United States Patent
Laughlin et al.

(10) Patent No.: US 12,194,023 B2
(45) Date of Patent: Jan. 14, 2025

(54) COMPOSITIONS AND METHODS FOR MODULAR CONTROL OF BIOORTHOGONAL LIGATION

(71) Applicants: The Research Foundation for The State University of New York, Albany, NY (US); Scott Laughlin, Roslyn Heights, NY (US); Pratik Kumar, St. James, NY (US); Ting Jiang, Centereach, NY (US); Wei Huang, Stony Brook, NY (US)

(72) Inventors: Scott Laughlin, Roslyn Heights, NY (US); Pratik Kumar, St. James, NY (US); Ting Jiang, Centereach, NY (US); Wei Huang, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/297,848

(22) PCT Filed: Nov. 27, 2019

(86) PCT No.: PCT/US2019/063714
§ 371 (c)(1),
(2) Date: May 27, 2021

(87) PCT Pub. No.: WO2020/113077
PCT Pub. Date: Jun. 4, 2020

(65) Prior Publication Data
US 2022/0218661 A1     Jul. 14, 2022

Related U.S. Application Data

(60) Provisional application No. 62/772,797, filed on Nov. 29, 2018.

(51) Int. Cl.
| | |
|---|---|
| A61K 31/403 | (2006.01) |
| A61K 31/4178 | (2006.01) |
| A61K 31/4188 | (2006.01) |
| A61K 47/54 | (2017.01) |

(52) U.S. Cl.
CPC ........ *A61K 31/403* (2013.01); *A61K 31/4178* (2013.01); *A61K 31/4188* (2013.01); *A61K 47/543* (2017.08); *A61K 47/545* (2017.08)

(58) Field of Classification Search
CPC ............. A61K 31/403; A61K 31/4178; A61K 31/4188; A61K 47/543; A61K 47/545; Y02P 20/55; C07D 205/12; C07D 495/04; C07D 487/10; C07D 209/02
See application file for complete search history.

(56) References Cited

U.S. PATENT DOCUMENTS

| | | | |
|---|---|---|---|
| 7,351,738 B2 | 4/2008 | Pulley et al. | |
| 7,361,688 B2 | 4/2008 | Maillard et al. | |
| 7,459,450 B2 | 12/2008 | Zhu et al. | |
| 7,772,178 B2 | 8/2010 | Malcolm et al. | |
| 7,790,730 B2 | 9/2010 | Kim et al. | |
| 7,902,157 B2 | 3/2011 | Burnett et al. | |
| 8,119,602 B2 | 2/2012 | Zhang et al. | |
| 8,124,584 B2 | 2/2012 | Miao et al. | |

(Continued)

FOREIGN PATENT DOCUMENTS

| | | |
|---|---|---|
| CN | 107281204 A | 10/2017 |
| CN | 107522673 B | 5/2020 |

(Continued)

OTHER PUBLICATIONS

STN Abstract for Registry No. 1242170-79-1. Published Sep. 21, 2010. (Year: 2010).*
ScienceOxygen. What is Boc organic chemistry. Retrieved from the Internet on Mar. 9, 2023, https://scienceoxygen.com/ what-is-boc-organic-chemistry/ Published Sep. 5, 2022. (Year: 2022).*
Wang et al. Photolabile 2-(2-Nitropheny)-propyloxycarbonyl (NPPOC) for stereoselective glycosylation and Its Application in Consecutive Assembly of Oligosaccharides. The Journal of Organic Chemistry, published 2022. (Year: 2022).*

(Continued)

*Primary Examiner* — Robert H Havlin
*Assistant Examiner* — Lauren Wells
(74) *Attorney, Agent, or Firm* — Gary J. Gershik

(57) ABSTRACT

The present invention provides a compound having the structure:

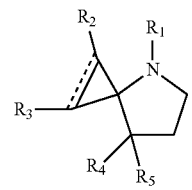

wherein $R_1$ is H or a protecting group;

$R_2$ and $R_3$ are each independently H, halo, $C_1$-$C_6$ alkyl, $C_2$-$C_6$ alkenyl, $C_2$-$C_6$ alkynyl, $C_1$-$C_6$ alkyl-C(O)NHR$_6$, $C_1$-$C_6$ alkyl-C(O)OR$_6$, wherein $R_6$ is H, $C_1$-$C_6$ alkyl, $C_2$-$C_6$ alkenyl or $C_2$-$C_6$ alkynyl, or $R_2$ and $R_3$ combine to form a 3-7 membered cycloalkyl, heterocycloalkyl, aryl or heteroaryl ring; and $R_4$ and $R_5$ are each independently halo.

17 Claims, 24 Drawing Sheets

(56) References Cited

U.S. PATENT DOCUMENTS

| | | |
|---|---|---|
| 8,329,727 B2 | 12/2012 | Bondy et al. |
| 8,426,403 B2 | 4/2013 | Zhu et al. |
| 8,470,773 B2 | 6/2013 | Gilbert et al. |
| 8,470,834 B2 | 6/2013 | Kwong et al. |
| 8,487,099 B2 | 7/2013 | Greenlee et al. |
| 8,530,466 B2 | 9/2013 | Masuda et al. |
| 8,715,638 B2 | 5/2014 | Kwong et al. |
| 8,735,604 B2 | 5/2014 | Gilbert et al. |
| 8,759,337 B2 | 6/2014 | Asberom et al. |
| 8,759,357 B2 | 6/2014 | Shipps, Jr. et al. |
| 8,765,757 B2 | 7/2014 | Chan et al. |
| 8,822,480 B2 | 9/2014 | Neelamkavil et al. |
| 8,846,600 B2 | 9/2014 | Darwish et al. |
| 9,012,643 B2 | 4/2015 | Diwu et al. |
| 9,242,983 B2 | 1/2016 | Bondy et al. |
| 9,315,505 B2 | 4/2016 | Ren et al. |
| 9,345,706 B2 | 5/2016 | Ren et al. |
| 9,624,205 B2 | 4/2017 | Campbell |
| 9,932,326 B2 | 4/2018 | Coats et al. |
| 10,155,726 B2 | 12/2018 | Wehn et al. |
| 10,226,535 B2 | 3/2019 | Yurkovetskiy et al. |
| 10,428,060 B2 | 10/2019 | Glenn et al. |
| 10,526,294 B2 | 1/2020 | Thomas et al. |
| 10,660,901 B2 | 5/2020 | Yin et al. |
| 10,806,737 B2 | 10/2020 | Crew et al. |
| 10,941,135 B2 | 3/2021 | Duncton et al. |
| 11,376,334 B2 | 7/2022 | Chuprakov et al. |
| 2009/0023916 A1 | 1/2009 | Fox et al. |
| 2015/0246893 A1 | 9/2015 | Devaraj et al. |
| 2018/0244643 A1 | 8/2018 | Devaraj et al. |

FOREIGN PATENT DOCUMENTS

| | | |
|---|---|---|
| WO | WO 2018/026551 A1 | 2/2018 |
| WO | WO 2018/187740 A1 | 10/2018 |
| WO | WO 2019/086142 A1 | 5/2019 |

OTHER PUBLICATIONS

Liu et al. Synthesis of photolabile o-nitroveratryloxycarbonyl (NVOC) protected peptide nucleic acid monomers. Tetrahedron 61 (2005) 7967-7973. (Year: 2005).*

STN Abstract for Registry No. 1242170-77-9. Published Sep. 21, 2010. (Year: 2010).*

STN Abstract for Registry No. 1242277-50-4. Published Sep. 22, 2010. (Year: 2010).*

International Preliminary Report on Patentability dated May 25, 2021, including Written Opinion of the International Searching Authority dated Mar. 12, 2020, in connection with PCT International Application No. PCT/US2019/063714.

International Search Report dated Mar. 12, 2020 in connection with PCT International Application No. PCT/US2019/063714.

Kumar, P. et al. "Lipidated cyclopropenes via a stable 3-N spirocyclopropene scaffold. " Tetrahedron Letters, vol. 59, iss. 37, Aug. 7, 2018, pp. 3435-3438.

PUBCHEM, Substance Record for SID 299275958, available date: Jan. 27, 2017.

Written Opinion (form PCT/ISA/237) dated Mar. 12, 2020 in connection with PCT International Application No. PCT/US2019/063714.

David M. Patterson et al, "Functionalized Cyclopropenes As Bioorthogonal Chemical Reporters" Journal of the American Chemical Society, Oct. 16, 2012, J. Am. Chem. Soc. 2012, 134, 45, 18638-18643.

Jonathan C.T. Carlson et al, "Unraveling Tetrazine-Triggered Bioorthogonal Elimination Enables Chemical Tools for Ultrafast Release and Universal Cleavage" Journal of the American Chemical Society, Jan. 31, 2018, J. Am. Chem. Soc. 2018, 140, 3603-3612.

Pratik Kumar et al,"Inexpensive multigram-scale synthesis of cyclic enamines and 3-N spirocyclopropyl systems" Organic & Biomolecular Chemistry, Dec. 21, 2017, Org. Biomol. Chem. 2018, 16, 652-656.

* cited by examiner

S15

S17

S16

S18

S19 (HELIOS 388Me)

10

11

COMPOSITIONS AND METHODS FOR MODULAR CONTROL OF BIOORTHOGONAL LIGATION

CROSS-REFERENCE TO RELATED APPLICATIONS

This application is a § 371 national stage of PCT International Application No. PCT/US2019/063714, filed Nov. 27, 2019, claiming the benefit of U.S. Provisional Application No. 62/772,797, filed Nov. 29, 2018, the contents of each of which are hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Over the last two decades, bioorthogonal reagents have enhanced our understanding of the structure and function of both genetically encoded biomolecules like proteins (Lang and Chin 2014), and non-genetically encoded biomolecules like lipids (Bumpus and Baskin 2017; Izquierdo and Delgado 2018), glycans (Agarwal et al. 2015; Lopez Aguilar et al. 2017), and nucleic acids (El-Sagheer and Brown 2010). Indeed, efforts in bioorthogonal chemistry have reached as far as the development of bioorthogonal radiopharmaceuticals (Zeng et al. 2013) and mimics of neurotransmitters GABA (Paulini and Reissig 1992) and glutamate (Kumar, Shukhman, and Laughlin 2016). Tagging biomolecules with bioorthogonal reagents is now routinely performed in solution, living cells, and whole-organisms by choosing from approximately two-dozen unique bioorthogonal chemistries (Patterson, Nazarova, and Prescher 2014). Significant effort has been devoted to inventing and optimizing current bioorthogonal reagents. Generally, such optimizations focus on creating bioorthogonal reagents that are faster, fluorogenic, or orthogonal to the already existing bioorthogonal repertoire (Liu, Liang, and Houk 2017; Ramil and Lin 2014; Row and Prescher 2018).

On the other hand, efforts to explore bioorthogonal reagents that permit control over their reaction in space and/or time are limited. Such "activatable" bioorthogonal reagents are unreactive to their bioorthogonal partner unless activated by a stimulus; for example, illumination by light or application of an enzyme. The light- and/or enzyme-dependent control furnishes the ability to decide when and where the bioorthogonal reaction will occur. Importantly, there exist approximately a dozen activatable click reactions (Herner and Lin 2016; Kaur, Singh, and Singh 2018; Tasdelen and Yagci 2013). However, most of them are not modular, generally require UV light, or do not meet the bioorthogonality standards crucial for biological applications.

Cyclopropenes have become popular bioorthogonal reagents due to their small size, inertness to biological nucleophiles, ability to be genetically encoded (Yu et al. 2012), and participation in cycloaddition reactions with 1,3-dipoles and inverse electron demand Diels-Alder (IEDDA) substrates such as s-tetrazines (Ravasco, Monteiro, and Trindade 2017), 1,2,4-triazines (Kamber et al. 2015), and o-quinones (Gahtory et al. 2018). Cyclopropenes are also useful synthetic targets due to their importance as synthetic intermediates (Edwards, Rubina, and Rubin 2016; Rubin, Rubina, and Gevorgyan 2006; Zhu, Wei, and Shi 2011), e.g., for polymerization (Elling, Su, and Xia 2016) or unnatural amino acids synthesis (F. Zhang and Fox 2006). Over the last decade, cyclopropenes have been appended to various biomolecules like glycans (Spute et al. 2014), lipids (Kaur, Singh, and Singh 2018; Yang et al. 2012), proteins (Z. Li et al. 2014; Patterson, Jones, and Prescher 2014), and nucleic acids (Šečkutė, Yang, and Devaraj 2013) to reveal their function in cells and whole organisms.

The technology is composed of a bicyclic cyclopropene scaffold with a variety of substitutions that modulate the molecules reactivity IEDDA substrates. It can do this in a modular fashion, meaning that a variety of activation methods can integrate into the technology to optimize it for a given application. Activatable cyclopropenes are unreactive toward their IEDDA reaction partner (e.g., s-tetrazines) until they are activated. The activation strategy is highly modular due to the cyclopropene's ability to be caged by various light- and enzyme-activatable groups. Of these biological applications, majority of them utilize tetrazine ligation where cyclopropenes act as dienophiles.

Historically, tetrazine ligation was first reported by Carboni and Lindsey. They observed that the characteristic red-violet color of the tetrazine disappears upon heating with olefins or acetylenic compounds (Carboni and Lindsey 1959) with concomitant evolution of nitrogen gas. Building upon this seminal study, Sauer and coworkers conducted thorough spectrometric studies to measure kinetic rate constants of the tetrazine ligation for a series of dienophiles with different electronic densities, steric constraints, and ring strains. This seminal study provided experimental values of the quantitative observations made by Carboni and Lindsey; it has set the basis for now routinely applied bioorthogonal tetrazine ligation (Thalhammer, Wallfahrer, and Sauer 1990). Both these studies found the rate of tetrazine ligation to increase with increasing electron density of the alkene dienophiles or with decreasing electron density of the tetrazines. Increasing the ring size of the cyclic dienophiles from three to eight, thereby decreasing the ring strain, decreases the rate of adduct formation. Interestingly, the trans form of the eight-member ring, trans-cyclooctene (fastest dienophile tested) and cyclooctyne do not follow this general trend.

Cyclopropene, the most strained ring, is only second to transcyclooctene. However, disubstituted 3,3-dimethyl cyclopropene display very diminished reactivity compared to their monosubstituted analog. This decrease in the reactivity is due to steric blocking of the incoming tetrazine. The IEDDA inactive 3,3-disubstituted cyclopropenes are active toward the 1,3-dipole cycloaddition, for example, in photoclick chemistry. Prescher and coworkers exploited this significant difference in reactivity between C3 mono- and di-substituted cyclopropenes for orthogonal labeling of proteins in vitro using a tetrazine and tetrazole respectively (Kamber et al. 2013), and with azides for SPAAC (Patterson et al. 2012).

SUMMARY OF THE INVENTION

The invention provides a compound having the structure:

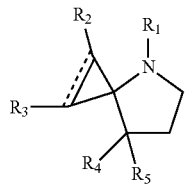

wherein
$R_1$ is H or a protecting group;
$R_2$ and $R_3$ are each independently H, halo, $C_1$-$C_6$ alkyl, $C_2$-$C_6$ alkenyl, $C_2$-$C_6$ alkynyl, $C_1$-$C_6$ alkyl-C(O)NHR$_6$, $C_1$-$C_6$ alkyl-C(O)OR$_6$,
    wherein $R_6$ is H, $C_1$-$C_6$ alkyl, $C_2$-$C_6$ alkenyl or $C_2$-$C_6$ alkynyl,
or $R_2$ and $R_3$ combine to form a 3-7 membered cycloalkyl, heterocycloalkyl, aryl or heteroaryl ring; and
$R_4$ and $R_5$ are each independently halo.

The present invention also provides compound having the structure:

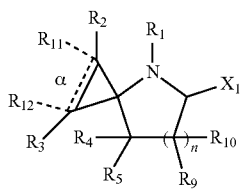

wherein
n is 0 or 1;
α is a bond which is absent or present,
    wherein when α is present, then $R_{11}$ and $R_{12}$ are absent and when a is absent, Ru and $R_{12}$ are present;
$X_1$ is H or $L_3$-$Y_3$,
    wherein $L_3$ is a chemical linker that is present or absent and $Y_3$ is a lipid, peptide, protein, sugar, nucleotide, antibody or imaging moiety;
$R_1$ is H or a protecting group;
$R_2$ and $R_3$ are each independently H, halo alkyl, alkenyl, alkynyl, alkyl-C(O)NHR$_{13}$, alkyl-C(O)OR$_{13}$,
    wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
    wherein $L_4$ is a chemical linker that is present or absent and $Y_4$ is a lipid, peptide, protein, sugar, nucleotide, antibody or imaging moiety;
$R_4$ and $R_5$ combine to form a carbonyl, or are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;
$R_9$ and $R_{10}$ are each independently H, halo, alkyl, —O(alkyl), O(alkylaryl), $CF_3$, $OCF_3$, $OCHF_2$ or $OSO_3^-$; and
$R_{11}$ and $R_{12}$, when present, combine to form a 5-6 membered substituted or unsubstituted cycloalkyl, heterocycloalkyl, aryl or heteroaryl ring which is fused to the cycopropanyl.

The present invention further provides a compound having the structure:

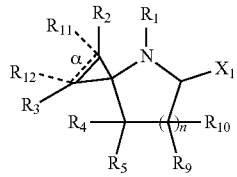

wherein
n is 0 or 1;
α is a bond which is absent or present,
    wherein when α is present, then $R_{11}$ and $R_{12}$ are absent and when α is absent, $R_{11}$ and $R_{12}$ are present;
$X_1$ is H or $L_3$-$Y_3$,
    wherein $L_3$ is a chemical linker and $Y_3$ is a lipid, peptide, protein, sugar, nucleotide, antibody or imaging moiety;
$R_1$ is H or a protecting group;
$R_2$ and $R_3$ are each independently H, halo alkyl, alkenyl, alkynyl, alkyl-C(O)NHR$_{13}$, alkyl-C(O)OR$_{13}$,
    wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
    wherein $L_4$ is a chemical linker that is present or absent and $Y_4$ is a lipid, peptide, protein, sugar, nucleotide, antibody or imaging moiety;
$R_4$ and $R_5$ are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;
$R_9$ and $R_{10}$ are each independently H, halo, alkyl, —O(alkyl), —O(alkylaryl), $CF_3$, $OCF_3$, $OCHF_2$ or $OSO_3^-$;
$R_{11}$ and $R_{12}$, when present, combine to form a 5-6 membered substituted or unsubstituted cycloalkyl, heterocycloalkyl, aryl or heteroaryl ring which is fused to the cycopropanyl.

BRIEF DESCRIPTION OF THE DRAWINGS

FIG. 7A—Synthesis of functionalized 3-N deprotected spirocyclopropenes and kinetic evaluation of their reaction with 1,2,4,5-tetrazine S10. (A) 3-N spirocyclopropene 4 carboxylic acid functionalization and subsequent amide linkage to 4-methyoxybenzylamine or NHi-PEG2-biotin.

FIG. 7B—Synthesis of functionalized 3-N deprotected spirocyclopropenes and kinetic evaluation of their reaction with 1,2,4,5-tetrazine S10. Pseudo 1st order kinetic analysis of the reaction between cyclopropane 10a and tetrazine S10.

FIG. 7C—Synthesis of functionalized 3-N deprotected spirocyclopropenes and kinetic evaluation of their reaction with 1,2,4,5-tetrazine S10. 2nd order rate constant calculation of the reaction between cyclopropene 10a and 3-phenyl-1,2.4,5-tetrazine pyrrolidinyl amide S10. The reactions under pseudo $1^{st}$ order conditions were conducted at rt in a 96-well plate. Reaction progress was monitored by the disappearance of characteristic tetrazine absorbance at 520 nm. Each well consisted of 10a (50/65/85 mM) and S10 (5 mM) in 1:1 MeCN/buffer (shown here for pH 8.0 in NH$_4$HCO$_3$ buffer). Plotting the normalized absorbance wrt the initial tetrazine absorbance against reaction time. and then fitting using the pseudo $1^{st}$ order rate equation A=A$_0$ exp(−k·[10a]·t) (A=absorbance at time t, A$_0$=initial absorbance, and k·[10a]=pseudo $1^{st}$ order rate constant) provided pseudo $1^{st}$ order rate constant. The $2^{nd}$ order rate constants were obtained by plotting pseudo $1^{st}$ order rates against the concentration of 10a.

FIG. 9A—Kinetic evaluation of ligation between cyclopropene 10a and 1,2,4,5-tetrazine S10. Incubation of cyclopropene 10a and 1,2,4,5-tetrazine S10 in 1:1 MeCN/buffer produced the ligated product S11.

FIG. 9B—2nd order rate constants for this ligation reaction were determined at pH 7.4.

FIG. 9C—2nd order rate constants for this ligation reaction were determined at pH 8.0.

FIG. 9D—2nd order rate constants for this ligation reaction were determined at pH 8.8.

FIG. 25. Scheme 9—Methods for synthesis of compounds S6, 1, 2, 3, S7, 4, 5a, and 6a.

DETAILED DESCRIPTION OF THE INVENTION

Figure 1:
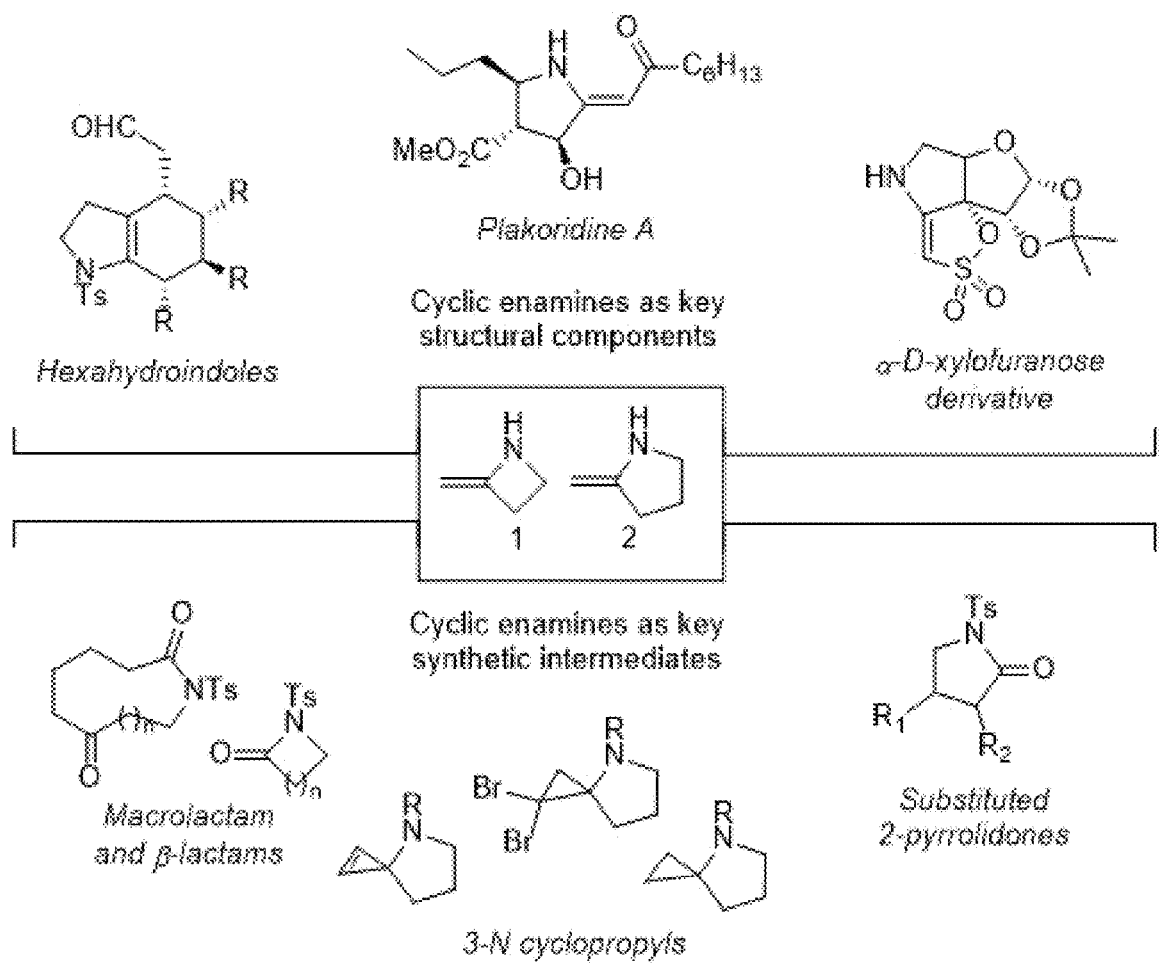
FIG. 1—An array of synthetic, naturally-occurring, and pharmaceutical molecules utilizes cyclic enamines as key motifs, Additionally, cyclic enamines containing an exocyclic double bond can provide access to 3-N spirocyclic systems.

The invention provides a compound having the structure:

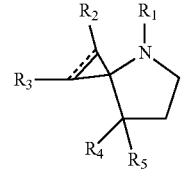

wherein

R$_1$ is H or a protecting group;

R$_2$ and R$_3$ are each independently H, halo, C$_1$-C$_6$ alkyl, C$_2$-C$_6$ alkenyl, C$_2$-C$_6$ alkynyl, C$_1$-C$_6$alkyl-C(O)NHR$_6$, C$_1$-C$_6$ alkyl-C(O)OR$_6$, wherein R$_6$ is H, C$_1$-C$_6$ alkyl, C$_2$-C$_6$ alkenyl or C$_2$-C$_6$ alkynyl, or R$_2$ and R$_3$ combine to form a 3-7 membered cycloalkyl, heterocycloalkyl, aryl or heteroaryl ring; and R$_4$ and R$_5$ are each independently halo.

In some embodiments, the compound wherein

R$_1$ is H, Boc or Nvoc;

R$_2$ and R$_3$ are each independently H, halo, C$_1$-C$_3$ alkyl, C$_2$-C$_3$alkenyl, C$_2$-C$_3$ alkynyl, C$_1$-C$_3$ alkyl-C(O)NHR$_6$, C$_1$-C$_3$ alkyl-C(O)OR$_6$, wherein R$_6$ is H, C$_1$-C$_3$ alkyl, C$_2$-C$_3$ alkenyl or C$_2$-C$_3$ alkynyl, or R$_2$ and R$_3$ combine to form a 3-7 membered cycloalkyl, heterocycloalkyl, aryl or heteroaryl ring; and R$_4$ and R$_5$ are each independently F, Cl or Br.

In some embodiments, the compound wherein

R$_1$ is H, Boc or Nvoc;

R$_2$ and R$_3$ are each independently H or C$_1$-C$_3$ alkyl; and

R$_4$ and R$_5$ are each F.

In some embodiments, the compound wherein R$_1$ is H.

In some embodiments, the compound wherein R$_1$ is Boc.

In some embodiments, the compound wherein R$_1$ is a light cleavable protecting group.

In some embodiments, the compound wherein R$_1$ is Nvoc.

In some embodiments, the compound having the structure:

[chemical structures]

In some embodiments, the compound having the structure:

[chemical structure with R$_7$, R$_8$, R$_2$, R$_1$, R$_3$, R$_4$, R$_5$]

wherein

R$_1$ is H;

R$_2$ and R$_3$ are each independently H, halo, C$_1$-C$_6$ alkyl, C$_2$-C$_6$ alkenyl, C$_2$-C$_6$ alkynyl, C$_1$-C$_6$ alkyl-C(O)NHR$_6$, C$_1$-C$_6$ alkyl-C(O)OR$_6$, wherein R$_6$ is H, C$_1$-C$_6$ alkyl, C$_2$-C$_6$ alkenyl or C$_2$-C$_6$ alkynyl;

R$_7$ and R$_8$ are each independently H or aryl; and

R$_4$ and R$_5$ are each independently halo.

In some embodiments, the compound wherein R$_7$ and R$_8$ are each independently H, phenyl or substituted phenyl.

In some embodiments, the compound wherein R$_7$ and R$_8$ are each independently H, phenyl or

[chemical structure with CO$_2$H]

In some embodiments, the compound having the structure:

[chemical structures]

In some embodiments, the compound having the structure:

[chemical structure with R$_2$, R$_1$, R$_3$, R$_4$, R$_5$]

wherein

R$_1$ is H or a protecting group;

R$_2$ and R$_3$ are each independently H or C$_1$-C$_6$ alkyl-C(O)NHR$_6$, wherein R$_6$ is C$_1$-C$_6$ alkylaryl or L$_1$-Y$_1$, wherein L$_1$ is a chemical linker that is present or absent and Y$_1$ is biotin or a lipid;

or R$_2$ and R$_3$ combine to form a 3-7 membered cycloalkyl, heterocycloalkyl, aryl or heteroaryl ring; and R$_4$ and R$_5$ are each independently halo.

In some embodiments, the compound having the structure:

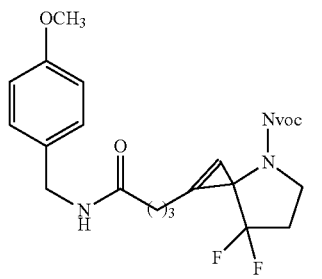

or

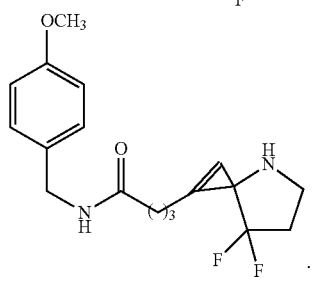

In some embodiments, the compound having the structure:

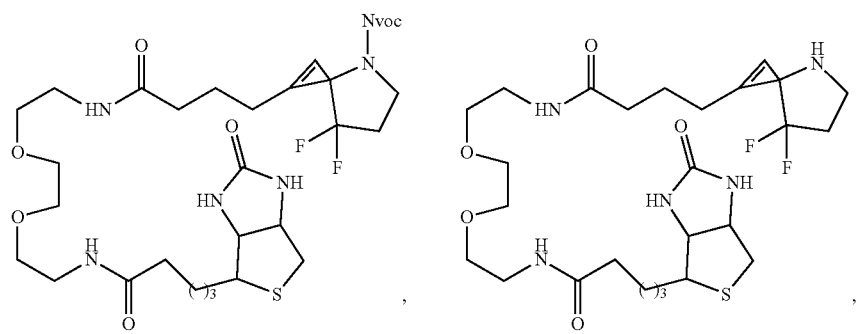

In some embodiments, the compound having the structure:

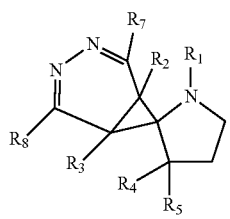

wherein $R_1$ is H;

$R_2$ and $R_3$ are each independently H or $C_1$-$C_6$ alkyl-C(O)NHR$_6$,
  wherein $R_6$ is $C_1$-$C_6$ alkylaryl or $L_1$-$Y_1$,
    wherein $L_1$ is a chemical linker that is present or absent and $Y_1$ is biotin or a lipid;

$R_7$ and $R_8$ are each independently H, aryl or $L_2$-$Y_2$,
    wherein $L_2$ is a chemical linker that is present or absent and $Y_2$ is bovine serum albumin protein; and $R_4$ and $R_5$ are each independently halo.

In some embodiments, the compound of the present invention which is a salt form of the compound.

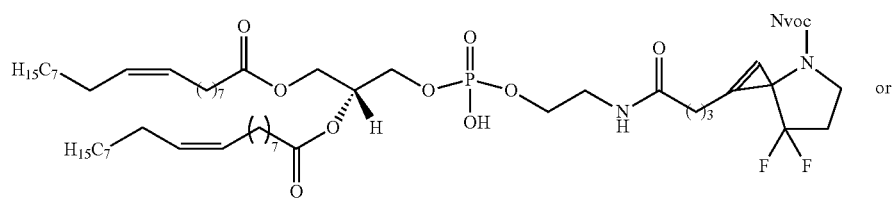

or

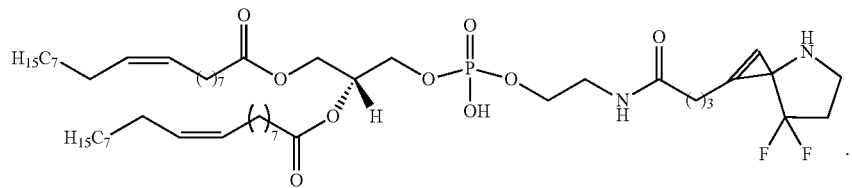

In some embodiments, a process for preparing the compound of the present invention comprising exposing a compound having the structure:

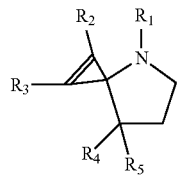

wherein
R₁ is a light cleavable protecting group;
R₂ and R₃ are each independently H, halo, C₁-C₆ alkyl, C₂-C₆ alkenyl, C₂-C₆ alkynyl, C₁-C₆ alkyl-C(O)NHR₆, C₁-C₆ alkyl-C(O)OR₆,
   wherein R₆ is H, C1-C₆ alkyl, C₂-C₆ alkenyl or C₂-C₆ alkynyl; and
R₄ and R₅ are each independently halo,
to light which is effective to cleave the amine protecting group in the presence of an unsubstituted or substituted tetrazine having the structure:

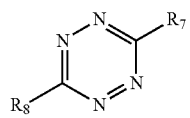

wherein R₈ and R₉ are each independently H or aryl, so as to thereby produce the compound.

In some embodiments, a process for preparing the compound of the present invention comprising exposing a compound having the structure:

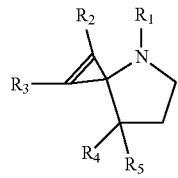

wherein
R₁ is a light cleavable protecting group;
R₂ and R₃ are each independently H or C₁-C₆ alkyl-C(O)NHR₆,
   wherein R₆ is C₁-C₆ alkylaryl or L₁-Y₁,
      wherein L₁ is a chemical linker that is present or absent and Y₁ is biotin or a lipid; and
R₄ and R₅ are each independently halo,
to light which is effective to cleave the amine protecting group in the presence of an unsubstituted or substituted tetrazine having the structure:

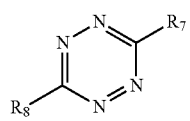

wherein R₇ and R₈ are each independently H, aryl or L₂-Y₂, wherein L₂ is a chemical linker that is present or absent and Y₂ is bovine serum
   albumin protein, so as to thereby produce the compound.

The present invention also provides compound having the structure:

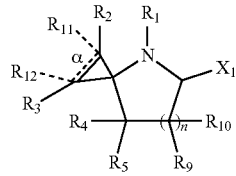

wherein
n is 0 or 1;
α is a bond which is absent or present,
   wherein when α is present, then R₁₁ and R₁₂ are absent and when α is absent, Ru and R₁₂ are present;
X₁ is H or L₃-Y₃,
   wherein L₃ is a chemical linker that is present or absent and Y₃ is a lipid, peptide, protein, sugar, nucleotide, antibody or imaging moiety;
R₁ is H or a protecting group;
R₂ and R₃ are each independently H, halo alkyl, alkenyl, alkynyl, alkyl-C(O)NHR₁₃, alkyl-C(O)OR₁₃,
   wherein R₁₃ is H or substituted or unsubstituted alkyl, alkenyl, alkynyl, heteroalkyl, amidoalkyl, amidoheteroalkyl, alklyaryl, alkylheteroaryl or L₄-Y₄,
      wherein L₄ is a chemical linker that is present or absent and Y₄ is a lipid, peptide, protein, sugar, nucleotide, antibody or imaging moiety;
R₄ and R₅ combine to form a carbonyl, or are each H, or one of R₄ and R₅ is H and the other is halo, —O(alkyl), —O(alkylaryl), CF₃, OCF₃, OCHF₂ or OSO₃⁻, or R₄ and R₅ are each independently halo, alkyl, —O(alkyl), CF₃, OCF₃, OCHF₂ or OSO₃⁻;
R₉ and R₁₀ are each independently H, halo, alkyl, —O(alkyl), O(alkylaryl), CF₃, OCF₃, OCHF₂ or OSO₃⁻; and
R₁₁ and R₁₂, when present, combine to form a 5-6 membered substituted or unsubstituted cycloalkyl, heterocycloalkyl, aryl or heteroaryl ring which is fused to the cycopropanyl.

In some embodiments, the compound wherein one of R₄ or R₅ or one of R₉ and R₁₀ is other than H.

In some embodiments, the compound wherein two of R₄ and R₅ are other than H and R₉ and R₁₀ are each H.

In some embodiments, the compound wherein two of R₉ and R₁₀ are other than H and R₄ and R₅ are each H.

In some embodiments, the compound wherein one of R₄ and R₅ is other than H and one of R₉ and R₁₀ is other than H.

In some embodiments, the compound having the structure:

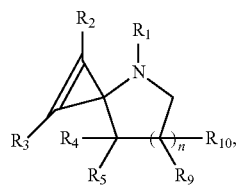

wherein n is 0 or 1;

$R_1$ is H or a protecting group;

$R_2$ and $R_3$ are each independently H, halo alkyl, alkenyl, alkynyl, alkyl-C(O)NHR$_{13}$, alkyl-C(O)OR$_{13}$, wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$, wherein $L_4$ is a chemical linker that is present or absent and $Y_4$ is a lipid, peptide, protein, sugar, nucleotide, antibody or imaging moiety;

$R_4$ and $R_5$ combine to form a carbonyl, or are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;

$R_9$ and $R_{10}$ are each independently H, halo, alkyl, —O(alkyl), —O(alkylaryl), $CF_3$, $OCF_3$, $OCHF_2$ or $OSO_3^-$.

In some embodiments, the compound wherein $R_1$ is H.

In some embodiments, the compound wherein $R_1$ is a light cleavable amine protecting group, an enzyme cleavable protecting group or a small molecule cleavable protecting group.

In some embodiments, the compound wherein $R_1$ is a carbamate protecting group having the structure

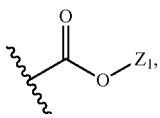

wherein $Z_1$ is alkylaryl, alkylheteroaryl or a pyranoside.

In some embodiments, the compound wherein $Z_1$ is

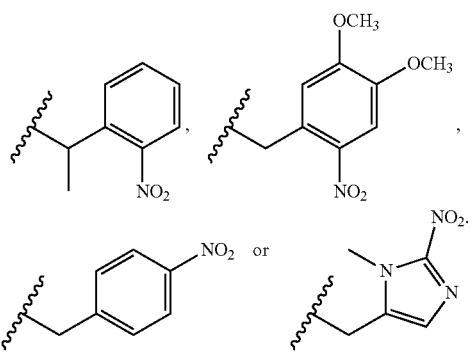

In some embodiments, the compound wherein $Z_1$ is

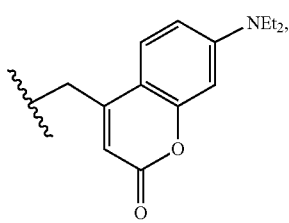

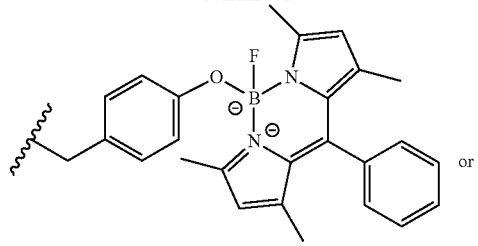

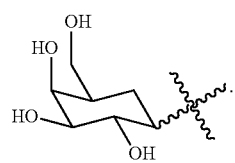

In some embodiments, the compound having the structure:

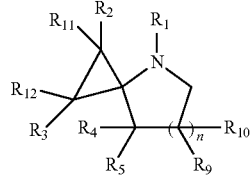

wherein n is 0 or 1;

$R_1$ is H;

$R_2$ and $R_3$ are each independently H, halo alkyl, alkenyl, alkynyl, alkyl-C(O)NHR$_{13}$, alkyl-C(O)OR$_{13}$, wherein $R_{13}$ is H or a substituted or unsubstituted alkyl, alkenyl, alkynyl, heteroalkyl, amidoalkyl, amidoheteroalkyl, alklyaryl, alkylheteroaryl or $L_4$-$Y_4$, wherein $L_4$ is a chemical linker that is present or absent and $Y_4$ is a lipid, peptide, protein, sugar, nucleotide, antibody or imaging moiety, $R_4$ and $R_5$ combine to form a carbonyl, or are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;

$R_9$ and $R_{10}$ are each independently H, halo, alkyl, —O(alkyl), —O(alkylaryl), $CF_3$, $OCF_3$, $OCHF_2$ or $OSO_3^-$, $R_{11}$ and $R_{12}$, when present, combine to form a 5-6 membered substituted or unsubstituted cycloalkyl, heterocycloalkyl, aryl or heteroaryl ring which is fused to the cycopropanyl.

In some embodiments, the compound wherein $R_{11}$ and $R_{12}$ combine to form a 6 membered substituted heteroaryl ring which is fused to the cycopropanyl.

In some embodiments, the compound wherein $R_{11}$ and $R_{12}$ combine to form a dihydropyridazine.

In some embodiments, the compound having the structure:

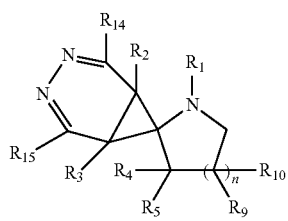

wherein
R$_{14}$ and R$_{15}$ are each independently H, halo alkyl, alkenyl, alkynyl, alkyl-C(O)NHR$_{16}$, alkyl-C(O)OR$_{16}$,
wherein R$_{16}$ is H, or a substituted or unsubstituted alkyl, alkenyl, alkynyl, heteroalkyl, amidoalkyl, amidoheteroalkyl, alklyaryl, alkylheteroaryl or L$_5$-Y$_5$,
wherein L$_5$ is a chemical linker that is present or absent and Y$_5$ is a lipid, peptide, protein, sugar, nucleotide, antibody or imaging moiety.

In some embodiments, the compound wherein R$_2$ and R$_3$ are each independently H, alkyl or C$_1$-C$_6$ alkyl-C(O)NHR$_{13}$, wherein R$_{13}$ is alkylaryl or L$_4$-Y$_4$.

In some embodiments, the compound wherein the aryl is substituted phenyl.

In some embodiments, the compound wherein the substituted phenyl is

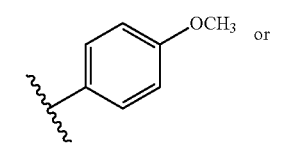 or

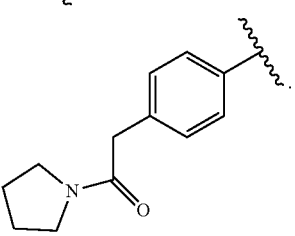

In some embodiments, the compound wherein the chemical linker L$_4$ or L$_5$ is an alkyl, alkenyl, alkynyl, alkylether, alkylthioether, alkylamino, alkylamido, alkylester, alkylaryl, alklyheteroaryl, aryl, heteroaryl, a natural amino acid, an unnatural amino acid, a disulfide or thioether containing linker or combinations thereof.

In some embodiments, the compound wherein Y$_4$ or Y$_N$ is

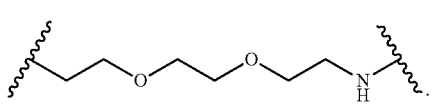 [SMILES: *CCOCCOCCN*]

In some embodiments, the compound wherein Y$_4$ or Y$_5$ is biotin, a phospholipid or tetramethylrhodamine.

In some embodiments, the compound wherein are each H, or one of R$_4$ and R$_5$ is H and the other is halo, —O(alkyl), —O(alkylaryl), CF$_3$, OCF$_3$, OCHF$_2$ or OSO$_3^-$, or R$_4$ and R$_5$ are each independently halo, alkyl, —O(alkyl), CF$_3$, OCF$_3$, OCHF$_2$ or OSO$_3^-$.

In some embodiments, the compound wherein one of R$_4$ and R$_5$ is H and the other is —O(alkylaryl).

In some embodiments, the compound wherein one of R$_9$ and R$_{10}$ is H and the other is —O(alkylaryl).

In some embodiments, the compound wherein the —O(alkylaryl) is

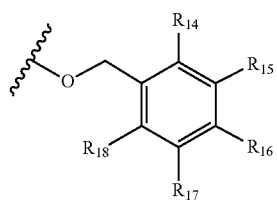

wherein R$_{14}$, R$_{15}$, R$_{16}$, R$_{17}$ and R$_{18}$ are each independently H, halo, alkyl, —O(alkyl), CF$_3$, OCF$_3$, OCHF$_2$, OSO$_3^-$, SO$_3$H, NO$_2$ or CN.

In some embodiments, the compound having the structure:

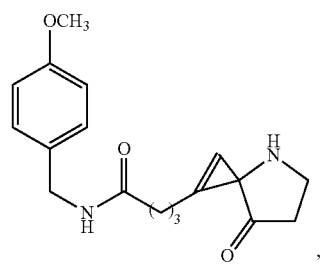

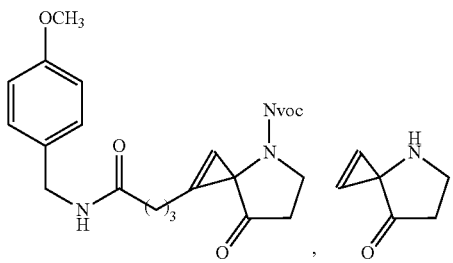

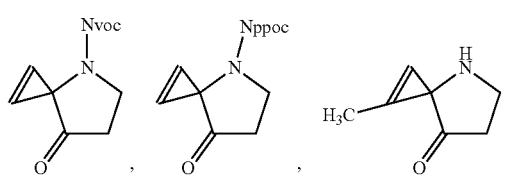

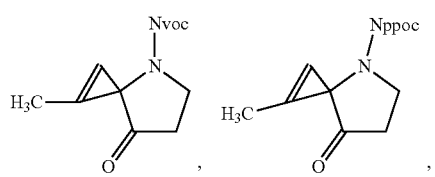

-continued
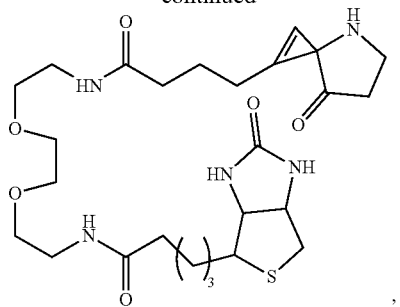
,
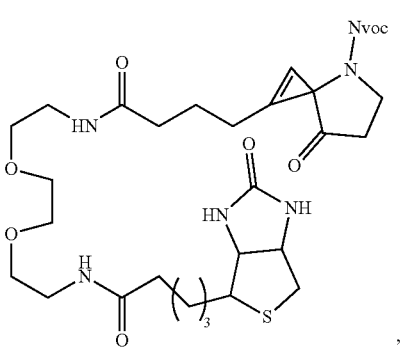
,
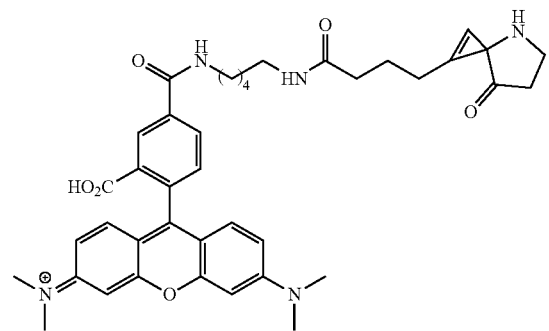
or
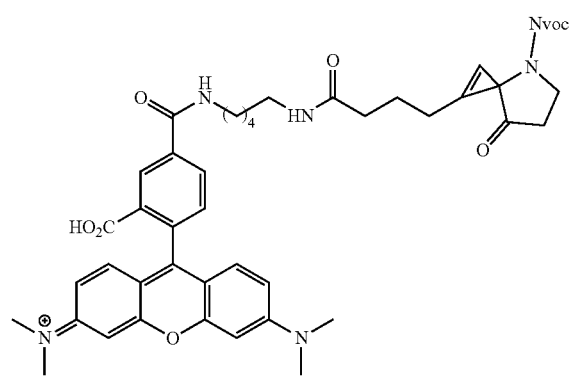
In some embodiments, the compound having the structure:
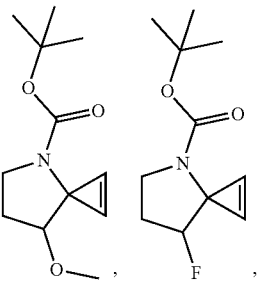
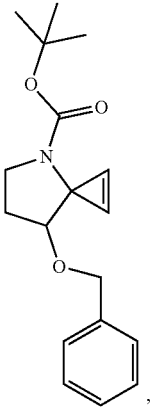
,
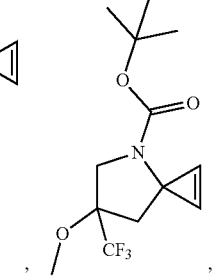
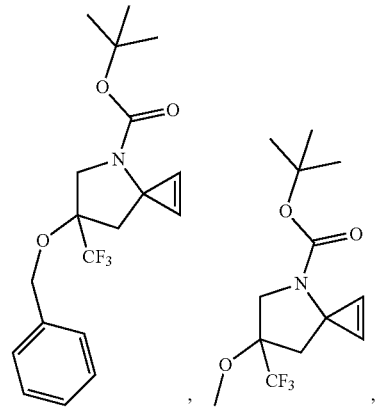
,
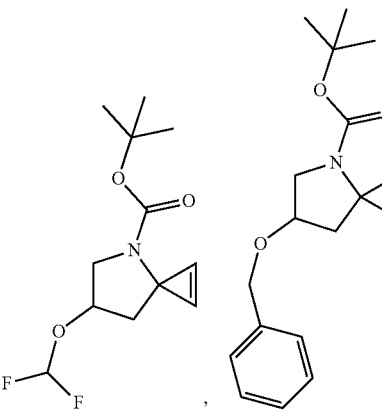
, -continued

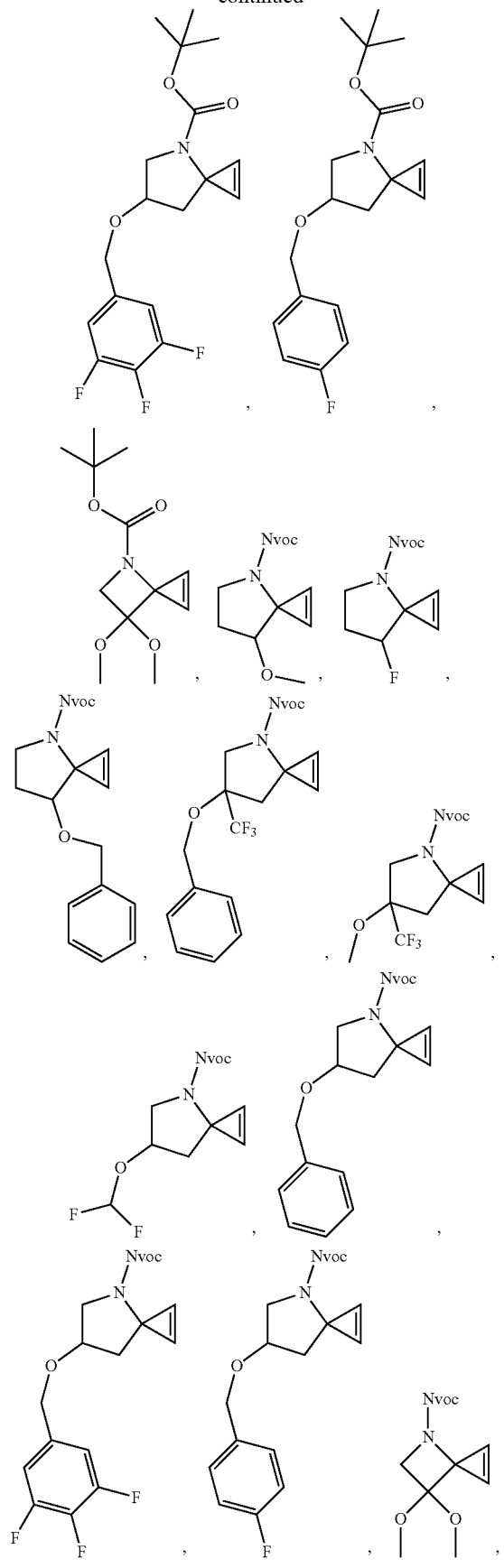

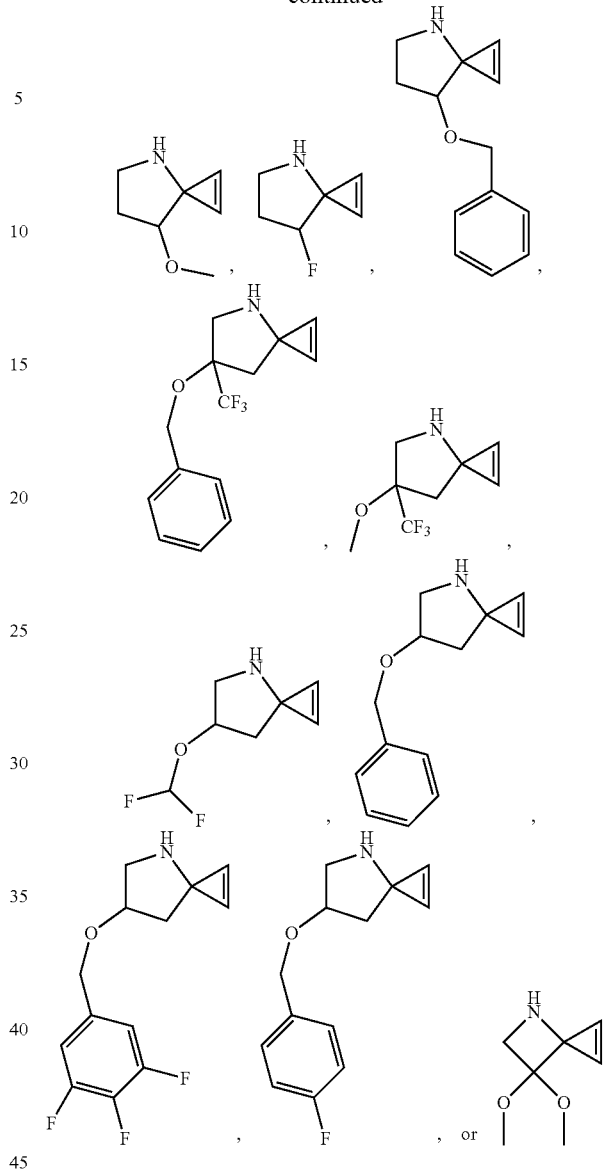

In some embodiments, the compound of the present invention which is a salt form of the compound.

In some embodiments, a process for preparing the compound of the present inventions comprising exposing a compound having the structure:

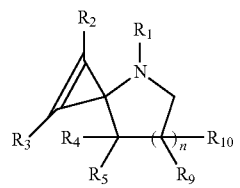

wherein n is 0 or 1;

$R_1$ is a light cleavable amine protecting group, an enzyme cleavable protecting group or a small molecule cleavable protecting group;

$R_2$ and $R_3$ are each independently H, halo alkyl, alkenyl, alkynyl, alkyl-C(O)NHR$_{13}$, alkyl-C(O)OR$_{13}$,
  wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
  wherein $L_4$ is a chemical linker that is present or absent and $Y_4$ is a lipid, peptide, protein, sugar, nucleotide, antibody or imaging moiety;
$R_4$ and $R_5$ combine to form a carbonyl, or are each H, or one of $R_4$ and $R_5$ is H and the other is halo, —O(alkyl), —O(alkylaryl), CF$_3$, OCF$_3$, OCHF$_2$ or OSO$_3^-$, or $R_4$ and $R_5$ are each independently halo, alkyl, —O(alkyl), CF$_3$, OCF$_3$, OCHF$_2$ or OSO$_3^-$;
$R_9$ and $R_{10}$ are each independently H, halo, alkyl, —O(alkyl), —O(alkylaryl), CF$_3$, OCF$_3$, OCHF$_2$ or OSO$_3^-$,
to light, an enzyme or s small molecule which is effective to cleave the amine protecting group in the presence of an unsubstituted or substituted tetrazine having the structure:

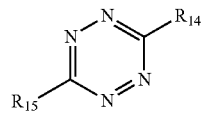

$R_{14}$ and $R_{15}$ are each independently H, halo alkyl, alkenyl, alkynyl, alkyl-C(O)NHR$_{16}$, alkyl-C(O)OR$_{16}$,
  wherein $R_{16}$ is H, or a substituted or unsubstituted alkyl, alkenyl, alkynyl, heteroalkyl, amidoalkyl, amidoheteroalkyl, alklyaryl, alkylheteroaryl or $L_5$-$Y_5$,
  wherein $L_5$ is a chemical linker that is present or absent and $Y_5$ is a lipid, peptide, protein, sugar, nucleotide, antibody or imaging moiety, so as to thereby produce the compound.

The present invention further provides a compound having the structure:

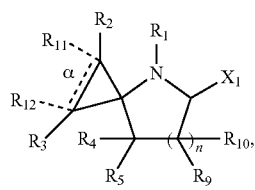

wherein
n is 0 or 1;
α is a bond which is absent or present,
  wherein when α is present, then $R_{11}$ and $R_{12}$ are absent and when α is absent, $R_{11}$ and $R_{12}$ are present;
$X_1$ is H or $L_3$-$Y_3$,
  wherein $L_3$ is a chemical linker and $Y_3$ is a lipid, peptide, protein, sugar, nucleotide, antibody or imaging moiety;
$R_1$ is H or a protecting group;
$R_2$ and $R_3$ are each independently H, halo alkyl, alkenyl, alkynyl, alkyl-C(O)NHR$_{13}$, alkyl-C(O)OR$_{13}$,
  wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
  wherein $L_4$ is a chemical linker that is present or absent and $Y_4$ is a lipid, peptide, protein, sugar, nucleotide, antibody or imaging moiety;
$R_4$ and $R_5$ are each H, or one of $R_4$ and $R_5$ is H and the other is halo, —O(alkyl), —O(alkylaryl), CF$_3$, OCF$_3$, OCHF$_2$ or OSO$_3^-$, or $R_4$ and $R_5$ are each independently halo, alkyl, —O(alkyl), CF$_3$, OCF$_3$, OCHF$_2$ or OSO$_3^-$;
$R_9$ and $R_{10}$ are each independently H, halo, alkyl, —O(alkyl), —O(alkylaryl), CF$_3$, OCF$_3$, OCHF$_2$ or OSO$_3^-$;
$R_{11}$ and $R_{12}$, when present, combine to form a 5-6 membered substituted or unsubstituted cycloalkyl, heterocycloalkyl, aryl or heteroaryl ring which is fused to the cycopropanyl.

In some embodiments, the compound having the structure:

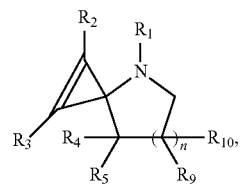

wherein
n is 0 or 1;
$R_1$ is H or a protecting group;
$R_2$ and $R_3$ are each independently H, halo alkyl, alkenyl, alkynyl, alkyl-C(O)NHR$_{13}$, alkyl-C(O)OR$_{13}$,
  wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
  wherein $L_4$ is a chemical linker that is present or absent and $Y_4$ is a lipid, peptide, protein, sugar, nucleotide, antibody or imaging moiety;
$R_4$ and $R_5$ are each H, or one of $R_4$ and $R_5$ is H and the other is halo, —O(alkyl), —O(alkylaryl), CF$_3$, OCF$_3$, OCHF$_2$ or OSO$_3^-$, or $R_4$ and $R_5$ are each independently halo, alkyl, —O(alkyl), CF$_3$, OCF$_3$, OCHF$_2$ or OSO$_3^-$;
$R_9$ and $R_{10}$ are each independently H, halo, alkyl, —O(alkyl), O(alkylaryl), CF$_3$, OCF$_3$, OCHF$_2$ or OSO$_3^-$.

In some embodiments, the compound wherein $R_1$ is H.

In some embodiments, the compound wherein $R_1$ is a light cleavable amine protecting group, an enzyme cleavable protecting group or a small molecule cleavable protecting group.

In some embodiments, the compound wherein $R_1$ is a carbamate protecting group having the structure

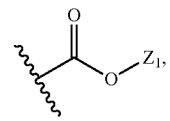

wherein $Z_1$ is alkylaryl, alkylheteroaryl or a pyranoside.
In some embodiments, the compound wherein $Z_1$ is

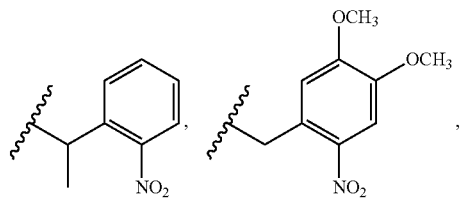

-continued

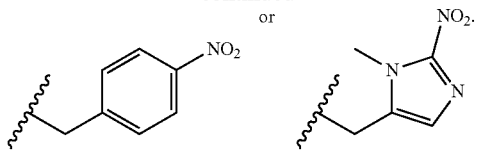

In some embodiments, the compound wherein $Z_1$ is

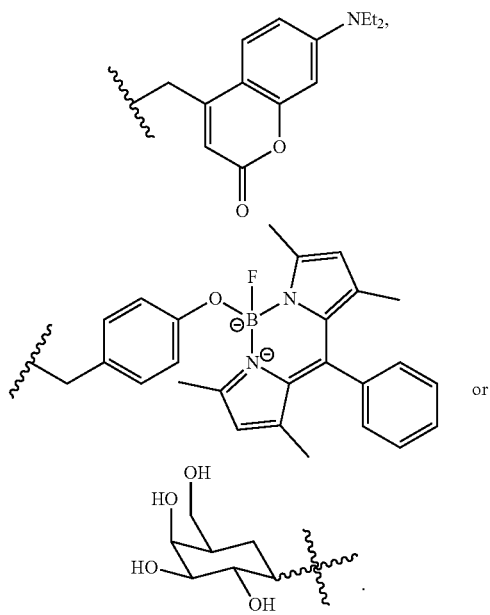

In some embodiments, the compound having the structure:

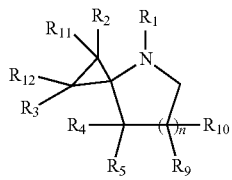

wherein n is 0 or 1;

$R_1$ is H;

$R_2$ and $R_3$ are each independently H, halo alkyl, alkenyl, alkynyl, alkyl-C(O)NHR$_{13}$, alkyl-C(O)OR$_{13}$,
  wherein R$_{13}$ is H or a substituted or unsubstituted alkyl, alkenyl, alkynyl, heteroalkyl, amidoalkyl, amidoheteroalkyl, alklyaryl, alkylheteroaryl or L$_4$-Y$_4$,
  wherein L$_4$ is a chemical linker that is present or absent and Y$_4$ is a lipid, peptide, protein, sugar, nucleotide, antibody or imaging moiety, $R_4$ and $R_5$ are each H, or one of $R_4$ and $R_5$ is H and the other is halo, —O(alkyl), —O(alkylaryl), CF$_3$, OCF$_3$, OCHF$_2$ or OSO$_3^-$, or $R_4$ and $R_5$ are each independently halo, alkyl, —O(alkyl), CF$_3$, OCF$_3$, OCHF$_2$ or OSO$_3^-$;

$R_9$ and $R_{10}$ are each independently H, halo, alkyl, —O(alkyl), —O(alkylaryl), CF$_3$, OCF$_3$, OCHF$_2$ or OSO$_3^-$, $R_{11}$ and $R_{12}$, when present, combine to form a 5-6 membered substituted or unsubstituted cycloalkyl, heterocycloalkyl, aryl or heteroaryl ring which is fused to the cycopropanyl.

In some embodiments, the compound wherein $R_{11}$ and $R_{12}$ combine to form a 6 membered substituted heteroaryl ring which is fused to the cycopropanyl.

In some embodiments, the compound wherein $R_{11}$ and $R_{12}$ combine to form a dihydropyridazine.

In some embodiments, the compound having the structure:

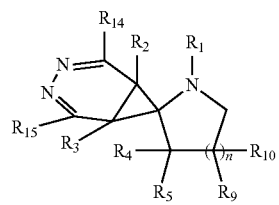

wherein $R_{14}$ and $R_{15}$ are each independently H, halo alkyl, alkenyl, alkynyl, alkyl-C(O)NHR$_{16}$, alkyl-C(O)OR$_{16}$,
  wherein R$_{16}$ is H, or a substituted or unsubstituted alkyl, alkenyl, alkynyl, heteroalkyl, amidoalkyl, amidoheteroalkyl, alklyaryl, alkylheteroaryl or L$_5$-Y$_5$,
  wherein L$_5$ is a chemical linker that is present or absent and Y$_5$ is a lipid, peptide, protein, sugar, nucleotide, antibody or imaging moiety.

In some embodiments, the compound wherein $R_2$ and $R_3$ are each independently H, alkyl or C$_1$-C$_6$ alkyl-C(O)NHR$_{13}$, wherein R$_{13}$ is alkylaryl or L$_4$-Y$_4$.

In some embodiments, the compound wherein the aryl is substituted phenyl.

In some embodiments, the compound wherein the substituted phenyl is

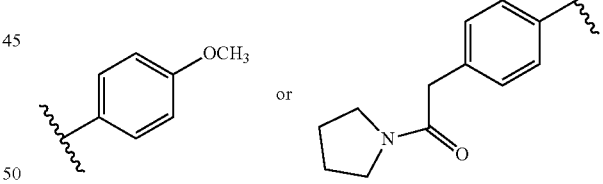

In some embodiments, the compound wherein the chemical linker L$_4$ or L$_5$ is an alkyl, alkenyl, alkynyl, alkylether, alkylthioether, alkylamino, alkylamido, alkylester, alkylaryl, alklyheteroaryl, aryl, heteroaryl, a natural amino acid, an unnatural amino acid, a disulfide or thioether containing linker or combinations thereof.

In some embodiments, the compound wherein Y$_4$ or Y$_5$ is

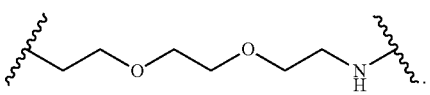 [SMILES: *CCOCCOCCN*]

In some embodiments, the compound wherein Y$_4$ or Y$_5$ is biotin, a phospholipid or tetramethylrhodamine.

In some embodiments, the compound wherein one of $R_4$ and $R_5$ is H and the other is —O(alkylaryl).

In some embodiments, the compound wherein one of $R_9$ and $R_{10}$ is H and the other is —O(alkylaryl).

In some embodiments, the compound wherein the —O(alkylaryl) is

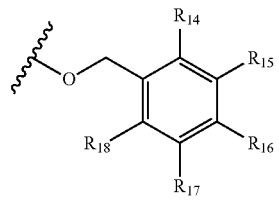

wherein $R_{14}$, $R_{15}$, $R_{16}$, $R^{17}$ and $R^{18}$ are each independently H, halo, alkyl, —O(alkyl), $CF_3$, $OCF_3$, $OCHF_2$, $OSO_3$, $SO_3H$, $NO_2$ or CN.

In some embodiments, the compound having the structure:

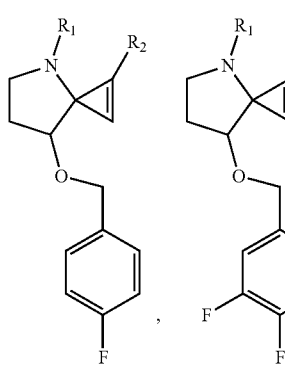
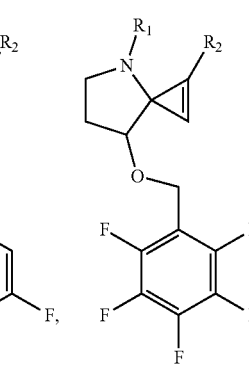
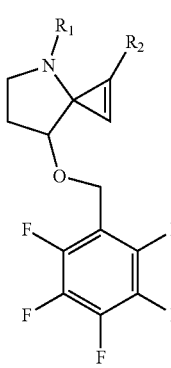

-continued

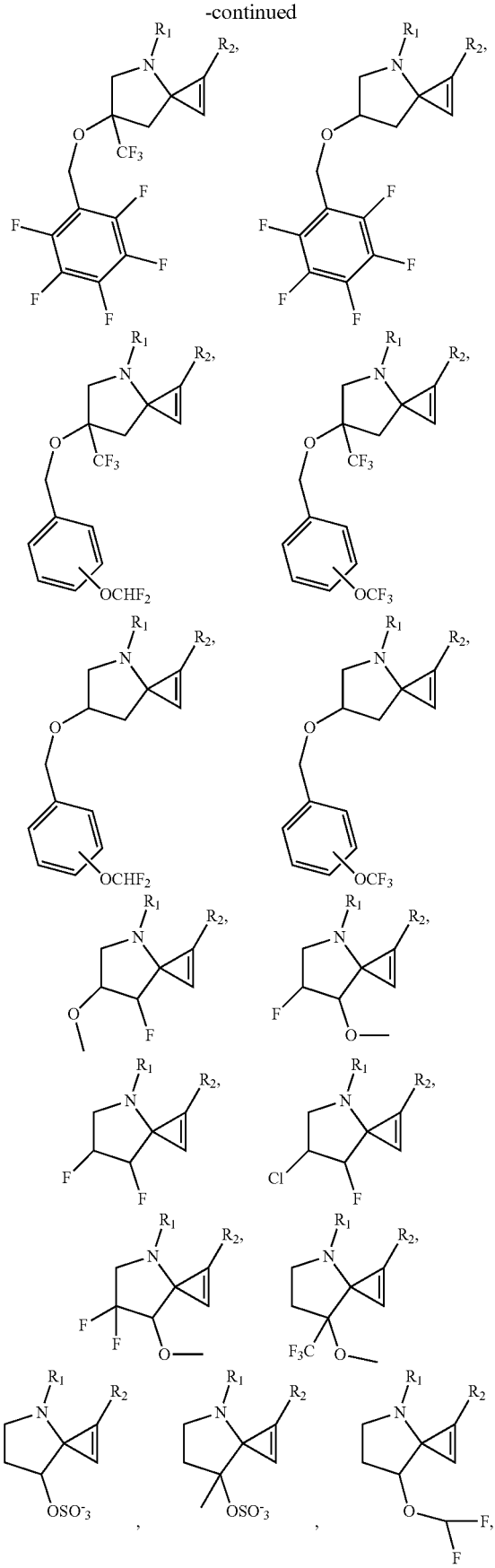

-continued
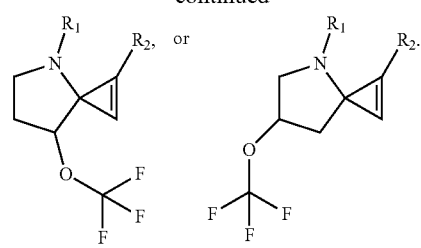
In some embodiments, the compound having the structure:
In some embodiments, the compound having the structure:
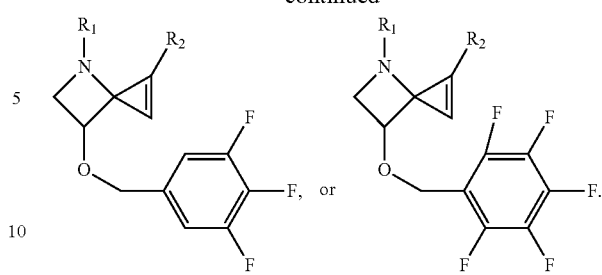
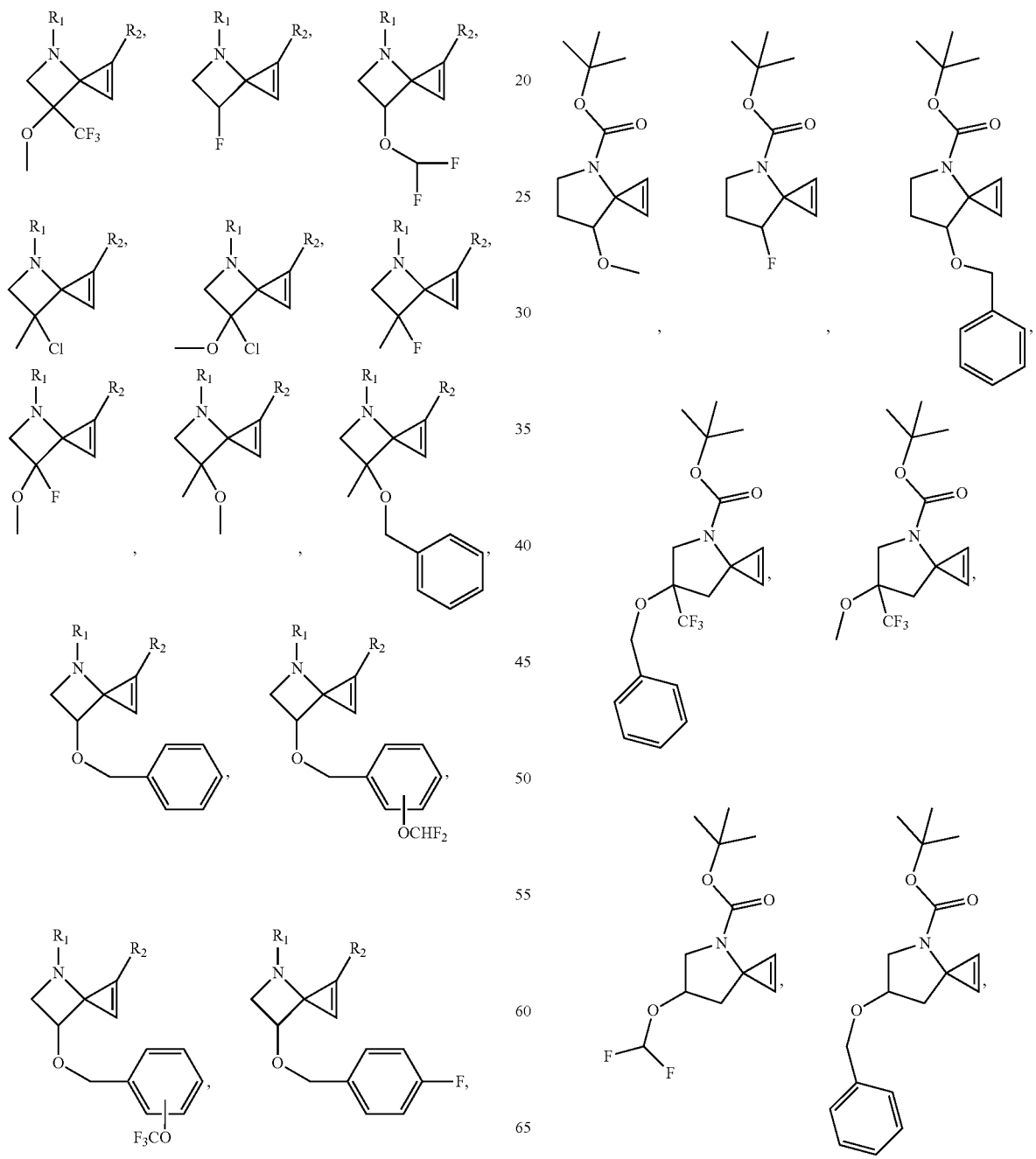

-continued
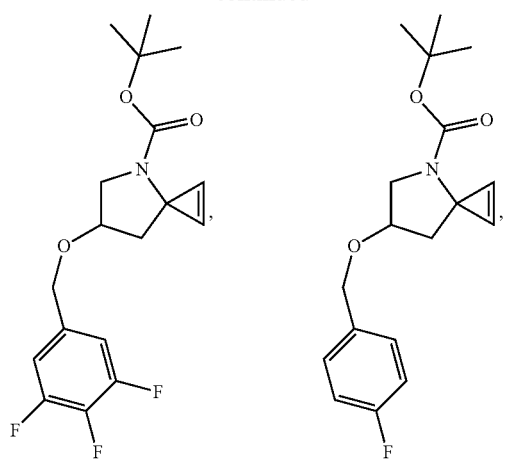
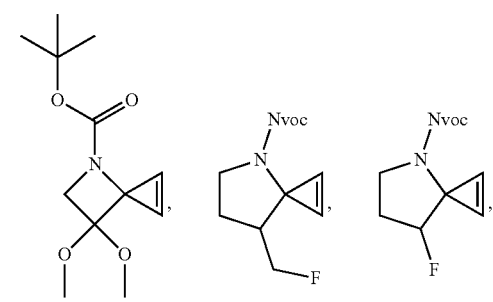
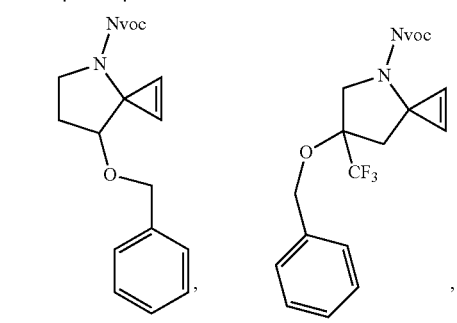
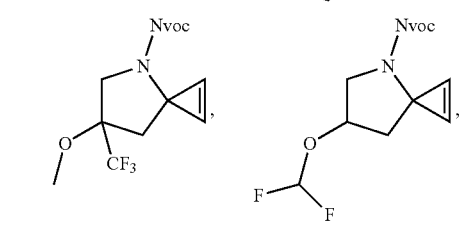
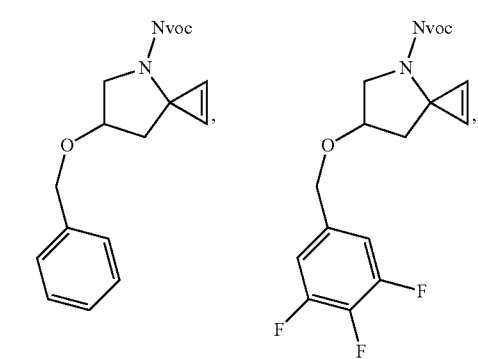
-continued
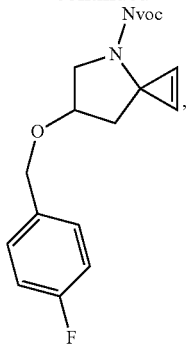
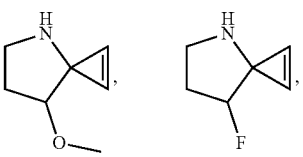
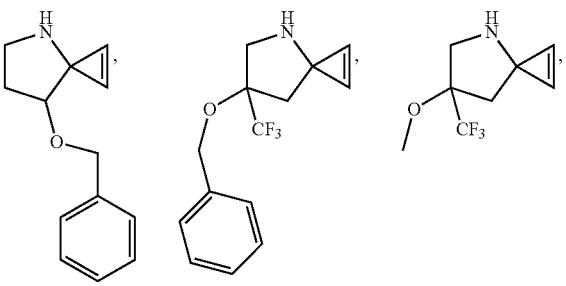
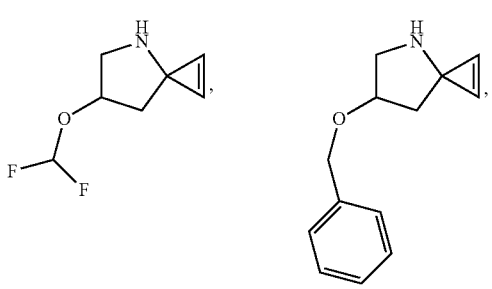
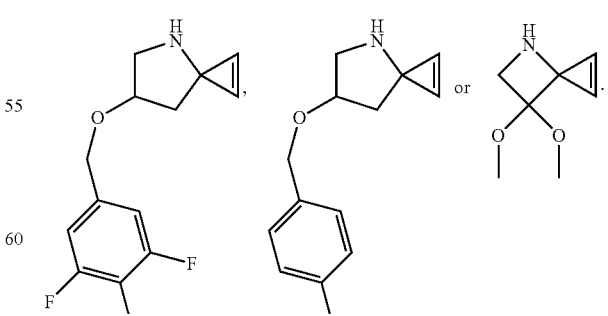
In some embodiments, the compound of the present invention which is a salt form of the compound.

In some embodiments, a process for preparing the compound of the present invention comprising exposing a compound having the structure:

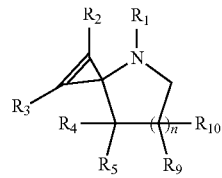

wherein n is 0 or 1;

R₁ is a light cleavable amine protecting group, an enzyme cleavable protecting group or a small molecule cleavable protecting group;

R₂ and R₃ are each independently H, halo alkyl, alkenyl, alkynyl, alkyl-C(O)NHR₁₃, alkyl-C(O)OR₁₃,
  wherein R₁₃ is H or substituted or unsubstituted alkyl, alkenyl, alkynyl, heteroalkyl, amidoalkyl, amidoheteroalkyl, alklyaryl, alkylheteroaryl or L₄-Y₄,
  wherein L₄ is a chemical linker that is present or absent and Y₄ is a lipid, peptide, protein, sugar, nucleotide, antibody or imaging moiety;

R₄ and R₅ are each H, or one of R₄ and R₅ is H and the other is halo, —O(alkyl), —O(alkylaryl), CF₃, OCF₃, OCHF₂ or OSO₃⁻, or R₄ and R₅ are each independently halo, alkyl, —O(alkyl), CF₃, OCF₃, OCHF₂ or OSO₃⁻;

R₉ and R₁₀ are each independently H, halo, alkyl, —O(alkyl), —O(alkylaryl), CF₃, OCF₃, OCHF₂ or OSO₃⁻, to light, an enzyme or a small molecule which is effective to cleave the amine protecting group in the presence of an unsubstituted or substituted tetrazine having the structure:

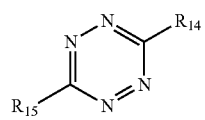

R₁₄ and R₁₅ are each independently H, halo alkyl, alkenyl, alkynyl, alkyl-C(O)NHR₁₆, alkyl-C(O)OR₁₆,
  wherein R₁₆ is H, or a substituted or unsubstituted alkyl, alkenyl, alkynyl, heteroalkyl, amidoalkyl, amidoheteroalkyl, alklyaryl, alkylheteroaryl or L₅-Y₅,
  wherein L₅ is a chemical linker and Y₅ is a lipid, peptide, protein, sugar, nucleotide, antibody or imaging moiety, so as to thereby produce the compound.

In some embodiments, a composition comprising the compound of the present invention and a carrier.

In some embodiments, a pharmaceutical composition comprising the compound of the present invention and a pharmaceutically acceptable carrier.

Embodiments of the invention described herein provide compositions and methods for modular control of bioorthogonal ligation. The compositions include 3-N-substituted spirocyclopropenes.

Embodiments of the invention include compound having the structure:

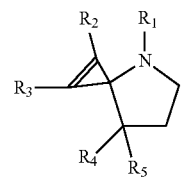

wherein:
R¹ is H or a protecting group;
R² and R³ are each independently substituted or unsubstituted C₀₋₆alkyl, C₀₋₆alkene, C₀₋₆alkyne, C₀₋₆CONHR₆, C₀₋₆COOR₆, halo, or R₂ and R₃ are cyclized to form a 3-7 membered substituted or unsubstituted alkyl, aryl, heteroalkyl or heteroaryl ring;
R₄ and R₅ are each independently halo; and
R₆ is substituted or unsubstituted C₀₋₆alkyl, C₀₋₆alkene, or C₀₋₆alkyne, According to further embodiments of Formula I, the composition wherein:
R₁ is H, Boc, or Nvoc;
R₂ and R₃ are each independently substituted or unsubstituted C₀₋₃alkyl, C₀₋₃alkene, C₀₋₃ alkyne, C₀₋₃CONHR₆, C₀₋₃COOR₆, halo, or R₂ and R₃ are cyclized to form a 5-7 membered substituted or unsubstituted alkyl, aryl, heteroalkyl or heteroaryl ring;
R₄ and R₅ are each independently F, Cl, or Br; and
R₆ is substituted or unsubstituted C₀₋₃alkyl, C₀₋₃alkene, or C₀₋₃alkyne.

In some embodiments, the compound wherein two of R₂, R₃, R₉ and R₁₀ are electron withdrawing groups.

In some embodiments, the compound wherein n is 0.

In some embodiments, the compound wherein n is 1.

In some embodiments, wherein R₂ and R₃ are each independently —H, —CH₃ or

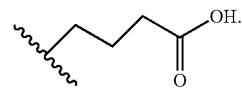 [SMILES: *CCCC(=O)O]

In some embodiments, the compound having the structure:

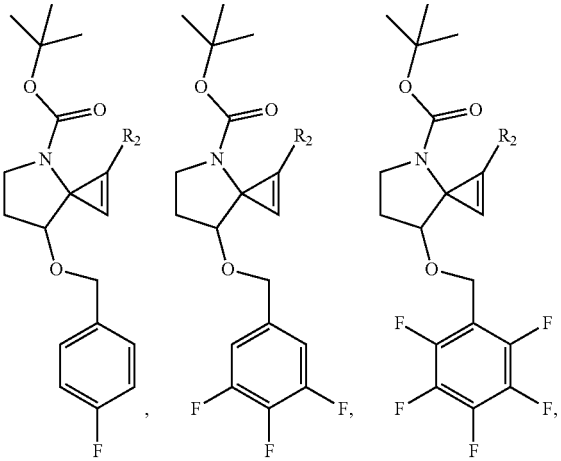

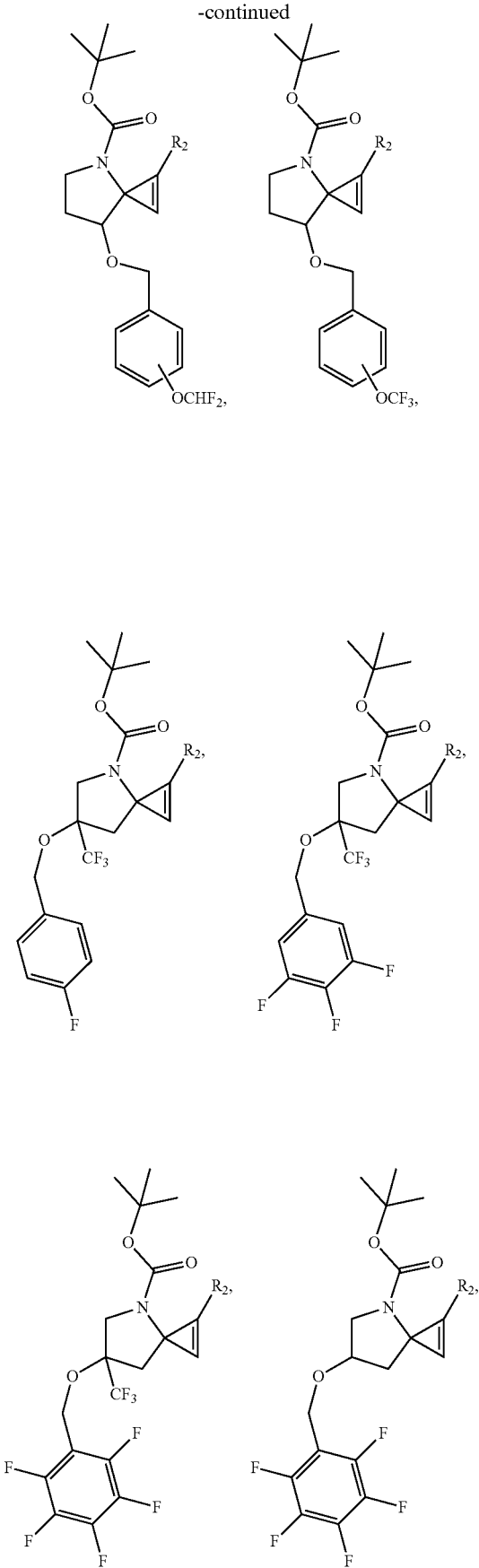
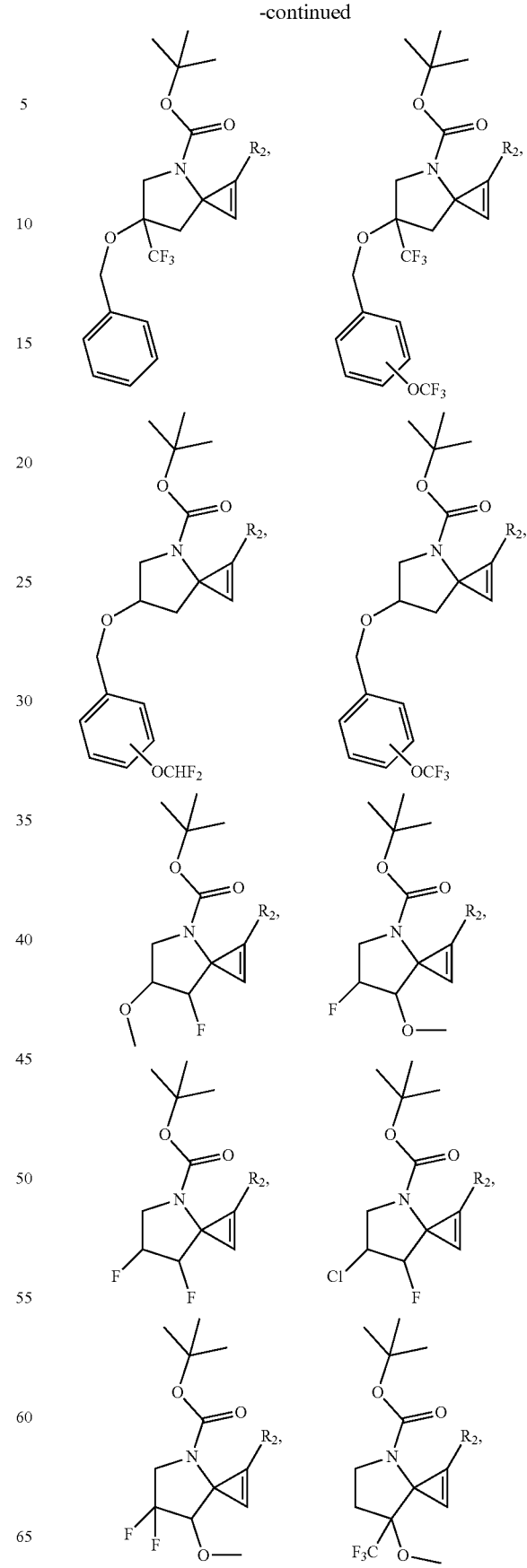

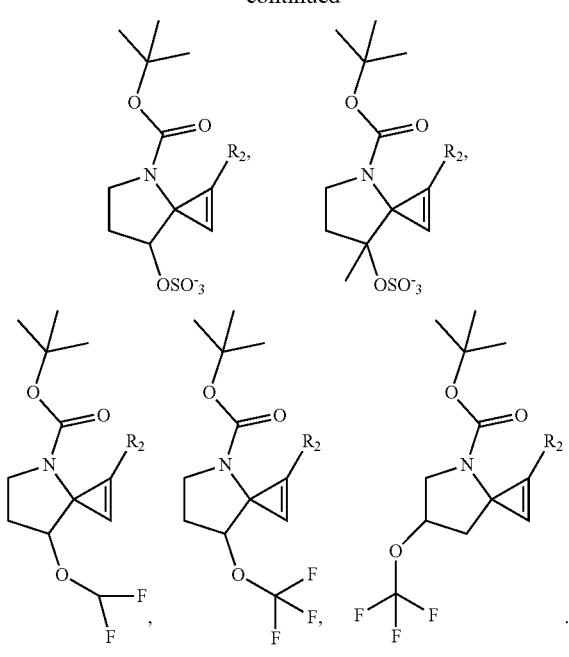
In some embodiments, the compound having the structure:
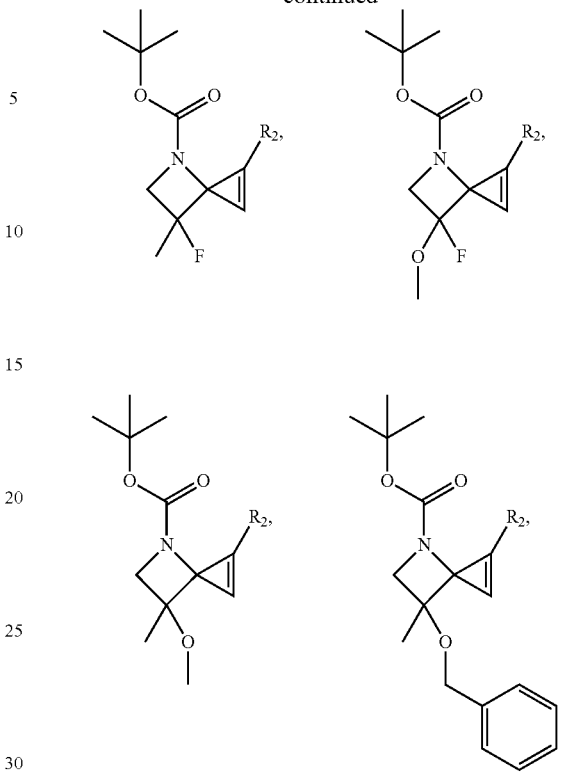
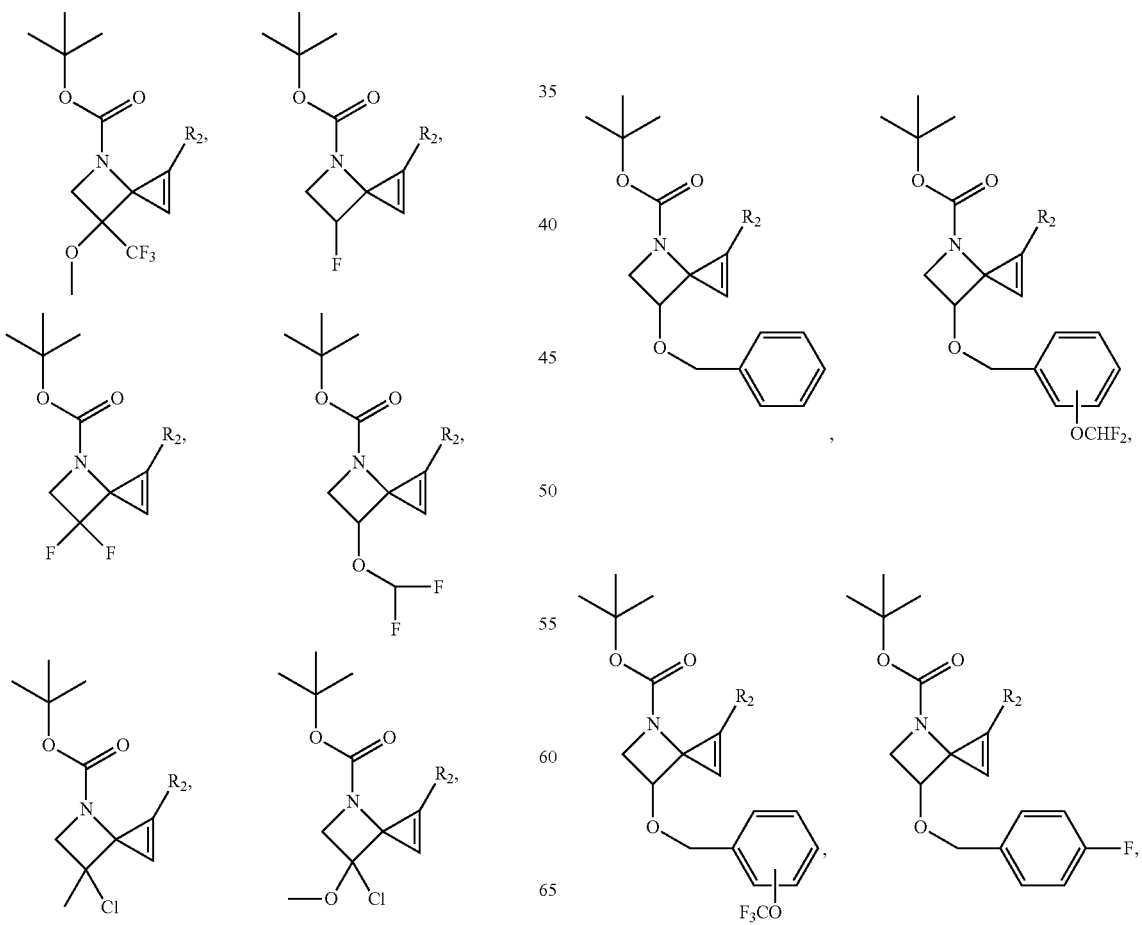

-continued

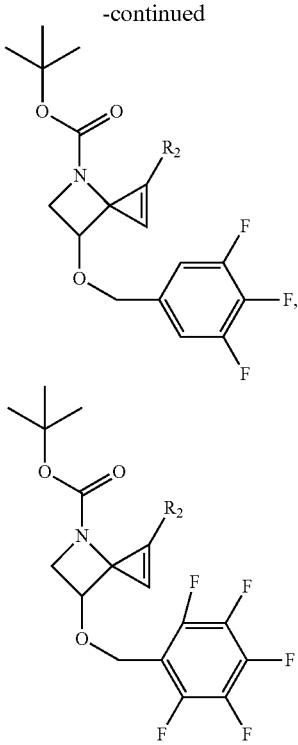

In some embodiments, the compound having the structure:

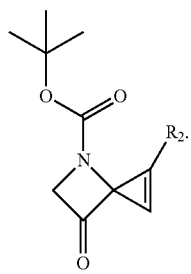

Embodiments of the invention provide the ability to control when and where a reaction occurs, which can target the reaction to cells, subcellular compartments, pattern the reaction on surfaces in diagnostic instruments, etc. It is able to do this in a modular fashion, meaning that a variety of activation methods can integrate into the technology to optimize it for a given application. The capability this technology provides does not exist in any existing products.

Bioorthogonal ligation reactions are of high interest to pharmaceutical companies for their utility in the development of new diagnostics and bioconjugate-based drugs. Embodiments of the invention provide the ability to control when and where the reaction occurs, which can target the reaction to cells, subcellular compartments, pattern the reaction on surfaces in diagnostic instruments, etc. The technology is composed of a bicyclic cyclopropene scaffold with a variety of substitutions that modulate the molecules reactivity with inverse electron demand Diels Alder substrates.

While the invention has been shown and described with reference to certain embodiments of the present invention thereof, it will be understood by those skilled in the art that various changes in from and details may be made therein without departing from the spirit and scope of the present invention and equivalents thereof.

In some embodiments, a method of imaging cells comprising:
a) contacting the cells with
1) a compound of the present invention bearing an enzyme cleavable $R_1$ protecting group;
2) an antibody-enzyme conjugate bearing an enzyme which is effective at cleaving the enzyme cleavable group; and
3) a lipid linked tetrazine containing a pro-fluorescent group;
b) detecting the location of the tetrazine; and
c) obtaining an image of the neuron cells based on the location of the tetrazine in the cells.

In some embodiments, a method of imaging neuron cells comprising:
a) contacting the cells with
1) a compound of the present invention bearing an enzyme cleavable $R_1$ protecting group;
2) an antibody-enzyme conjugate bearing an enzyme which is effective at cleaving the enzyme cleavable group; and
3) a lipid linked tetrazine containing a pro-fluorescent group;
b) detecting in the subject the location of the tetrazine; and
c) obtaining an image of the neuron cells based on the location of the tetrazine in the cells.

In some embodiments, a method of imaging neuron cells comprising:
a) contacting the cells with:
1) a compound having the structure:

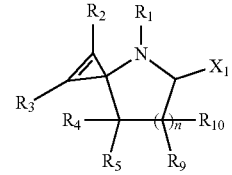

wherein
n is 0 or 1;
$X_1$ is H or $L_3$-$Y_3$,
wherein $L_3$ is a chemical linker that is present or absent and $Y_3$ is a lipid;
$R_1$ is an enzyme cleavable protecting group;
$R_2$ and $R_3$ are each independently H, halo alkyl, alkenyl, alkynyl, alkyl-C(O)NHR$_{13}$, alkyl-C(O)OR$_{13}$,
wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
wherein $L_4$ is a chemical linker that is present or absent and $Y_4$ is a lipid;
$R_4$ and $R_5$ are each halo, or combine to form a carbonyl, or are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;
$R_9$ and $R_{10}$ are each independently H, halo, alkyl, —O(alkyl), —O(alkylaryl), $CF_3$, $OCF_3$, $OCHF_2$ or $OSO_3^-$, wherein one of $R_2$ or $R_3$ is $C_1$-$C_6$ alkyl-C(O)NH$R_{13}$ or alkyl-C(O)O$R_{13}$ wherein $R_{13}$ is $L_4$-$Y_4$, or $X_1$ is $L_3$-$Y_3$;

2) an antibody-enzyme conjugate bearing an enzyme which is effective at cleaving the enzyme cleavable group; and 3) a lipid linked tetrazine containing a pro-fluorescent group, In an embodiment of the above method, wherein the compound is exposed to the antibody-enzyme conjugate at the synaptic cleft, thereby cleaving the enzyme cleavable group.

In an embodiment of the above method, wherein the deprotected compound reacts with the lipid linked pro-fluorescent tetrazine to form an inverse electron demand Diels-Alder (IEDDA) product.

In an embodiment of the above method, wherein the reaction activates the fluorescence pro-fluorescent group on the lipid linked tetrazine.

In an embodiment of the above method, wherein a fluorescence imaging device is used to detect the location of the activated pro-fluorescent group on the lipid linked tetrazine.

Protecting Group

The term "cleavable protecting group" as used herein refer to a cleavable protecting group that is cleaved by a cleaving agent (e.g., enzyme, nucleophilic/basic reagent, reducing agent, photo-irradiation, electrophilic/acidic reagent, organometallic and metal reagent, oxidizing reagent). In a mixture of two or more different cleaving agents the cleavable protecting group is cleaved by only one agent is not cleaved by any other different cleaving agent in the mixture of two or more cleaving agents.

Target Cells

The term "target cells" refers to the cells that are involved in a pathology and so are preferred targets for imaging. Target cells can be, for example and without limitation, neural cells, nerve cells or neurons.

Imaging Agent

As used herein, the term "imaging agent" refers to any agent or portion (i.e. imaging moiety) of an agent that is used in medical imaging to visualize or enhance the visualization of the body including, but not limited to, internal organs, cells, cancer cells, cellular processes, tumors, and/or normal tissue. Imaging agents or imaging moieties include, but are not limited to, positron-emission tomography (PET) imaging agents, fluorescence imaging agents, x-ray imaging agents, MRI imaging agents or Nuclear Medicine Imaging Agents. Imaging agents or moieties include, but are not limited to, any compositions useful for imaging neurons.

Pro-Fluorescent Tetrazines

"Pro-fluorescent Tetrazines" include, but are not limited to, any tetrazine containing a quenched fluorophore which is restored upon bioorthogonal reaction, i.e. reaction with an uncaged cyclopropane. Examples include fluorogenic BODIPY probes, fluorogenic coumarin probes, and fluorogenic xanthene probes and those recited in Oliveira, B. L. et al. *Chem. Soc. Rev.* 2017, 46, 4895, the entire contents of which are hereby incorporate by reference.

Chemical Linker

The term "chemical linker" refers to a chemical moiety or bond that covalently attaches two or more molecules, such as a small molecule and an imaging moiety. The linker may be a cleavable linkers, e.g. pH-sensitive (acid-labile) linker, disulfide linker, a peptide linker, a β-glucuronide linkers or a hydrazine linker. The linker may be a non-cleavable linker, e.g. thioether, maleimidocaproyl, maleimidomethyl cyclohexane-1carboxylate, alkyl, alkylamido or amide linker.

Covalent bonding of the imaging moiety. chemical linker and small molecule can occur through the formation of amide, ester or imino bonds between acid, aldehyde, hydroxy, amino, or hydrazo groups.

Linkage may be achieved by any means known to those in the art, such as genetic fusion, covalent chemical attachment, noncovalent attachment (e.g., adsorption) or a combination of such means. Selection of a method for linking will vary depending, in part, on the chemical nature of the targeting moiety.

Linkage may be achieved by covalent attachment, using any of a variety of appropriate methods. For example, the small molecule and imaging moiety may be linked using bifunctional reagents (linkers) that are capable of reacting with both the targeting moiety and imaging moiety and forming a bridge between the two.

The term "non-covalent linker" is used in accordance with its ordinary meaning and refers to a divalent moiety which includes at least two molecules that are not covalently linked to each other but do interact with each other via a non-covalent bond (e.g. electrostatic interactions (e.g. ionic bond, hydrogen bond, halogen bond) or van der Waals interactions (e.g. dipole-dipole, dipole-induced dipole, London dispersion).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(O), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation).

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Exemplary linkers are described in U.S. Patent Application No. 2012/0322741 A1, U.S. Patent Application No. 2018/0289828 A1 and U.S. Pat. No. 8,461,117 B2 the contents of which are hereby incorporated by reference.

Antibody

An "antibody" as used herein is defined broadly as a protein that characteristically immunoreacts with an epitope (antigenic determinant) of an antigen. As is known in the art, the basic structural unit of an antibody is composed of two identical heavy chains and two identical light chains, in which each heavy and light chain consists of amino terminal variable regions and carboxy terminal constant regions. The antibodies of the present invention include polyclonal antibodies, monoclonal antibodies (mAbs), chimeric antibodies, CDR-grafted antibodies, humanized antibodies, human antibodies, catalytic antibodies, multispecific antibodies, as well as fragments, regions or derivatives thereof provided by known techniques, including, for example, enzymatic cleavage, peptide synthesis or recombinant techniques.

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., *Nature* 352:624-28 (1991) and Marks et al., *J. Mol. Biol.* 222(3): 581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art [Kozbor et al., *Immunol. Today* 4:72 (1983); Cole et al., in *Monoclonal Antibodies and Cancer Therapy*, Alan R. Liss, Inc. 77-96 (1985)].

The term "epitope" refers to a portion of a molecule (the antigen) that is capable of being bound by a binding agent, e.g., an antibody, at one or more of the binding agent's antigen binding regions. Epitopes usually consist of specific three-dimensional structural characteristics, as well as specific charge characteristics.

"Humanized antibodies" means antibodies that contain minimal sequence derived from non-human immunoglobulin sequences. For the most part, humanized antibodies are human immunoglobulins (recipient antibody) in which residues from a hyper variable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-25 (1986); Riechmann et al., *Nature* 332:323-27 (1988); and Presta, *Curro Opin. Struct. Biol.* 2:593-96 (1992), each of which is incorporated herein by reference.

Also encompassed by the term "antibody" are xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598, the entire contents of which are incorporated herein by reference.

Those skilled in the art will be aware of how to produce antibody molecules of the present invention. For example, polyclonal antisera or monoclonal antibodies can be made using standard methods. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

Other Definitions

As used herein, the term "amino acid" refers to any natural or unnatural amino acid including its salt form, ester derivative, protected amine derivative and/or its isomeric forms. Amino Acids comprise, by way of non-limiting example: Agmatine, Alanine Beta-Alanine, Arginine, Asparagine, Aspartic Acid, Cysteine, Glutamine, Glutamic Acid, Glycine, Histidine, Isoleucine, Leucine, Lysine, Methionine, Phenylalanine, Phenyl Beta-Alanine, Proline, Serine, Threonine, Tryptophan, Tyrosine, and Valine. The amino acids may be L or D amino acids.

The terms "peptide", "polypeptide", peptidomimetic and "protein" are used to refer to a polymer of amino acid residues. The terms apply to amino acid polymers in which one or more amino acid residues is an artificial chemical mimetic of a corresponding naturally occurring amino acid, as well as to naturally occurring amino acid polymers. These terms also encompass the term "antibody". "Peptide" is often used to refer to polymers of fewer amino acid residues than "polypeptides" or "proteins". A protein can contain two or more polypeptides, which may be the same or different from one another.

As used herein, the term "oligopeptide" refers to a peptide comprising of between 2 and 20 amino acids and includes dipeptides, tripeptides, tetrapeptides, pentapeptides, etc.

An amino acid or oligopeptide may be covalently bonded to an amine of another molecule through an amide linkage, resulting in the loss of an "OH" from the amino acid or oligopeptide.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halo" or "halogen" refers to F, Cl, Br, and I.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As sued herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons and five hydrogens.

The term "benzyl" is intended to mean a —CH$_2$R$_1$ group wherein the R$_1$ is a phenyl group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. R$_1$, R$_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described—in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric coated to prevent release of the active ingredient compounds before they reach the small intestine. Materials that may be used as enteric coatings include, but are not limited to, sugars, fatty acids, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to general Schemes. Variations on the following general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

While the invention has been shown and described with reference to certain embodiments of the present invention thereof, it will be understood by those skilled in the art that various changes in from and details may be made therein without departing from the spirit and scope of the present invention and equivalents thereof.

Each embodiment disclosed herein is contemplated as being applicable to each of the other disclosed embodiments. Thus, all combinations of the various elements described herein are within the scope of the invention.

The following publications including the supplemental information of each are hereby incorporated by reference in their entirety: (1) Org. Biomol. Chem. 2018, 16, 4081; (2) Tetrahedron Lett. 2018, 59, 3435; (3) Org. Biomol. Chem. 2018, 16, 652; (4) Org. Lett. 2019, 21, 3721; and (5) CHEMBIOCHEM 2019, 20, 2222-2226.

Example 1. Synthesis of Precursor Compounds

Cyclic enamines are valuable building. blocks for the preparation of synthetic, naturally-occurring, and pharmacologically active molecules (Granik, Makarov, and Párkányi 1998; Guo, Clift, and Thomson 2012; Mukherjee et al. 2007; Stork et al. 1963; Xie, Zhu, and Zhou 2011; R. Borrmann et al. 2017). For example, they are key components of synthetic azacyclic hexahydroindoles, (Chintalapudi et al. 2016) the naturally-occurring alkaloid Plakoridine A (T.-Y. Lin et al. 2016), and a pharmaceutically relevant derivative of the sugar α-D-xylofuranose (Cordeiro et al. 2006) (FIG. 1). Naturally, chemists have devoted considerable effort to developing strategies for the synthesis of cyclic enamines. Among the cyclic enamines, those containing an exocyclic double bond, like azetidine enamine 1 and pyrrolidine enamine 2 (FIG. 1), have garnered attention (Chintalapudi et al. 2016; Lu and Li 2006; Lu et al. 2008; Campbell et al. 2015; Hazelden et al. 2016; Wolf et al. 2002; H. Jiang et al. 2016) for their wide use as precursors in the syntheses of biologically active molecules ranging from β-lactams (Lu and Li 2006; De Kimpe and Boeykens 1994) and macrolactams (Lu et al. 2008) to unnatural amino acids (Wolf et al. 2002) and substituted 2-pyrrolidines. (T.-Y. Lin et al. 2016) Our interest in cyclic enamines 1 and 2 stems from their potential use as intermediates in the creation of 3-N spirocyclopropyl (i.e., 4-azaspiro[2.n] alkane) and 3-N spirocyclopropenyl (i.e., 4-azaspiro[2.n] alkene) systems, which have utility in diverse subfields of chemistry as synthons for cyclin-dependent kinase 2 (Brasca et al. 2007) and tyrosine kinase inhibitors (Xi Hing 2012), monomers for both ROM polymerization (Elling, Su, and Xia 2016; R. Singh, Czekelius, and Schrock 2006) and poly-cyclopropane-based materials, (DeBoer 1973) and reagents in the bioorthogonal tetrazine ligation (Ravasco, Monteiro, and Trindade 2017; Kamber et al. 2013; Yang et al. 2014).

Traditionally, cyclic enamines like compounds 1 and 2 have been synthesized in modest yields by cyclization of the respective halo-imine precursors with strong bases. (Abbaspour Tehrani and De Kimpe 2000; Mangelinckx, Boeykens, and De Kimpe 2008; Sulmon, De Kimpe, and Schamp 1988) Unfortunately, these strategies are limited in their substrate scope by their use of strong base and requirement for a quaternary carbon adjacent to the amine to prevent elimination of the halogen.

More recently, catalysts based on copper (Lu et al. 2008; Campbell et al. 2015) and palladium (Hazelden et al. 2016; H. Jiang et al. 2016; Greenaway et al. 2012) have significantly improved the reaction yields for the formation of cyclic enamines and have provided access to new cyclic enamine scaffolds; however, they require multistep syntheses of the precursors required for the catalytic step. Additionally, the scalability of these reactions has not been determined, and the combined cost of the catalyst and multiple step synthesis of the precursor molecules can be prohibitive when multigram quantities of cyclic enamines like 1 and 2 are required.

Figure 2:
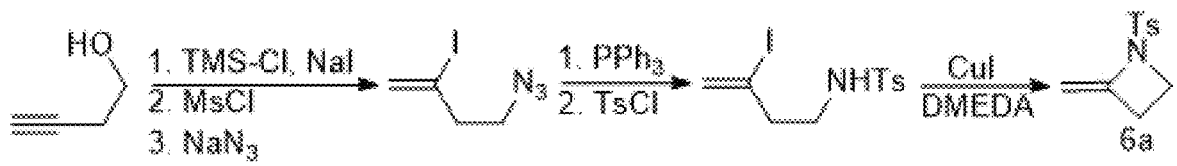
FIG. 2—Initial attempts to synthesize the protected enamine 6a in six steps were high yielding only at 100-150 mg scale. The reaction yields were significantly reduced upon scale up.

Thus, in our initial foray into the synthesis of enamines 1 and 2, we explored the scalability of a metal-catalysed Ullman-type coupling, recently described by Li and co-workers, (Lu et al. 2008) to produce protected enamine 6a in six steps from commercially available 3-butyn-1-ol (FIG. 2). Our initial attempt to synthesize the enamine 6a was successful on the 100-150 mg scale, with yields of 90-92% for the final step, consistent with those reported by Li and co-workers, and an overall yield of 34-39% over six steps. However, five separate attempts to scale up the preparation of enamine 6a to 500 mg scale quantities resulted in significant loss of material in the final copper-mediated coupling step, with yields of 45-53%. Our attempts to improve the yield for the copper catalysed coupling by optimizing the reaction duration, temperature, or amount of catalyst did not improve the yield. An extensive survey of the literature for alternative, gram-scale syntheses of molecules like cyclic enamines 1 and 2 did not yield useful synthetic precedents, so we devised the strategy described in this report for the large-scale synthesis of molecules similar to protected enamine 6a.

In our search for suitable starting materials for these transformations, we were intrigued by the possibility of leveraging economical, alcohol-based substrates for alkene production via a straightforward elimination reaction. Surveying the literature for N-heterocyclic rings with a methylene alcohol on the α-position, we identified prolinol, a commercially available inexpensive alcohol analogue of the amino acid proline, as an ideal substrate for our initial attempts to incorporate the alkene functionalization to form protected enamine 6b (Scheme 1). Importantly, formation of an alkene adjacent to a nitrogen atom can lead to an imine rearrangement product, which can be suppressed by protecting the nitrogen with an electron withdrawing protecting group.

Thus, we chose to begin with the electron withdrawing tosyl group for nitrogen protection prior to establishing the applicability of the approach to more conventional, and less electron withdrawing, nitrogen protecting groups.

Scheme 1 - Synthesis of N-tosyl protected enamines 6a-d in multigram-scale quantities using inexpensive and commercially available reagents

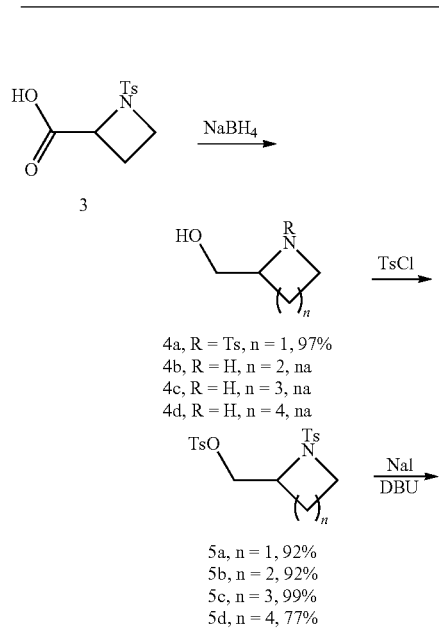

Scheme 2 - Methods for the synthesis of compounds 3, 4, 5a-5d, and 6a-6d

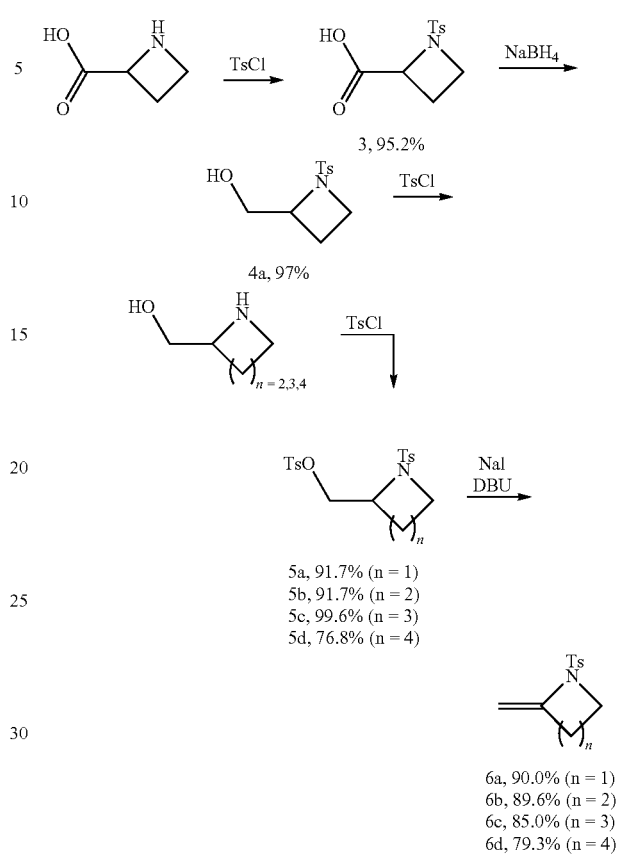

Exploration of this synthetic route began with the synthesis of the N,O-bistosylated prolinol 5b (Scheme 1) in one step from prolinol using TsCl in 94.4% yield (1.0 g scale with respect to prolinol). The yield was consistent upon scaling up to the multigram scale (13.0 g scale with respect to prolinol, 91.7% yield). Next, we performed the elimination to obtain N-tosyl protected enamine 6b using in situ activation with NaI in presence of the bulky base DBU under refluxing conditions, a method previously developed by Maier and co-workers for olefin synthesis (Phukan, Bauer, and Maier 2003). Our initial attempt afforded the 5-membered enamine 6b in 92% yield (1.0 g scale). Importantly, we observed consistent reaction yields upon scaling up this reaction (37.0 g scale, 89.6% yield). Repeating this reaction three more times with different batches of 5b on different days provided similar yields for 6b (88-93% yield).

Buoyed by the initial success of this strategy to prepare gram-scale quantities of enamine 6b in high-yields, we tested its generality in the preparation of cyclic enamines containing varying ring sizes (Scheme 1, compounds 6a-d). N,O-bistosylated compounds 5a and 5c were synthesized starting from the relatively inexpensive and commercially available 2-azetidinecarboxylic acid or piperidine-2-methanol. For 5a, we prepared the N-tosyl protected 3 in 95.2% yield (Scheme 1, Scheme 2). Subsequent reduction of the carboxylic acid group using NaBH$_4$ afforded the alcohol 4a in 97% yield. Compound 4a was then N,O-bistosylated using TsCl to obtain 5a in 92% yield. N,O-bistosylated 5c was obtained in one step using TsCl in 99.6% yield. Subsequent elimination of the tosylate under the above-mentioned conditions afforded the enamines 6a and 6c in 90% (30 g scale) and 85% (18.0 g scale) yields respectively. Further, N,O-bistosylation afforded 5d in 77% yield, which, upon subsequent elimination, afforded enamine 6d in 79% yield.

With an inexpensive two to four-step synthesis for enamines 6a-d in hand, the effect of alternative N-protecting groups on the stability and yields of these N-protected enamines was tested. Importantly, the strength of the electron withdrawing nature of the N-protecting group has been shown to greatly affect the synthetic yields of enamines in previously-described methods. (Lu and Li 2006). For example, when the enamine 6a was synthesized by Li and co-workers using their Ullman-type coupling strategy (FIG. 2) the yield for enamine formation reduced by half when Boc was used for N-protection instead of tosyl (Lu and Li 2006). Additionally, most of the reported procedures for cyclic enamine syntheses have used only tosyl-protection of the amine, (Chintalapudi et al. 2016; Lu and Li 2006; Lu et al. 2008; Campbell et al. 2015; Hazelden et al. 2016; Greenaway et al. 2012) so the stability and yields for the formation of N-protected enamines with other strategies are unknown.

Using the same reaction conditions employed for the N-tosyl protected compound 5a-d, we attempted eliminations of activated alcohol analogues of N-Boc, N-trifluoroacetamide, N-mesyl, and N-benzoyl prolinols 5e-h (Scheme 3). N-Boc, N-trifluoroacetamide, and N-mesyl tosylated prolinols (Scheme 3, Scheme 4) afforded the Boc protected enamine 6e and the volatile enamines 6f and 6g in 71% (15 g scale), 45% (5 g scale), and 55% (2.5 g) yields respectively, whereas the Bz-protected activated alcohol 5 h was not stable to the elimination conditions and produced no observable enamine product 6 h. Further, tosylation of trityl protected prolinol to obtain N-trityl enamine was unsuccessful, possibly due to the steric hindrance provided by the bulky trityl group. Importantly, the reaction's compatibility with deprotection conditions for removal of protecting groups that are gentler than Ts provides a significant advantatest 2ge over strategies that require Ts protection, especially when using these enamines as precursors for sensitive or complex targets.

Scheme 3 - Use of alternative N-protecting groups for synthesis of enamines 6e-h in multigram-scale quantities

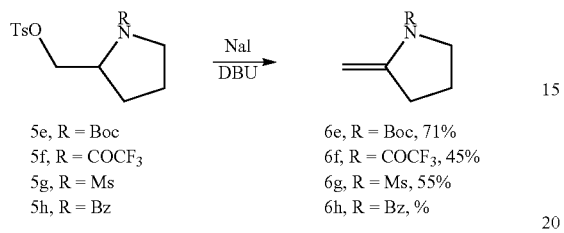

5e, R = Boc
5f, R = COCF₃
5g, R = Ms
5h, R = Bz

6e, R = Boc, 71%
6f, R = COCF₃, 45%
6g, R = Ms, 55%
6h, R = Bz, %

Scheme 4 - Methods for synthesis of compounds 4e, 5e-h and 6e-g

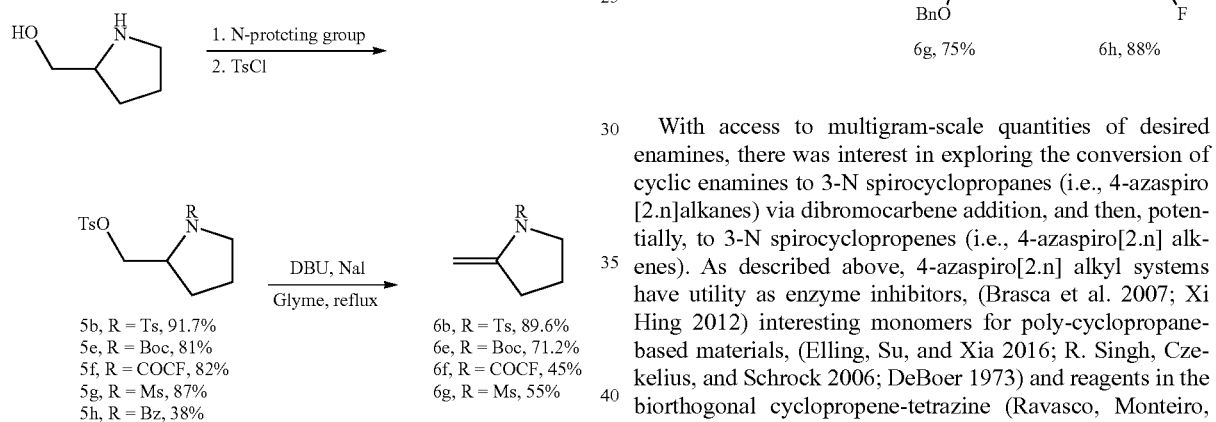

5b, R = Ts, 91.7%
5e, R = Boc, 81%
5f, R = COCF, 82%
5g, R = Ms, 87%
5h, R = Bz, 38%

6b, R = Ts, 89.6%
6e, R = Boc, 71.2%
6f, R = COCF, 45%
6g, R = Ms, 55%

The enamine formation's compatibility with substitutions around the pyrrolidine ring (Scheme 5) was tested. Towards this, the tosylated alcohol analogues of N-Boc benzylether pyrrolidine 5i and N-Boc difluoropyrrolidine 5j were prepared from the corresponding alcohols in 40% and 78.3% yields respectively. Subsequent elimination produced the enamines 6i-j in 75% and 87.5% yields. Compatibility of this NaI/DBU-mediated elimination with heteroatom substitutions at different ring position should be straightforward to extend to other ring sizes and substitutions for generating a diverse array of enamines.

Scheme 5 - Tolerance towards ring substitutions on the synthesis of cyclic enamines 6i-j

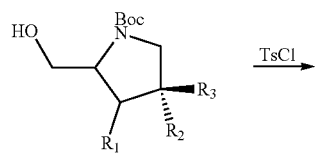

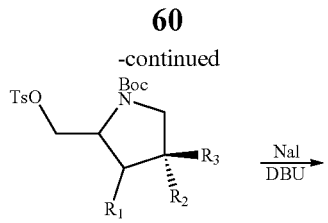

5g, R₁ = OBn, R₂ = H, 40%
5h, R₁ = H, R₂ = F, 78%

6g, 75%    6h, 88%

With access to multigram-scale quantities of desired enamines, there was interest in exploring the conversion of cyclic enamines to 3-N spirocyclopropanes (i.e., 4-azaspiro[2.n]alkanes) via dibromocarbene addition, and then, potentially, to 3-N spirocyclopropenes (i.e., 4-azaspiro[2.n] alkenes). As described above, 4-azaspiro[2.n] alkyl systems have utility as enzyme inhibitors, (Brasca et al. 2007; Xi Hing 2012) interesting monomers for poly-cyclopropane-based materials, (Elling, Su, and Xia 2016; R. Singh, Czekelius, and Schrock 2006; DeBoer 1973) and reagents in the biorthogonal cyclopropene-tetrazine (Ravasco, Monteiro, and Trindade 2017; Kamber et al. 2013; Yang et al. 2014) ligation. To the best of our knowledge, there are only a handful of reports describing the synthesis of 4-azaspiro [2.n] alkanes. Most of these strategies utilized carbenoid insertion on lactams or cyanoesters using a combination of Grignard reagents and titanium catalysts (K. W. Lin et al. 2006; Madelaine, Six, and Buriez 2007; Laroche et al. 2005; Bertus and Szymoniak 2003). Others utilized the cyclization reaction between an amine and nitrile present on a cyclopropane ring using a strong base (Brasca et al. 2007). carbenoid insertion on enamines flanked by aromatic rings using zinc catalyst (Fardis et al. 2006). or palladium-catalysed alkene and isocyanate reaction (Shintani et al. 2010).

We employed the cyclic enamines in the preparation of 4-azaspiro[2.n] alkanes by insertion of a dibromocarbene generated using bromoform and NaOH (Scheme 6). Both the N-tosylated enamines 6a-c and N-Boc enamine 6e produced the corresponding dibromo-4-azaspiro[2.n]alkanes 7a-d in 49%, 65.2%, 40% and 37.6% yields respectively, and boc de-protection of 7d proceeded in excellent yield (99%) to the free amine cyclopropane 9. To the best of our knowledge, this is the first report of dibromo-4-azaspiro [2.n] alkanes. Furthermore, 7a adds another entry to the short list of 4-azaspiro[2.n] alkanes with a spiro[2.3] hexane spirocyclic system.

Scheme 6 -Cyclic enamines 6a-d provide access to 4-azaspiro[2.n] alkane synthons

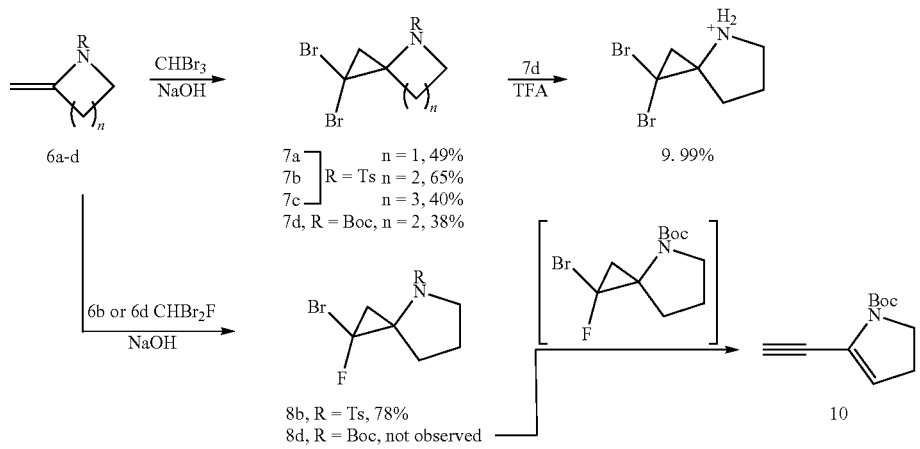

Cyclic enamine conversion to a mixed bromo-fluoro-cyclopropane was then explored. The tosylated enamine 6b formed the desired 1-bromo-1-fluoro-4-azaspiro[2.4] heptane 8b in 78% yield. However, subjecting the weaker electron withdrawing N-Boc-protected enamine 6e to base-mediated bromofluorocarbene insertion resulted in a rearrangement-elimination to generate 10. Ultimately, having access to the halogen-containing synthons (7a-d, 8b, and 9) opens the door for further functionalization with these N-heterocycles.

In addition to the dibromocyclopropanes 0.7a-d, the corresponding monobromo cyclopropanes present useful substrates for additional functionalization of the scaffold. Accordingly, we explored the conversion of dibromo precursors to the corresponding monobromo cyclopropanes. We evaluated several strategies for the reduction of dibromocyclopropane 7b to 11b (Table S1, ESI). Importantly, this reaction required complete consumption of the dibromo starting material for purification of the monobromo product as they have the same retention factor on silica gel in all solvent systems tested. The best strategy employed lithium-halogen exchange using n-BuLi at −85° C. and subsequent quenching with a proton source like ammonium chloride to produce 11b in 60% yield (Scheme 7). These conditions applied to compound 7a produced the azetidine analogue bromo-4-azaspiro[2,3] hexane 11a in 49% yield.

Scheme 7 - Methods for synthesis of compounds S2-3

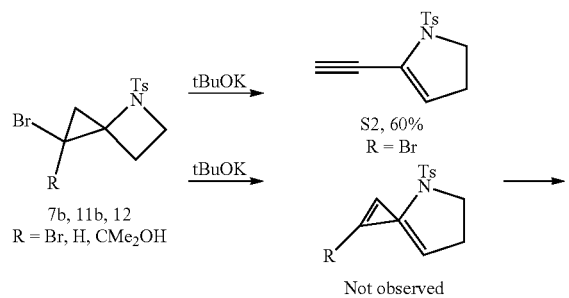

-continued

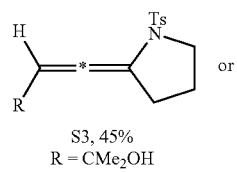

S3, 45%
R = CMe$_2$OH

Reaction consumed starting material and produced a complex mixture of products that could not be identified
R = H Finally, 11b was subjected to potassium tert-butoxide in an effort to achieve the elimination, but instead produced a complex mixture of products that could not be identified. Subjecting the spirocyclic dibromo-4-azaspiro[2,4] heptane 7b to the similar elimination resulted in the alkyne rearrangement product, dihydropyrrole derivative. This ring opening rearrangement is thought to proceed via an electron deficient intermediate (Walsh 2005), so we attempted the elimination with electron withdrawing fluoro substitution on the cyclopropene ring 8b only to produce the alkyne rearrangement product S2 again. We further increased the electron withdrawing nature of the substitution by creating the difluoro substituted spirocyclopropane using enamine 6j (Scheme 3). However, subjecting the enamine 6j to carbene addition produced the fluoro-eliminated pyrrole S1 (Scheme 5) as the major product. Previous reports have observed that addition of alkyl groups can impart stability (Yang et al. 2012) to cyclopropenes in solution, so we attempted the elimination with a monobromocyclopropane bearing a bulky tertiary alcohol group 12, which resulted in the formation of the allene rearrangement product, tetrahydropyrrole derivative S3 (Scheme 9, ESI). Finally, we explored elimination with N-trifluoroacetate 6f, a substrate bearing more heavily electron withdrawing N-protecting group. In this case, the reaction produced a crude reaction mixture with a characteristic cyclopropene peak in the $^1$H NMR spectrum at 6.4 ppm. However, attempts at purification via Flash chromatography resulted in isolation of only the alkyne rearrangement product. These results suggest that forming a 4-azaspiro[2.n] alkene system requires the addition of stronger electron withdrawing components to promote long-term stability, which may be accomplished by appending electron withdrawing groups to positions closer to the quaternary carbon to form the offending electron deficient intermediate.

Scheme 8 - Spirocyclic 3-N dibromocyclopropanes can be converted to corresponding monobromo versions with added functionalization.

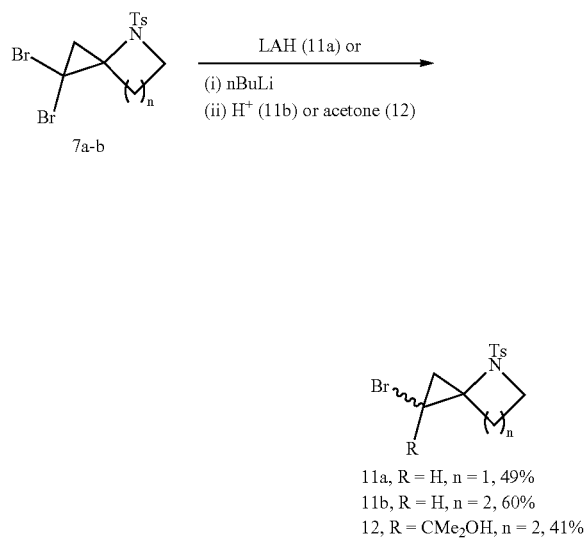

11a, R = H, n = 1, 49%
11b, R = H, n = 2, 60%
12, R = CMe₂OH, n = 2, 41%

We have devised an inexpensive, catalyst-free, multi-gram-scale and high yielding synthesis of protected cyclic enamines with varying ring sizes. Additionally, we described a route for the preparation of pharmacologically relevant 4-azaspiro[2.n] alkanes with an azetidine ring. This route produced novel dihalo and mono-halo 4-azaspiro[2.n] alkanes, which provide possibilities for further functionalization using established halide chemistry.

Example 2. Synthesis of Dihalo Compounds

Considerable effort has gone into the development of bioorthogonal reagents with faster kinetics or unique and mutually orthogonal reactivities (Patterson, Nazarova, and Prescher 2014; Jie Li and Chen 2016; Patterson et al. 2012). Conversely, there have been few reagents developed for activating bioorthogonal reactivity in space and time. Such activatable biorthogonal reagents remain dormant until activated, generally by light or an enzyme. This furnishes the ability to exert control over when and where they can react with their biorthogonal partners. For example, a photoactivatable bioorthogonal reagent-coated surface would allow users to decide both when the reagent can be activated by illumination and where on the surface activation can occur for the reagent to participate in the bioorthogonal ligation. Examples include the tetrazole-alkene photoclick chemistry (Yu, Ho, and Lin 2011; Ramil and Lin 2014; Yu et al. 2012), although recent concerns of side reactions with biological nucleophiles limit its usage in systems requiring strict bioorthogonality (Z. Li et al. 2016). Innovative work by Popik and coworkers exploited intrinsic photoinduced decarboxylation of cyclopropenone to create a photoactivatable cyclooctyne for Cu-free click chemistry (Poloukhtine et al. 2009; Orski et al. 2010), and Fox and coworkers created a redox-activatable tetrazine based on oxidation of dihydrotetrazine to tetrazine by exposure to the enzyme Horse Radish Peroxidase or a photosensitizer (H. Zhang et al. 2016). Finally, Carrico and coworkers produced a variant of the Staudinger ligation that is activated by light. (Shah, Laughlin, and Carrico 2016) With the exception of the photoactivated Staudinger ligation, each activation strategy takes advantage of intrinsic properties of the reagents, making it challenging to tailor the caging strategy to a desired application. Here we describe a strategy employing a carbamate cage that will permit control of reactivity with a wide array of carbamate-linked photocleavable protecting groups. This strategy engineers control of the ligation between 1,2,4,5-tetrazines and cyclopropenes that will enable the use of convenient fluorogenic tetrazine reagents (Meimetis et al. 2014) as well as a diverse set of caging groups that will permit tailoring the reaction's activation method to the desired application.

Figure 3:
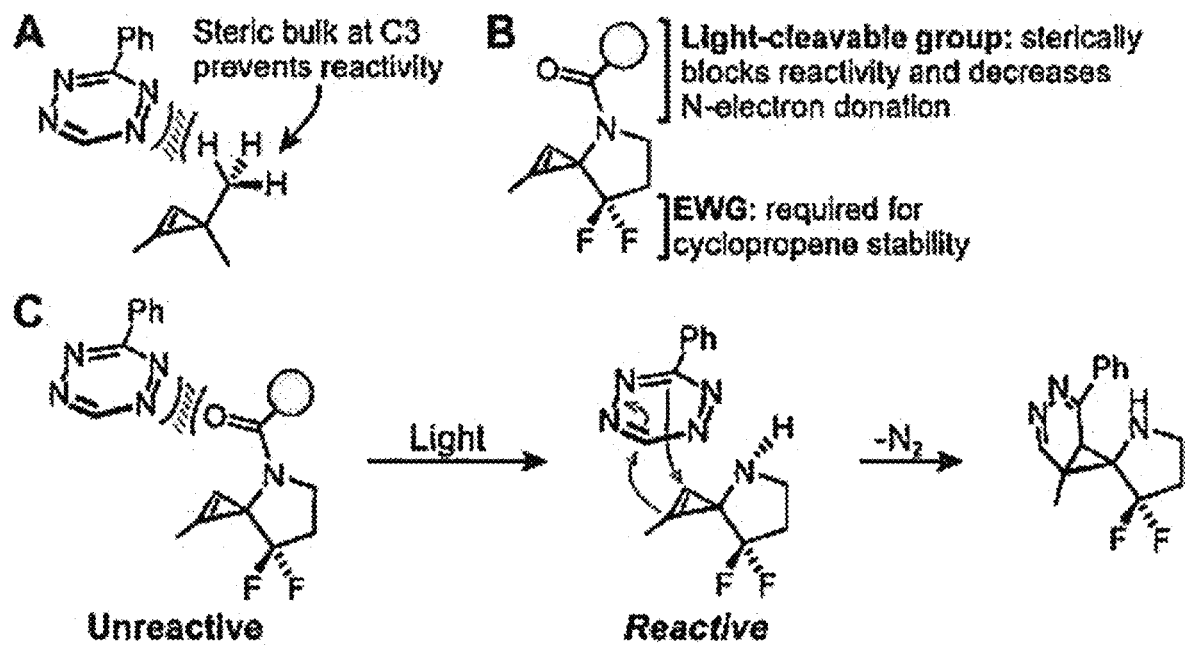
FIG. 3A—Leveraging sluggish reactivity between C3-disubstituted cyclopropenes and tetrazines to create an activatable ligation. Cyclopropenes with C3 substitutions as small as a methyl group react very sluggishly with tetrazines.
FIG. 3B—Leveraging sluggish reactivity between C3-disubstituted cyclopropenes and tetrazines to create an activatable ligation. Installation of a bulky light-cleavable protecting group serves as a removable inhibitor of reactivity. In molecules with this scaffold, positioning electron withdrawing groups (EWG) at the other cyclopropene C3 was necessary for stability.
FIG. 3C—Leveraging sluggish reactivity between C3-disubstituted cyclopropenes and tetrazines to create an activatable ligation. Light removes a bulky protecting group, activating reactivity between cyclopropane and tetrazine to permit ligation.

The strategy for controlling the cyclopropene-tetrazine ligation exploits previous reports that this reaction proceeds >7000 times slower when the cyclopropene is disubstituted vs. monosubstituted at the 3-position (Thalhammer, Wallfahrer, and Sauer 1990; Kamber et al. 2013). This dramatic rate difference is due to unfavorable steric interactions between the C3 substituents and tetrazine in the transition state (Kamber et al. 2013) (FIG. 3a). We reasoned that a nitrogen, positioned at C3 of the cyclopropane in a bicyclic system, would adopt a pyramidal geometry that is amenable to the tetrazine's approach. Importantly, the introduction of nitrogen to C3 is likely to have a notable effect on the electronics of the cyclopropene. Moreover, the nitrogen's addition is key to the molecule's design and distinguishes the scaffold from known cyclopropenes (e.g., spiro[2.3] hex-1-ene (Yu and Lin 2014)) structurally, electronically, and with respect to the molecule's synthetic strategy. Indeed, there is only one previous report of a 3N-modified cyclopropenes, the cyclopropane amino acids synthesized by Fox and coworkers (F. Zhang and Fox 2006), and in its synthesis the nitrogen was installed after formation of the cyclopropene. We hypothesized that the resulting 4-azaspiro[2,n] alkene, hereafter termed 3N-spirocyclopropene, would be unreactive when the nitrogen is modified with a bulky protecting group and reactive when the protecting group was removed (FIG. 3b-c). As an additional level of control, the increased electron withdrawing effect of a carbamate-protected vs. free nitrogen to decrease the electron density in the cyclopropane, resulting in further deceleration of the protected cyclopropene's reaction with tetrazines.

Initial synthetic efforts focused on 3-N spirocyclopropene without electron withdrawing groups. However, in these reactions, we obtained only rearrangement products resulting from cyclopropene ring opening. (Kumar, Zainul, and Laughlin 2018) To mitigate ring opening, a difluoro group was installed to destabilize the partial positive charge that would be formed along the ring opening reaction coordinate. The synthesis began with an elimination of Boc-protected, tosylated difluoroprolinol 1 to produce enamine 2. A subsequent dibromocarbene addition produced dibromocyclopropane 3 in good yield. Finally, conversion to the monobromocyclopropane (Scheme 9) and subsequent elimination afforded cyclopropene 4 in modest yield over two steps (Scheme 10).

Scheme 9 - Methods for synthesis of compounds S6, 1,2, 3, S7, 4, 5a, and 6a

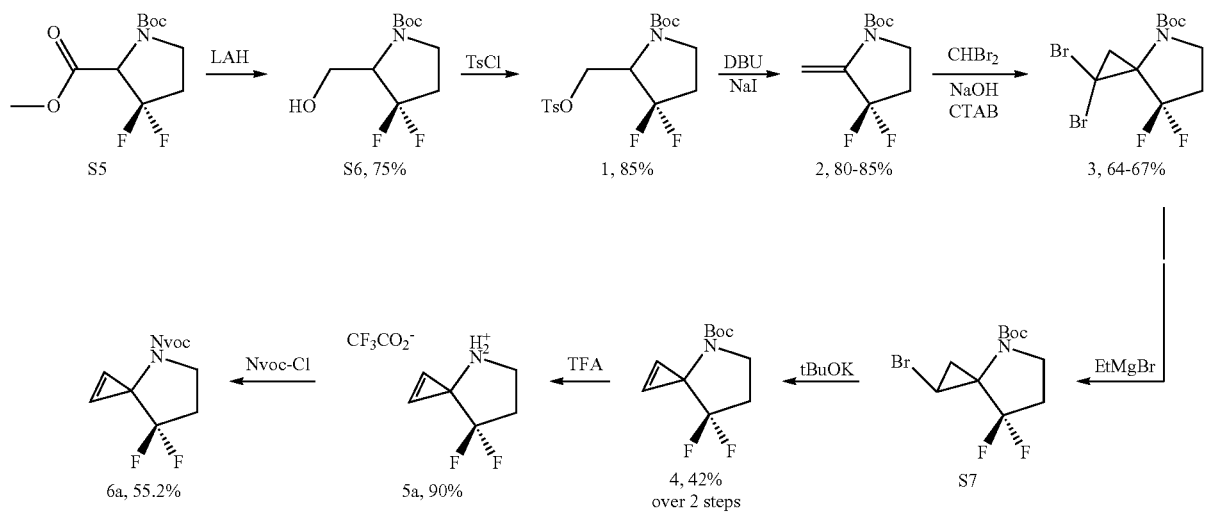

Scheme 10 - Synthesis of Boc-protected 3-N, difluoro spirocyclopropene

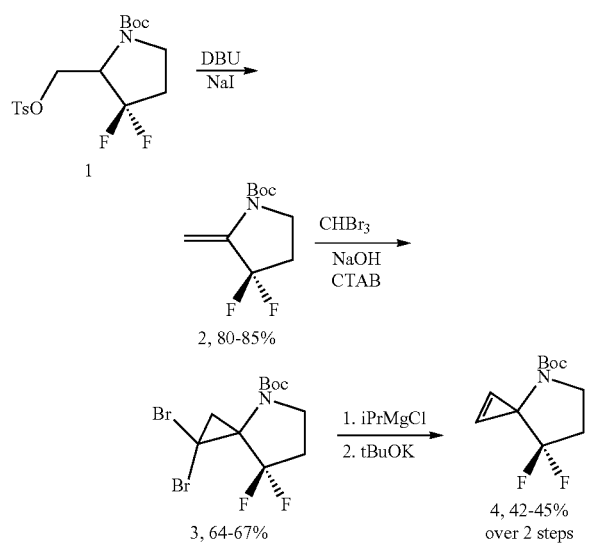

Figure 4:
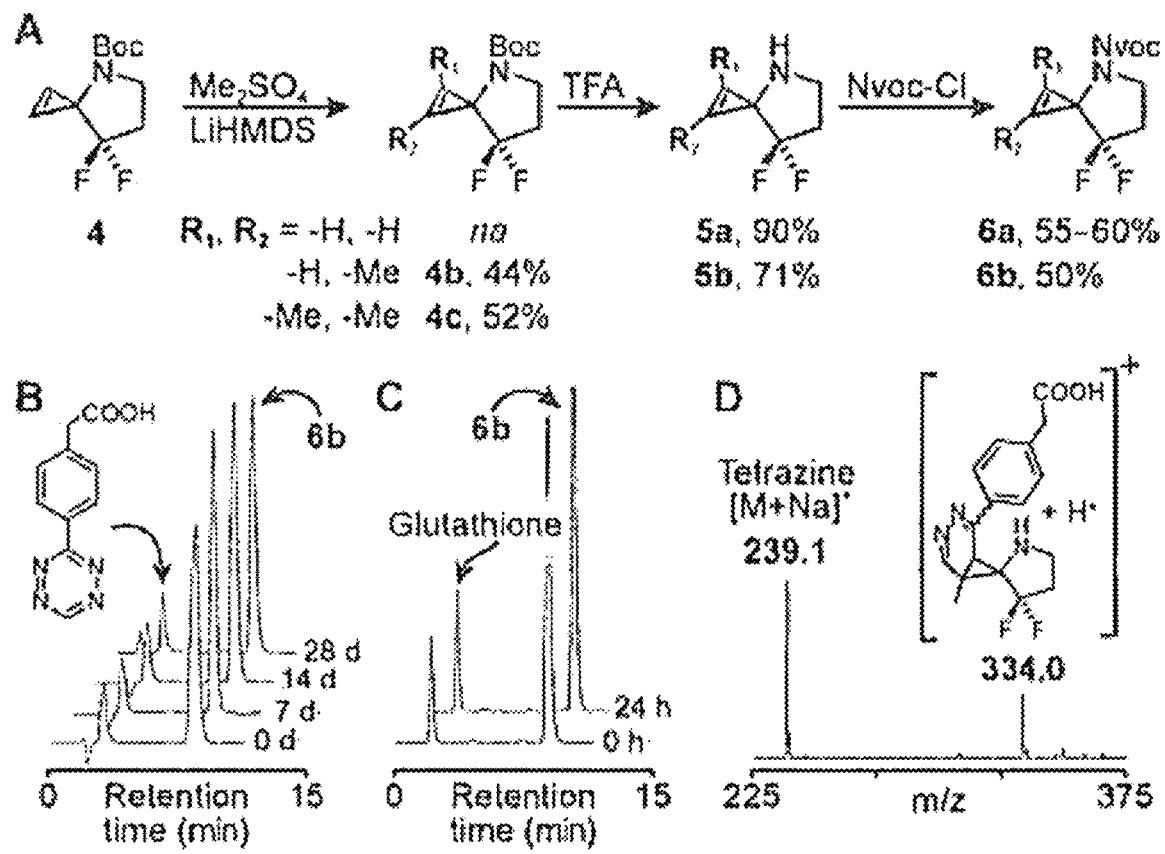
FIG. 4A—Synthesis and reactivity of C1/2-modified 3-N spirocyclopropenes. (A) Cyclopropene 4 is amenable to modifications at the C1/C2 positions and subsequent N-functionalization with light-cleavable protecting groups.
FIG. 4B—HPLC traces showing lack of reaction in 50% (v/v) MeCN in pH 7.4 PBS between Nvoc-protected cyclopropene 6b (2 mM) and tetrazine S9 (0.5 mM) for at least 4 weeks.
FIG. 4C—HPLC traces showing lack of reaction in 50% (v/v) MeCN in pH 7.4 PBS between 6b (2.5 mM) and glutathione (10 mM) for at least 24 h.
FIG. 4D—The reaction between 3-N deprotected cyclopropene 5b and tetrazine S9 showed formation of the cycloadduct in a mass spectrometry assay (m/z=334.0).
Figure 5:
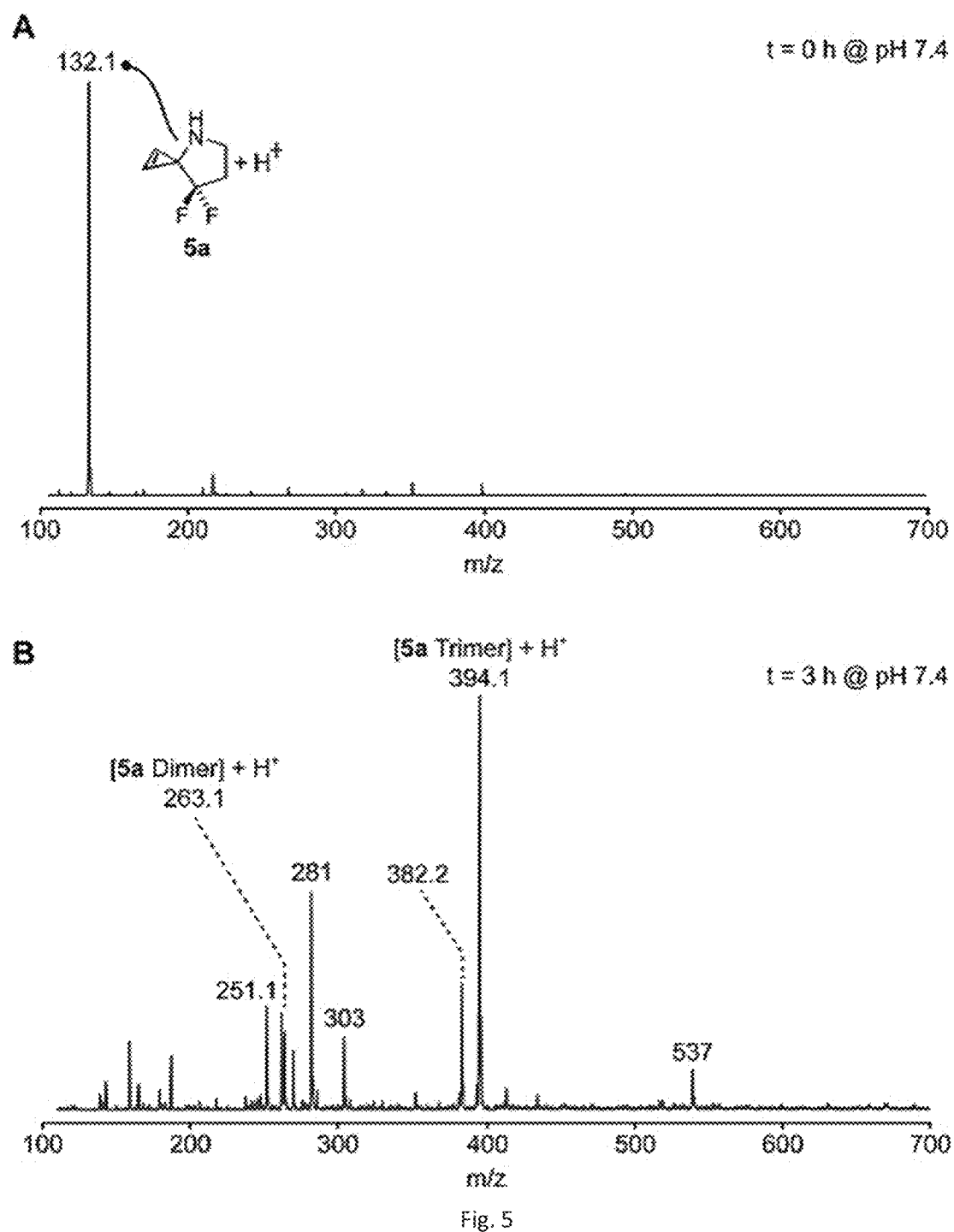
FIG. 5A—Degradation of cyclopropene 5a at neutral pH. (A-B) ESI-MS of 5a after incubation at pH 7.4 for 0 h FIG. 5B—Degradation of cyclopropene 5a at neutral pH. (A-B) ESI-MS of 5a after incubation at pH 7.4 for 3 h.

Boc-protected 4 was stable for at least 6 months at −20° C., and its free amine counterpart 5a (FIG. 4a) was stable for at least 6 months as a pH 1 aqueous solution at room temperature. Upon neutralization, the free amine cyclopropene 5a displayed reactivity with a 1,2,4,5-tetrazine in a mass spectrometry-based assay. However, it was prone to degradation at neutral pH over several hours, presumably via polymerization as evidenced by the generation of dimer and trimer species according to mass spectrometry analysis (FIG. 5). This result is consistent with previous reports of cyclopropane decomposition with C1 and C2=H (FIG. 4a, compound 5a: $R_1/R_2$=H) (Dowd and Gold 1969; Yang et al. 2012). Unfortunately, notable degradation on the hour timescale prohibited accurate determination of reaction rates and limited the utility of the molecule with unmodified C1/2. Thus, we sought cyclopropene modification strategies that would stabilize the cyclopropene scaffold.

Previous reports of cyclopropene tag stability have shown that decoration of the cyclopropene C1/2 with alkyl groups can produce substantial improvements to their stability in solution. (Yang et al. 2012) Thus, to improve on the stability of 4, variants were synthesized with substituents at the C1 and/or C2-position of the cyclopropene. Reaction of 4 with LiHMDS and dimethylsulfate produced a mixture of mono- and di-substituted cyclopropane (compounds 4b and 4c in FIG. 4a, respectively), which could be N-Boc deprotected to produce compounds 5a/5b and subsequently decorated with the Nvoc light-cleavable protecting group to produce 6a/6b (FIG. 4a). It was found that both the protected and free amine versions of the monomethyl cyclopropane (compounds 4b-6b) were stable at neutral pH and room temperature for at least several days, enabling analysis of their reactivity with tetrazines and biological nucleophiles.

Figure 6:
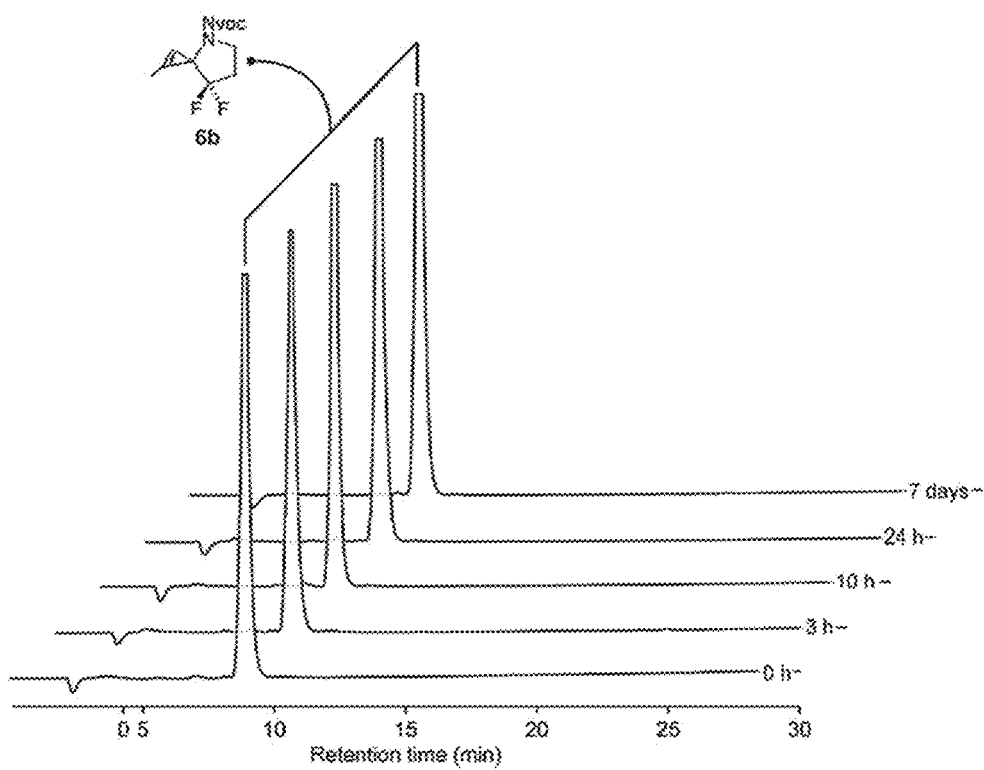
FIG. 6—Stability of Nvoc-protected 6b at 37° C. HPLC-based assay showed no decomposition products for at least 7 days. The HPLC peaks were confirmed to be the expected, unreacted 6b by mass spectrometry analysis.

A lack of reactivity between N-protected cyclopropene 6b and tetrazine is critical to this strategy's success as an activatable bioorthogonal ligation. Thus began an analysis of the molecule's properties with an evaluation of the reactivity between Nvoc-protected compound 6b and 1,2,4,5-tetrazine S9. Critically, we did not observe any decomposition or ligation between 6b and S9 for at least 4 weeks, at which point the experiment was terminated with no observed reaction (FIG. 4b). Additionally, it was found that 6b was stable in a 1:1 PBS:MeCN solution at 37° C. for at least 7 days (FIG. 6), and displayed no reactivity or decomposition when exposed to 10 mM L-glutathione, the highest physiologically-relevant concentration of this biological nucleophile (X. Jiang et al. 2017) (FIG. 4c). Importantly, however, removal of the protecting group permitted the cyclopropene-tetrazine ligation to proceed (FIG. 4d).

Figure 7:
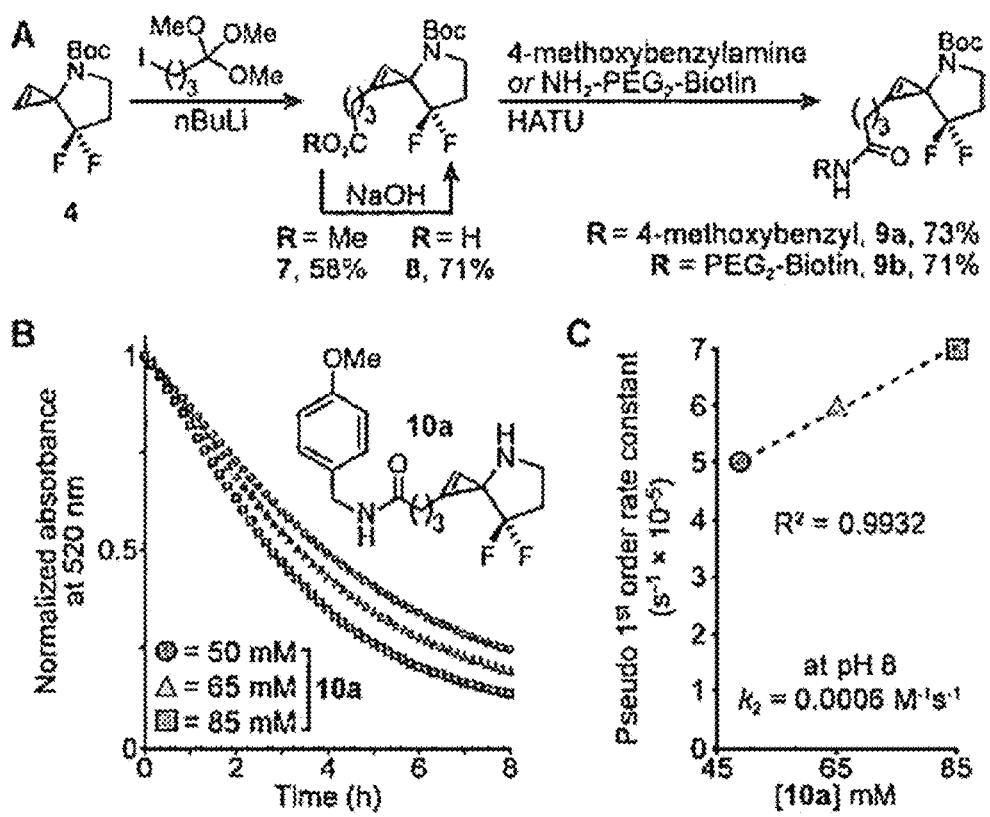

Next, it was sought to modify 4 with carboxyl functionality to both impart stability and provide a functionalization handle to the molecule. Modification of 4 with trimethyl 4-iodoorthobutyrate in the presence of n-BuLi produced the resulting methyl ester 7, and the subsequent saponification produced the carboxylic acid 8, both in modest yield. To this ester, we conjugated either p-methoxybenzylamine, for use in rate determination experiments, or biotin, for use in ligations to tetrazine-laden proteins, to produce 9a and 9b in good yield (FIG. 7a). These were then deprotected to produce free amines 10a and 10b, and the biotin derivative was decorated with the light-cleavable Nvoc group to produce compound 11 (Scheme 11 and FIG. 8b).

Scheme 11 - Methods for synthesis of compounds 9b, 10b, and 11

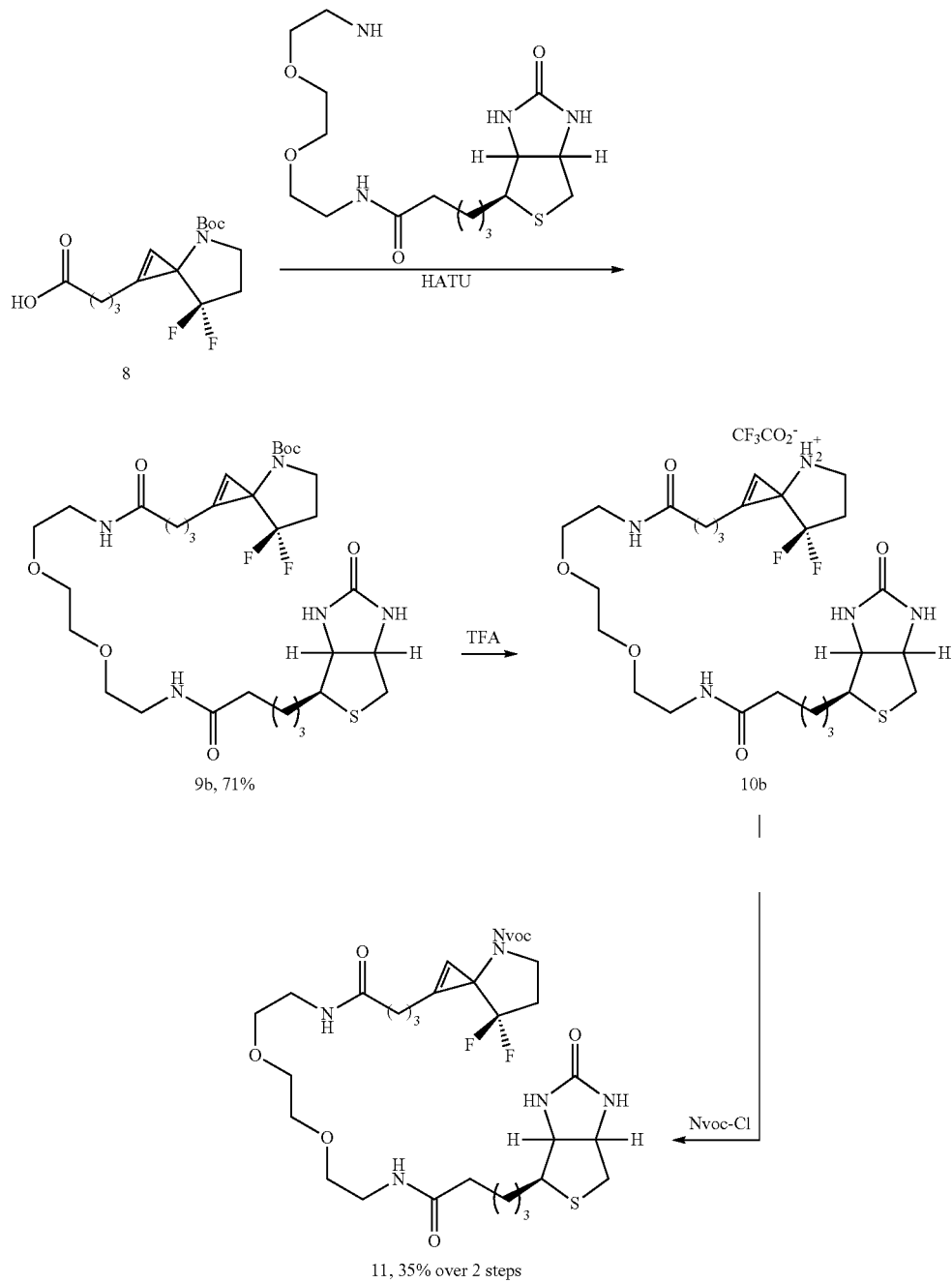

Figure 9:
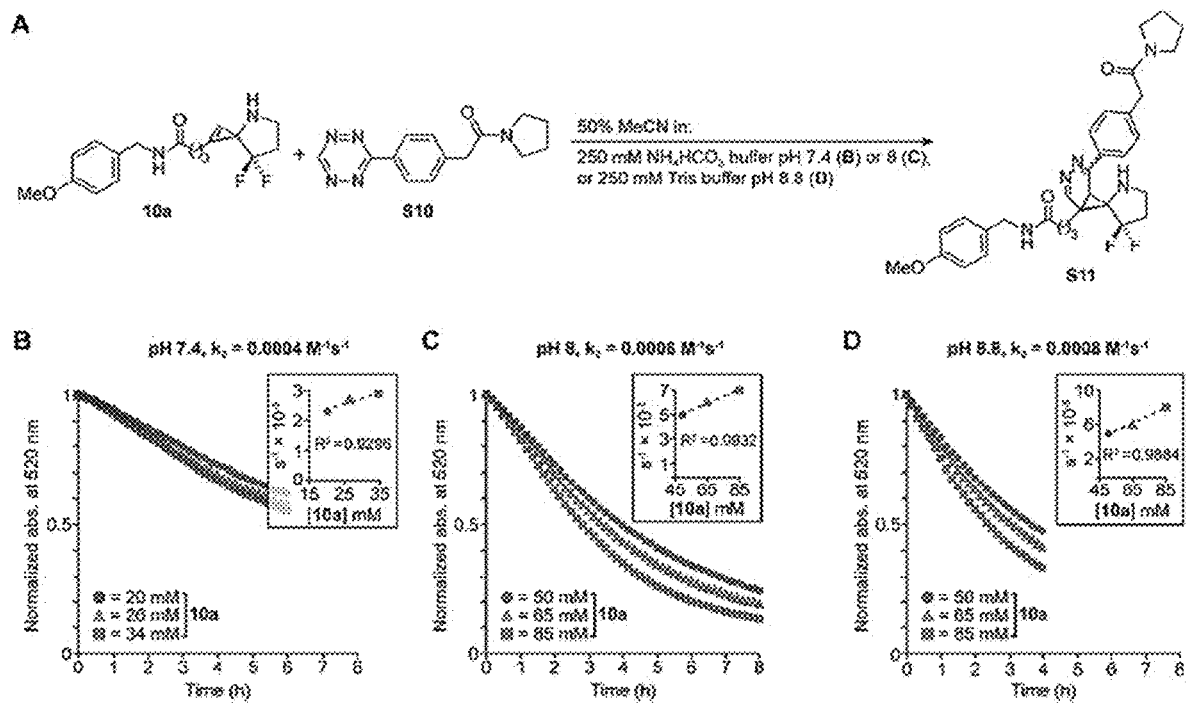
Figure 10:
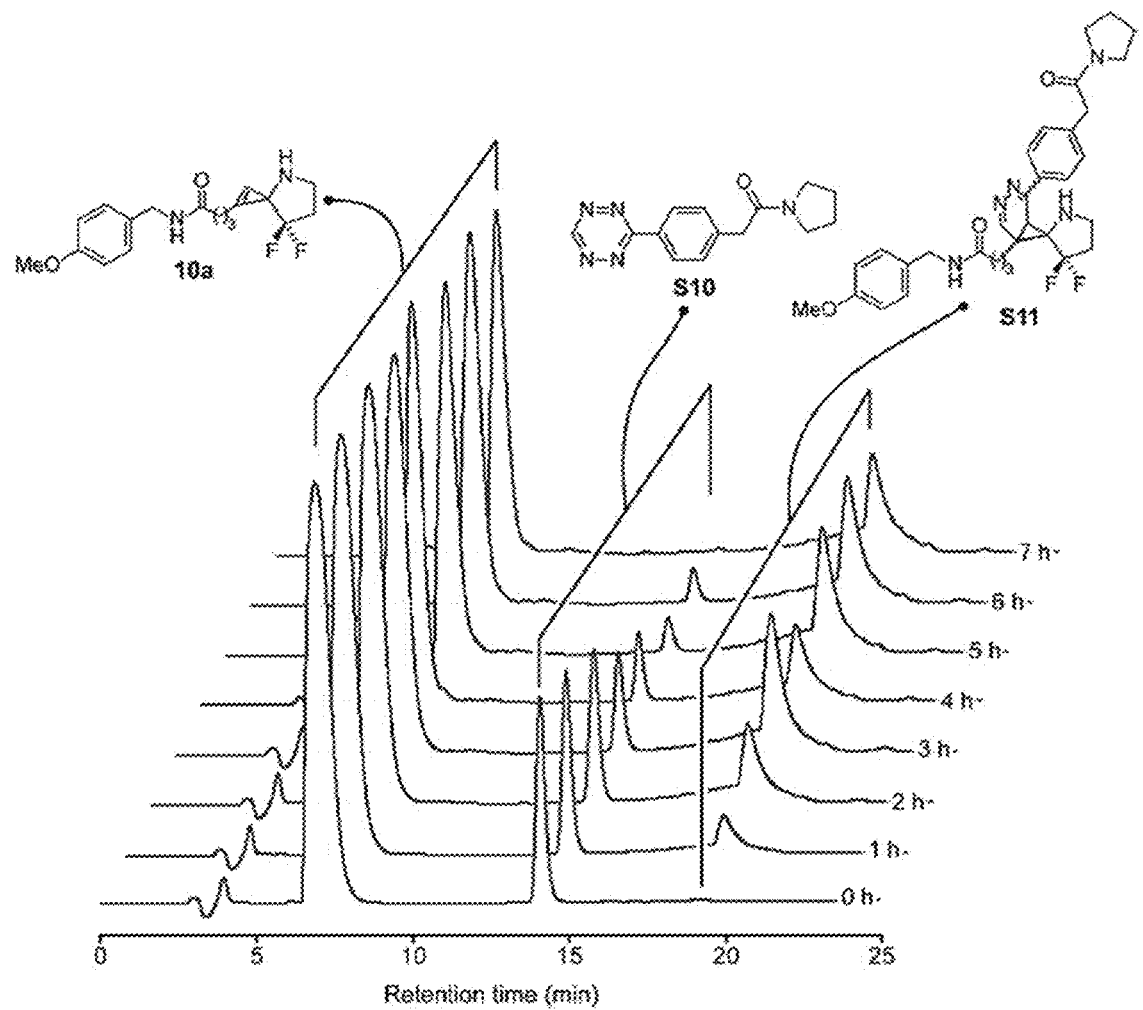
FIG. 10—HPLC-based analysis of the ligation between 10a and S10. A reaction mixture consisting of 10a (50 mM) and S10 (5 mM) in 1:1 MeCN/NH4HCO3 buffer (pH=8.0) was incubated in the dark at rt. At each designated time point (0 h, 1 h, 2 h, 3 h, 4 h, 5 h, 6 h, and 7 h), a 10 μL aliquot was withdrawn from the reaction mixture and subjected to HPLC. The ligated product S11 peak was observed and confirmed by NMR and mass spectrometry analysis. (Scheme 7, S87).

With compound 10a in hand, it was sought to evaluate the kinetic parameters of its ligation with tetrazine. We measured pseudo $1^{st}$ order rate constants at three concentrations of 10a in buffers at pH 7.4, 8.0, and 8.8, by monitoring the disappearance of the characteristic tetrazine absorbance at 520 nm (FIG. 7b). Analysis of these results revealed that the reaction at pH 7.4 has a $2^{nd}$ order rate constant of 0.0004 $M^{-1}s^{-1}$, which increased to 0.0006 $M^{-1}s^{-1}$ at pH 8.0 and 0.0009 $M^{-1}s^{-1}$ at pH 8.8 (FIG. 7c and FIG. 9). The acceleration in the reaction rate at higher pH is likely the result of increased electron donation and/or reduced steric interactions that occur upon neutralization of a greater fraction of the nitrogen. These results were consistent with a separate HPLC-based assay evaluating pseudo $1^{st}$ order kinetics (FIG. 10), which also allowed us to confirm the formation of the ligation product (Scheme 12). The observed $2^{nd}$ order rate constant puts this spirocyclopropene in the same order of magnitude as the original, Cu-free click reactions with cyclooctyne (Agard, Prescher, and Bertozzi 2004). Additionally, the acceleration in rate with increasing pH suggests that next generation reagents with lowered $pK_a$ values are an avenue for future reaction rate improvements.

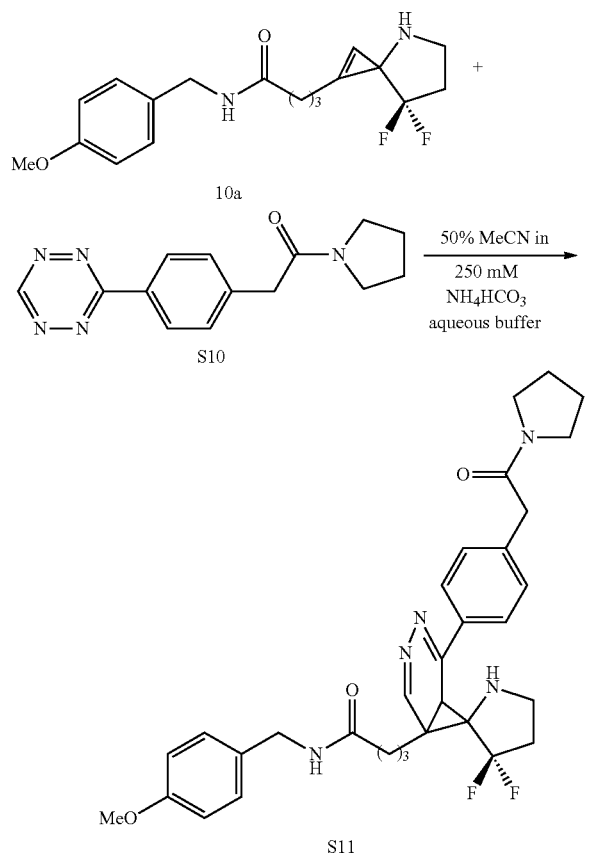

Scheme 12 - Methods for synthesis of compound S11

Figure 8:
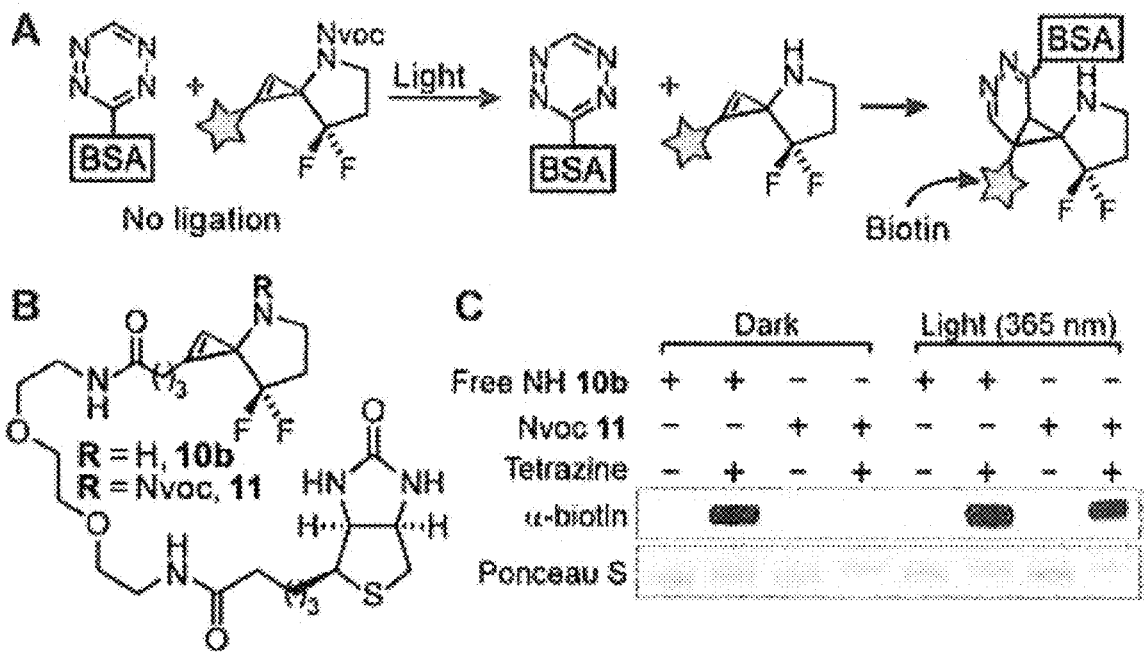
FIG. 8A—Light-controlled bioorthogonal reactivity of 3-N spirocyclopropenes. (A) Nvoc-protected cyclopropene 11 did not display any ligation to tetrazine-modified BSA. Upon exposure to 365 nm light cyclopropane 11 generates 3N-deprotected cyclopropene 10b which ligates to the tetrazine-modified BSA protein.
FIG. 8B—Molecular structures of biotin containing 3-N deprotected cyclopropene 10b and Nvoc protected 3-N cyclopropene 11.
FIG. 8C—Chemiluminescence and Ponceau analysis of ligation between the tetrazine-modified BSA and cyclopropenes 10b or 11. No signal was detected for the Nvoc-caged 11 in the absence of light. whereas a strong signal was observed for the same compound after the sample was exposed to 365 nm light. Each reaction contains 5.0 μg of protein (BSA or tetrazine modified BSA) and 500 nM cyclopropene (10b or 11) were either kept in dark or exposed to 365 nm light for 4 h in PBS (pH 7.4). The reactions were incubated at rt for 12-14 h and subjected to western-blot.

Lastly, this ligation was studied in biological contexts and to determine the success of the ligation after light activation. A solution of tetrazine-modified bovine serum albumin (BSA) was prepared and evaluated its reactivity with the biotin-conjugated free-amine or Nvoc-protected cyclopropenes 10b and 11 in a Western blot assay (FIG. 8a-b). Incubation of 500 nM of Nvoc-protected cyclopropane 11 with tetrazine-BSA in the dark produced no observable ligation products according to Western blot analysis (FIG. 8c), consistent with the observed long-term lack of reactivity in solution (i.e., FIG. 4b). Additionally, the Nvoc-protected cyclopropane 11 and free amine cyclopropene 10b displayed no reactivity with unmodified BSA in light or dark exposure situations. However, upon exposure of 500 nM Nvoc-protected cyclopropene 11 to light at 365 nm we observed ligation to BSA-tetrazine, indicating that 11 can be activated in situ (FIG. 8c).

In conclusion, a cyclopropene scaffold was developed whose activity can be controlled by addition or removal of a light-cleavable protecting group. The cyclopropene's reactivity could impact other areas of chemistry, such as in the creation of new polymers for materials applications (e.g., in ring opening metastasis polymerizations (Elling, Su, and Xia 2016). Given the popularity of nitrogen as a target for light-removable protecting groups in biology (Klan et al. 2013; Grimm et al. 2016) (e.g., N-linked photocleavable protecting groups with varying properties based on coumarins (Klan et al. 2013; Furuta et al. 1999; Ellis-Davies 2007), RuBi cage (Cabrera et al. 2017), nitroindonilyl, (Canepari et al. 2001; Amatrudo et al. 2015; Kantevari et al. 2016) 2-nitrobenzyl (Ellis-Davies 2007; Stutz and Pitsch 1999), and thiochromone S,S-dioxides (Kitani et al. 2008), this activatable cyclopropane scaffold is amenable to control via additional wavelengths of light through the application of the desired protecting group. The kinetics of this reaction with 1,2,4,5-tetrazine is sluggish relative to recent bioorthogonal ligations that have been optimized for speed, but this reagent provides control of reactivity in space and time that can be tuned to the particular application through the selection of an appropriate light-cleavable protecting group.

Additionally, kinetics for these reactions are currently being optimized with analogs that lower the molecule's $pK_a$ and decrease the strength of the rate-decelerating electron withdrawing groups on the spiro ring system.

Example 3. Synthesis of Additional Dihalo Compounds

Cyclopropenes are popular bioorthogonal reagents for exploring native biomolecules' roles in biology (Ravasco, Monteiro, and Trindade 2017). They have been used extensively with sugars, (Patterson, Jones, and Prescher 2014; Cole et al. 2013; Späte et al. 2014; Smith et al. 2018; Z. Li et al. 2014) proteins, (Smith et al. 2018; Z. Li et al. 2014; Kamber et al. 2013; Patterson et al. 2012; Yu, Ho, and Lin 2011) oligonucleotides, (Yang et al. 2014; Eggert and Kath-Schorr 2016) neurotransmitters, (Paulini and Reissig 1992; Kumar, Shukhman, and Laughlin 2016) and, to a limited extent, lipids (Yang et al. 2012; Baird et al. 1992). The application of cyclopropenes to lipid biology is particularly interesting because lipids are one of the few biomolecules with naturally occurring cyclopropene-containing metabolites, including sterculynic acid, (Baird et al. 1992) sterculic acid, (Nunn 1952) and malvalic acid (Macfarlane, Shenstone, and Vickery 1957).

Figure 11:
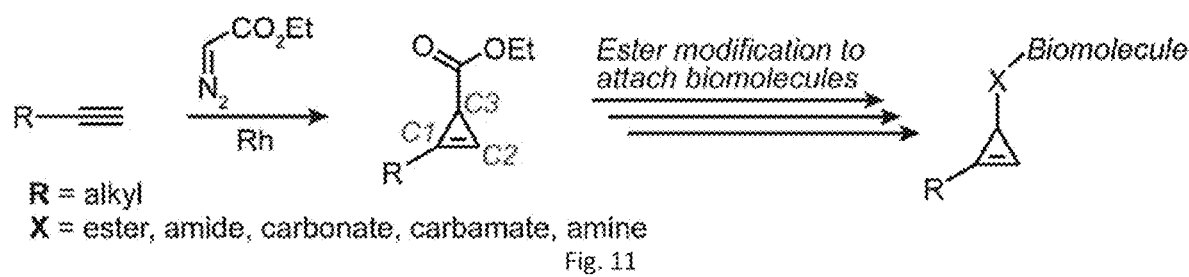
FIG. 11—Current strategies to append cyclopropene handles onto biomolecules proceed via modification at the cyclopropene C3 position. Cyclopropenes are first prepared via rhodium catalysed addition of ethyl diazoacetate to alkynes, which are then modified at C3 to append biomolecules such as lipids.

Produced in plants, these naturally occurring cyclopropene-bearing lipids have diverse functions, from promoting liver tumor formation (D. J. Lee et al. 1968) to exhibiting anti-parasitic properties, likely through their inhibition of lipid metabolism (Hao et al. 2016). Similarly fascinating, unnatural cyclopropene-modified lipids have found applications in bioorthogonal chemistry, including, for example, Devaraj and co-workers' preparation of a C3 lipidated cyclopropene (see FIG. 11 for cyclopropene carbon numbering) and demonstration of its use as a tool for live-cell imaging of mammalian cells (Yang et al. 2012).

Unfortunately, lipidation of cyclopropenes for biorthogonal chemistry applications is typically restricted to addition of the lipid to the C3 position of the cyclopropene. This is due to the limited number of synthetic procedures that enable direct derivatization of cyclopropenes with biomolecules at C1 or C2. For example, it is possible to generate a cyclopropene that is already modified at C1 with an alkyl alcohol by the rhodium catalyzed addition of ethyl diazoacetate to a protected alcoholic alkyne (R=protected alkyl alcohol, FIG. 11). The protected alcohol could then be deprotected and oxidized to obtain a carboxylic acid handle for further elaboration. However, examples of the oxidation of such cyclopropene C1-alcohols to the corresponding cyclopropene C1-acid are challenging and rare in the literature. (Kumar, Shukhman, and Laughlin 2016; Kogen et al. 2000) Alternatively, the functionalization handle could be installed using a lipid-modified protected alkyne precursor (R=functional group protected lipid, FIG. 11), but such functionalized alkyne lipids are commercially uncommon, expensive and difficult to synthesize (e.g., Avanti® polar lipids offers four alkyne-modified lipids and the cheapest is ~$150/mg). There are also strategies for cyclopropene modification at C1/C2 on intact cyclopropenes to obtain secondary alcohols (Kim, Sherrill, and Rubin 2010; Edwards, Rubina, and Rubin 2016; Liao, Yan, and Fox 2004) but they require challenging conjugation conditions to attach lipids via an ether or, after a non-trivial oxidation, a ketone.

Methods for the addition of bulky biomolecules such as lipids at the C1/2 position of a cyclopropene, instead of C3, would be desirable for several reasons. For example, C1/C2 derivatization strategies will expand the accessible cyclopropene chemical space. Additionally, substituting C1/C2 has been shown to increase the stability of cyclopropenes (Yang et al. 2014). As a result, lipidation at C1/C2 could serve the dual purpose of stabilizing the cyclopropene while minimizing the size at C3 to limit negative steric effects on the cyclopropene's reactivity with 1,2,4,5-tetrazines. Indeed, modifications of C1/C2 place the substituent orthogonal to the approach of the tetrazine along the ligation's reaction coordinate, resulting in only modest reaction rate deceleration relative to unmodified cyclopropenes. For example, Ye and co-workers demonstrated that C1 methylation of a C3-amide-containing cyclopropene produced only a modest decrease of 9% in cyclopropene's ligation rate (Xiong et al. 2015). Conversely, di-substitutions at C3 cause substantial deceleration or complete inhibition of the cyclopropene-tetrazine ligation (Ravasco, Monteiro, and Trindade 2017; Kamber et al. 2013; Thalhammer, Wallfahrer, and Sauer 1990).

Finally, lipidation at C3 is not directly compatible with our recently described 'caged cyclopropene' strategy, which provides external control over the cyclopropene-tetrazine ligation (FIG. 12A) (Kumar, Jiang, Li, et al. 2018). These caged cyclopropenes were inspired by the >7500-fold difference in reaction rate between C3 mono-substituted and C3 di-substituted cyclopropenes. (Sauer et al. 1998; Thalhammer, Wallfahrer, and Sauer 1990) Essentially, a carbamate-caged 3-N spirocyclopropene mimics the unreactive C3 di-substituted cyclopropene, whereas the uncaged, 3-N spirocyclopropene mimics the more reactive C3 di-substituted cyclopropene, with the addition of an electron withdrawing group at C3 critical to prevent the ring opening isomerization to an allene or alkyne (Kumar, Zainul, and Laughlin 2018). The constraints of the spirocyclopropene scaffold complicate efforts to append biomolecules at C3, which contains the required electron withdrawing group. As a result, biomolecules such as lipids must be appended to C1/C2 or elsewhere on the scaffold to create target compounds like CpL1 or CpL2 (FIG. 12B), and both options possess few synthetic precedents.

Figure 12:
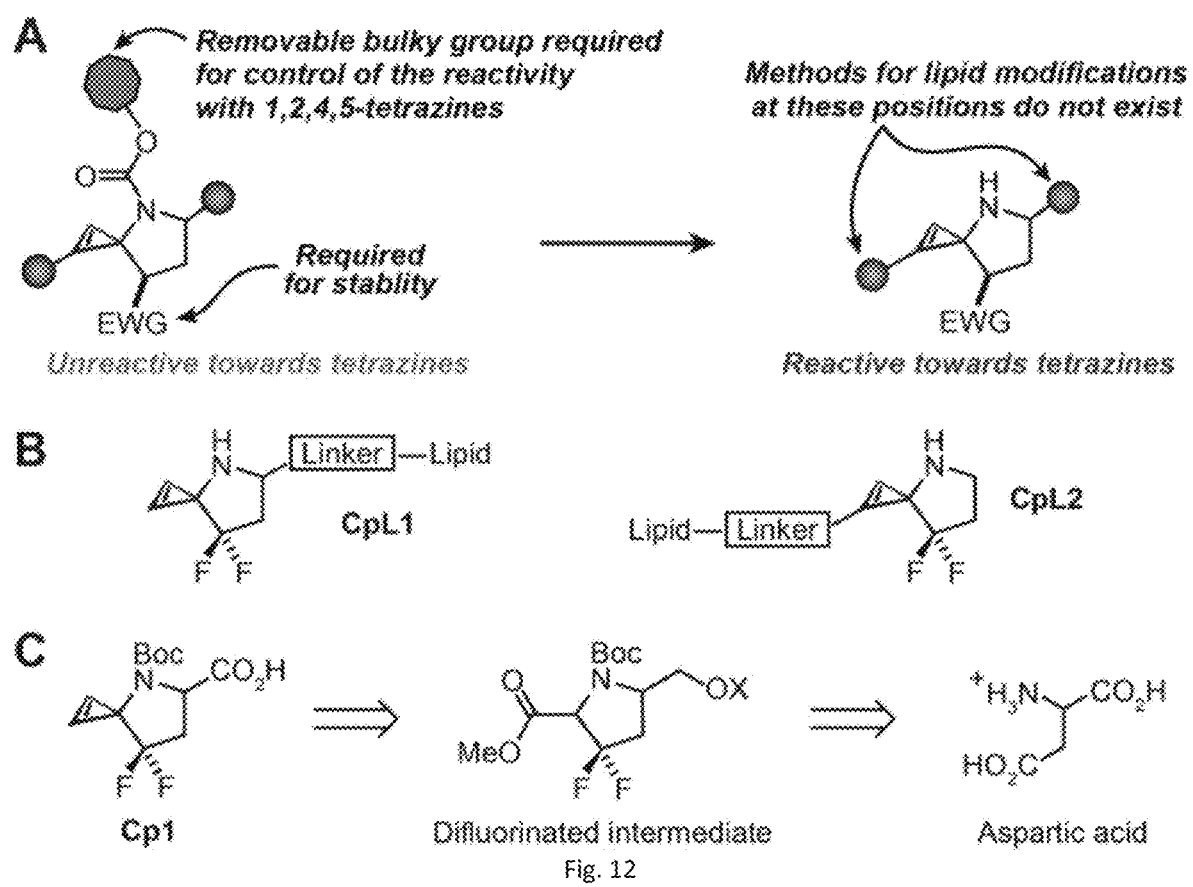
FIG. 12A—Photocaged 3-N cyclopropenes allow light-mediated control of cyclopropene-tetrazine bioorthogonal ligation. Such 3-N cyclopropene formation require an EWG to prevent rearrangement to an alkyne or allene. Installing a linker on the EWG-stabilized 3-N spirocyclopropenes will enable an alternative to currently available C3 modification for attaching lipids (or other biomolecules) to cyclopropenes.
FIG. 12B—Lipids can be attached to 3-N cyclopropenes either at C1/C2.
FIG. 12C—Lipids can be attached on the pyrrolidine ring. Retrosynthetic analysis for Cp1 identified aspartic acid as an inexpensive starting point with the 'difluorinated intermediate' as a key scaffold.

To begin, modification of the caged cyclopropene scaffold on the pyrrolidine ring of the spirocyclic framework represents the best possible option: no rate deceleration from the addition of a bulky group adjacent to the tetrazine approach trajectory, and we would not have to alter the nature of the difluoromethylene substituent at the cyclopropene C3. To explore this possibility, it was sought to synthesize difluorinated spirocyclopropene Cp1, which contains a carboxylic acid-bearing linker on the carbon adjacent to the caged nitrogen group (FIG. 12C).

The synthesis of 6 began with a NaBH$_4$-mediated reduction of bis-protected L-aspartic acid 1 to the corresponding alcohol S1 (Scheme 13), which we protected using TBDPSCl to obtain 2 in 92% yield over two steps (Scheme 14). Then, 2 was subjected to Pd-mediated deprotection of the benzyl ester to give carboxylic acid 3 in 85% yield, activated the resulting acid using CDI, and proceeded directly to the Mg-mediated production of β-keto ester 4 in 80% yield over two steps. The acidity of the methylene sandwiched between the ketone and ester groups allowed us to convert 4 to the corresponding diazo compound 5. Subsequently, compound 5 was cyclized using Rh insertion (Moreau and Sorensen 2007) with a non-stereoselective catalyst (Adams and Spero 1991) to obtain the five membered, 3-oxopyrrolidine-2-carboxylate based scaffold, 6 in 96% yield as a mixture of diastereomers.

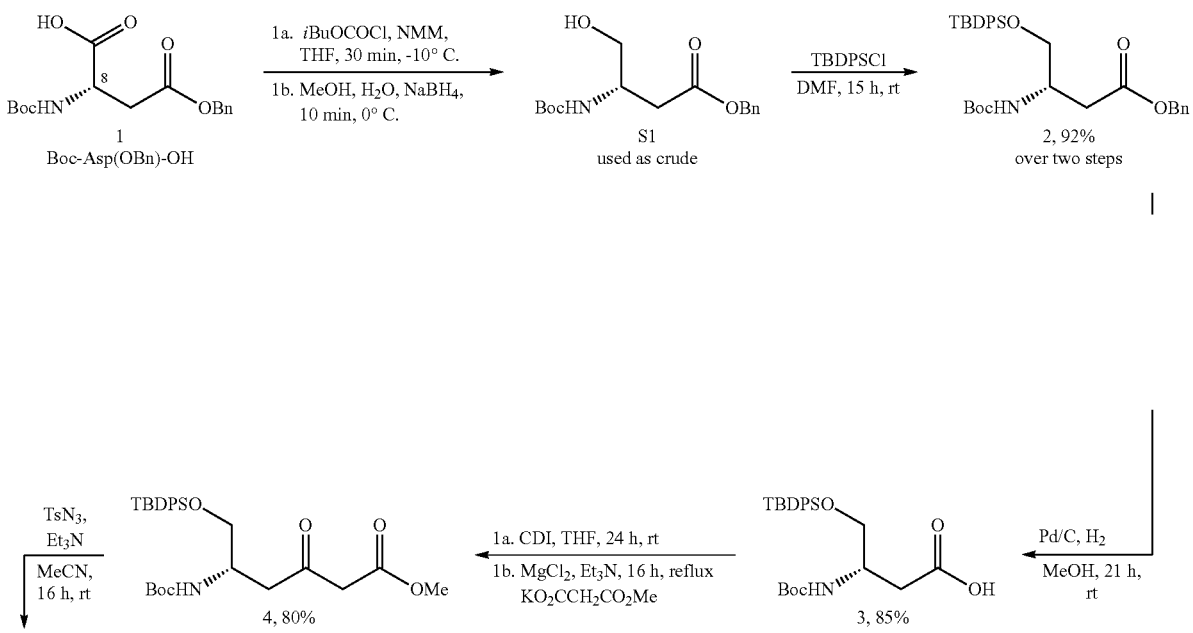

Scheme 13 - Synthesis and characterization of compound S1, and 2-6

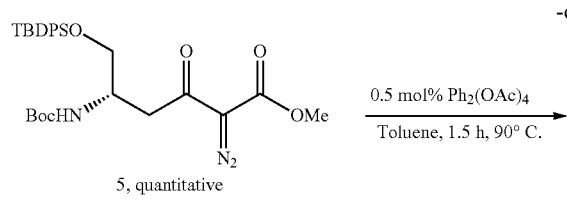
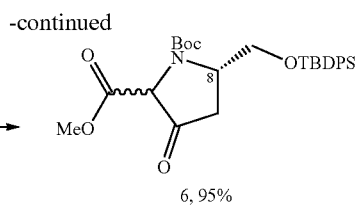

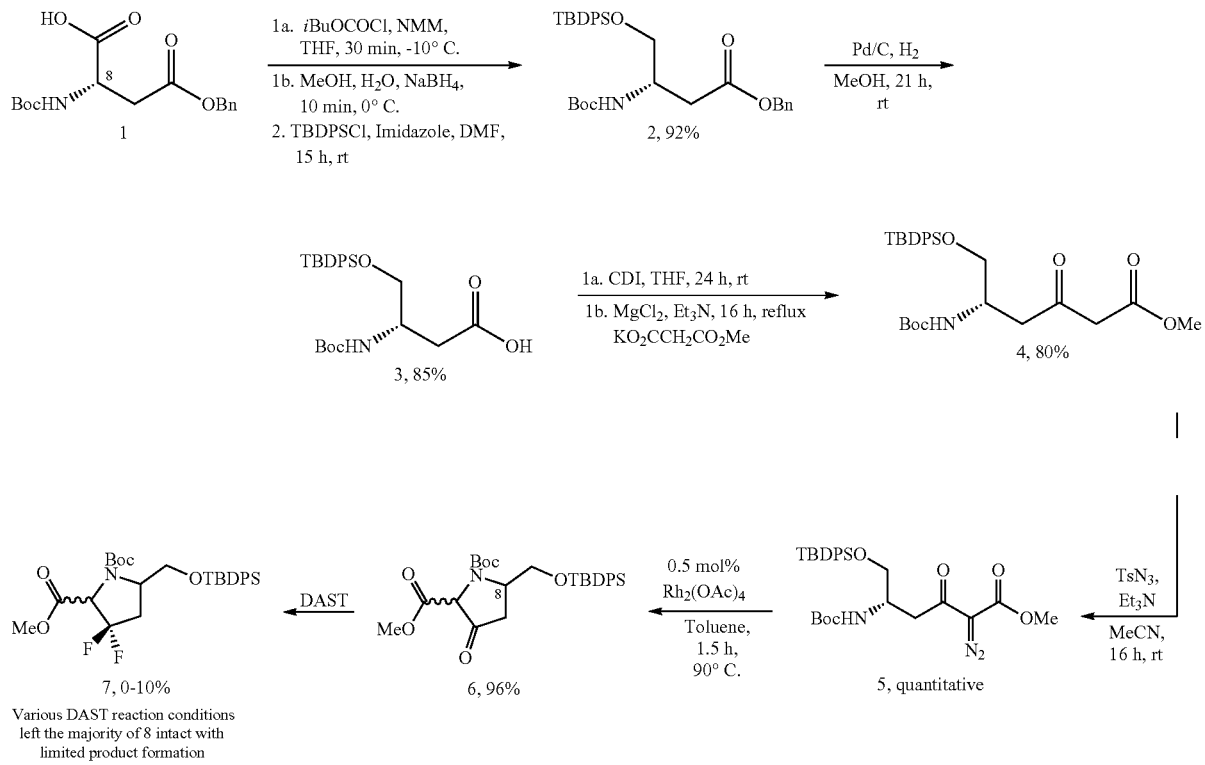

Scheme 14 - Synthesis of five-membered scaffold 6 with linker for 3-N spirocyclopropene formation.

The ketone intermediate 6 was an ideal candidate for installation of the difluoro group, which is necessary for stability of the cyclopropene in this bicyclic scaffold (Kumar, Zainul, and Laughlin 2018). To perform the difluorination, DAST was used, which has been successfully used to carry out difluorinations of similar proline analogs. (Doebelin, He, and Kamenecka 2016) Our initial attempts using equimolar equivalents of DAST at low or room temperature for varying amounts of time produced no reaction. Doubling the molar equivalents of DAST and adding it under cold conditions afforded 7 in 5% yield and tripling the DAST equivalents improved the yield to 10%. However, extensive efforts to further optimize the reaction through alterations to time, solvents, and temperature, or through the use of a different fluorinating agent Selectfluor, produced no further improvement to the reaction's yield.

It was hypothesized that the bulky TBDPS group limits DAST's access to the ketone, so we switched to the less bulky MOM protecting group (Scheme 15). For these transformations, diazo 5 was stable to the requisite de- and re-protection conditions, proceeding without issue to give deprotected alcohol S2 in 90% yield. Interestingly, this is only the second report of fluoride-mediated silyl ether deprotection in the presence of diazo functionality and the first report employing TBAF deprotection of TBDPS in these systems (Abid et al. 2015). Next, we MOM-protected the free alcohol S2 to obtain S3 in 68% yield. Subsequent rhodium catalyzed cyclization afforded S4, the MOM-protected derivative of 7, in 93% yield as a mixture of diastereomers. However, despite the diminutive MOM protecting group, our extensive efforts at difluorinating ketone S4 produced S5 with yields in the 5% range and never fully consumed the starting material. Ultimately, although a maximum yield of 10% for the difluorinated 7 may have been acceptable at late stages in the synthesis, it was not feasible to carry out the next nine linear steps to generate the desired lipidated cyclopropenes. Further, as described earlier, the alkyne containing ceramides and phospholipids are either non-existent or difficult to synthesize, suggesting that rhodium-catalyzed cyclopropenation with an alkyne lipid would not be straightforward; therefore, the possibility of lipidation at C1/C2, after the formation of the cyclopropene scaffold was explored.

Scheme 15 - Synthesis and characterization of compounds S2-S5

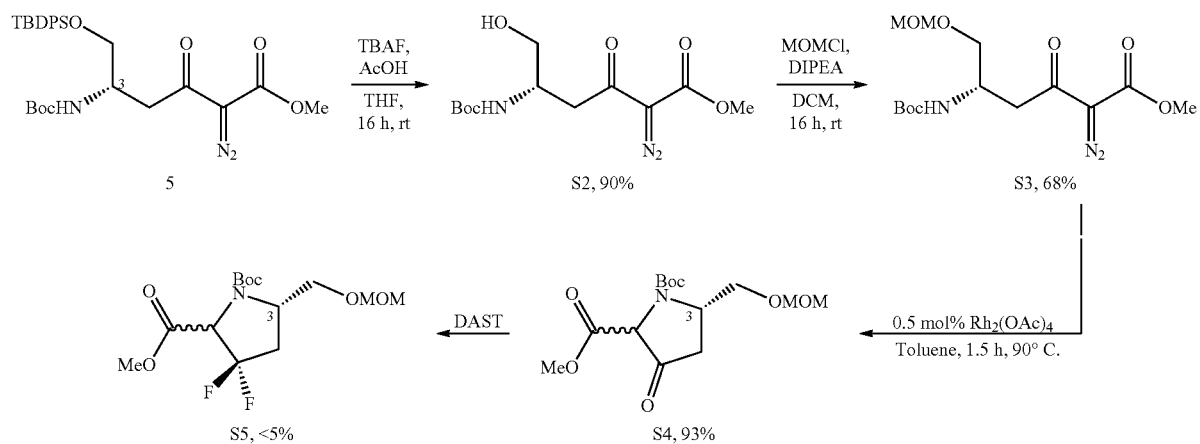

Methods for attaching an amine or acid handle at the C1/C2 position of an intact cyclopropene were, with one exception, unprecedented in the literature. The one exception is our recently reported orthoformate strategy that installs an ester in one step from the corresponding cyclopropene (Kumar, Jiang, Li, et al. 2018). Here, a variety of electrophiles were explored in an effort to expand the scope for installation of carboxylic acid functionality on 15 (Scheme 16). For example, we attempted to install an alcohol using oxirane or paraformaldehyde after treatment of the cyclopropene with n-BuLi, but this produced only unreacted starting material. A reaction with a tosyl-activated alcohol linked to dihydrooxazole-protected carboxylic acid was explored. This reagent should participate in base-mediated substitution of the tosylate at the cyclopropene C1/C2, and the dihydrooxazole could be subsequently hydrolysed to the carboxylic acid. However, our attempts at nucleophilic substitution using n-BuLi produced a mixture of unreacted starting material and oxazole decomposition. Ultimately, of all electrophiles tested, the iodo-orthoformates were the only electrophile that efficiently modified C1/C2 on the cyclopropene, producing the orthoformate-modified cyclopropene in high yield that quantitatively hydrolysed to the corresponding ester upon silica gel chromatography, and, after saponification, produced the spiro-cyclopropene acid 16 (Scheme 17).

Scheme 16 - Attempts at installation of linker at C1 on cyclopropene 15

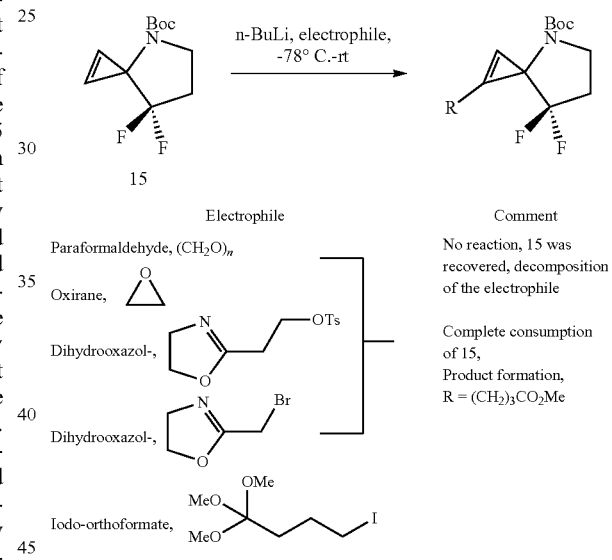

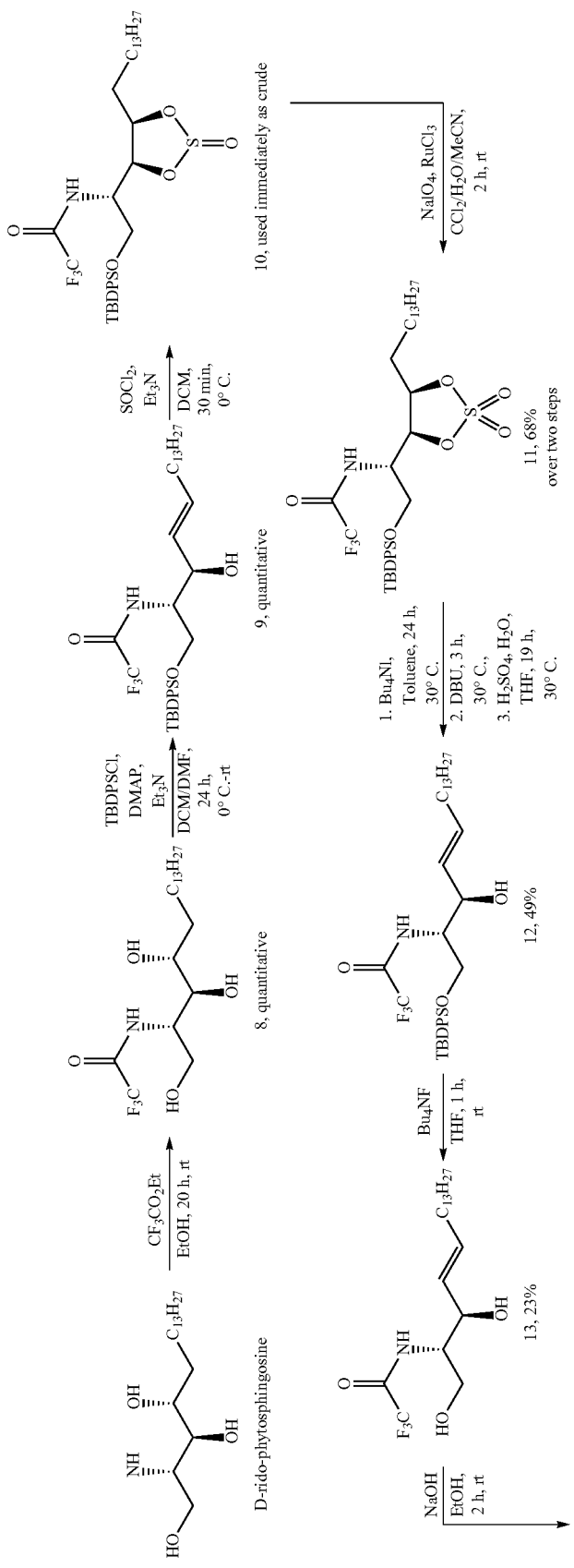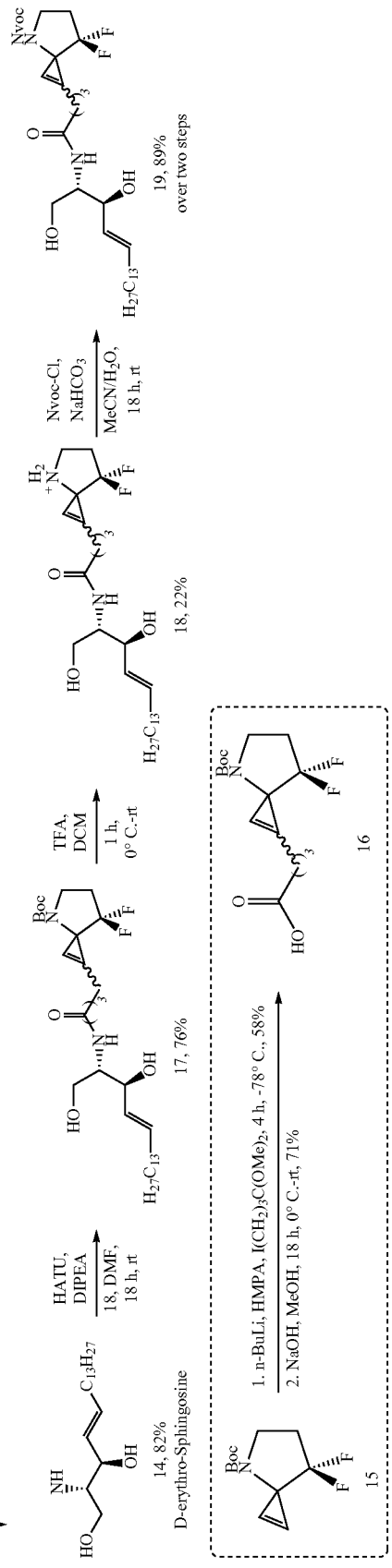

Finally, lipidation of the carboxylic-acid-modified cyclopropene C1 with two different classes of bioactive lipids was expored: ceramide and phospholipid. Ceramides are important components of a eukaryotic cell lipidome. They make up sphingomyelin, a major bilayer lipid, and control a variety of cellular signaling processes. (Bieberich 2008; Morad and Cabot 2013) Consequently, functionalized ceramides, such as a fluorophore-modified BODIPY-ceramide, are employed for tracking the biological functions of ceramides in the cell. Bioorthogonal chemistry-based applications include a recently described trans-cyclooctene-containing ceramide analog that Schepartz and co-workers used for super-resolution imaging of the Golgi in living cells. (Erdmann et al. 2014) The availability of a cyclopropene analog of ceramide will further increase the available options for bioorthogonal reagents that can be used to study ceramide dynamics.

To obtain a C1-ceramide containing spirocyclopropene we started from D-ribo-phytosphingosine, a commercially available reagent (Scheme 18 and Scheme 17). Ceramides are sphingosines where the amine on the sphingosine contains hydrophobic residues via an amide linkage. We converted D-ribo-phytosphingosine to D-erythro-sphingosine using slight modifications to the synthetic strategy reported by Kim and co-workers (Y. M. Lee et al. 2011). Briefly, the dual protection of the amine group on D-ribo-phytosphingosine using ethyl trifluoroacetate to obtain 8, and the primary alcohol with TBDPSCl to obtain 9 proceeded in quantitative yield. Next, we converted 9 to cyclic sulfite 10 with thionyl chloride. However, this cyclic sulfite to be unstable to silica gel and overnight storage. Therefore, the compound was subjected immediately to ruthenium-periodate oxidation to obtain the cyclic sulfate 11 in 68% yield over two steps. Additionally, the trityl protected analogues were unstable to the required thionyl chloride/ruthenium-periodate conditions, so we proceeded with ethyl trifluoroacetate protected analogs instead. The 11-12 reaction sequence was performed in one pot because our attempts to purify the intermediates resulted in substantially lower overall yields due to their decomposition on silica gel. Essentially, cyclic sulfate 11 was converted to the sulfate ester-iodide using $Bu_4NI$, dehydrohalogentated the intermediate using DBU to produce the sulfate alkene, and hydrolysed the sulfate under acidic conditions to obtain 12 in 49% yield over three steps. Then, this N,O-bis protected sphingosine 12 was TBDPS-deprotected using the fluoride source $Bu_4NF$ to obtain a 23% yield of 13, which was converted to the D-erythro-sphingosine 14 by base-mediated hydrolysis in 82% yield.

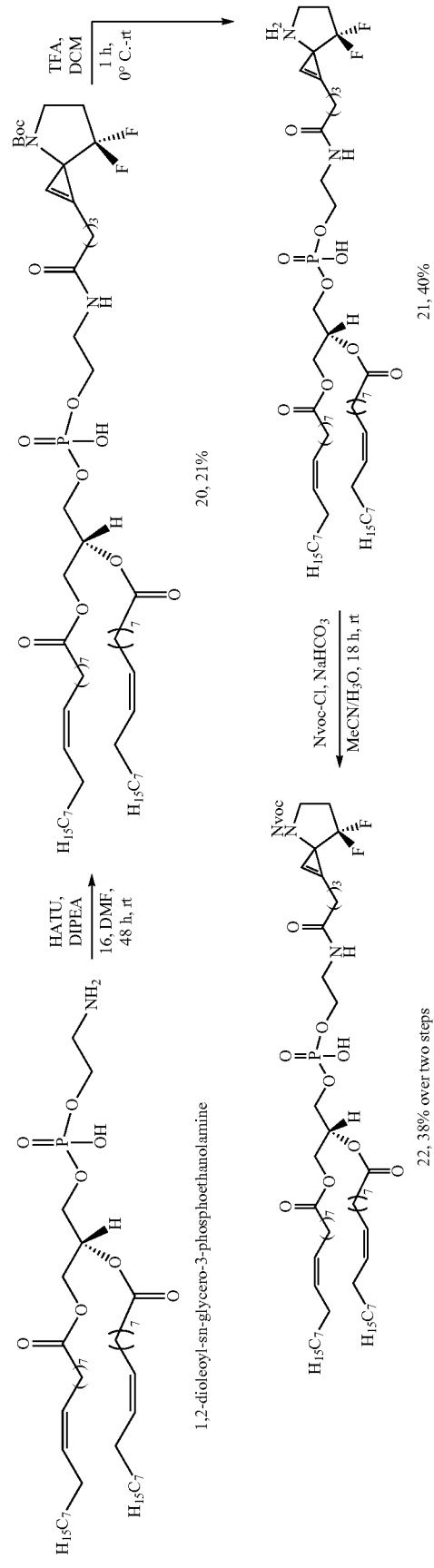

The free amine sphingosine 14 was coupled to the 3-N spirocyclopropene acid 16 using HATU to obtain the C1-ceramide Boc-cyclopropene 17 in 76% yield. Finally, the lipidated-cyclopropene was Boc-deprotected to obtain free amine C1-ceramidated 3-N spirocyclopropene 18 in 22% yield. Importantly, the low yields of 18 are due to difficulties inherent to the purification of this charged lipid, not decomposition, because similar cyclopropene scaffolds, including the Boc- and Nvoc-protected variants of 18, have survived acidic HPLC and deprotection conditions unscathed (Kumar, Zainul, and Laughlin 2018). Separately, the Nvoc photocaged version was prepared directly without purifying the Boc-deprotected intermediate 18 to obtain 19 in 89% yield over two steps.

Like ceramides, phospholipids represent another important class of biologically relevant lipids. The amphiphilic character of phospholipids makes them a major component of the lipid bilayer in the cell plasma membrane. The availability of a photocaged, cyclopropene-containing phospholipid will permit its applications as a bioorthogonal probe to study membrane biology. We installed a commercially available phospholipid, 1,2-dioleoyl-sn-glycero-3-phosphoethanolamine (18:1 (Δ9-cis) PE), at the C1 position of cyclopropene 16 to obtain C1 phospholipidated 3-N spirocyclopropene 20 in 21% yield, which, upon Boc deprotection, afforded 21 in 40% yield. Similar to the photocaged ceramide cyclopropene lipid, the Nvoc photocaged version 22 was prepared without purifying the Boc-deprotected intermediate 21 to obtain 22 in 38% yield over two steps (Scheme 18). However, the amounts obtained complicated our efforts at full spectroscopic characterization other than HRMS due to the complexity of the molecule, modest reaction yields, and high cost of the phospholipid starting material.

In summary, two biologically relevant, C1-lipidated cyclopropenes were prepared using an acid functionalized 3-N spirocyclopropene scaffold. Both the C1-ceramide- and phospholipid-linked spirocyclopropene represent the first examples of cyclopropene modifications with biomolecules on the alkenic C1/C2 position.

Example 4. Synthesis of Compounds with Varied Protecting Groups

Bioorthogonal reactions enable the functions of biomolecules like glycans (Spite et al. 2014), lipids (Yang et al. 2012), proteins (Lang and Chin 2014), neurotransmitters (Paulini and Reissig 1992; Kumar, Shukhman, and Laughlin 2016), and nucleic acids (Eggert and Kath-Schorr 2016), to be imaged, perturbed, and quantified. The benefits of rapid kinetics for these reactions were apparent early in their evolution, and rapid kinetics have been the focus of their optimization (Patterson, Nazarova, and Prescher 2014; Ravasco, Monteiro, and Trindade 2017; Debets, van Hest, and Rutjes 2013). However, the complex biological systems in which bioorthogonal reactions are employed also demand control over when and where the reactions occur in order to target reactivity to distinct cell types or biological processes. For example, proteomic analyses of post-translational modifications in a whole-organism disease model would benefit from restricting the bioorthogonally tagged molecules only to disease-relevant cell populations. However, such reactivity targeting of bioorthogonal reactions has been less well explored than both kinetic optimization and the development of mutually orthogonal reactions (Row and Prescher 2018; Patterson et al. 2012).

Nevertheless, there have been several pioneering strategies for activating bioorthogonal reactivity with light, or, more rarely, through the action of an enzyme. Notable among these are reports of light-triggered cyclooctyne or phosphine reactivity by Popik (Poloukhtine et al. 2009) and Carrico (Shah, Laughlin, and Carrico 2016), light-triggered tetrazole conversion to an alkene-reactive nitrile imine by Lin (Yu, Ho, and Lin 2011), and light-/enzyme-triggered dihydrotetrazine oxidation to tetrazine by Fox (H. Zhang et al. 2016). However, one limitation of these approaches is that they cannot easily be tailored to an experiment's requirements by adapting other reactivity activation methods, like activation by other enzymes, other wavelengths, or reaction-based indicators of cellular metabolites (e.g., $H_2O_2$, $H_2S$, or $Fe^{2+}$ when using reaction-based probes as developed by Chang and others (Spangler et al. 2016; M. H. Lee et al. 2012; Yik-Sham Chung et al. 2018). Granted, it is possible to tailor these reagents to activate at different wavelengths, albeit with some sacrifice to uncaging efficiency, but they have not been used with diverse, off-the-shelf or next-generation photolabile groups designed specifically for rapid uncaging rates, long-wavelength uncaging, large two-photon cross sections, and high stability in vivo. Accordingly, there is a need for reactions that enable the use of separate reaction caging groups that have been specifically optimized to the uncaging task (Kumar and Laughlin 2019).

Figure 13:
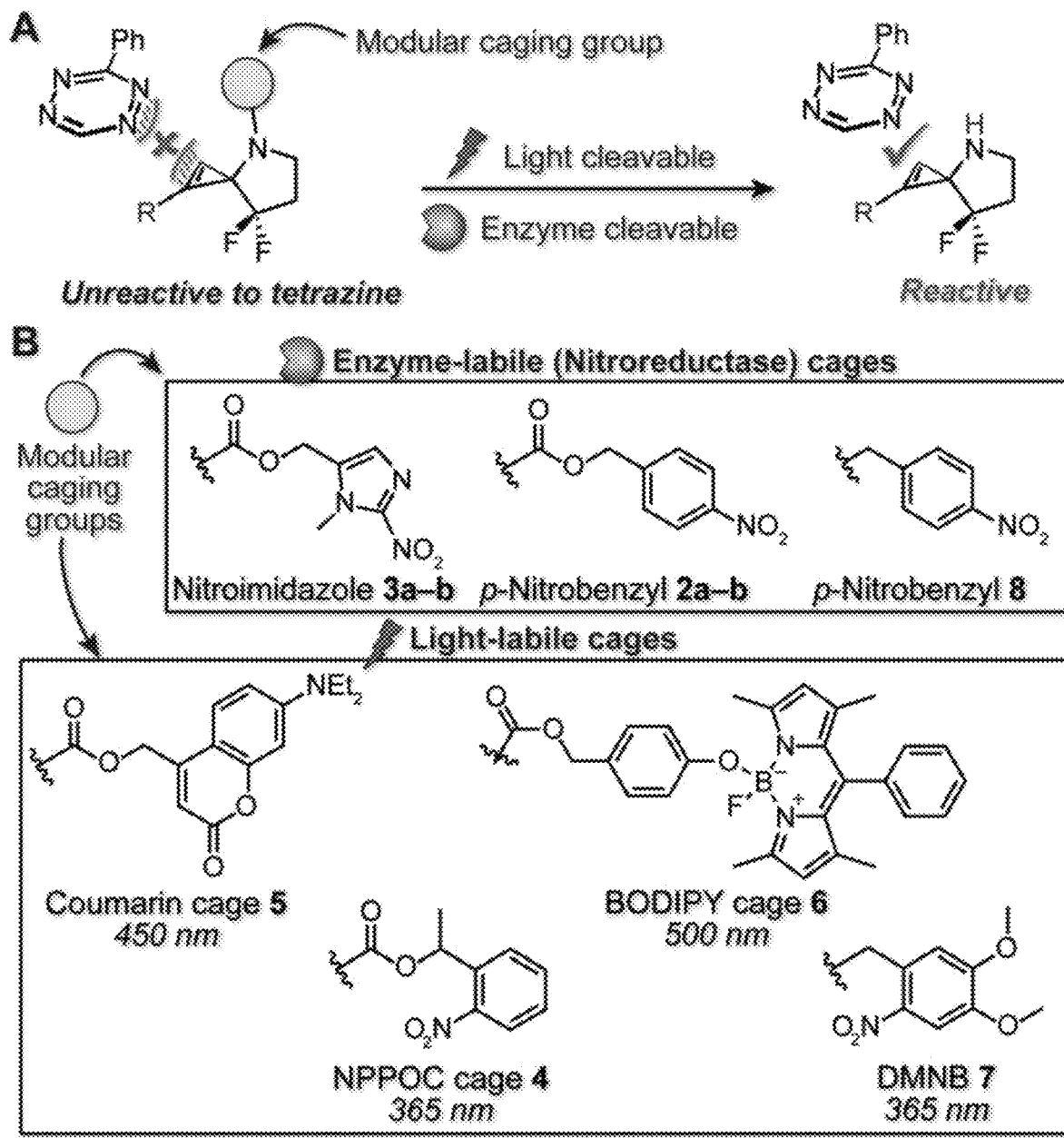
FIG. 13A—Diverse and modular caging strategies for controlling IEDDA cyclopropene-tetrazine bioorthogonal ligation. Attaching enzyme- or photolabile groups at the cyclopropene nitrogen prevents ligation. Uncaging liberates free amine cyclopropene, which ligates with tetrazine.
FIG. 13B—it was found that this caging works with a panel of enzyme and photocages that are linked through either a carbamate or an amine.

Herein is describe a modular bioorthogonal caging strategy built upon a recently reported cyclopropene scaffold (Kumar, Jiang, Li, et al. 2018). In this scaffold, a difluoro group stabilizes the cyclopropene by suppressing ring opening (Kumar, Zainul, and Laughlin 2018), and the carbamate-based cage on the nitrogen stifles its reactivity with s-tetrazines until removed, at which point the ligation proceeds (FIG. 13A). Previously, we showed this UV activation of cyclopropene reactivity in the context of proteins; activation of caged cyclopropene by 365 nm light allowed it to undergo ligation with tetrazine modified proteins (Kumar, Jiang, Li, et al. 2018). In this communication, we show that the activation of caged cyclopropenes is modular and not limited to UV light. This modular activation has several advantages. For example, current strategies that enable switching from UV to green-light-based activation for an activatable bioorthogonal reagent generally require redesigning the entire probe. The modular reactivity-caged cyclopropenes we describe allow one-step switching of the caging group because the core cyclopropene is unaltered.

Given the diverse array of nitrogen-linked enzyme- and light-labile groups, there are many potential bioorthogonal caging modalities to explore. Herein, we discuss the development of reactivity-caged cyclopropenes that can be activated by a broader range of wavelengths (UV-green) as well as by enzymes (FIGS. 13B and 14), while maintaining the cyclopropene's low reactivity in the caged form. Further, we show the ease with which the activation strategy can be manipulated to obtain caged cyclopropene probes with the desired activation modality. Lastly, we describe a lipidated photocaged cyclopropene that enables fixed-cell imaging.

The activation strategy's modularity began by assessing cyclopropene caging using enzyme-labile groups because there is only one enzyme-controlled bioorthogonal reaction: the peroxidase oxidation of dihydrotetrazine to tetrazine. Furthermore, the ability to use a desired enzyme to activate bioorthogonal reactions could expand the ways in which bioorthogonal chemistries are used. For example, an enzyme that is absent in eukaryotes could be expressed to guide the bioorthogonal reaction to the appropriate cells or subcellular compartments. Additionally, the activation strategy could be tailored to report on the activity of an endogenous enzyme. Finally, tethering an uncaging enzyme, either in vitro or in vivo, to an antibody directed against an epitope could target the reaction to the epitope's precise location. We used nitroreductase-labile cages, which fall under the first approach, being non-native to eukaryotes. Nitroreductase is an ideal test candidate because it can be expressed tissue specifically to activate fluorophores and prodrugs in several eukaryotic species including zebrafish, Xenopus, and mice (Curado, Stainier, and Anderson 2008; Kaya et al. 2012; Drabek et al. 1997).

Figure 14:
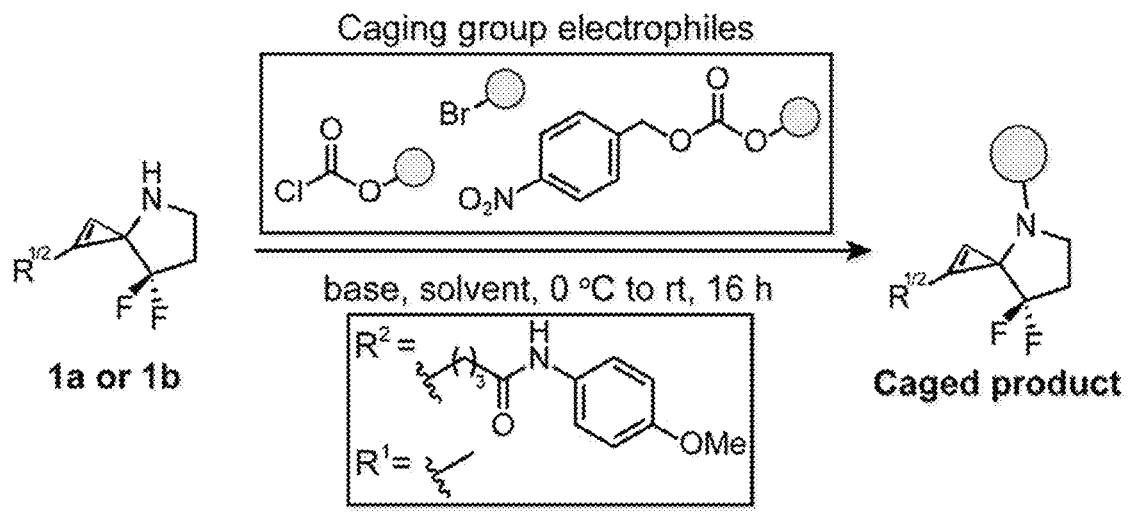
FIG. 14—Free amine cyclopropene can be protected by using multiple routes. We used chloroformates, p-nitrobenzylformates, and bromides to append enzyme- or photolabile protecting groups and obtain a series of caged cyclopropenes.
Figure 15:
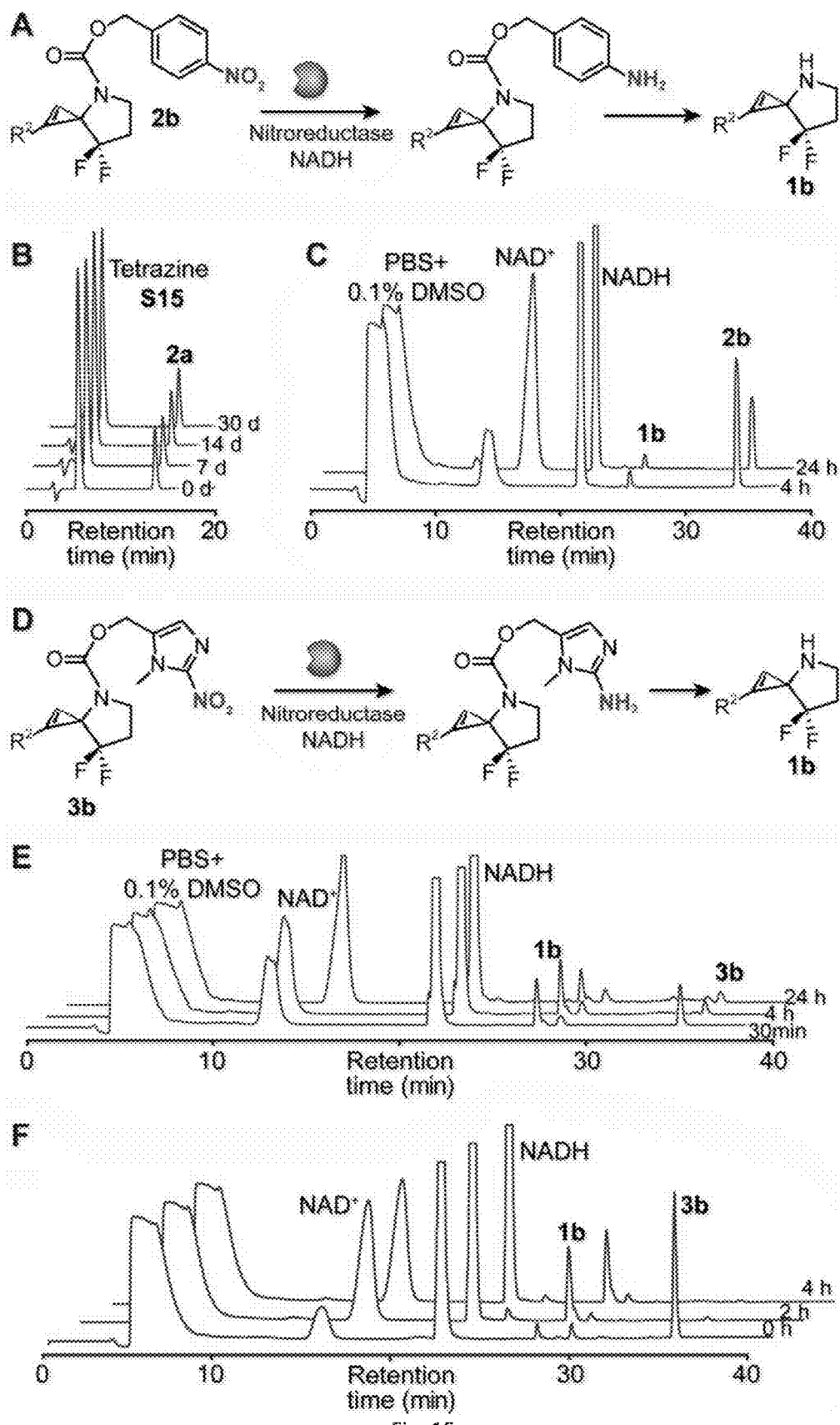
FIG. 15A—HPLC analyses of mixtures containing enzyme-caged cyclopropenes confirmed the prevention of cyclopropene-tetrazine ligation and provided insights into the substrate's uncaging efficiency. (A) Exposure to nitroreductase produces the free amine cyclopropene 1b, but the uncaging does not progress efficiently.
FIG. 15B—p-nitrobenzyl caged cyclopropene 2a does not react with excess tetrazine S15 for at least a month.
FIG. 15C—HPLC analyses of mixtures containing enzyme-caged cyclopropenes confirmed the prevention of cyclopropene-tetrazine ligation and provided insights into the substrate's uncaging efficiency. (C) Exposure to nitroreductase produces the free amine cyclopropene 1b, but the uncaging does not progress efficiently.
FIG. 15D—The rate of uncaging to obtain 1b increased dramatically upon switching to the nitroimidazole-caged cyclopropene 3b.
FIG. 15E—The rate of uncaging to obtain 1b increased dramatically upon switching to the nitroimidazole-caged cyclopropene 3b.
FIG. 15F—Switching to an engineered nitroreductase further improves the uncaging of 3b.

To assess the generality of the enzyme-caging approach, we explored two nitroreductase-labile groups that are widely used in cancer prodrugs (Searle et al. 2004) and turn-on fluorophores: (Grimm et al. 2016; Gruber et al. 2018) carbamate-linked p-nitrobenzyl and p-nitroimidazole. The cage's release mechanism is straightforward; nitroreductase reduces the nitro group to an amine, which leads to rearrangement and, in the case of the carbamate linkage, decarboxylation and subsequent release of the secondary amine cyclopropene (FIG. 15A). The nitroreductase-caged cyclopropenes from cyclopropenes were prepared from 1a or 1b (FIG. 14). The p-nitrobenzyl chloroformate S3 was installed on cyclopropene-NH 1a to obtain nitrobenzyl-caged cyclopropene 2a with a modest yield over two steps (41%). Nitroimidazole-caged cyclopropene 3a was also obtained in modest yield over two steps (35%) by attaching 1a to p-nitrophenyl activated nitroimidazole S5. Similarly, starting from the cyclopropene 1b, nitrobenzyl- or nitroimidazole-caged 2b and 3b were obtained in 71 and 14% yield, respectively.

The first critical experiment to determine the modularity of the approach was to determine if the reactivity-caged cyclopropenes were indeed unreactive to tetrazine. To evaluate this, we mixed 1 mM nitrobenzyl-(2a, FIG. 15B) or nitroimidazole caged cyclopropene with 4 mM tetrazine S15 in MeCN/phosphate-buffered saline (PBS; 1:1, pH 7.4) and assayed for reaction by HPLC. Importantly, we observed no reaction between the caged cyclopropenes and tetrazine over the one month time course; this indicated that these structurally diverse cages are effective at stifling reactivity and are stable over long periods in buffered solution (FIG. 15B). Interestingly, tetrazine S15 was stable under these conditions over long time periods, unlike structurally similar tetrazines that were reported to rapidly decompose in PBS or PBS+serum at 37° C. (Karver, Weissleder, and Hilderbrand 2011) To address this disparity and confirm the stability of tetrazine S15 and a related tetrazine (S16), we acquired 1H NMR spectra of these molecules in CD$_3$CN/[D]PBS (1:1, pH 7.4):1% DMSO or irradiation with 560/40 nm light at room temperature or 37° C. In no case did we observe substantial decomposition of the tetrazine over the 14-day time course. Additionally, the cyclopropenes are stable to the biological nucleophile l-glutathione. We found no decomposition over 24 h upon exposing 1 mm of each cyclopropene to 10 mm l-glutathione in MeCN/PBS (1:1, pH 7.4), the highest concentration known to occur in cells.

Next, we explored the efficiency of enzymatic activation in a direct HPLC assay. Interestingly, reports of such direct analyses of nitroreductase uncaging efficacies are rare. (Vorobyeva et al. 2015) Most uses of the nitroreductase cage explore indirect effects like cell death in nitroreductase-activated prodrugs (Curado, Stainier, and Anderson 2008; Kaya et al. 2012; Drabek et al. 1997) or fluorescence from nitroreductase-activated fluorophore (Grimm et al. 2016; Gruber et al. 2018). For this assay, we used the C1-p-methoxybenzyl-modified cyclopropenes 2b and 3b to increase the absorbance of the uncaged cyclopropene 1b to acceptable levels for HPLC analyses. We analyzed a solution containing 100 mm p-nitrobenzyl-caged 2b with nitroreductase and NADH after 4 and 24 h (FIG. 15C). MS showed that the caged cyclopropene was consumed over the first 4 h with the concomitant production of the uncaged product 1b. Interestingly, between 4 and 24 h, there was no difference in the amount of product formed or starting material consumed; this is consistent with the reported slow uncaging of the p-nitrobenzyl moiety. (Sebej et al. 2013) We switched to the nitroimidazole-caged cyclopropene 3b (FIGS. 15D and 15E) to uncage more efficiently (Yik-Sham Chung et al. 2018) Between 0 and 4 h, we found a dramatic improvement in the uncaging efficiency (57% higher conversion for 3b over 2b).

Figure 16:
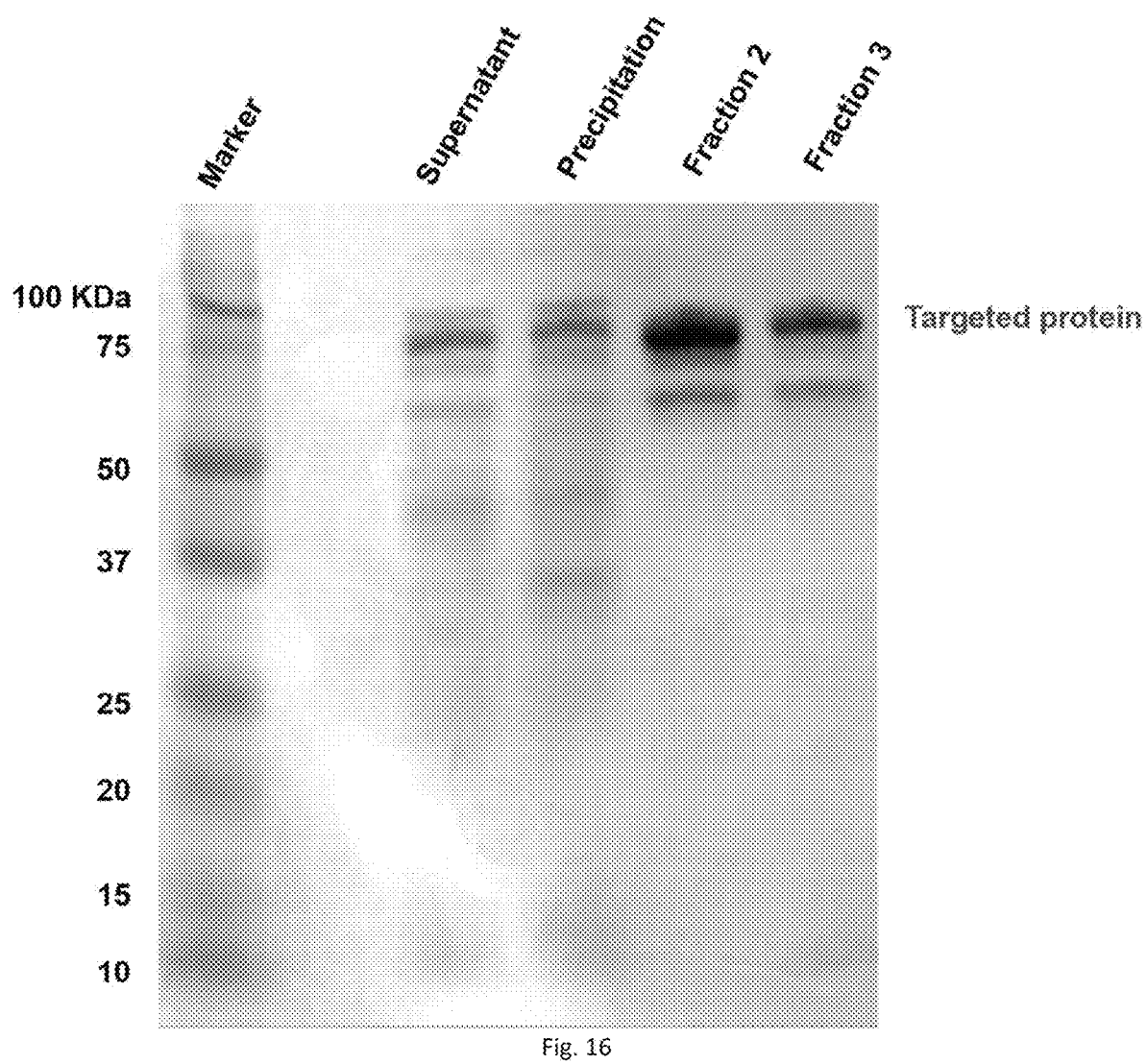
FIG. 16—Protein gel of the targeted tdNfsB(F124W)-mCherry. Supernatant, precipitation, fraction 2 and fraction 3 is loaded on the SDS page gel. Staining was performed with Comassie blue. Targeted protein ~82.3 KDa was successfully purified.

Having evaluated two nitroreductase substrates, it was sought to improve uncaging efficiency by using an engineered nitroreductase that was recently developed by Lavis and co-workers (Gruber et al. 2018). This optimized nitroreductase was cloned, expressed and purified this (FIG. 16), and then tested its ability to uncage 3b. Interestingly, the uncaging of nitro-imidazole caged 3b proceeds with almost all of the 3b converted into 1b within 4 hours (FIG. 15F). Collectively, the results with the nitroreductase cages and optimized nitroreductase show that the bioorthogonal reaction caging functions with a wide array of carbamate-linked caging groups, that these reagents are stable in solution over long time periods, and that the nitroimidazole and optimized nitroreductase are more efficient at uncaging these cyclopropenes.

Next, the modularity of caging with both classic and modern photocages was explored. Specifically, we tested 3'-nitrophenylpropyloxycarbonyl (NPPOC) (Kumar, Jiang, Li, et al. 2018), which is rapidly cleaved with 365 nm light, a feature frequently exploited in systems requiring high-fidelity uncaging such as DNA modification (Olejniczak, Carling, and Almutairi 2015; Sebej et al. 2013); coumarin, with its large molar absorptivity, longer-wavelength uncaging (405 nm), high release rates and, more importantly, compatibility with two-photon uncaging (Wong et al. 2017; Kantevari et al. 2010) BODIPY (500 nm); (Goswami et al. 2015; Umeda et al. 2014); and DMNB (365 nm), a classic photocage that linked to the cyclopropene through an amine as opposed to a carbamate (FIG. 13B).

The synthesis of each photocleavable group followed the same general protocol as that performed for the nitroreductase cages (FIG. 14). Essentially, chloroformate- or p-nitrophenyl-activated caging group alcohols were added to the free amine cyclopropene 1b to form carbamates 5-6 in modest yields (Scheme 19). We evaluated the efficacy of each cage at preventing tetrazine ligation in the HPLC assay described above. No reaction was observed between any photolabile cyclopropene 4-6 (1 mm) and tetrazine S15 (4 mm) or l-glutathione (10 mm) in MeCN/PBS (1:1) for at least one month (24 h for glutathione; FIG. 4A). Collectively, these results from diverse caging structures confirm the modular nature of this bioorthogonal caging strategy.

Scheme 19 - Methods synthesis of compounds 4, 5, S11, S12, S13 and 6

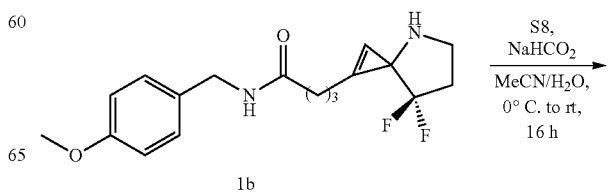

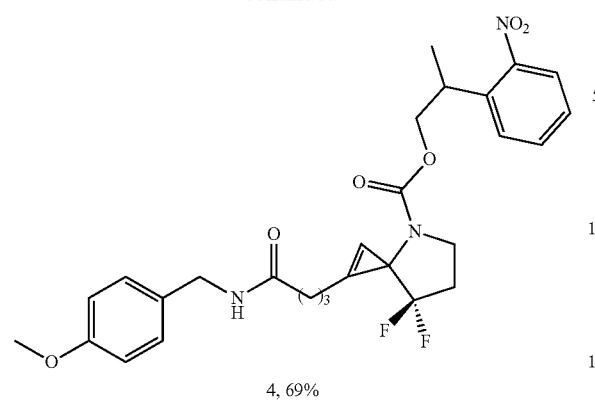
4, 69%
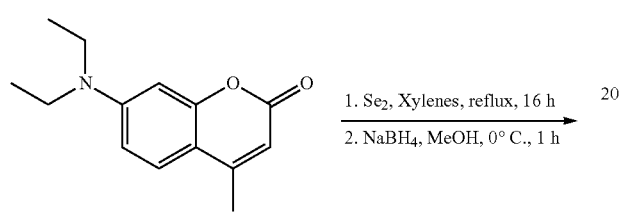
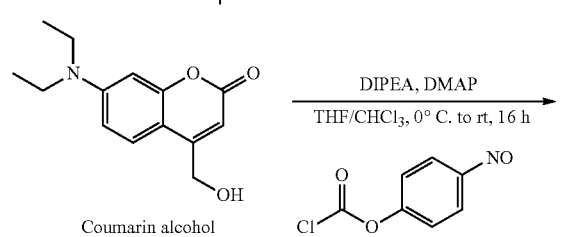
S10
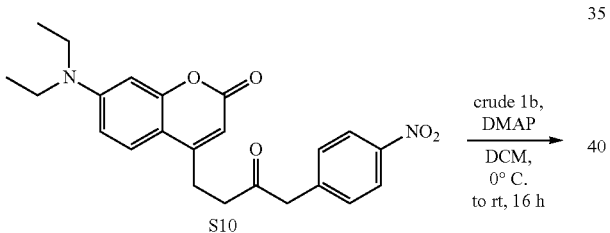
5, 33% over two steps
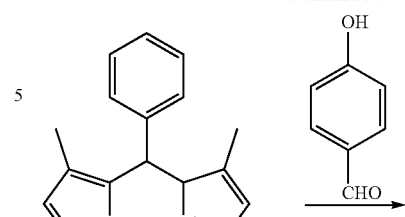
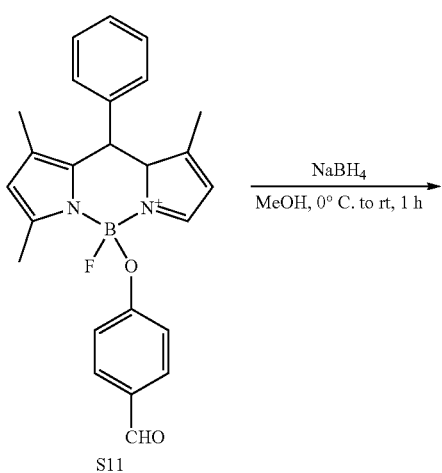
S11
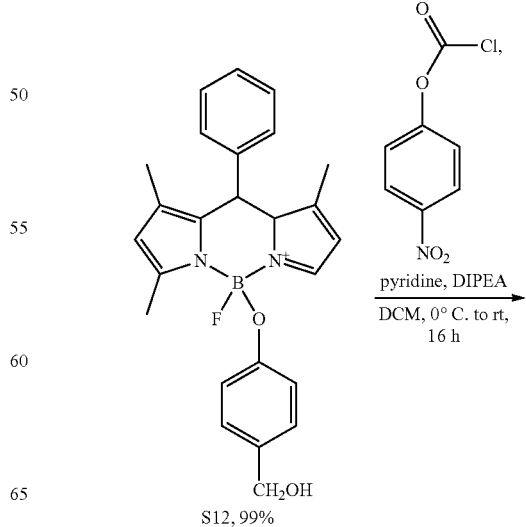
S12, 99%

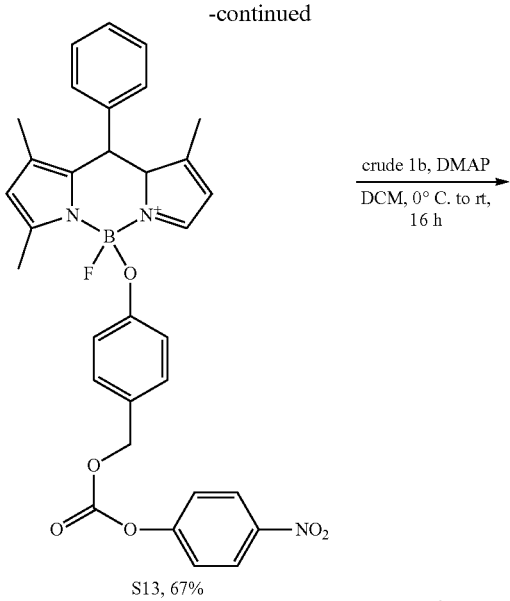

S13, 67%

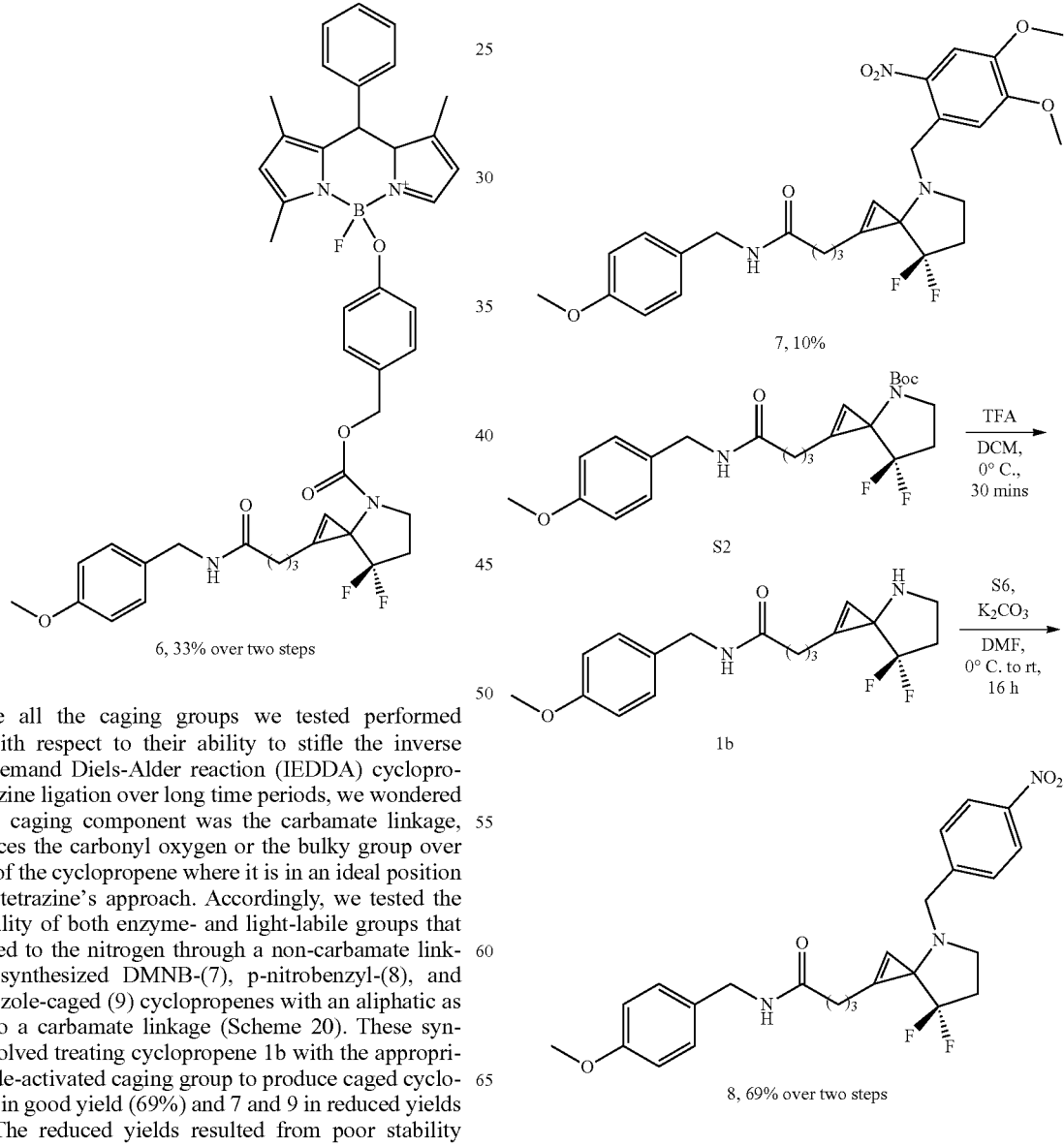

during purification, foreshadowing our challenges in using aliphatic linkages for cyclopropene caging groups. We evaluated the reactivity of non-carbamate-caged cyclopropene 8 (1 mm) with tetrazine S15 (4 mm) for 24 h. Interestingly, we observed no ligation. However, we did note substantial cyclopropene decomposition over 24 h. The lack of tetrazine reactivity is encouraging and leaves open the possibility of exploring cyclopropene scaffolds with improved stability for caging groups attached through aliphatic linkages.

Scheme 20 - Methods for synthesis of compounds 7, 8, and 9

Because all the caging groups we tested performed equally with respect to their ability to stifle the inverse electron demand Diels-Alder reaction (IEDDA) cyclopropene-tetrazine ligation over long time periods, we wondered if the key caging component was the carbamate linkage, which places the carbonyl oxygen or the bulky group over the plane of the cyclopropene where it is in an ideal position to inhibit tetrazine's approach. Accordingly, we tested the caging ability of both enzyme- and light-labile groups that are attached to the nitrogen through a non-carbamate linkage. We synthesized DMNB-(7), p-nitrobenzyl-(8), and nitroimidazole-caged (9) cyclopropenes with an aliphatic as opposed to a carbamate linkage (Scheme 20). These syntheses involved treating cyclopropene 1b with the appropriate bromide-activated caging group to produce caged cyclopropene 8 in good yield (69%) and 7 and 9 in reduced yields (<10%). The reduced yields resulted from poor stability

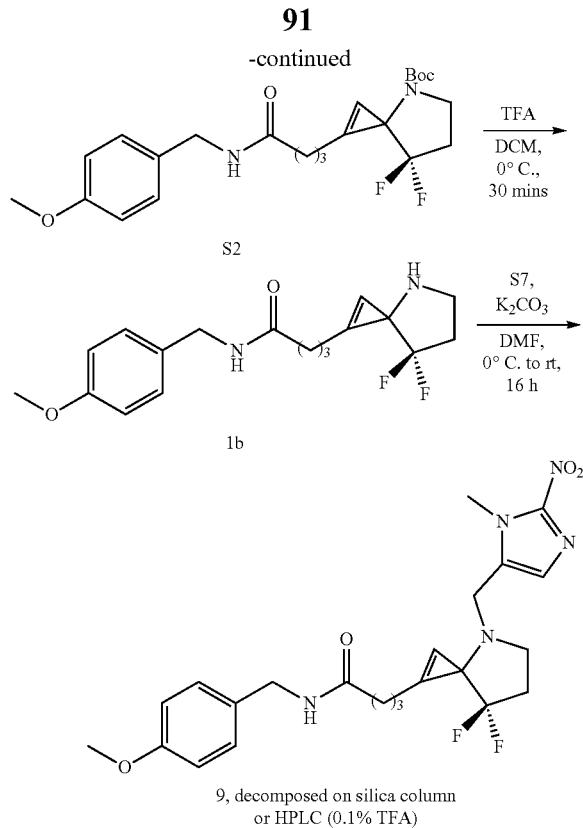

Figure 17:
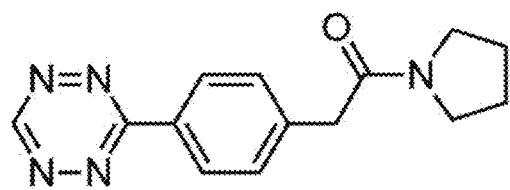
FIG. 17—Molecular structures of tetrazines used for (1) NMR based stability experiments (S15, S16), or (2) determining second order rate constants of their reaction with cyclopropene 1b (515, S17, S18), or (3) fixed cell imaging (S19). The results of NMR stability experiments and kinetics experiments are described below. The synthesis of tetrazine S19 (also known as HELIOS 388Me) was carried as described previously (Meimetis et al., 2014).
Figure 17:
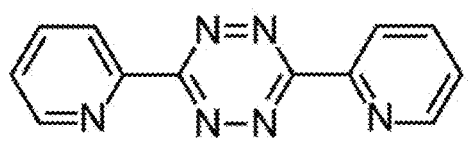
Figure 17:
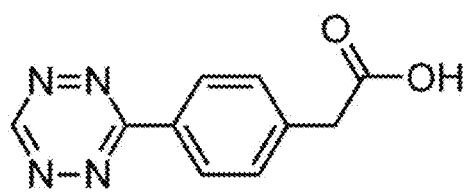
Figure 17:
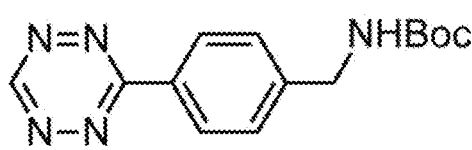
Figure 17:
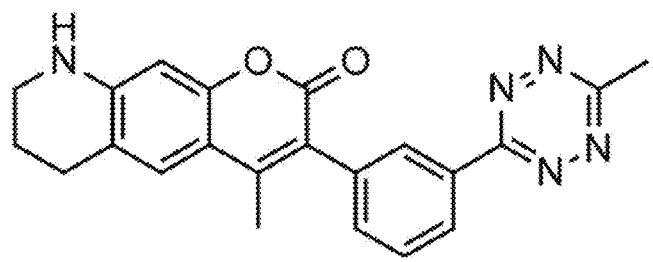
Figure 18:
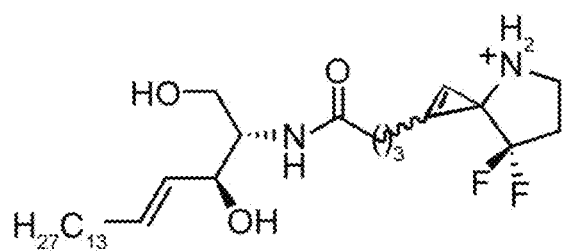
FIG. 18—Molecular structures of lipidated cyclopropenes used for fixed-cell imaging of HEK293T cells. The synthesis of lipidated cycloporpenes 10 and 11 was recently reported by us (Kumar, Jiang, Zainul et al., 2018).
Figure 18:
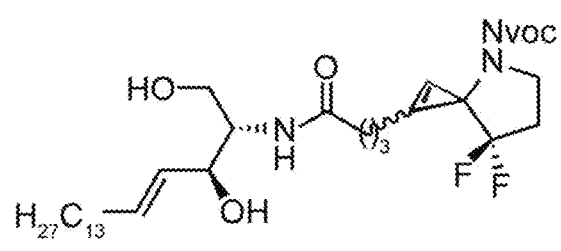
Figure 19:
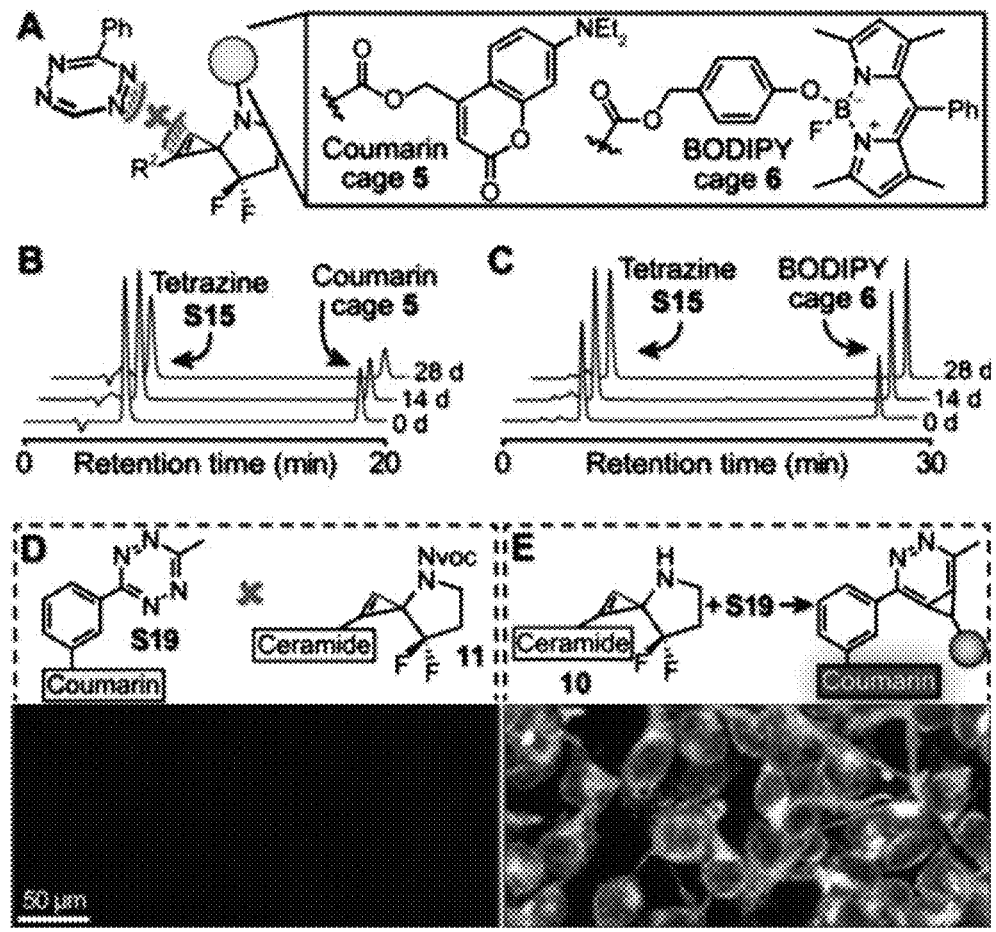
FIG. 19A—HPLC analyses of mixtures containing 1 mm photocaged cyclopropane 4-6 and 4 mm tetrazine S15 showed no ligation.
FIG. 19B—Coumarin caged cyclopropenes did not react with tetrazine S15 in MeCN/PBS (1:1, pH 7.4) for at least one month.
FIG. 19C—BODIPY-caged cyclopropenes did not react with tetrazine S15 in MeCN/PBS (1:1, pH 7.4) for at least one month.
FIG. 19D—HEK293 cells were fixed and then incubated with pro-fluorescent tetrazine S19 and caged cyclopropane lipid 11; the labelling of cellular membranes was assayed by confocal microscopy. Images represent a maximum intensity projection of a confocal z stack.
FIG. 19E—HEK293 cells were fixed and then incubated with liberated cyclopropene 10; the labelling of cellular membranes was assayed by confocal microscopy. Images represent a maximum intensity projection of a confocal z stack.

Finally, fixed HEK293 cells were treated with an nitroveratryloxycarbonyl (Nvoc)-caged cyclopropene-ceramide conjugate, 11 (Kumar, Jiang, Zainul, et al. 2018) and a profluorescent coumarin tetrazine (Meimetis et al. 2014) S19 (FIGS. 17 and 18). In this experiment, the ceramide conjugate marks the cell's secretory pathway membranes and its reaction with tetrazine is revealed by the coumarin's fluorescence turn-on. Importantly, we observed no coumarin fluorescence in cells treated with the photocaged cyclopropene (FIG. 19D) but clear coumarin fluorescence in cells incubated with the uncaged cyclopropene ceramide 10 (FIG. 19E), thus indicating effective caging and post-release reactivity of the cyclopropene scaffold.

Additionally, we evaluated the kinetics of the reactivity of the uncaged cyclopropene with tetrazines other than S15. We determined the pseudo-first-order rate constants for reaction with dipyridyl tetrazine S17 and a Boc-protected amino tetrazine S18 to be $1.7 \times 10^{-4}$ and $1.4 \times 10^{-4}$ $M^{-1}s^{-1}$, respectively, of the order of the original cyclooctyne-azide and Staudinger-Bertozzi ligation reaction kinetics as well as consistent with results of $4 \times 10^{-4}$ $M^{-1}s^{-1}$ obtained for reaction of the uncaged cyclopropene with tetrazine S15 (Meimetis et al. 2014).

In conclusion, two structurally distinct nitroreductase cages and four classic or modern light-labile caging groups attached through a carbamate linkage served as effective cages. Cages linked aliphatically to the cyclopropene's nitrogen produced molecules with poor stability in neutral buffer but were effective at caging the ligation, albeit on much shorter timescales. These results suggest that the carbamate linkage can serve as a general strategy for caging this bioorthogonal ligation with other cages that can be removed by enzyme-, light-, or even small-molecule metabolites (e.g., $H_2O_2$, $H_2S$, or $Fe^{2+}$) (Spangler et al. 2016; M. H. Lee et al. 2012; Yik-Sham Chung et al. 2018), thus providing a new dimension of control for bioorthogonal chemistries. Of note is that our cyclopropene caging strategy is fundamentally different from the many examples of caged metabolites that contain bioorthogonal tags (Zengeya et al. 2016; H. Li, Fan, and Chen 2016; Dieterich et al. 2006). For example, Bertozzi and co-workers developed a caged, protease-substrate-tagged azidosugar that is not metabolically incorporated into the cell's glycans until liberated by the appropriate protease (Chang et al. 2010). However, this protease-substrate-tagged azidosugar is caged with respect to its recognition by biosynthetic machinery, not with respect to the bioorthogonal ligation. The caged cyclopropenes reported here are fundamentally different from such approaches because they represent caging the bioorthogonal reaction itself.

Example 5. Synthesis of Carbonyl Compounds

Although significant effort has been devoted to developing newer (Patterson et al. 2012; Row and Prescher 2018; Levandowski et al. 2018; Herner and Lin 2016; Devaraj, Weissleder, and Hilderbrand 2008), faster (Blackman, Royzen, and Fox 2008; A. Borrmann et al. 2015; Gahtory et al. 2018) and mutually orthogonal bioorthogonal reagents (Narayanam et al. 2016; Kamber et al. 2013; Ramil and Lin 2014; Jinbo Li et al. 2018; Wu and Devaraj 2016), only a limited subset allow for activation of their bioorthogonal reactivities (Kumar and Laughlin 2019). Activatable bioorthogonal reagents are initially unreactive to their bioorthogonal reaction partner, but upon activation by an external stimulus (e.g., light or an enzyme), they generate a reactive bioorthogonal reagent, providing control over their bioorthogonal reactivity. The usefulness of spatiotemporal control over activatable bioorthogonal reactions has led to the identification of almost a dozen activatable variants of popular bioorthogonal reagents for applications in materials chemistry and biology (Jinbo Li et al. 2018; Tasdelen and Yagci 2013; K. Singh et al. 2018; H. Zhang et al. 2016). However, many of these reagents can be activated only through exposure to UV light, making them ill-suited for biological purposes.

Currently, there are few activatable bioorthogonal reagents whose activation strategy can be tailored to their application's requirements. These include the cyclopropenone-caged dibenzocyclooctyne of Popik and co-workers that undergoes photodecarbonylation for strain-promoted azide-alkyne click chemistry (Poloukhtine et al. 2009), photoactivatable tetrazoles of Lin and co-workers that, upon photolysis, generate reactive nitrile imines for 1,3-dipolar cycloaddition (Herner and Lin 2016), photocaged phosphines of Carrico and co-workers for photoactivatable Staudinger-Bertozzi ligation (Shah, Laughlin, and Carrico 2016) photo- or enzyme-mediated tetrazine production by Fox and co-workers by oxidation of dihydrotetrazine for inverse electron demand Diels-Alder (IEDDA) reactions (H. Zhang et al. 2016) and our recently described photocaged cyclopropenes that are unreactive to their IEDDA reaction partner, s-tetrazines, unless they are activated by light (FIG. 20) (Kumar, Jiang, Li, et al. 2018).

The molecular design of each of these bioorthogonal reagents determines the ease of tuning the activation strategy. For example, cyclopropenone-caged dibenzocyclooctynes undergo decarbonylation by both UV and two-photon wavelengths (Kumar, Jiang, Li, et al. 2018), but such decarbonylation cannot be activated by red-shifted one-photon wavelengths or enzymes. Similarly, photolysis of tetrazoles for photoclick chemistry generates reactive nitrile imines upon UV illumination, by certain redshifted one-photon wavelengths (Kumar, Jiang, Li, et al. 2018), and by two-photon illumination (Yu et al. 2013), but enzymatic activation is not currently possible. Importantly, both the redshifted- and two-photon activated tetrazoles require synthesis of the corresponding tetrazole from scratch and not through an easy manipulation of a single core tetrazole skeleton. With regard to oxidative activation of dihydrotetrazine to tetrazine, enzymatic strategies are possible (e.g., HRP), as is activation by multiple one photon wavelengths. However, the strict requirement of an air and water stable dihydrotetrazine/tetrazine pair currently limits the scope of this method. Additionally, light activation requires the addition of a photosensitizer.

On the other hand, the caging strategy of both the photocaged Staudinger-Bertozzi phosphines and our recently described caged cyclopropenes (FIG. 20) enables easy switching between different light activation wavelengths or enzymatic activation. This is because both these strategies utilize commercially available or known photocages or enzyme cages to block the reactivity of the bioorthogonal reagents without altering the core molecular design. This allows relatively easy, one-step manipulation of the activating group.

Figure 20:
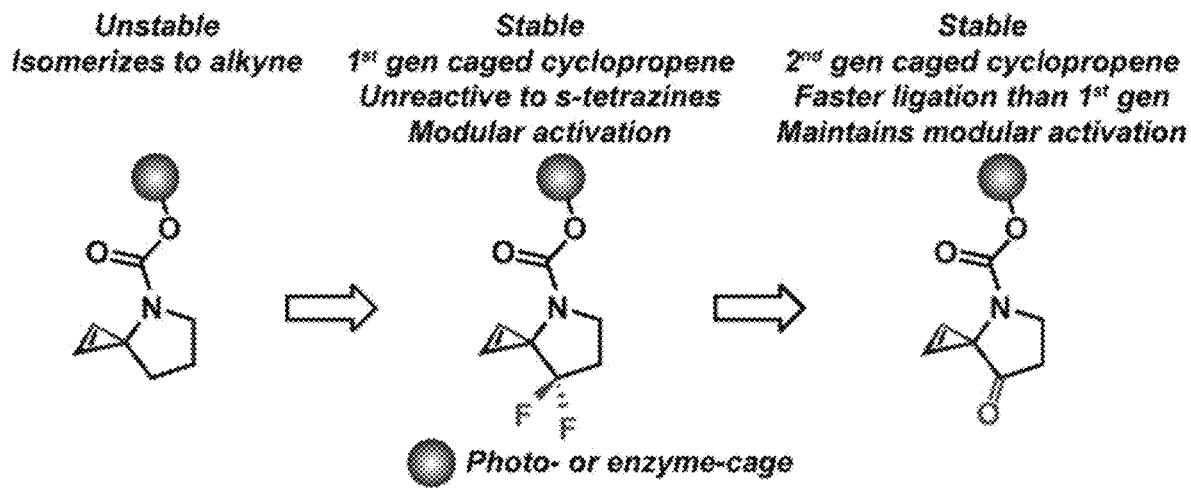
FIG. 20—C3 electron-withdrawing group and C3-nitrogen are keys to the stability and activatability of caged cyclopropenes, respectively. Second-generation caged cyclopropenes are stable and maintain the modular activatability of first-generation compounds but exhibit faster ligation rates.

In this report, we describe an alteration of the first generation caged cyclopropene that improved the ligation rate of the uncaged cyclopropene with s-tetrazines by ≤270-fold. We achieve this by replacing the cyclopropene C3-difluoro with a C3-ketone while maintaining the C3-nitrogen atom that permits modular activation (FIG. 20). We describe the synthesis of these second-generation caged cyclopropenes and evaluate their stability and reactivity toward biological nucleophiles and s-tetrazines. Additionally, we assess the caging modularity by evaluating the efficacy of different cages, and we synthesize caged cyclopropenes that are functionalized with useful biomolecules and fluorophores.

Having the C3-nitrogen atom in the spirocyclic cyclopropene system is key to the activation strategy as it serves as an anchor for linking photo- or enzyme-labile cages, thereby hindering IEEDA tetrazine-cyclopropene ligation (Kumar, Jiang, Li, et al. 2018). However, such C3-nitrogen-containing cyclopropenes are rare and difficult to synthesize (Kumar, Zainul, and Laughlin 2018) and generally also require installation of an inductively electron-withdrawing group at the C3 position. For example, the nonactivatable spirocyclic cyclopropene scaffold in which a cyclopropene and a cyclobutane are fused together at the cyclopropene C3 is known, (Yu and Lin 2014) but our attempts to install a nitrogen atom at C3 resulted in ring opening isomerization of cyclopropenes to form alkynes or allenes. (Kumar, Zainul, and Laughlin 2018)

Conversely, installing the C3-difluoro inhibits such ring-opening isomerization (Kumar, Jiang, Li, et al. 2018). These first-generation caged cyclopropenes have excellent modularity of activation (T. Jiang et al. 2019) but exhibit relatively slow ligation kinetics with s-tetrazines (k2=0.0004 M$^{-1}$s$^{-1}$) in a buffered solution at neutral pH. A modular activatable cyclopropene system with an improved tetrazine ligation rate can greatly expand the possible applications of cyclopropenes in which spatial and/or temporal control is a high priority. We hypothesized that replacing the C3-difluoro with a C3-ketone moiety should increase this ligation rate due to the relatively weaker inductive power (–I) of a ketone. Previously, the rate of cyclopropene-tetrazine ligation has been shown to increase with a decrease in the –I of C3 substituents; however, such an improvement comes at the cost of cyclopropene stability (Ravasco, Monteiro, and Trindade 2017).

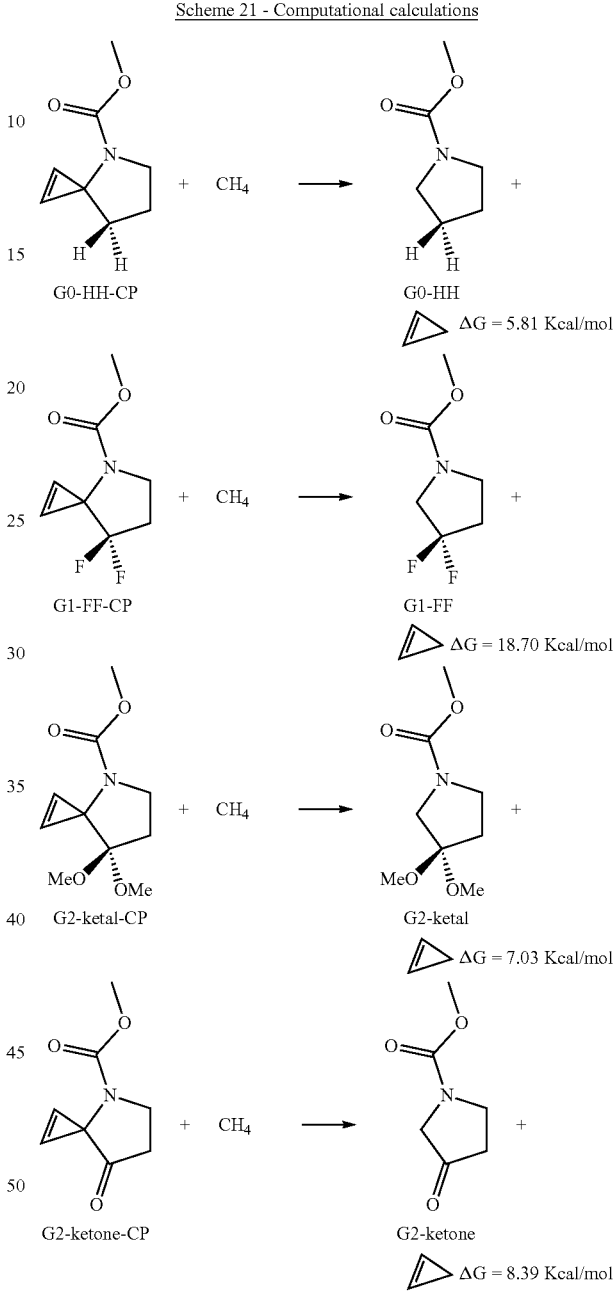

Scheme 21 - Computational calculations

To estimate the relative stability of the C3-ketone (G2-ketone-CP) versus the stable C3-difluoro (G1-FF-CP) and the unstable C3-dihydrogen (G0-HH-CP), we performed DFT-based computations to calculate their ring separation energies (Scheme 21) (Kao and Radom 1978). Under isodesmic reaction conditions, the stability of C3-ketone (ΔG=8.4 kcal/mol) was predicted to be better than that of the unstable C3-dihydrogen (ΔG=5.8 kcal/mol) but worse than that of C3-difluoro (ΔG=18.7 kcal/mol). With more confidence in our hypothesis, we attempted the C3-ketone synthesis via a C3-ketal (G2-ketal-CP; ΔG=7.0 kcal/mol) starting from oxo-pyrrolidinone S3 (Scheme 22). Our initial attempt to protect ketone S3 using ethylene glycol to obtain cyclic ketal S4 resulted in only unreacted starting material S3 (Table 2 and Scheme 23). However, switching to the more flexible acyclic ketal 1 was successful. Several reaction conditions were explored in an attempt to optimize the reaction. Employing weak acid catalyst PPTS in MeOH at rt afforded only unreacted starting material (Table 2, entry 1).

TABLE 2

Optimization Conditions for the Protection of Ketone in 3-Oxopyrrolidine Derivative S3 via Acid Catalysis To Obtain Ketal 1.

| entry | catalyst,[a] equiv | CH(OMe)$_3$ (equiv) | solvent[b] | temp (° C.) | time (h) | yield[c] (%) | comments[d] |
|---|---|---|---|---|---|---|---|
| 1 | PPTS, 0.2 | 0 | MeOH | 55 | 24 | 0 | unreacted |
| 2 | PTSA, 0.1 | 9 | THF | rt | 16 | 0 | unreacted |
| 3 | PTSA, 0.1 | 9 | THF | 85 | 16 | 0 | unreacted |
| 4 | PTSA, 0.1 | 9 | THF | 110 | 24 | 0 | unreacted |
| 5 | PTSA, 0.2 | 9 | THF | 110 | 24 | 0 | unreacted |
| 6 | PTSA, 0.2 | 35 | MeOH | rt | 16 | 50 | 0.4 g scale |
| 7 | PTSA, 0.2 | 35 | MeOH | rt | 16 | 40 | 1.0 g scale |
| 8 | H$_2$SO$_4$, 0.3 | 30 | MeOH | rt | 14 | 43.7 | 1.0 g scale |
| 9 | H$_2$SO$_4$, 0.3 | 30 | MeOH | rt | 14 | 50-55 | 8.0 g scale |

[a]Pyridine p-toluenesulfonic acid (PPTS), p-toluenesulfonic acid monohydrate (PTSA), or conentrated H$_2$SO$_4$.
[b]Dry MeOH.
[c]Referes to the isolated yield of silica-gel chromatography.
[d]Refers to S3. Entries 3-5 were conducted under relux conditions.

Similarly, PTSA in THF provided only unreacted starting material both at rt and under reflux conditions (Table 2, entries 2-4). However, increasing the number of equivalents of trimethyl orthoformate and switching to MeOH afforded 1 in 50% yield (Table 2, entry 6). Scaling up the reaction (1 g scale) reduced the yield to 40% (Table 2, entry 7). Switching to a stronger proton donor, H$_2$SO$_4$, afforded 1 in 44% yield, which increased slightly to 50-55% upon scaling up the reaction (Table 2, entries 8 and 9).

Scheme 22-Synthetic procedures of S3

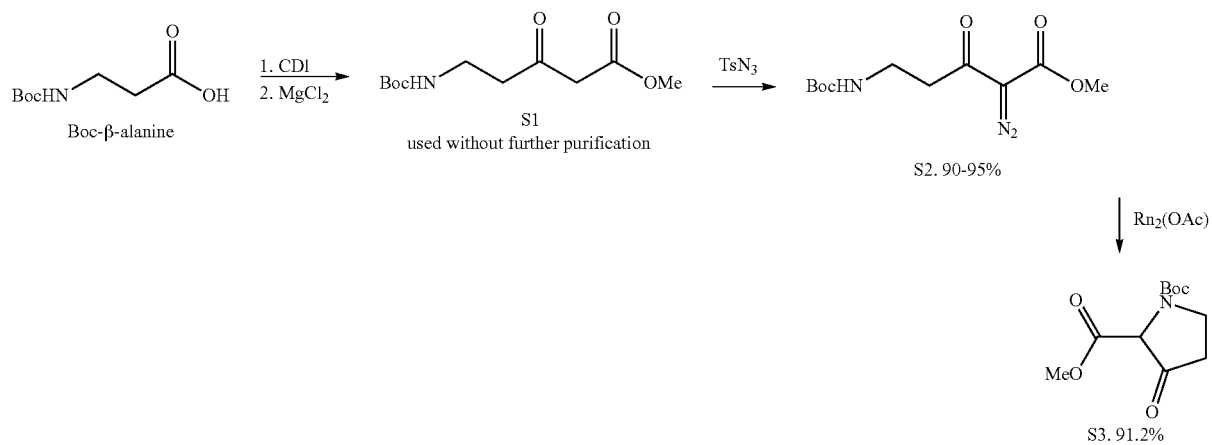

Scheme 23-Synthetic procedures for S4 and 1

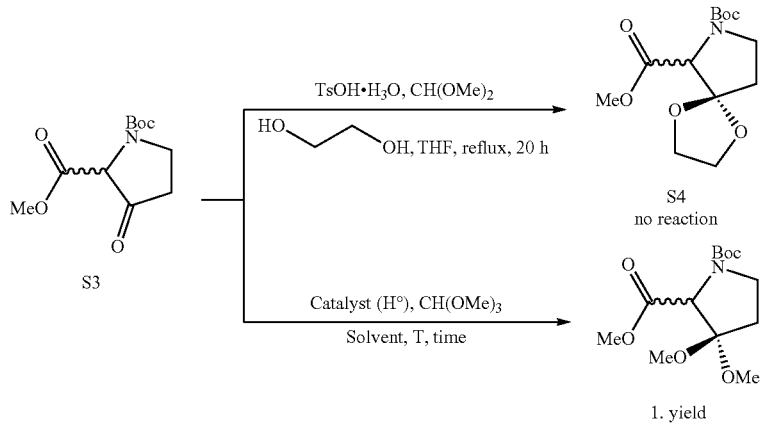

Next, we utilized ketal 1 to build the 3-N spirocyclic framework, dibromo-4-azaspiro[2.4]heptane derivative 5, via cyclic enamine 4 (Scheme 24 and Scheme 25). Briefly, ester 1 was reduced to alcohol 2 using LAH in high yields of 87-92%. Tosylation using TsCl at rt produced negligible product but, at elevated temperatures, provided tosylated alcohol 3 in 85-88% yield using Et$_3$N in DCM or in neat pyridine (Table 3).

TABLE 3

Optimization conditions for tosyl activation of alcohol 3 to 4.

| TsCl (eq) | Solvent | T (° C.) | Time (h) | Yield (%) | Comments |
|---|---|---|---|---|---|
| 1.2 | DCM | rt | 16-24 | 45-50 | Unreacted 3 was recovered |
| 1.2 | DCM | 45 | 16 | 85 | Some unreacted 3 |
| 3.0 | Pyridine | 50 | 20 | 86.2 | |

Subjecting 3 to one-pot NaI activation and DBU elimination afforded 3-N enamine 4 in high yields of 90-95% (up to 7 g scale). Such enamines are currently prepared in moderate to high yields at subgram scale by multistep synthesis using either strong bases (Abbaspour Tehrani and De Kimpe 2000; Mangelinckx, Boeykens, and De Kimpe 2008; Sulmon, De Kimpe, and Schamp 1988) under harsh conditions or copper (Lu et al. 2008; Campbell et al. 2015) and palladium (Hazelden et al. 2016; Greenaway et al. 2012; H. Jiang et al. 2016) catalysts. ESI-MS analyses of t-BuOK/CHBr$_3$-mediated carbene addition on ketal enamine 4 confirmed the formation of 3-N dibromospirocyclopropane 5. However, even with more equivalents of t-BuOK or at extended reaction times, we did not achieve complete conversion, which is critical for purification of 5 as both 4 and 5 have the same retention factor on silica gel. Upon utilizing a biphasic medium containing NaOH and employing phase-transfer catalyst CTAB, we achieved complete conversion of the ketal enamine to 3-N dibromo-spirocyclopropane 5. The yield varied from 65 to 85% (based on more than seven repetitions) depending on the scale of the reaction.

Scheme 24-Utilizing a Ketal Group To Stabilize the 3-NCyclopropene[a]

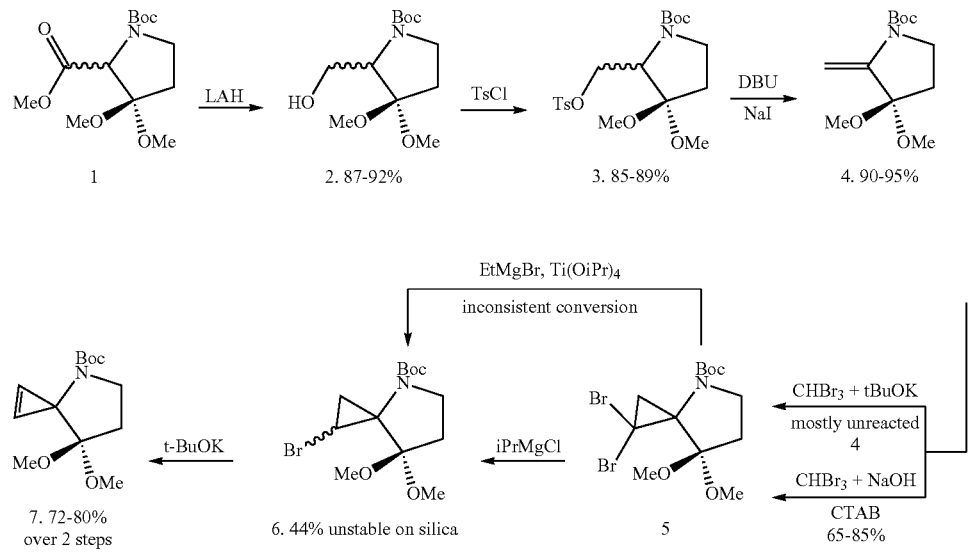

Scheme 25-Synthetic procedures for preparing 7

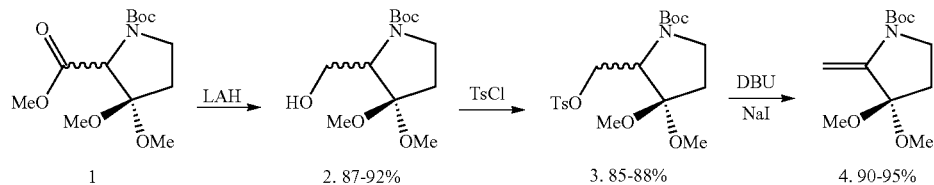

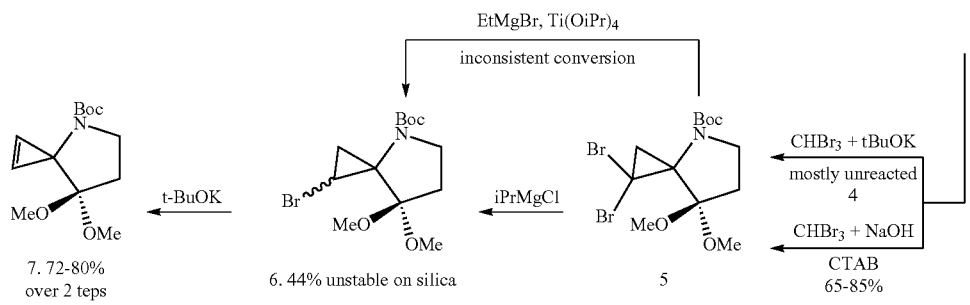

Initial attempts at Ti(OiPr)$_4$-catalyzed EtMgBr hydrodehalogenation (Al Dulayymi et al. 2000) of 5 under ice-cold or rt conditions did not generate 3-N monobromo 6 (Table 4, entries 1 and 2). Increasing both the reaction time and the number of reagent equivalents provided 6 in moderate yields (Table 4, entries 3 and 4) which improved 2-fold upon switching to iPrMgCl under cold conditions (Vu et al. 2002) (Table 4, entry 5). However, we observed this conversion to be time sensitive (Table 4, entry 6), which has also been reported earlier for a similar reaction but different substrates. In addition, the unstable nature of 6 on silica gel [ketal 6 partially hydrolyzes to ketone S5 (Scheme 25 and Table 5)] prompted us to carry out the subsequent elimination by t-BuOK on the crude 6, which ultimately afforded 3-N cyclopropene 7 in an excellent yield of 72-80% over two steps.

Next, it was established that 3-N cyclopropene 7 is amenable to base-mediated C1/C2 substitution (8), remains stable upon conversion to C3-ketone 3-N cyclopropenes (9a and 9b), remains stable upon N-deprotection (10a), and can be N-reprotected (11) (Scheme 26). Applying the LHMDS/Me$_2$SO$_4$ strategy of Rubin and co-workers (Kim, Sherrill, and Rubin 2010) for 3-methyl-3-carboxamide cyclopropenes' C1/C2 methylation, 7 was methylated to obtain 8 in a high yield of 80%. Our attempts at ketal deprotection under mildly acidic conditions using catalytic amounts of PTSA under both ice-cold and rt conditions either did not produce any reaction (7 to 9a) or produced unidentifiable reaction products (8 to 9b). Additionally, one-pot conversion to directly obtain uncaged ketones 10a and 10b by employing an organic acid (TFA) or an aqueous inorganic acid (2 M HCl) resulted in complete decomposition of starting mate- Scheme 26-Synthesis of C3-Ketone 3-N Cyclopropene and Subsequent Photocaging

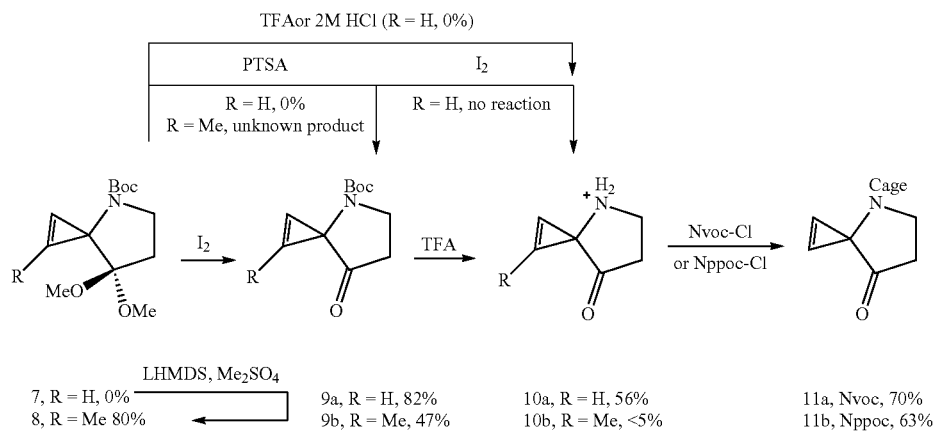

rials. Thus, we carried out the ketal deprotection using catalytic 12, which proceeds under neutral conditions (Sun et al. 2004). Both cyclopropene ketals 7 and 8 were converted to the corresponding ketones under rt or ice-cold conditions in 82% and 47% yields, respectively. TFA deprotection of cyclopropene ketone 9a afforded uncaged 3-N cyclopropene 10a in 56% yield, which could be N-reprotected by a popular, photolabile NVOC or NPPOC group to give 3-N cyclopropene 11a and 11b in 70% and 63% yields, respectively. On the other hand, uncaged C1-methylated cyclopropene 10b was detected via ESI-MS and HPLC upon TFA deprotection of 9a, but we were unable to isolate it. The stability of both ketal and ketone 3-N cyclopropenes in solution, on silica gel, and upon concentration at room temperature verified our initial hypothesis about the stability of this compound.

TABLE 4

Optimization Conditions for Grignard Reagent-Mediated Conversion of Dibromo 5 to Monobromo.

| entry | RmgX, equiv | Ti(OiPr)$_4$ (equiv) | solvent[a] | temp (° C.) | time (min) | yield[b] (%) |
|---|---|---|---|---|---|---|
| 1 | EtMgBr, 1.2 | 0.1 | THF | 0-4 | 20 | 0[c] |
| 2 | EtMgBr, 1.2 | 0.1 | THF | rt | 45 | 0[d] |
| 3 | EtMgBr, 1.5 | 0.2 | THF | rt | 45 | 25[e] |
| 4 | EtMgBr, 1.2 | 0.1[f] | THF | rt | 240 | 21[e] |
| 5 | iPrMgCl, 1.2 | 0 | DCM | −78 | 11-15 | 44 |
| 6 | iPrMgCl, 1.2 | 0 | DCM | −78 | >18 | 0[g] |

[a] Dry solvents.
[b] Refers to the isolated yield of silica-gel chromatography. 5 and 6 have identical $R_f$ values.
[c] Unreacted 5 was recovered.
[d] ESI-MS analyses (10 μL of reaction mixture quenched with saturated NH$_4$Cl) confirmed partial conversion to 6; however, upon isolation, only 5 was confirmed by NMR.
[e] Complete consumption of 5. Yield is for 6 only. 6a is not included in this yield.
[f] Reagents were replenished every 0.5 h.
[g] ESI-MS analyses showed the absence of 5 or 6.

TABLE 5

Optimization conditions for Grignard reagent mediated mono-bromo formation from 5.

| Grignard reaagent | Ti(OiPr)$_\lambda$ | Solvent | T(° C). | Time | Yield (%) | Comments |
|---|---|---|---|---|---|---|
| EtMgBr (1.2 eq) | 0.1 eq | Dry THF | 0-4 | 20 min | — | No reaction, Unreacted 5 |
| EtMgBr (1.2 eq) | 0.1 eq | Dry THF | rt | 45 min | — | unreacted 5, and 6 |
| EtMgBr (1.5 eq) | 0.2 eq | Dry THF | rt | 45 min | 25 | No 5, 6 + S5 upon column |
| EtMgBr (1.2 eq) every 0.5 h | 0.1 eq every 0.5 h | Dry THF | rt | 4 h | 21 | No 5, 6 + S5 upon column |
| PrMgCl (1.2 eq) | — | Dry DCM | −78 | 11-15 min | 44 | No 5, 6 upon column |
| iPrMgCl (1.2 eq) | — | Dry DCM | −78 | >15 min | 0 | No 5 or 6 |

It was determined if the ketal 3-N cyclopropene 7 is amenable to modification with an acid linker to append biomolecules and fluorophores to the scaffold (Scheme 27). We obtained the acid from ester 12, which, in turn, was obtained via n-BuLi-mediated iodo-orthoformate S6 (Scheme 27) substitution in 75% yield. To the best of our knowledge, this is the only method to directly install an ester functionality onto C1/C2 of a cyclopropene. (Kumar, Jiang, Zainul, et al. 2018) Moreover, ketal-ester 12 upon saponification and acid workup directly afforded ketone cyclopropene 13 in 62% yield. Ketone 3-N cyclopropene acid 13 can be easily appended to amines. Accordingly, we attached p-methoxybenzylamine, biotin, and tetramethylrhodamine via HATU coupling to obtain 14a and 14b in 68% and 54% yields, respectively. Subsequent Boc deprotection by TFA afforded 15a and 15b in 66% and 79% yields, respectively. To avoid multiple reverse-phase HPLC purification, 14c was used as the crude and purified after TFA deprotection to give 15c in 39% yield over two steps. As mentioned previously, 3-N cyclopropene-tagged molecules can be reprotected to give 16b and 16c in 18% (over two steps from 14b) and 76% yields, respectively.

(FIG. 21B), or with 10 mM L-glutathione at rt or 37° C. did not show any new or decomposition peaks (FIG. 21C). Lastly, incubating 1 mM 11 with 4.0 mM tetrazine 17 did not produce any new significant peak for 2 months in a 1:1 $H_2O$/MeCN solvent (FIG. 21D) but, surprisingly, produced the ligated product in a 1:1 PBS/MeCN solvent (FIG. 21E). However, the rate of this ligation is extremely slow (~1% cyclopropene 11 reacted in 5 h, 3.5% in 24 h, and 7.5% over 2 days) compared to that of uncaged ketone 10a (k2=0.11 $M^{-1}s^{-1}$ at pH 7.4 in a 1:1 MeOH/PBS solvent). This rate was obtained by recording the disappearance of the characteristic 520 nm tetrazine absorbance in an ultraviolet-visible assay. It should be noted that cyclopropene 10a exhibits slight absorbance at 520 nm and, at high concentrations (i.e., ≥90 mM but not 10 mM), instability that produces a minor but highly colored byproduct that is too diluted to be observed by 1H NMR. Taking these factors into account in the kinetic analysis, we determined the second-order rate constants with tetrazine S17 and 3,6-di-2-pyridyl-1,2,4,5-tetrazine to be 0.11 and 0.05 $M^{-1}s^{-1}$, respectively (FIG. 21F). The more sluggish kinetics with 3,6-di-2-pyridyl-1,2,4,5-tetrazine than with S17 was expected on the basis of literature reports Scheme 27-C3-Ketal Cyclopropene Is Amenable to Modification with an Acid Linker for Tagging Molecules of Interest

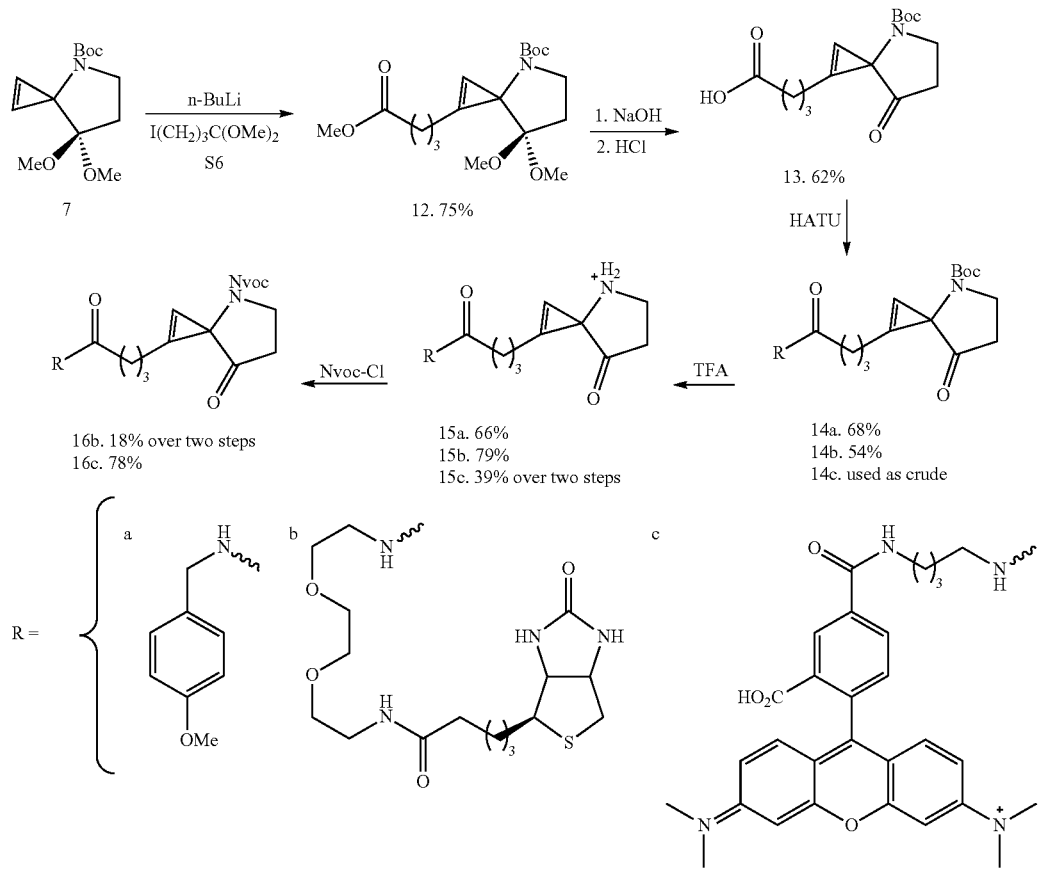

Figure 21:
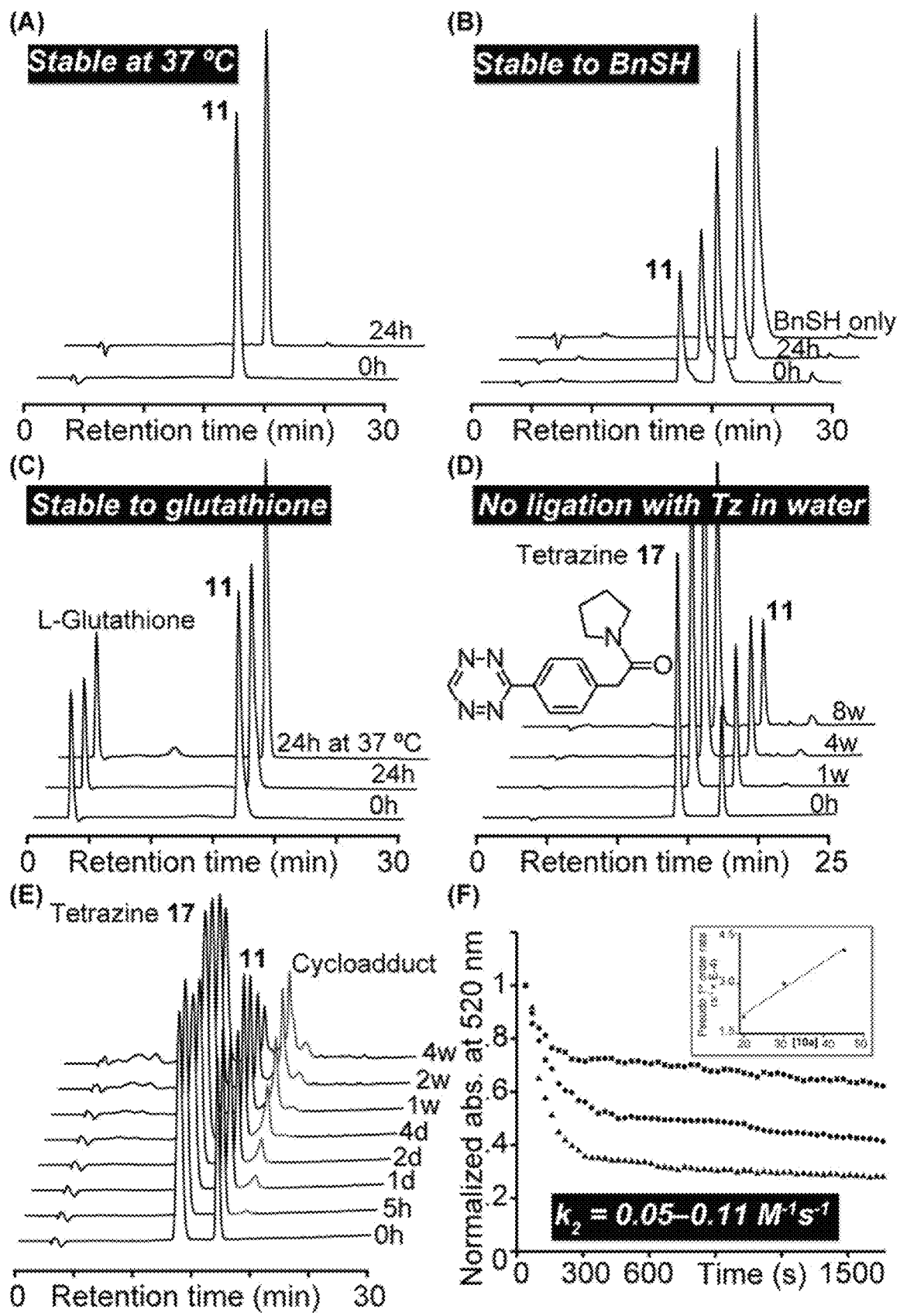
FIG. 21A—HPLC analyses of mixtures in a 1:1 PBS/MeCN solvent containing 2.5 mM photocaged cyclopropene 11 showing (A) stability at 37° C.
FIG. 21B—HPLC analyses of mixtures in a 1:1 PBS/MeCN solvent containing 2.5 mM photocaged cyclopropene 11 showing stability toward 10 mM BnSH.
FIG. 21C—HPLC analyses of mixtures in a 1:1 PBS/MeCN solvent containing 2.5 mM photocaged cyclopropene 11 showing stability toward reduced L-glutathione at rt and 37° C.
FIG. 21D—HPLC analyses of mixtures in a 1:1 PBS/MeCN solvent containing 2.5 mM photocaged cyclopropene 11 showing no ligation with 4 mM tetrazine 17 with 1 mM 11 in a 1:1 H$_2$O/MeCN solvent, and (E) extremely slow ligation of 1 mM 11 with 4 mM 17 in a 1:1 PBS/MeCN solvent.
FIG. 21E—HPLC analyses of mixtures in a 1:1 PBS/MeCN solvent containing 2.5 mM photocaged cyclopropene 11 showing extremely slow ligation of 1 mM 11 with 4 mM 17 in a 1:1 PBS/MeCN solvent.
FIG. 21F—HPLC analyses of mixtures in a 1:1 PBS/MeCN solvent containing 2.5 mM photocaged cyclopropene 11 showing the <270-fold faster kinetics of uncaged cyclopropene 10a compared to that of a first-generation compound. h=hour, d=day, and w=week.

The stability of these compounds was copared to those of common potential reaction partners in biological systems. Nvoc-photocaged C3 ketone cyclopropene 11 is stable toward biological nucleophiles for 24 h ($H_2O$, thiols, and amines) as measured by an HPLC assay in a 1:1 MeCN/PBS solvent (FIG. 21). Incubating 2.5 mM 11 for 24 h either by itself at 37° C. (FIG. 21A), with 10 mM benzyl mercaptan of cyclopropene kinetics with this tetrazine (T. Jiang et al. 2019; Ravasco, Monteiro, and Trindade 2017; Yang et al. 2014). This rate of uncaged ketone cyclopropene (0.05-0.11 $M^{-1}s^{-1}$) is substantially higher than that of the caged version and 125-270-fold higher than that of the first generation cyclopropene, thereby improving its potential for applications that require faster ligation kinetics, spatial and/or temporal control, and small bioorthogonal tags like cyclopropene (Patterson et al. 2012; Ravasco, Monteiro, and Trindade 2017; Yang et al. 2014; Kumar, Shukhman, and Laughlin 2016).

In conclusion, replacing the C3-difluoro moiety of the first generation caged cyclopropene with a C3-ketone moiety via the C3-ketal allows synthesis of stable 3-N cyclopropenes. The 3-N cyclopropene can be substituted at C1/C2 with an acid linker to tag biomolecules of interest. The second-generation 3-N cyclopropene maintains its modularity to allow easy attachment of photocages or enzyme cages and is stable to common biological nucleophiles at high concentrations, and its ligation rate is 5270-fold faster than that of the first generation of caged cyclopropenes.

Example 6. Synthesis of Mono and Di-Substituted Compounds

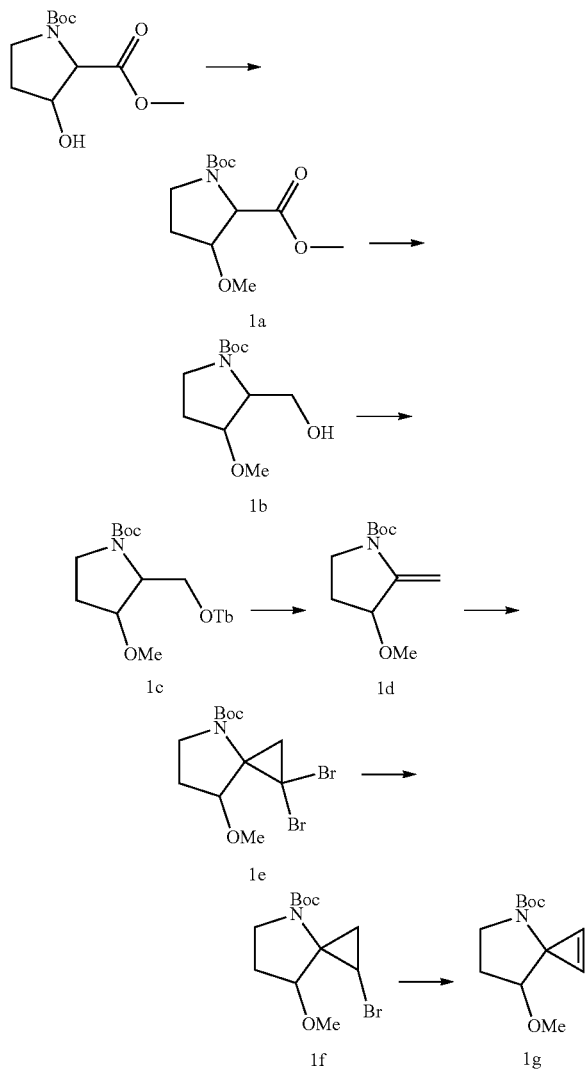

Scheme 28

1-(tert-butyl) 2-methyl 3-methoxypyrrolidine-1,2-dicarboxylate (1a): To a solution of 1-(tert-butyl) 2-methyl 3-hydroxypyrrolidine-1,2-dicarboxylate (4.26 g, 17.37 mmol, 1 eq) and MeI (2.16 ml, 34.70 mmol, 2 eq) in anhydrous DMF (43 mL) was added NaH (0.83 g, 20.75 mmol, 1.2 eq) in portions at −10° C. The resulting suspension was gradually warmed to rt and stirred overnight. The reaction mixture was cooled down using an ice-bath and quenched by dropwise addition of saturated aq. NH$_4$Cl. Excess DMF was removed in vacuo and the reaction mixture was diluted with DCM and water. The organic layer was collected and the aqueous layer was further washed with DCM. The combined organic layers were washed with brine, dried over anhydrous Na$_2$SO$_4$, concentrated in vacuo, and purified by flash chromatography (20% EtOAc/hexanes (v/v)) to obtain 1a as a colorless oil (3.0 g, 67%). $^1$H NMR (38:62 rotamers, 400 MHz, CDCl$_3$): δ=4.16 (2×d, J=7.1 Hz, 1H), 3.86-3.78 (m, 1H), 3.41 (s, 3H), 3.33-3.24 (m, 1H), 3.09-3.02 (m, 4H), 1.80-1.69 (m, 2H), 1.11 (2×s, 9H). $^{13}$C NMR (38:62 rotamers, 101 MHz, CDCl$_3$): δ=169.85, 169.74, 153.59, 153.07, 80.68, 79.81, 79.18, 61.52, 60.84, 57.47, 57.43, 51.07, 51.03, 43.39, 42.93, 28.91, 28.22, 27.73, 27.61. HRMS (ESI): Calcd for C$_{12}$H$_{21}$NO$_5$Na [M+Na]$^+$: 282.1312, found: 281.1314.

1-(tert-butyl) 2-methyl 3-methoxypyrrolidine-1,2-dicarboxylate (1b): To an ice-cold solution of 1a (3.0 g, 11.57 mmol, 1 eq) in anhydrous THF (30 mL) was added LAH (483 mg, 12.73 mmol, 1.1 eq) in portions. The resulting suspension was stirred for 30 min at 0° C. The reaction was quenched with ice cold water, diluted with DCM (10 mL) and separated. The organic layer was collected and the aqueous layer was further washed with DCM. The combined organic layers were washed with brine, dried over anhydrous Na$_2$SO$_4$, concentrated in vacuo, and purified by flash chromatography (20% EtOAc/hexanes (v/v)) to obtain 1b as a colourless oil (2.34 g, 87%). $^1$H NMR (mixture of isomers, 500 MHz, CDCl$_3$): δ=4.18-4.14 (m, 0.6H), 3.88-3.52 (m, 4H), 3.23-3.14 (m, 5H), 2.83-2.72 (m, 0.4H), 1.91-1.75 (m, 2H), 1.27 (s, 9H). $^{13}$C NMR (mixture of isomers, 126 MHz, CDCl$_3$): δ=155.79, 155.63, 154.36, 154.18, 82.68, 81.92, 81.38, 80.79, 79.72, 79.54, 79.46, 79.18, 64.21, 64.12, 63.35, 62.29, 61.93, 61.46, 61.07, 59.08, 58.81, 57.35, 57.16, 55.99, 55.85, 44.89, 44.45, 44.17, 43.16, 29.10, 28.37, 28.12, 27.70. COSY NMR (500 MHz, CDCl$_3$, attached) was obtained under the same conditions. $^{13}$C DEPT-135 NMR (mixture of isomers, 126 MHz, CDCl$_3$): δ=(up) 82.80, 82.04, 81.51, 80.91, 64.33, 64.24, 61.59, 58.94, 57.48, 57.28, 56.11, 55.97, 28.24; (down) 63.48, 62.42, 62.05, 61.19, 45.02, 44.56, 44.30, 43.28, 29.23, 28.49, 27.82. HRMS (ESI): Calcd for C$_{11}$H$_{21}$NO$_4$Na [M+Na]$^+$: 254.1363, found: 254.1366.

tert-butyl 3-methoxy-2-((tosyloxy)methyl)pyrrolidine-1-carboxylate (1c): To an ice-cold solution of 1b (2.03 g, 8.78 mmol, 1 eq) in anhydrous pyridine (44 mL) was added TsCl (8.37 g, 43.88 mmol, 5 eq). The reaction mixture was then warmed to rt and stirred overnight. The reaction mixture was diluted with water and the crude product extracted with DCM (4×30 mL). The combined organic layers were washed with brine, dried over anhydrous Na$_2$SO$_4$, concentrated in vacuo, and purified by flash chromatography (10% EtOAc/hexanes (v/v)) to obtain 1c as a colourless oil (2.52 g, 75%). $^1$H NMR (500 MHz, CDCl$_3$): δ=7.60 (d, J=7.9 Hz, 2H), 7.18 (d, J=7.8 Hz, 2H), 4.07-3.97 (m, 2H), 3.84 (br s, 1H), 3.74 (br s, 1H), 3.15 (br s, 2H), 3.08 (s, 3H), 2.26 (s, 3H), 1.87-1.67 (m, 2H), 1.24 (s, 9H). $^{13}$C NMR (126 MHz, CDCl$_3$): δ=153.99, 153.78, 144.41, 144.25, 132.69, 129.69, 129.45, 127.55, 127.46, 79.69, 79.31, 79.22, 78.53, 66.88, 66.41, 61.07, 57.25, 56.73, 56.03, 53.34, 43.66, 43.02, 28.69, 27.95, 21.20. COSY NMR (500 MHz, CDCl$_3$, attached) was obtained under the same conditions. $^{13}$C DEPT-135 NMR (126 MHz, CDCl$_3$): δ=(up) 129.90, 129.65, 127.76, 127.66, 79.42, 78.72, 57.46, 56.93, 56.23, 28.15, 21.41; (down) 67.09, 66.60, 43.87, 43.22, 28.91. HRMS (ESI): Calcd for C$_{18}$H$_{27}$NO$_6$SNa [M+Na]$^+$: 408.1451, found: 408.1456.

tert-butyl 3-methoxy-2-methylenepyrrolidine-1-carboxylate (1d): To a solution of 1c (4.11 g, 10.66 mmol, 1 eq) in glyme (115 mL) was added NaI (4.79 g, 31.96 mmol, 3 eq), and DBU (3.2 ml, 21.44 mmol, 2 eq). The reaction mixture was heated to 95° C. for 3 h, diluted with water (20 mL), and extracted with Et$_2$O (3×30 mL). The combined organic layers were washed with brine, dried over anhydrous Na$_2$SO$_4$, concentrated in vacuo, and used directly without any further purification to obtain 1d as a pale-yellow oil (0.57 g). We found the alkene to be unstable on silica and, therefore, used it without the flash chromatography for future production of 1d. $^1$H NMR (500 MHz, CDCl$_3$): δ=5.34 (s, 1H), 4.37 (s, 1H), 3.87-3.85 (m, 1H), 3.53-3.44 (m, 2H), 3.19 (s, 3H), 1.85-1.78 (m, 1H), 1.74-1.69 (m, 1H), 1.35 (s, 9H). $^{13}$C NMR (126 MHz, CDCl$_3$): δ=152.61, 143.63, 93.49, 82.13, 80.18, 65.56, 55.64, 46.61, 28.10. HRMS (ESI): Calcd for C$_{11}$H$_{19}$NO$_3$Na [M+Na]$^+$: 236.1257, found: 236.1254. $^1$H NMR (500 MHz, CDCl$_3$): δ=5.34 (s, 1H), 4.37 (s, 1H), 3.87-3.85 (m, 1H), 3.53-3.44 (m, 2H), 3.19 (s, 3H), 1.85-1.78 (m, 1H), 1.74-1.69 (m, 1H), 1.35 (s, 9H). $^{13}$C NMR (126 MHz, CDCl$_3$): δ=152.61, 143.63, 93.49, 82.13, 80.18, 65.56, 55.64, 46.61, 28.10. HRMS (ESI): Calcd for C$_{11}$H$_{19}$NO$_3$Na [M+Na]$^+$: 236.1257, found: 236.1254.

tert-butyl 1,1-dibromo-7-methoxy-4-azaspiro[2.4]heptane-4-carboxylate (1e): To a solution of 1d (0.956 g, 4.48 mmol, 1 eq) in CHBr$_3$ (1.62 mL, 20.00 mmol, 4 eq) was added CTAB (246 mg, 0.68 mmol, 0.15 eq) and the mixture was stirred vigorously. To this was added NaOH (392 μL, 50% w/v, 25 M) dropwise. The brown-black reaction mixture was stirred for 13 h at rt. To this reaction was added additional CHBr$_3$ and CTAB based on TLC and the process was repeated until complete consumption of reactant. Complete consumption of reactant was a necessity as the product have the same R$_f$ as the reactant. Upon completion, the reaction mixture was diluted with DCM and water. The organic layer was collected, washed with brine, and concentrated under reduced pressure. The crude obtained was purified by flash chromatography (30 g silica, 10%-20% EtOAc/hexanes (v/v)) to obtain 1e as a light-yellow oil (270 mg, 4% over two steps). $^1$H NMR (700 MHz, CDCl$_3$): δ=3.82 (d, J=7.0 Hz, 1H), 3.36-3.34 (m, 2H), 3.33-3.25 (m, 4H), 2.11 (d, J=14.0 Hz, 1H), 1.98-1.89 (m, 2H), 1.34 (s, 9H). $^{13}$C NMR (176 MHz, CDCl$_3$): δ=154.76, 116.52, 82.74, 79.13, 56.84, 53.52, 46.81, 42.76, 32.03, 29.80, 28.66, 22.79, 14.22. MS (ESI): Calcd for C$_{12}$H$_{19}$Br$_2$NO$_3$ [M+Na]$^+$: 411.9330, found: 411.9306.

tert-butyl 1,1-dibromo-7-methoxy-4-azaspiro[2.4]heptane-4-carboxylate (1f): To a solution of 1e (270 mg, 0.7 mmol, 1.0 eq) in anhydrous DCM (14.0 mL) under N$_2$ at −78° C. was dropwise added 2M iPrMgCl (0.42 mL, 0.84 mmol, 1.2 eq) and the mixture was stirred at the same temperature for 13 mins. The reaction was quenched with by saturated NH$_4$Cl. The organic layer was collected and the aqueous layer was further washed with DCM. The combined organic layers were dried over anhydrous Na$_2$SO$_4$, concentrated in vacuo, and purified by flash chromatography (15% EtOAc/hexanes (v/v)) to give crude 1f (90 mg) which was used without further purification. The formation of 1f was confirmed by MS. MS (ESI): Calcd for C$_{12}$H$_{20}$BrNO$_3$ [M+H]$^+$: 306.1, found: 249.9 [M−C(CH$_3$)$_3$+2H]$^+$.

tert-butyl 7-methoxy-4-azaspiro[2.4]hept-1-ene-4-carboxylate (1g): The crude if (90 mg, 0.29 mmol, 1.0 eq) was dissolved in THF (5.0 mL) and cooled down to −78° C. To this solution was added tBuOK (50 mg, 0.45 mmol, 1.5 eq) and the reaction was allowed gradually warming to rt. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo, and purified by flash chromatography (30% EtOAc/hexanes(v/v)) to obtain 1g (51 mg, 32% over two steps) as a pale-yellow oil that solidified upon storage at −20° C. $^1$H NMR (500 MHz, CDCl$_3$): δ=7.48-7.39 (br, 2H), 3.46-3.39 (m, 2H), 3.38-3.36 (m, 1H), 3.28 (s, 3H), 2.12-2.08 (m, 1H), 1.85-1.82 (m, 1H), 1.37 (s, 9H). $^{13}$C NMR (126 MHz, CDCl$_3$): δ=154.76, 116.52, 115.73, 82.74, 79.14, 56.84, 53.52, 46.81, 42.76, 32.03, 29.80, 28.66, 28.15, 22.79, 14.22. HRMS (ESI): Calcd for C$_{12}$H$_{19}$NO$_3$Na [M+Na]$^+$: 248.1257, found: 248.1225.

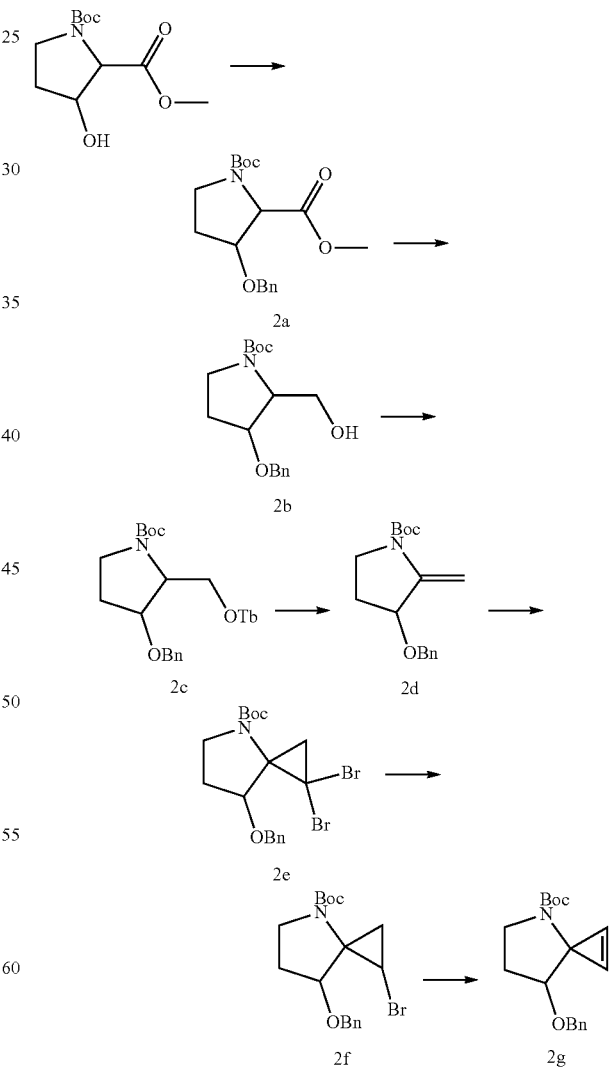

Scheme 29

1-(tert-butyl) 2-methyl 3-(benzyloxy)pyrrolidine-1,2-dicarboxylate (2a): To a solution of 1-(tert-butyl) 2-methyl 3-hydroxypyrrolidine-1,2-dicarboxylate (3.00 g, 12.23 mmol, 1 eq) tetrabutylammonium iodide (1.36 g, 3.67 mmol, 0.3 eq) and benzyl bromide (2.2 ml, 18.35 mmol, 1.5 eq) in THF (80 mL) was added NaH (0.60 g, 14.68 mmol, 1.2 eq) in portions at 0° C. The resulting suspension was gradually warmed to rt and stirred for 4 h. Then additional benzyl bromide (0.67 ml, 5.50 mmol, 0.45 eq) was added and the mixture was stirred for 15 h. The reaction mixture was cooled down using an ice-bath and quenched by dropwise addition of saturated aq. NH4Cl. Excess THF was removed in vacuo and the reaction mixture was diluted with DCM and water. The organic layer was collected and the aqueous layer was further washed with DCM. The combined organic layers were washed with brine, dried over anhydrous Na$_2$SO$_4$, concentrated in vacuo, and purified by flash chromatography (5% EtOAc/hexanes (v/v)) to obtain 2a (2.98 g, 72%)%), which is a mixture of diastereomers. MS (ESI): Calcd for C$_{18}$H$_{26}$NO$_5$ [M+H]$^+$: 336.2, found: 236.1 [M-Boc+2H]$^+$.

tert-butyl 3-(benzyloxy)-2-(hydroxymethyl)pyrrolidine-1-carboxylate (2b): The preparation of 2b followed similar procedure for 1b using 2a (0.69 g, 2.06 mmol, 1 eq), dry THF (10 ml) and LAH (86 mg, 2.27 mmol, 1.1 eq). After workup with 2M HCl and extracted with DCM, the organic layer was collected and dried over Na$_2$SO$_4$, concentrated in vacuo, the crude 2b was obtained (0.63 g). The formation of 2b was confirmed by MS. MS (ESI): Calcd for C$_{17}$H$_{26}$NO$_4$ [M+H]$^+$: 308.2, found: 308.2.

tert-butyl 3-(benzyloxy)-2-((tosyloxy)methyl)pyrrolidine-1-carboxylate (2c): The preparation of 2c followed similar procedure for 1e using the crude 2b (4.00 g, 13.00 mmol, 1 eq), TsCl (12.4 g, 65.04 mmol, 5 eq) in pyridine (40 ml). The reaction crude was purified by flash chromatography (0% to 20% EtOAc/hexanes (v/v)) to obtain 2c (4.64 g, 70% over two steps). $^1$H NMR (400 MHz, CDCl$_3$): δ=7.76 (d, 2H, J=7.84 Hz), 7.33-7.23 (m, 7H), 4.54-4.47 (m, 2H), 4.24 (br, 2H), 4.15-4.10 (m, 1H), 4.04-4.03 (m, 1H), 3.40-3.27 (br, 2H), 2.43 and 2.40 (each s, 3H in total), 2.04-1.97 (m, 2H), 1.45 and 1.41 (each s, 9H in total). MS (ESI): Calcd for C$_{24}$H$_{32}$NO$_6$S [M+H]$^+$: 462.2, found: 362.1 [M-Boc+2H]$^+$.

tert-butyl 3-(benzyloxy)-2-methylenepyrrolidine-1-carboxylate (2d): To the solution of 2c (0.40 g, 0.87 mmol, 1 eq) in dry THF (8 ml), tBuOK (0.20 g, 1.74 mmol, 2 eq) was added in one portion and the reaction mixture was stirred for overnight. The reaction was quenched by adding H$_2$O, followed by extraction with ether. The organic layer was collected and washed with brine twice, dried over Na$_2$SO$_4$, concentrated in vacuo, the crude 2d was obtained (0.20 g). The crude 2d was used without further purification. $^1$H NMR (400 MHz, CDCl$_3$): δ=7.35-7.28 (m, 5H), 5.52-5.48 (br, 1H), 4.69 and 4.66 (each s, 1H in total), 4.59-4.51 (m, 2H), 4.24-4.22 (m, 1H), 3.76-3.65 (m, 1H), 3.64-3.60 (m, 1H), 1.99-1.93 (m, 2H), 1.51 (s, 9H). MS (ESI): Calcd for C$_{17}$H$_{24}$NO$_3$ [M+H]$^+$: 290.2, found: 290.1.

tert-butyl 7-(benzyloxy)-1,1-dibromo-4-azaspiro[2.4]heptane-4-carboxylate (2e): The preparation of 2e followed similar procedure for 1e using crude 2d (2.29 g, 7.90 mmol, 1 eq), CTAB (0.044 g, 0.19 mmol, 0.015 eq), bromoform (1.42 ml, 15.80 mmol, 2 eq) and 50% NaOH (4 ml). The reaction crude was purified by flash chromatography (10% EtOAc/hexanes (v/v)) to obtain 2e (1.50 g, 33% over two steps). MS (ESI): Calcd for C$_{18}$H$_{24}$Br$_2$NO$_3$ [M+H]$^+$: 462.0, found: 405.9 [M-C(CH$_3$)$_3$+2H]$^+$.

tert-butyl 7-(benzyloxy)-1-bromo-4-azaspiro[2.4]heptane-4-carboxylate (2f): The preparation of 2f followed similar procedure for 1f using 2e (1.50 g, 3.25 mmol, 1 eq), 2M iPrMgCl (1.95 ml, 3.90 mmol, 1.2 eq) in dry THF (30 ml). The reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 2f (1.29 g), which was used without further purification. The formation of 2f was confirmed by MS. MS (ESI): Calcd for C$_{18}$H$_{25}$BrNO$_3$ [M+H]$^+$: 382.1, found: 326.0 [M-C(CH$_3$)$_3$+2H]$^+$.

tert-butyl 7-(benzyloxy)-4-azaspiro[2.4]hept-1-ene-4-carboxylate (2g): To the solution of crude 2f (1.29 g, 3.38 mmol, 1 eq) in dry THF (30 ml) at 0° C., tBuOK (0.63 g, 5.63 mmol, 1.6 eq) was added in one portion. The reaction was slowly warmed to r.t. and stirred overnight. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo, and purified by flash chromatography (10-20% EtOAc/hexanes(v/v)) to obtain 2g (0.58 g, 59% over two steps). $^1$H NMR (400 MHz, CDCl$_3$): δ=7.54-7.28 (m, 7H), 4.56-4.46 (m, 2H), 3.58-3.37 (m, 3H), 2.17-2.09 (m, 1H), 1.97-1.89 (m, 1H), 1.40 (s, 9H). $^{13}$C NMR (101 MHz, CDCl$_3$): δ=154.85, 138.67, 128.48, 127.67, 127.61, 116.94, 80.58, 79.17, 70.93, 47.01, 42.86, 29.84, 28.70. MS (ESI): Calcd for C$_{18}$H$_{24}$NO$_3$ [M+H]$^+$: 302.2, found: 302.2.

Scheme 30

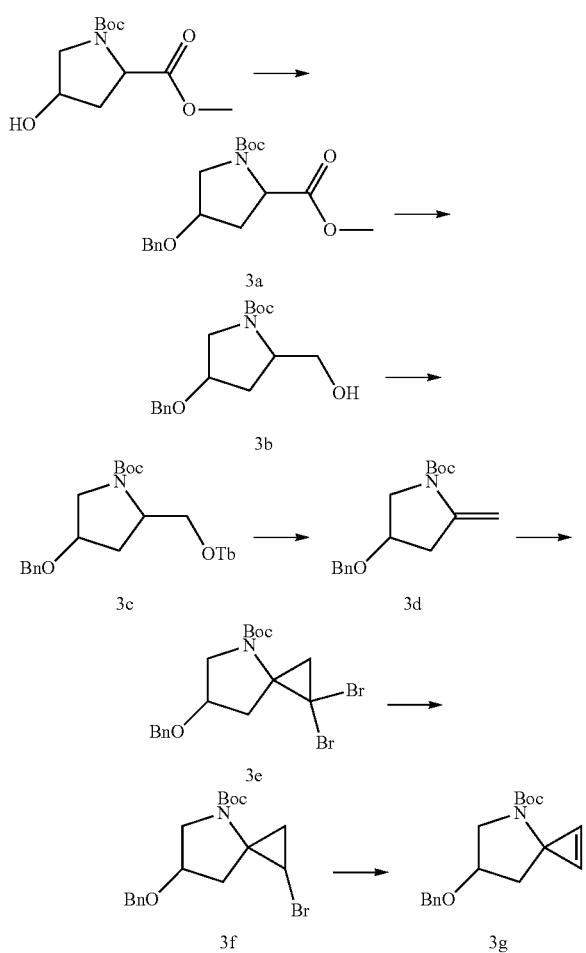

1-(tert-butyl) 2-methyl 4-(benzyloxy)pyrrolidine-1,2-dicarboxylate (3a): The preparation of 3a followed similar procedure for 2a using 1-(tert-butyl) 2-methyl 4-hydroxypyrrolidine-1,2-dicarboxylate (5.40 g, 22.04 mmol, 1 eq), tetrabutylammonium iodide (2.44 g, 6.61 mmol, 0.3 eq), benzyl bromide (4.0 ml, 33.06 mmol, 1.5 eq), THF (140 mL) and NaH (1.60 g, 26.45 mmol, 1.2 eq). The reaction crude was purified by flash chromatography (10-30% EtOAc/hexanes(v/v)) to obtain 3a (4.50 g, 61%, mixture of diastereomers). $^1$H NMR (400 MHz, CDCl$_3$): δ=7.37-7.27 (m, 5H), 4.55-4.34 (m, 3H), 4.20-4.09 (m, 1H), 3.73-3.52 (m, 5H), 2.44-2.31 (m, 1H), 2.10-2.03 (m, 1H), 1.47, 1.45, 1.42 and 1.40 (each s, 9H in total). $^{13}$C NMR (101 MHz, CDCl$_3$): δ=173.75, 154.50, 153.89, 137.89, 137.81, 128.49, 127.81, 127.96, 127.78, 127.69, 127.08, 80.31, 80.14, 76.13, 75.81, 71.33, 71.23, 65.44, 58.15, 57.73, 52.35, 52.13, 52.00, 51.45, 36.83, 35.69, 28.51, 28.37. MS (ESI): Calcd for C$_{18}$H$_{26}$NO$_5$ [M+H]$^+$: 336.2, found: 336.1.

tert-butyl 4-(benzyloxy)-2-(hydroxymethyl)pyrrolidine-1-carboxylate (3b): The preparation of 3b followed similar procedure for 1b using 3a (7.6 g, 22.66 mmol, 1 eq), LAH (0.95 g, 24.93 mmol, 1.1 eq) in THF (110 ml). After workup with 2M HCl and extracted with DCM, the organic layer was collected and dried over Na$_2$SO$_4$, concentrated in vacuo, the crude 3b was obtained (6.70 g). The formation of 3b was confirmed by MS. MS (ESI): Calcd for C17H$_{26}$NO$_4$ [M+H]$^+$: 308.2, found: 308.2.

tert-butyl 4-(benzyloxy)-2-((tosyloxy)methyl)pyrrolidine-1-carboxylate (3c): The preparation of 3c followed similar procedure for 1c using the crude 3b (6.70 g, 21.80 mmol, 1 eq), TsCl (20.70 g, 108.95 mmol, 5 eq) in pyridine (60 ml). The reaction crude was purified by flash chromatography (20% to 30% EtOAc/hexanes (v/v)) to obtain 3c (3.45 g, 33% over two steps, mixture of diastereomers). $^1$H NMR (500 MHz, CDCl$_3$): δ=7.76 (d, 2H, J=7.85 Hz), 7.33-7.26 (m, 7H), 4.48-4.40 (m, 2H), 4.33-4.32 (m, 0.5H), 4.16-4.05 (m, 3.5H), 3.72-3.70 (m, 0.5H), 3.50-3.39 (m, 1H), 3.28-3.26 (m, 0.5H), 2.43 and 2.40 (each s, 3H in total), 2.17-2.04 (m, 2H), 1.40 and 1.35 (each s, 9H in total). $^{13}$C NMR (126 MHz, CDCl$_3$): δ=154.59, 154.28, 145.08, 144.90, 137.98, 132.94, 130.03, 129.93, 128.58, 128.06, 127.98, 127.90, 127.80, 127.76, 80.30, 79.98, 76.60, 75.87, 71.26, 71.14, 70.88, 70.63, 70.39, 54.94, 54.85, 52.35, 51.55, 35.25, 33.90, 28.49, 28.39, 21.75. MS (ESI): Calcd for C$_{24}$H$_{32}$NO$_6$S [M+H]$^+$: 462.2, found: 462.2.

tert-butyl 4-(benzyloxy)-2-methylenepyrrolidine-1-carboxylate (3d): The preparation of 3d followed similar procedure for 1d using 3c (3.45 g, 7.47 mmol, 1 eq), NaI (3.36 g, 22.41 mmol, 3 eq), DBU (2.23 ml, 14.94 mmol, 2 eq) in glyme (50 ml). The reaction was quenched by adding H$_2$O, followed by extraction with ether. The organic layer was collected and washed with brine twice, dried over Na$_2$SO$_4$, concentrated in vacuo, the crude 3d was obtained (1.66 g). The crude 3d was used without further purification. $^1$H NMR (500 MHz, CNCD$_3$): δ=7.37-7.29 (m, 5H), 5.20 (br, 1H), 4.50 (d, 2H, J=3.3 Hz), 4.30 (s, 2H), 4.04-4.01 (m, 1H), 3.74-3.70 (m, 1H), 3.66-3.63 (dd, 1H), 2.77-2.72 (m, 1H), 2.66 and 2.62 (each s, 1H in total), 1.47 (s, 9H). $^{13}$C NMR (126 MHz, CNCD$_3$): δ=140.48, 130.23, 129.58, 129.43, 91.61, 75.38, 72.08, 56.60, 29.35.

tert-butyl 6-(benzyloxy)-1,1-dibromo-4-azaspiro[2.4]heptane-4-carboxylate (3e): The preparation of 3e followed similar procedure for 1e using crude 3d (1.66 g, 5.72 mmol, 1 eq), CTAB (0.031 g, 0.085 mmol, 0.015 eq), bromoform (1.03 ml, 11.44 mmol, 2 eq) and 50% NaOH (2.9 ml). The reaction crude was purified by flash chromatography (10% EtOAc/hexanes (v/v)) to obtain 3e (0.71 g, 21% over two steps). $^1$H NMR (500 MHz, CDCl$_3$): δ=7.38-7.29 (m, 5H), 4.55 (s, 2H), 4.29-4.24 (m, 1H), 3.72-3.55 (br and m, 3H), 2.58-2.54 (m, 1H), 2.25-2.21 (m, 1H), 1.88 (d, 1H, J=9.5 Hz), 1.41 (s, 9H). $^{13}$C NMR (126 MHz, CDCl$_3$): δ=153.68, 137.79, 128.66, 128.07, 127.96, 74.44, 71.96, 53.56, 52.73, 50.86, 35.71, 28.50. MS (ESI): Calcd for C$_{18}$H$_{24}$Br$_2$NO$_3$ [M+H]$^+$: 462.0, found: 405.9 [M-C(CH$_3$)$_3$+2H]$^+$.

tert-butyl 6-(benzyloxy)-1-bromo-4-azaspiro[2.4]heptane-4-carboxylate (3f): The preparation of 3f followed similar procedure for 1f using 3e (0.58 g, 1.27 mmol, 1 eq), 2.0 M iPrMgCl (0.76 ml, 1.52 mmol, 1.2 eq) in dry THF (10 ml). The reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 3f (0.51 g), which was used without further purification. The formation of 3f was confirmed by MS. MS (ESI): Calcd for C$_{18}$H$_{24}$BrNNaO$_3$ [M+Na]$^+$: 404.1, found: 404.0.

tert-butyl 6-(benzyloxy)-4-azaspiro[2.4]hept-1-ene-4-carboxylate (3g): To the solution of crude 3f (0.51 g, 1.34 mmol, 1 eq) in dry THF (10 ml) at −78° C., tBuOK (0.21 g, 1.86 mmol, 1.4 eq) was added in one portion. The reaction mixture was slowly warmed to r.t. and stirred overnight. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo. We could clearly see the right mass corresponding to 3g on the MS in the crude. However, we cannot isolate it from the crude by using silica gel chromatography. Ring open byproduct, which was unable to be identified, was obtained by Prep. TLC using 10:90:5 EtOAc/hexanes/triethylamine (v/v/v) as the eluent. The formation of 3g was confirmed by MS. MS (ESI): Calcd for C$_{18}$H$_{24}$NO$_3$ [M+H]$^+$: 302.2, found: 302.1.

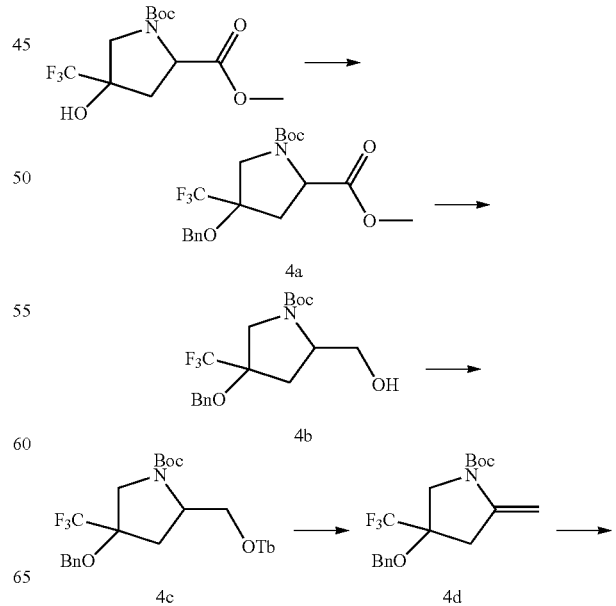

Scheme 31

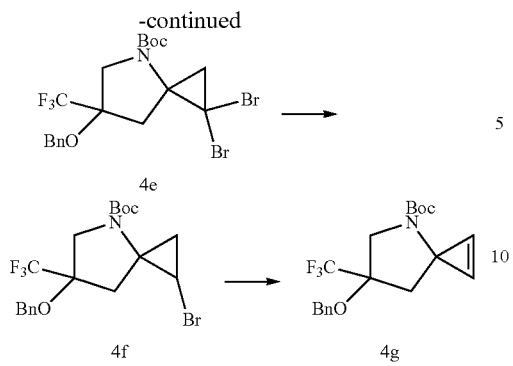

1-(tert-butyl) 2-methyl 4-(benzyloxy)-4-(trifluoromethyl) pyrrolidine-1,2-dicarboxylate (4a): The preparation of 4a followed similar procedure for 2a using 1-(tert-butyl) 2-methyl 4-hydroxy-4-(trifluoromethyl)pyrrolidine-1,2-dicarboxylate (2.07 g, 6.61 mmol, 1 eq), tetrabutylammonium iodide (0.73 g, 1.98 mmol, 0.3 eq), benzyl bromide (1.2 ml, 10.11 mmol, 1.5 eq), THF (40 mL) and NaH (0.32 g, 7.92 mmol, 1.2 eq). The reaction crude was purified by flash chromatography (10-20% EtOAc/hexanes(v/v)) to obtain 4a (1.60 g, 60%, a mixture of diastereomers). $^1$H NMR (500 MHz, CDCl$_3$): δ=7.35-7.26 (m, 5H), 4.68-4.46 and 4.40-4.36 (each m, 3H in total), 4.22-4.20, 4.04-4.00 and 3.91-3.88 (each m, 1H in total), 3.81-3.75, 3.69-3.64 and 3.56 and 3.52 (two m and two s, 4H in total), 2.67-2.50 and 2.32-2.26 (each m, 1H in total), 1.57, 1.50, 1.49, 1.44 and 1.42 (each s, 9H in total). MS (ESI): Calcd for C$_{19}$H$_{25}$F$_3$NO$_5$ [M+H]$^+$: 404.2, found: 348.1 [M-C(CH$_3$)$_3$+2H]$^+$.

tert-butyl 4-(benzyloxy)-2-(hydroxymethyl)-4-(trifluoromethyl)pyrrolidine-1-carboxylate (4b): The preparation of 4b followed similar procedure for 1b using 4a (1.6 g, 3.97 mmol, 1 eq), LAH (0.17 g, 4.37 mmol, 1.1 eq) in THF (20 ml). After workup with 2M HCl and extracted with DCM, the organic layer was collected and dried over Na$_2$SO$_4$, concentrated in vacuo, the crude 4b (1.57 g) was obtained and used without further purification. The formation of 4b was confirmed by MS. MS (ESI): Calcd for C$_{18}$H$_{25}$F$_3$NO$_4$ [M+H]$^+$: 376.2, found: 320.2 [M-C(CH$_3$)$_3$+2H]$^+$.

tert-butyl 4-(benzyloxy)-2-((tosyloxy)methyl)-4-(trifluoromethyl)pyrrolidine-1-carboxylate (4c): The preparation of 4c followed similar procedure for 1c using the crude 4b (1.57 g, 4.20 mmol, 1 eq), TsCl (4.00 g, 20.99 mmol, 5 eq) in pyridine (10 ml). The reaction crude was purified by flash chromatography (10% to 20% EtOAc/hexanes (v/v)) to obtain 4c (1.40 g, 66% over two steps, a mixture of diastereomers). $^1$H NMR (500 MHz, CDCl$_3$): δ=7.78 and 7.70 (each d, 2H in total, J=8.25 and 6.2 Hz), 7.35-7.23 (m, 7H), 4.64-4.54 (m, 2H), 4.40-4.39, 4.31-3.97 and 3.83-3.63 (each m, 5H in total), 2.44-2.36 (m, 5H), 1.42 and 1.38 (each s, 9H in total). $^{13}$C NMR (126 MHz, CDCl$_3$): δ=153.87, 145.10, 137.01, 132.85, 130.08, 130.03, 128.66, 128.16, 128.00, 127.79, 80.95, 69.62, 69.28, 68.08, 55.36, 55.11, 52.14, 50.91, 33.31, 31.56, 28.39, 21.76. MS (ESI): Calcd for C$_{25}$H$_{31}$F$_3$NO$_6$S [M+H]$^+$: 530.2, found: 474.1 [M-C(CH$_3$)$_3$+2H]$^+$.

tert-butyl 4-(benzyloxy)-2-methylene-4-(trifluoromethyl) pyrrolidine-1-carboxylate (4d): The preparation of 4d followed similar procedure for 1d using 4c (1.27 g, 2.40 mmol, 1 eq), NaI (1.08 g, 7.21 mmol, 3 eq), DBU (0.72 ml, 4.81 mmol, 2 eq) in glyme (15 ml). The reaction was quenched by adding H$_2$O, followed by extraction with ether. The organic layer was collected and washed with brine twice, dried over Na$_2$SO$_4$, concentrated in vacuo, the crude 4d was obtained (0.73 g). The crude 4d was used without further purification. $^1$H NMR (500 MHz, CNCD$_3$): δ=7.37-7.31 (m, 5H), 5.28 (br, 1H), 4.68 (t, 2H), 4.41 (s, 1H), 4.00 (d, 1H, J=12.65 Hz), 3.89 (d, 1H, J=12.60 Hz), 3.09-3.00 (m, 2H), 1.38 (s, 9H). $^{13}$C NMR (126 MHz, CNCD$_3$): δ=137.68, 128.48, 127.95, 127.67, 90.93, 67.34, 53.26, 27.44. MS (ESI): Calcd for C$_{18}$H$_{23}$F$_3$NO$_3$ [M+H]$^+$: 358.2, found: 358.1.

tert-butyl 6-(benzyloxy)-1,1-dibromo-6-(trifluoromethyl)-4-azaspiro[2.4]heptane-4-carboxylate (4e): The preparation of 4e followed similar procedure for 1e using crude 4d (0.37 g, 1.03 mmol, 1 eq), CTAB (0.005 g, 0.015 mmol, 0.015 eq), bromoform (0.18 ml, 2.06 mmol, 2 eq) and 50% NaOH (0.52 ml). The reaction crude was purified by flash chromatography (5-10% EtOAc/hexanes (v/v)) to obtain 4e (0.32 g, 52% over two steps). $^1$H NMR (500 MHz, CDCl$_3$): δ=7.45-7.29 (m, 5H), 4.79 and 4.67 (each dd, 2H in total), 4.22-4.21, 3.74 and 3.55-3.53 (br, d and br, 2H in total, J=12.65 Hz), 2.93 (d, 0.56H, J=15.05 Hz), 2.76 (d, 0.45H, J=14.4 Hz), 2.63 (d, 0.46H, J=14.35 Hz), 2.52 (d, 0.54H, J=14.70 Hz), 1.90, 1.88, 1.85 and 1.84 (each s, 1H in total), 1.55 (s, 1H), 1.46 and 1.44 (s, 9H). $^{13}$C NMR (126 MHz, CDCl$_3$): δ=153.06, 137.27, 137.12, 128.68, 128.53, 128.15, 128.02, 127.72, 127.48, 126.48, 83.48, 83.25, 68.29, 67.92, 51.35, 35.47, 34.99, 28.42, 28.09. MS (ESI): Calcd for C$_{19}$H$_{26}$Br$_2$F$_3$N$_2$O$_3$ [M+NH$_4$]$^+$: 547.0, found: 547.0.

tert-butyl 6-(benzyloxy)-1-bromo-6-(trifluoromethyl)-4-azaspiro[2.4]heptane-4-carboxylate (4f): The preparation of 4f followed similar procedure for 1f using 4e (0.32 g, 0.62 mmol, 1 eq), 2.0 M iPrMgCl (0.37 ml, 0.74 mmol, 1.2 eq) in dry THF (6 ml). The reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 4f (0.28 g), which was used without further purification. The formation of 4f was confirmed by MS. MS (ESI): Calcd for C$_{19}$H$_{27}$BrF$_3$N$_2$O$_3$ [M+NH$_4$]$^+$: 467.1, found: 467.1.

tert-butyl 6-(benzyloxy)-6-(trifluoromethyl)-4-azaspiro [2.4]hept-1-ene-4-carboxylate (4g): The preparation of 4g followed similar procedure for 2g using crude 4f (285 mg, 0.63 mmol, 1 eq), tBuOK (107 mg, 0.95 mmol, 1.5 eq). Additional tBuOK was added if necessary and the reaction was monitored by MS. The reaction crude was purified by flash chromatography (10% to 20% EtOAc/hexanes (v/v)) to obtain 4g (128 mg, 56% over two steps, mixture of enantiomers). $^1$H NMR (400 MHz, CDCl$_3$): δ=7.45-7.27 (m, 7H), 4.69 (q, 2H), 3.79-3.73 (m, 2H), 2.41 (d, 1H, J=13.96 Hz), 2.05 (d, 1H, J=13.96 Hz), 1.41 (s, 9H). $^{13}$C NMR (101 MHz, CDCl$_3$): δ=153.95, 137.73, 129.98, 128.60, 128.41, 127.98, 127.67, 127.48, 127.14, 124.30, 121.46, 118.94, 117.33, 81.69, 81.41, 79.94, 67.70, 51.02, 42.70, 39.66, 29.82, 29.55, 28.59, 28.44. MS (ESI): Calcd for C$_{19}$H$_{22}$F$_3$KNO$_3$ [M+K]$^+$: 408.1, found: 408.1.

Scheme 32

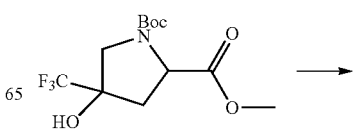

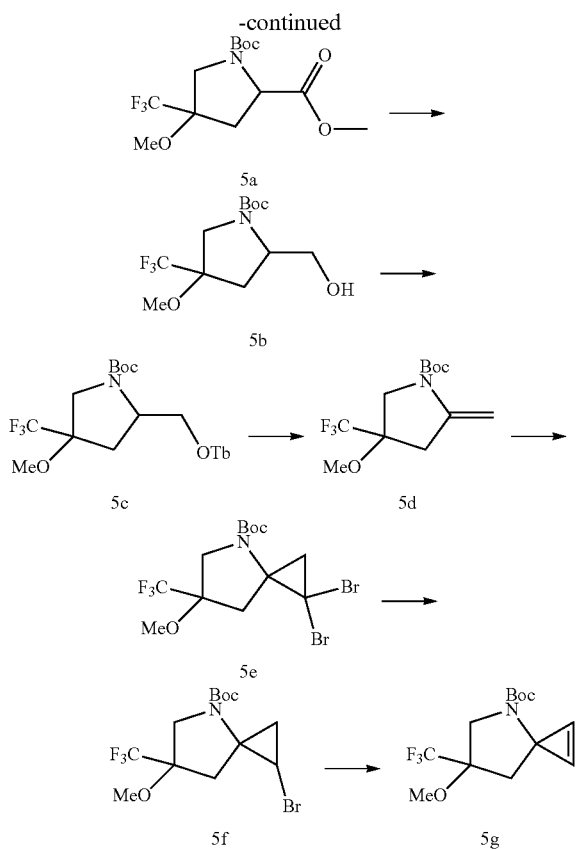

1-(tert-butyl) 2-methyl 4-methoxy-4-(trifluoromethyl) pyrrolidine-1,2-dicarboxylate (5a): The preparation of 5a followed similar procedure for 1a using 1-(tert-butyl) 2-methyl 4-hydroxy-4-(trifluoromethyl)pyrrolidine-1,2-dicarboxylate (2.93 g, 9.34 mmol, 1 eq), MeI (1.16 ml, 18.64 mmol, 2 eq) in dry DMF (30 mL) and NaH (0.45 g, 11.21 mmol, 1.2 eq). The reaction crude was purified by flash chromatography (10-20% EtOAc/hexanes(v/v)) to obtain 5a (2.21 g, 72%, a mixture of diastereomers). $^1$H NMR (500 MHz, CDCl$_3$): δ=4.56-4.54 and 4.46-4.34 (each m, 1H in total), 4.04-4.01, 3.89-3.87 and 3.77-3.74 (each m, 4H in total), 3.69-3.59 (m, 1H in total), 3.41 and 3.36 (each s, 3H in total), 2.58-2.38, 2.25-2.17 (each m, 2H in total), 1.48, 1.47, 1.42, 1.41 (each s, 9H in total). $^{13}$C NMR (126 MHz, CDCl$_3$): δ=172.49, 171.89, 171.57, 153.90, 153.60, 153.51, 126.16, 123.88, 83.76, 83.53, 82.69, 82.46, 81.14, 81.02, 80.88, 58.05, 57.92, 57.73, 57.57, 53.39, 53.26, 52.64, 52.55, 52.44, 52.36, 50.38, 49.69, 48.99, 48.67, 36.40, 36.02, 34.72, 34.18, 28.48, 28.35, 28.31. MS (ESI): Calcd for $C_{13}H_{21}F_3NO_5$ [M+H]$^+$: 328.1, found: 272.0 [M-C(CH$_3$)$_3$+2H]$^+$.

tert-butyl 2-(hydroxymethyl)-4-methoxy-4-(trifluoromethyl)pyrrolidine-1-carboxylate (5b): The preparation of 5b followed similar procedure for 1b using 5a (2.21 g, 6.75 mmol, 1 eq), LAH (282 mg, 7.43 mmol, 1.1 eq) in THF (30 ml). After workup with 2M HCl and extracted with DCM, the organic layer was collected and dried over Na$_2$SO$_4$, concentrated in vacuo, the crude 5b (1.74 g) was obtained and used without further purification. The formation of 5b was confirmed by MS. MS (ESI): Calcd for $C_{12}H_{21}F_3NO_4$ [M+H]$^+$: 300.1, found: 244.1 [M-C(CH$_3$)$_3$+2H]$^+$.

tert-butyl 4-methoxy-2-((tosyloxy)methyl)-4-(trifluoromethyl)pyrrolidine-1-carboxylate (5c): The preparation of 5c followed similar procedure for 1c using the crude 5b (1.74 g, 5.81 mmol, 1 eq), TsCl (5.52 g, 28.95 mmol, 5 eq) in pyridine (10 ml). The reaction crude was purified by flash chromatography (10% to 20% EtOAc/hexanes (v/v)) to obtain 5c (2.13 g, 69% over two steps, a mixture of diastereomers). $^1$H NMR (500 MHz, CDCl$_3$): δ=7.79-7.75 (m, 2H), 7.35-7.34 (m, 2H), 4.37-4.36, 4.21-4.09, 3.94-3.84 and 3.70-3.68 (each m, 4H in total), 3.55-3.49, 3.35-3.31 and 3.18-3.15 (each m, 4H in total), 2.44 (s, 3H), 2.31-2.12 (m, 2H), 1.40 (s, 9H). $^{13}$C NMR (126 MHz, CDCl$_3$): δ=154.31, 153.91, 153.73, 145.22, 145.10, 132.85, 130.04, 128.09, 127.99, 81.18, 80.96, 80.87, 69.79, 69.34, 69.27, 68.96, 55.25, 54.98, 53.35, 52.94, 51.82, 50.63, 50.45, 34.82, 32.48, 32.30, 30.55, 28.36, 21.75. MS (ESI): Calcd for $C_{19}H_{30}F_3N_2O_6S$ [M+NH$_4$]$^+$: 471.2, found: 471.1.

tert-butyl 4-methoxy-2-methylene-4-(trifluoromethyl)pyrrolidine-1-carboxylate (5d): The preparation of 5d followed similar procedure for 1d using 5c (2.13 g, 4.70 mmol, 1 eq), NaI (2.11 g, 14.10 mmol, 3 eq), DBU (1.41 ml, 9.40 mmol, 2 eq) in glyme (30 ml). The reaction was quenched by adding H$_2$O, followed by extraction with ether. The organic layer was collected and washed with brine twice, dried over Na$_2$SO$_4$, concentrated in vacuo, the crude 5d was obtained (1.08 g). The crude 5d was used without further purification. $^1$H NMR (400 MHz, CNCD$_3$): δ=5.25 (br, 1H), 4.38 (s, 1H), 3.89, 3.86, 3.82 and 3.79 (each s, 2H in total), 3.40 (s, 3H), 2.99-2.89 (m, 2H), 1.48 (s, 9H). $^{13}$C NMR (101 MHz, CNCD$_3$): δ=152.89, 142.56, 127.66, 124.83, 91.69, 69.84, 53.90, 53.46, 28.33.

tert-butyl 1,1-dibromo-6-methoxy-6-(trifluoromethyl)-4-azaspiro[2.4]heptane-4-carboxylate (5e): The preparation of 5e followed similar procedure for 1e using crude 5d (1.08 g, 3.83 mmol, 1 eq), CTAB (21 mg, 0.057 mmol, 0.015 eq), bromoform (0.69 ml, 7.66 mmol, 2 eq) and 50% NaOH (1.95 ml). The reaction crude was purified by flash chromatography (5-10% EtOAc/hexanes (v/v)) to obtain 5e (358 mg, 17% over two steps). MS (ESI): Calcd for $C_{13}H_{18}Br_2F_3NNaO_3$ [M+Na]$^+$: 475.9, found: 475.9.

tert-butyl 1-bromo-6-methoxy-6-(trifluoromethyl)-4-azaspiro[2.4]heptane-4-carboxylate (5f): The preparation of 5f followed similar procedure for 1f using 5e (358 mg, 0.79 mmol, 1 eq), 2.0 M iPrMgCl (0.48 ml, 0.95 mmol, 1.2 eq) in dry THF (8 ml). The reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 5f (307 mg), which was used without further purification. The formation of 5f was confirmed by MS. MS (ESI): Calcd for $C_{13}H_{20}BrF_3NO_3$ [M+H]$^+$: 374.1, found: 274.0 [M-Boc+2H]$^+$.

tert-butyl 6-methoxy-6-(trifluoromethyl)-4-azaspiro[2.4] hept-1-ene-4-carboxylate (5g): The preparation of 5g followed similar procedure for 2g using crude 5f (307 mg, 0.79 mmol, 1 eq), tBuOK (133 mg, 1.19 mmol, 1.5 eq) in dry THF (8 ml). Additional tBuOK was added if necessary and the reaction was monitored by MS. The reaction crude was purified by flash chromatography (10% to 20% EtOAc/hexanes (v/v)) to obtain 5g (183 mg, 79% over two steps). $^1$H NMR (700 MHz, CDCl$_3$): δ=7.53-7.41 (br, 2H), 3.66 (s, 2H), 3.46 (s, 3H), 2.32 (d, 1H, J=14.0 Hz), 1.93 (d, 1H, J=14.0 Hz), 1.41 (s, 9H). MS (EST): Calcd for $C_{13}H_{19}F_3NO_3$ [M+H]$^+$: 294.1, found: 294.1.

Scheme 33

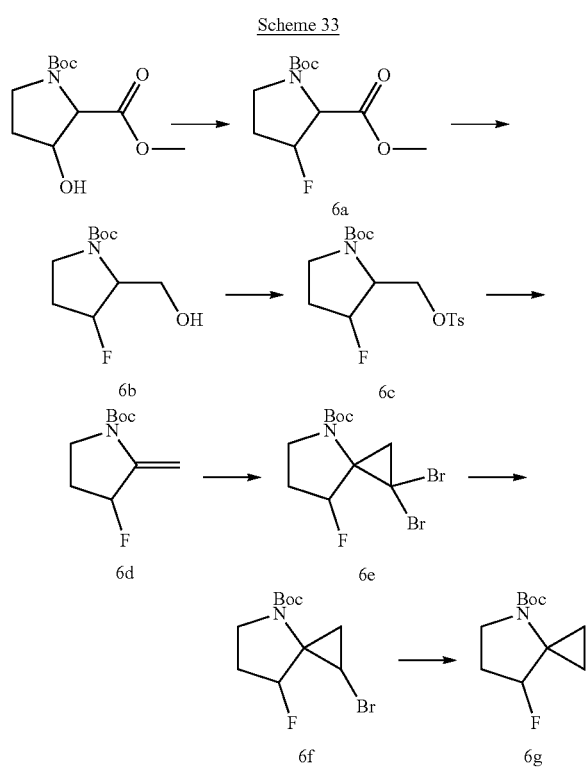

1-(tert-butyl) 2-methyl 3-fluoropyrrolidine-1,2-dicarboxylate (6a): To a solution of 1-(tert-butyl) 2-methyl 3-hydroxypyrrolidine-1,2-dicarboxylate (664 mg, 2.71 mmol, 1 eq) in dry DCM (5.3 ml) was added DAST (0.54 ml, 4.09 mmol, 1.5 eq) at −78° C. The reaction mixture was warmed to r.t. and stirred overnight. The excess DAST was carefully quenched with ice cold saturated NaHCO$_3$ and the reaction mixture was extracted with DCM. The combined organic layers were washed with brine, dried over anhydrous Na$_2$SO$_4$, concentrated in vacuo, and purified by flash chromatography (10% to 20% EtOAc/hexanes (v/v)) to obtain 6a (549 mg, 82%, a mixture of diastereomers). H NMR (700 MHz, CDCl$_3$): δ=5.17-5.16 and 5.09-5.08 (each m, 1H in total), 4.57, 4.54, 4.45 and 4.42 (each s, 1H in total), 3.74-3.70 and 3.67-3.64 (each m, 4H in total), 3.55-3.48 (m, 1H), 2.20-2.02 (m, 1H), 1.45, 1.44, 1.40, 1.39 (each s, 9H in total). $^{13}$C NMR (176 MHz, CDCl$_3$): δ=171.19, 170.88, 170.14, 170.05, 170.00, 169.91, 154.36, 153.95, 153.61, 153.44, 129.48, 129.37, 124.82, 124.72, 95.73, 94.75, 94.68, 93.70, 80.45, 80.26, 80.22, 66.64, 66.36, 66.27, 66.01, 65.87, 53.58, 53.34, 52.71, 52.56, 52.37, 52.24, 44.39, 44.07, 31.31, 31.19, 30.56, 30.43, 28.48, 28.44, 28.35, 28.31. MS (ESI): Calcd for C$_{11}$H$_{19}$FNO$_4$ [M+H]$^+$: 248.1, found: 192.1 [M-C(CH$_3$)$_3$+2H]$^+$.

tert-butyl 3-fluoro-2-(hydroxymethyl)pyrrolidine-1-carboxylate (6b): The preparation of 6b followed similar procedure for 1b using 6a (549 mg, 2.22 mmol, 1 eq), LAH (93 mg, 2.44 mmol, 1.1 eq) in THF (10 mL). The reaction was quenched with ice cold water, diluted with DCM (10 mL) and separated. The organic layer was collected and the aqueous layer was further washed with DCM. The combined organic layers were washed with brine, dried over anhydrous Na$_2$SO$_4$, concentrated in vacuo, to obtain crude 6b (468 mg). The formation of 6b was confirmed by MS. MS (ESI): Calcd for C$_{10}$H$_{19}$FNO$_3$ [M+H]$^+$: 220.1, found: 164.1 [M-C(CH$_3$)$_3$+2H]$^+$.

tert-butyl 3-fluoro-2-((tosyloxy)methyl)pyrrolidine-1-carboxylate (6c): The preparation of 6c followed similar procedure for 1c using the crude 6b (468 mg, 2.13 mmol, 1 eq), TsCl (2.03 g, 10.65 mmol, 5 eq) in pyridine (10 ml). The reaction crude was purified by flash chromatography (10% to 30% EtOAc/hexanes (v/v)) to obtain 6c (765 mg, 92% over two steps). $^1$H NMR (700 MHz, CDCl$_3$): δ=7.76-7.74 (m, 2H), 7.37-7.33 (m, 2H), 5.13 and 5.06 (each s, 1H in total), 4.19-4.10 (m, 2H), 4.03-4.00 and 3.92-3.89 (each m, 1H in total), 3.50-3.41 (m, 2H), 2.45-2.43 (m, 3H), 2.16-1.99 (m, 2H), 1.42, 1.38 and 1.36 (each s, 9H in total). $^{13}$C NMR (176 MHz, CDCl$_3$): δ=154.50, 153.86, 153.75, 145.45, 145.24, 132.59, 132.55, 130.17, 130.14, 128.00, 95.56, 95.07, 94.54, 94.06, 80.67, 80.33, 67.69, 67.63, 67.58, 62.79, 62.66, 62.52, 44.91, 44.57, 31.18, 31.06, 30.05, 29.93, 28.54, 28.48, 28.44, 28.38, 21.79. MS (ESI): Calcd for C$_{17}$H$_{25}$FNO$_5$S [M+H]$^+$: 374.1, found: 318.1 [M-C(CH$_3$)$_3$+2H]$^+$.

tert-butyl 3-fluoro-2-methylenepyrrolidine-1-carboxylate (6d): To a solution of 6c (706 mg, 1.89 mmol, 1 eq) in glyme (30 mL) was added NaI (850 mg, 5.67 mmol, 3 eq), and DBU (565 μl, 3.78 mmol, 2 eq). The reaction mixture was heated to 95° C. for 3 h, diluted with water, and extracted with Et$_2$O. The combined organic layers were washed with brine, dried over anhydrous Na$_2$SO$_4$, concentrated in vacuo, and used directly without any further purification to obtain crude 6d (332 mg) and used it without further purification. $^1$H NMR (500 MHz, CDCl$_3$): δ=5.55 (br, 1H), 5.28-5.27 (m, 0.5H), 5.17-5.16 (m, 0.5H), 4.75 (d, 1H, J=4.40 Hz), 3.76-3.68 (m, 2H), 2.17-1.94 (m, 2H), 1.51 (s, 9H).

tert-butyl 1,1-dibromo-7-fluoro-4-azaspiro[2.4]heptane-4-carboxylate (6e): The preparation of 6e followed similar procedure for 1e using crude 6d (332 mg, 1.65 mmol, 1 eq), CTAB (6 mg, 0.016 mmol, 0.01 eq), bromoform (0.30 ml, 3.33 mmol, 2 eq) and 50% NaOH (0.7 g in 0.7 ml H$_2$O). The reaction crude was purified by flash chromatography (5-10% EtOAc/hexanes (v/v)) to obtain 6e (292 mg, 47% over two steps, a mixture of diastereomers). $^1$H NMR (500 MHz, CDCl$_3$): δ=5.05-5.04 (m, 0.5H), 4.94 (d, 0.5H, J=3.70 Hz), 3.78 (br, 1H), 3.63-3.13 (br and m, 2H in total), 2.14-2.04 (m, 2H), 1.35 (s, 9H). $^{13}$C NMR (176 MHz, CDCl$_3$): δ=153.84, 97.57, 96.51, 95.89, 81.27, 80.37, 54.50, 54.35, 53.47, 46.56, 45.30, 31.67, 31.60, 28.67, 28.45, 28.41, 28.35, 28.31, 28.23. MS (ESI): Calcd for C$_{11}$H$_{17}$Br$_2$FNO$_2$ [M+H]$^+$: 374.0, found: 317.9 [M-C(CH$_3$)$_3$+2H]$^+$.

tert-butyl 1-bromo-7-fluoro-4-azaspiro[2.4]heptane-4-carboxylate (6f): The preparation of 6f followed similar procedure for 1f using 6e (189 mg, 0.51 mmol, 1 eq), 2.0 M iPrMgCl (0.3 ml, 0.60 mmol, 1.2 eq) in dry THF (5 ml). The reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 6f (150 mg), which was used without further purification. The formation of 6f was confirmed by MS. MS (ESI): Calcd for C$_{11}$H$_{18}$BrFNO$_2$ [M+H]$^+$: 294.0, found: 238.0 [M-C(CH$_3$)$_3$+2H]$^+$.

tert-butyl 7-fluoro-4-azaspiro[2.4]hept-1-ene-4-carboxylate (6g): The preparation of 6g followed similar procedure for 2g using crude 6f (150 mg, 0.51 mmol, 1 eq), tBuOK (86 mg, 0.77 mmol, 1.5 eq) in dry THF (10 ml). Additional tBuOK was added if necessary and the reaction was monitored by MS. The reaction crude was purified by flash chromatography (10% to 20% EtOAc/hexanes (v/v)) to obtain 6g (18 mg, 17% over two steps). $^1$H NMR (700 MHz, CDCl$_3$): δ=7.50-7.41 (br, 2H), 4.44-4.43 (m, 0.5H), 4.36-4.35 (m, 0.5H), 3.57-3.55 (m, 2H), 2.22-2.07 (m, 2H), 1.39

(s, 9H). ¹³C NMR (176 MHz, CDCl₃): δ=154.63, 115.78, 115.22, 98.92, 97.90, 79.50, 47.50, 47.35, 43.25, 36.76, 29.83, 29.39, 29.27, 28.64, 28.11, 24.81, 23.50. MS (ESI): Calcd for $C_{11}H_{16}FKNO_3$ [M+K]⁺: 252.1, found: 252.0.

Scheme 34

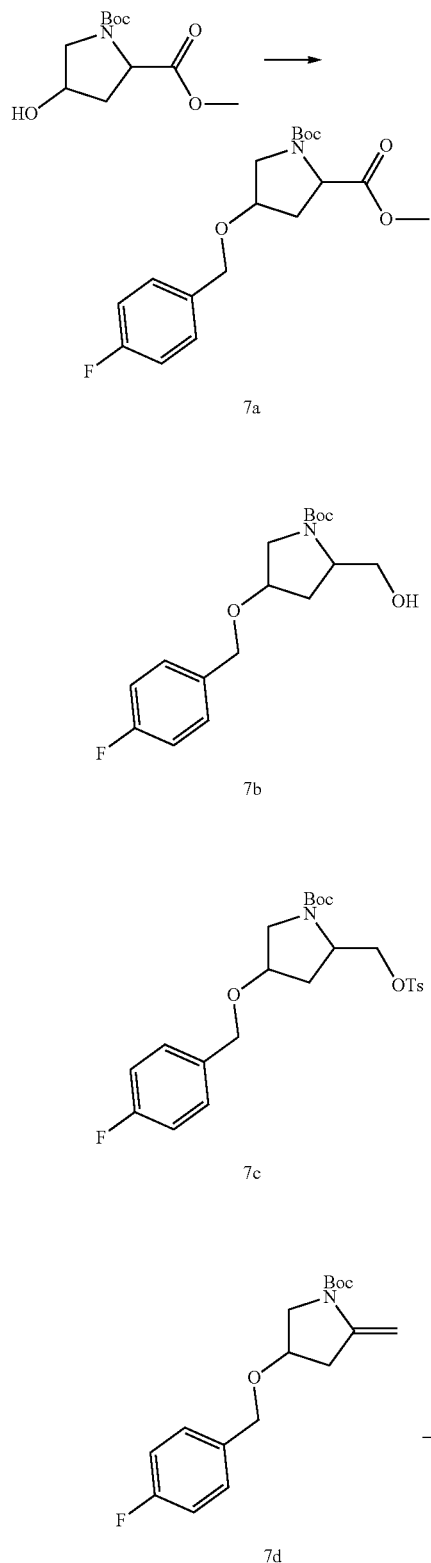

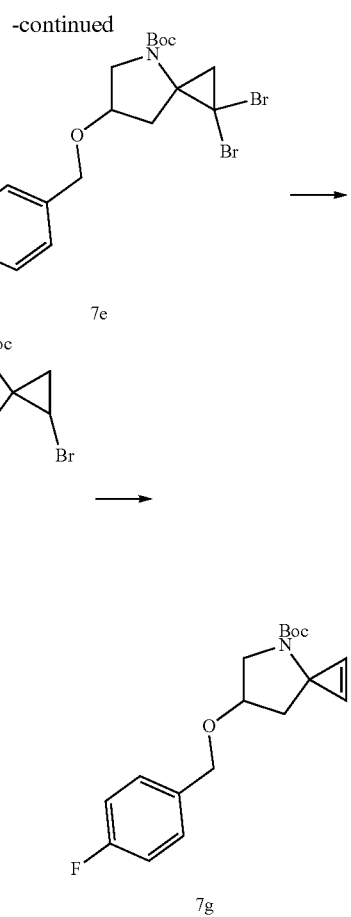

1-(tert-butyl) 2-methyl 4-((4-fluorobenzyl)oxy)pyrrolidine-1,2-dicarboxylate (7a): The preparation of 7a followed similar procedure for 2a using 1-(tert-butyl) 2-methyl 4-hydroxypyrrolidine-1,2-dicarboxylate (5.40 g, 22.04 mmol, 1 eq), tetrabutylammonium iodide (2.44 g, 6.61 mmol, 0.3 eq), 4-fluorobenzyl bromide (4.2 ml, 33.06 mmol, 1.5 eq), THF (140 mL) and NaH (1.60 g, 26.45 mmol, 1.2 eq). The reaction crude was purified by flash chromatography (10-30% EtOAc/hexanes(v/v)) to obtain 7a (6.50 g, 84%). ¹H NMR (400 MHz, CDCl₃): δ=7.29-7.26 (m, 2H), 7.04-7.00 (m, 2H), 4.50-4.33 (m, 3H), 4.18-4.09 (m, 1H), 3.73-3.50 (m, 5H), 2.41-2.31 (m, 1H), 2.09-2.04 (m, 1H), 1.47, 1.45, 1.40 (each s, 9H in total). ¹³C NMR (101 MHz, CDCl₃): δ=173.71, 173.48, 163.75, 161.31, 154.48, 153.90, 133.60, 129.56, 129.47, 129.38, 115.59, 115.38, 80.39, 76.22, 70.65, 70.56, 58.11, 57.70, 52.37, 52.16, 51.96, 51.40, 36.82, 35.65, 28.50, 28.36, 28.28. MS (ESI): Calcd for $C_{18}H_{25}FNO_5$ [M+H]⁺: 354.2, found: 354.1 [M-Boc+2H]⁺.

tert-butyl 4-((4-fluorobenzyl)oxy)-2-(hydroxymethyl)pyrrolidine-1-carboxylate (7b): The preparation of 7b followed similar procedure for 1b using 7a (2.80 g, 7.92 mmol, 1 eq), LAH (331 mg, 8.71 mmol, 1.1 eq) in THF (30 ml). After workup with 2M HCl and extracted with DCM, the organic layer was collected and dried over Na₂SO₄, concentrated in vacuo, the crude 7b was obtained (2.52 g). The formation of 7b was confirmed by MS. MS (ESI): Calcd for $C_{17}H_{25}FNO_4$ [M+H]: 326.2, found: 270.0 [M-C(CH₃)₃+2H]⁺.

tert-butyl 4-((4-fluorobenzyl)oxy)-2-((tosyloxy)methyl)pyrrolidine-1-carboxylate (7c): The preparation of 7c followed similar procedure for 1c using the crude 7b (2.52 g, 7.74 mmol, 1 eq), TsCl (7.36 g, 38.7 mmol, 5 eq) in pyridine (20 ml). The reaction crude was purified by flash chromatography (20% to 30% EtOAc/hexanes (v/v)) to obtain 7c (3.00 g, 79% over two steps). $^1$H NMR (700 MHz, CDCl$_3$): δ=7.74 (s, 2H), 7.34-7.26 (m, 4H), 7.02-7.01 (m, 2H), 4.46-4.38 (m, 2H), 4.33-4.31 (m, 0.5H), 4.16-4.04 (m, 3.5H), 3.71-3.70 (m, 0.5H), 3.47-3.39 (m, 1H), 3.28-3.26 (m, 0.5H), 2.43 and 2.40 (s, 3H in total), 2.15-2.04 (m, 2H), 1.40 and 1.34 (each s, 9H in total). $^{13}$C NMR (176 MHz, CDCl$_3$): δ=163.18, 161.78, 154.56, 154.27, 145.12, 144.95, 133.79, 133.71, 132.86, 130.03, 129.93, 129.58, 129.54, 129.49, 129.44, 128.02, 127.96, 115.49, 115.37, 80.34, 80.02, 76.63, 75.95, 70.60, 70.56, 70.43, 70.37, 54.93, 54.82, 52.28, 51.47, 35.23, 33.86, 28.48, 28.35, 21.74.

tert-butyl 4-((4-fluorobenzyl)oxy)-2-methylenepyrrolidine-1-carboxylate (7d): The preparation of 7d followed similar procedure for 1d using 7c (1.92 g, 4.01 mmol, 1 eq), NaI (1.80 g, 12.03 mmol, 3 eq), DBU (1.20 ml, 8.02 mmol, 2 eq) in glyme (27 ml). The reaction was quenched by adding H$_2$O, followed by extraction with ether. The organic layer was collected and washed with brine twice, dried over Na$_2$SO$_4$, concentrated in vacuo, the crude 7d was obtained (925 mg). The crude 7d was used without further purification. $^1$H NMR (400 MHz, CNCD$_3$): δ=7.37-7.32 (m, 2H), 7.11-7.06 (m, 2H), 5.19 (br, 1H), 4.47 (s, 2H), 4.30 (s, 1H), 4.03-4.02 (m, 1H), 3.73-3.62 (m, 2H), 2.77-2.72 (m, 1H), 2.65 and 2.61 (each s, 1H in total), 1.47 (s, 9H).

tert-butyl 1,1-dibromo-6-((4-fluorobenzyl)oxy)-4-azaspiro[2.4]heptane-4-carboxylate (7e): The preparation of 7e followed similar procedure for 1e using crude 7d (925 mg, 3.01 mmol, 1 eq), CTAB (16.5 mg, 0.045 mmol, 0.015 eq), bromoform (0.54 ml, 6.02 mmol, 2 eq) and 50% NaOH (1.48 ml). The reaction crude was purified by flash chromatography (10% EtOAc/hexanes (v/v)) to obtain 7e (499 mg, 26% over two steps). $^1$H NMR (500 MHz, CDCl$_3$): δ=7.33-7.30 (m, 2H), 7.06-7.02 (m, 2H), 4.51 (s, 2H), 4.27-4.22 (m, 1H), 3.78-3.54 (m, 2H), 2.57-2.54 (m, 1H), 2.24-2.20 (m, 1H), 1.88 (d, 1H, J=9.50 Hz), 1.60 (s, 1H), 1.43 (s, 9H). $^{13}$C NMR (126 MHz, CDCl$_3$): δ=163.59, 161.63, 153.67, 133.58, 133.56, 129.74, 129.67, 115.62, 115.45, 74.52, 71.24, 53.56, 52.62, 50.82, 35.64, 28.50, 28.19. MS (ESI): Calcd for C$_{18}$H$_{23}$Br$_2$FNO$_3$ [M+H]$^+$: 480.0, found: 423.9 [M-C(CH$_3$)$_3$+2H]$^+$.

tert-butyl 1-bromo-6-((4-fluorobenzyl)oxy)-4-azaspiro[2.4]heptane-4-carboxylate (7f): The preparation of 7f followed similar procedure for 1f using 7e (170 mg, 0.36 mmol, 1 eq), 2.0 M iPrMgCl (0.21 ml, 0.42 mmol, 1.2 eq) in dry THF (4 ml). Additional iPrMgCl was added if necessary and the reaction was monitored by MS. After the complete consumption of the starting material, the reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 7f (140 mg), which was used without further purification. The formation of 7f was confirmed by MS. MS (ESI): Calcd for C$_{18}$H$_{24}$BrFNO$_3$ [M+H]$^+$: 400.1, found: 300.1 [M-Boc+2H]$^+$.

tert-butyl 6-((4-fluorobenzyl)oxy)-4-azaspiro[2.4]hept-1-ene-4-carboxylate (7g): To the solution of crude 7f (140 mg, 0.35 mmol, 1 eq) in dry THF (4 ml) at −78° C., tBuOK (59 mg, 0.53 mmol, 1.5 eq) was added in one portion. The reaction mixture was slowly warmed to r.t. and stirred overnight. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo. We could clearly see the right mass corresponding to 7g on the MS in the crude. However, we cannot isolate it from the crude by using silica gel chromatography.

The formation of 7g was confirmed by MS. MS (ESI): Calcd for C$_{18}$H$_{22}$FKNO$_3$ [M+K]$^+$: 358.1, found: 358.1.

Scheme 35

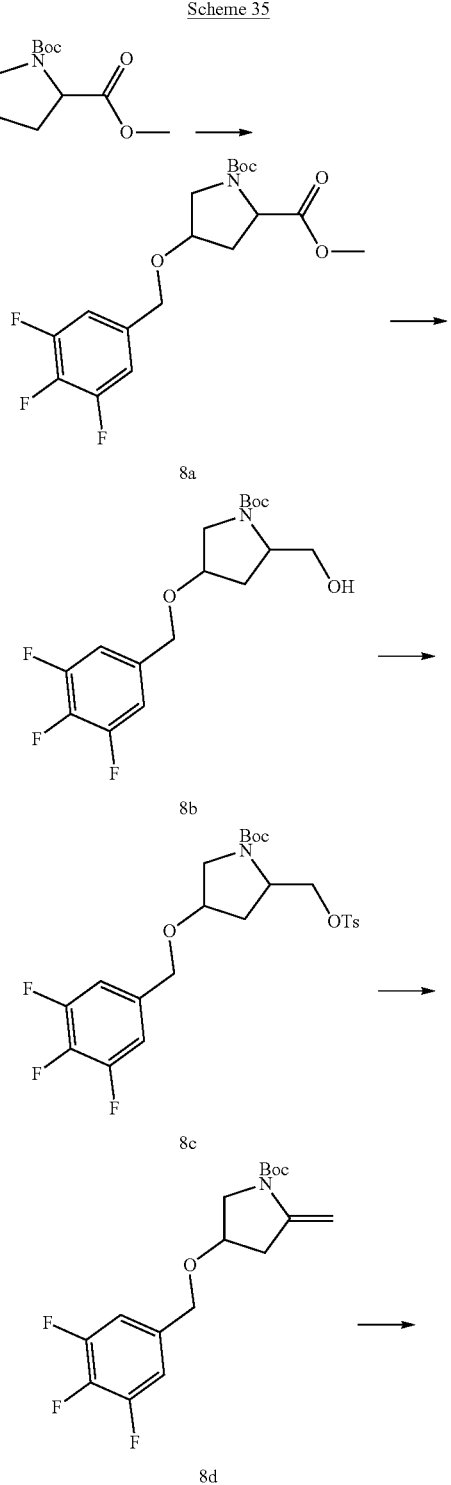

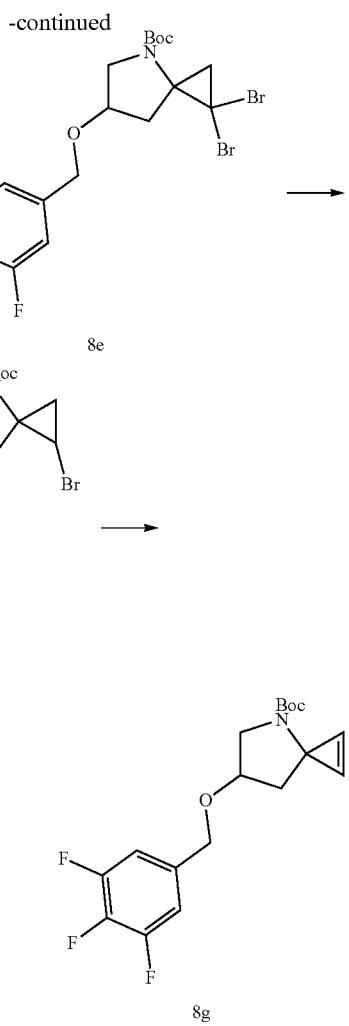

1-(tert-butyl) 2-methyl 4-((3,4,5-trifluorobenzyl)oxy)pyrrolidine-1,2-dicarboxylate (8a): The preparation of 8a followed similar procedure for 2a using 1-(tert-butyl) 2-methyl 4-hydroxypyrrolidine-1,2-dicarboxylate (3.63 g, 14.80 mmol, 1 eq), tetrabutylammonium iodide (1.64 g, 4.44 mmol, 0.3 eq), 3,4,5-trifluorobenzyl bromide (5.0 g, 22.20 mmol, 1.5 eq), THF (100 mL) and NaH (711 mg, 17.76 mmol, 1.2 eq). The reaction crude was purified by flash chromatography (10-30% EtOAc/hexanes(v/v)) to obtain 8a (4.16 g, 72%). $^1$H NMR (400 MHz, CDCl$_3$): δ=6.93 (t, 2H), 4.47-4.34 (m, 3H), 4.15 (br, 1H), 3.74-3.51 (m, 5H), 2.43-2.33 (m, 1H), 2.13-2.04 (m, 1H), 1.46, 1.41 (each s, 9H in total). $^{13}$C NMR (101 MHz, CDCl$_3$): δ=173.60, 173.38, 153.91, 150.10, 140.48, 137.98, 134.30, 111.29, 111.07, 80.59, 69.66, 69.53, 58.07, 57.67, 52.45, 52.24, 51.85, 51.25, 36.85, 35.62, 28.51, 28.37.

tert-butyl 2-(hydroxymethyl)-4-((3,4,5-trifluorobenzyl)oxy)pyrrolidine-1-carboxylate (8b): The preparation of 8b followed similar procedure for 1b using 8a (4.16 g, 10.68 mmol, 1 eq), LAH (446 mg, 11.75 mmol, 1.1 eq) in THF (54 ml). After workup with 2M HCl and extracted with DCM, the organic layer was collected and dried over Na$_2$SO$_4$, concentrated in vacuo, the crude 8b was obtained (3.95 g).

tert-butyl 2-((tosyloxy)methyl)-4-((3,4,5-trifluorobenzyl)oxy)pyrrolidine-1-carboxylate (8c): The preparation of 8c followed similar procedure for 1c using the crude 8b (3.95 g, 10.68 mmol, 1 eq), TsCl (10.10 g, 53.40 mmol, 5 eq) in pyridine (20 ml). The reaction crude was purified by flash chromatography (20% to 25% EtOAc/hexanes (v/v)) to obtain 7c (4.48 g, 81% over two steps). $^1$H NMR (700 MHz, CDCl$_3$): δ=7.75 (t, 2H), 7.35-7.32 (m, 2H), 6.91-6.89 (m, 2H), 4.43-4.32 (m, 2.5H), 4.16-4.04 (m, 3.5H), 3.73-3.71 (m, 0.5H), 3.48-3.41 (m, 1H), 3.27-3.25 (m, 0.5H), 2.43 (s, 3H), 2.17-2.07 (m, 2H), 1.40 and 1.34 (each s, 9H in total). $^{13}$C NMR (176 MHz, CDCl$_3$): δ=154.52, 154.30, 152.02, 151.99, 150.62, 150.60, 150.56, 145.19, 145.02, 139.94, 139.85, 139.76, 138.51, 138.42, 138.34, 134.49, 132.82, 130.06, 129.97, 128.09, 127.96, 111.23, 111.16, 80.52, 80.19, 76.56, 70.56, 70.33, 69.53, 69.37, 54.93, 54.84, 52.21, 51.36, 35.22, 33.80, 28.47, 28.33, 21.74.

tert-butyl 2-methylene-4-((3,4,5-trifluorobenzyl)oxy)pyrrolidine-1-carboxylate (8d): The preparation of 8d followed similar procedure for 1d using 8c (3.28 g, 6.36 mmol, 1 eq), NaI (2.86 g, 19.08 mmol, 3 eq), DBU (1.90 ml, 12.72 mmol, 2 eq) in glyme (43 ml). The reaction was quenched by adding H$_2$O, followed by extraction with ether. The organic layer was collected and washed with brine twice, dried over Na$_2$SO$_4$, concentrated in vacuo, the crude 8d was obtained (1.85 g). The crude 8d was used without further purification. $^1$H NMR (500 MHz, CNCD$_3$): δ=7.08 (t, 2H), 5.20 (br, 1H), 4.46 (s, 2H), 4.31 (s, 1H), 4.04-4.02 (m, 1H), 3.74-3.63 (m, 2H), 2.78-2.73 (m, 1H), 2.66 and 2.62 (each s, 1H in total), 1.47 (s, 9H).

tert-butyl 1,1-dibromo-6-((3,4,5-trifluorobenzyl)oxy)-4-azaspiro[2.4]heptane-4-carboxylate (8e): The preparation of 8e followed similar procedure for 1e using crude 8d (1.85 g, 5.40 mmol, 1 eq), CTAB (30 mg, 0.081 mmol, 0.015 eq), bromoform (0.98 ml, 10.80 mmol, 2 eq) and 50% NaOH (2.75 ml). The reaction crude was purified by flash chromatography (5-10% EtOAc/hexanes (v/v)) to obtain 8e (945 mg, 29% over two steps). $^1$H NMR (400 MHz, CDCl$_3$): δ=6.97 (t, 2H), 4.46 (s, 2H), 4.27-4.21 (m, 1H), 3.83-3.53 (m, 2H), 2.61-2.56 (m, 1H), 2.25-2.20 (m, 1H), 1.90 (d, 1H, J=9.48 Hz), 1.60 (s, 1H), 1.44 (s, 9H). $^{13}$C NMR (101 MHz, CDCl$_3$): δ=153.67, 152.69, 152.65, 152.55, 150.20, 150.16, 150.10, 150.06, 140.53, 138.03, 134.28, 134.23, 111.45, 111.39, 111.29, 111.23, 75.11, 70.10, 53.56, 52.54, 50.75, 35.51, 28.49. MS (ESI): Calcd for C$_{18}$H$_{21}$Br$_2$F$_3$NO$_3$ [M+H]$^+$: 516.0, found: 460.0 [M-C(CH$_3$)$_3$+2H]$^+$.

tert-butyl 1-bromo-6-((3,4,5-trifluorobenzyl)oxy)-4-azaspiro[2.4]heptane-4-carboxylate (8f): The preparation of 8f followed similar procedure for 1f using 8e (590 mg, 1.15 mmol, 1 eq), 2.0 M iPrMgCl (0.69 ml, 1.38 mmol, 1.2 eq) in dry THF (11 ml). Additional iPrMgCl was added if necessary and the reaction was monitored by MS. After the complete consumption of the starting material, the reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 8f (507 mg), which was used without further purification. The formation of 8f was confirmed by MS. MS (ESI): Calcd for C$_{18}$H$_{22}$BrF$_3$NO$_3$ [M+H]$^+$: 436.1, found: 380.0 [M-C(CH$_3$)$_3$+2H]$^+$.

tert-butyl 6-((3,4,5-trifluorobenzyl)oxy)-4-azaspiro[2.4]hept-1-ene-4-carboxylate (8g): To the solution of crude 8f (507 mg, 1.15 mmol, 1 eq) in dry THF (4 ml) at −78° C., tBuOK (196 mg, 1.73 mmol, 1.5 eq) was added in one portion. The reaction mixture was slowly warmed to r.t. and stirred overnight. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo. We could clearly see the right mass corresponding to 8g on the MS in the crude. However, we cannot isolate it from the crude by using silica gel chromatography. The formation of 8g was confirmed by MS. MS (ESI): Calcd for C$_{18}$H$_{20}$F$_3$KNO$_3$ [M+K]$^+$: 394.1, found: 394.0.

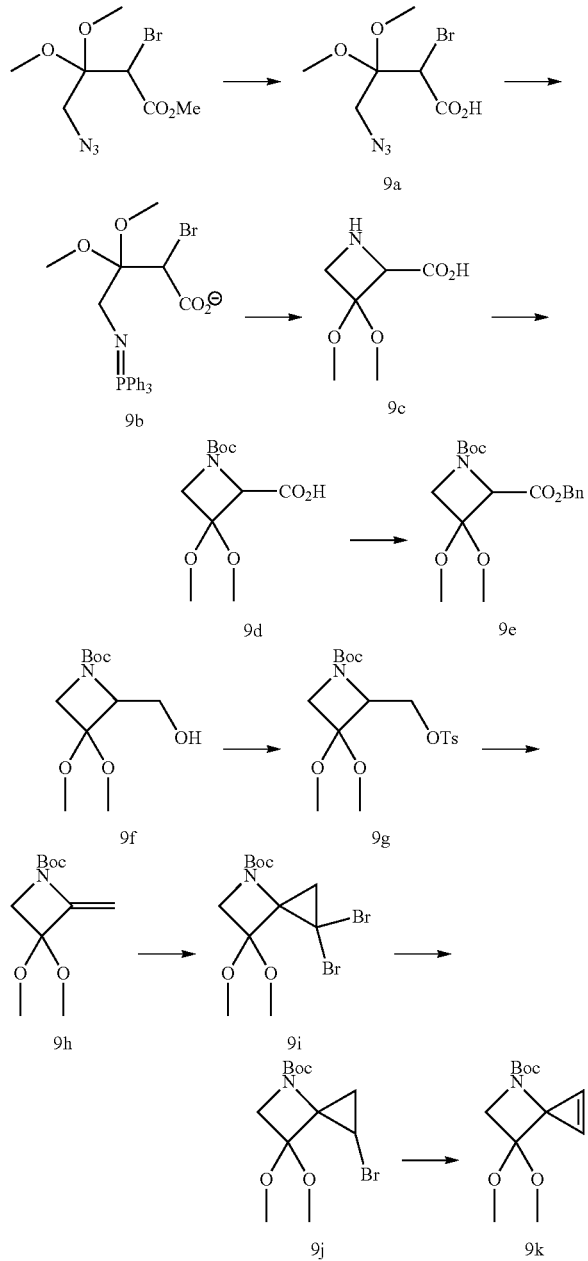

Scheme 36

4-azido-2-bromo-3,3-dimethoxybutanoic acid (9a): Into a solution of methyl 4-azido-2-bromo-3,3-dimethoxybutanoate (574 mg, 2.04 mmol, 1 eq) in MeOH (6 ml), 1N NaOH (6 ml) was added slowly. The mixture was stirred at room temperature for overnight and the completion of the reaction was confirmed by TLC. The resulting crude was first washed by DCM and then carefully neutralized to pH 2-3 using 2N HCl. The aqueous layer was extracted by DCM twice. Then the combined organic layers were dried over Na$_2$SO$_4$. After concentrated in vacuo, 9a (500 mg) was obtained and used for next step without further purification. $^1$H NMR (400 MHz, CDCl$_3$): δ=4.57 (s, 1H), 3.77 (q, 2H), 3.44 (s, 3H), 3.38 (s, 3H).

2-bromo-3,3-dimethoxy-4-((triphenyl-15-phosphanylidene)amino)butanoate (9b): Into a solution of crude 9a (2.70 g, 10.10 mmol, 1 eq) in THF (10 ml), triethylamine (5.6 ml, 40.40 mmol, 4 eq) was added followed by adding of PPh$_3$ (2.65 g, 10.10 mmol, 1 eq). The resulting mixture was stirred for 17 hours at room temperature. The crude 9b was obtained by filtration as a white solid. After dried at room temperature for 48 h, crude 9b (3.30 g) was used for next step without further purification.

3,3-dimethoxyazetidine-2-carboxylic acid (9c): In to a solution of crude 9b (1.92 g, 3.82 mmol, 1 eq) in THF/H$_2$O (1:1 v/v, 15 ml), NaOH (323 mg, 8.03 mmol, 2.1 eq) was added and the resulting mixture was stirred for 4 h at 85° C. The resulting solution was washed by DCM and concentrated in vacuo to obtain the crude 9c, which was used for next step without further purification. The formation of 9c was confirmed by MS. MS (ESI): Calcd for C$_6$H$_{10}$NNa$_2$O$_4$ [M+Na]$^+$: 206.0, found: 206.1.

1-(tert-butoxycarbonyl)-3,3-dimethoxyazetidine-2-carboxylic acid (9d): Into a solution of crude 9c in 25% NaOH (25 ml), 30% Boc$_2$O (20 ml) was added and the resulting mixture was stirred for 2 days at room temperature before neutralized to pH 6-7. The aqueous layer was extracted with DCM twice and the combined organic layers were dried over Na$_2$SO$_4$. After concentrated in vacuo, crude 9d (900 mg) was obtained and used for next step without further purification. The formation of 9d was confirmed by MS. MS (ESI): Calcd for C$_{11}$H$_{23}$N$_2$O$_6$ [M+NH$_4$]$^+$: 279.2, found: 279.0.

2-benzyl 1-(tert-butyl) 3,3-dimethoxyazetidine-1,2-dicarboxylate (9e): Into an ice-cold solution of crude 9d (921 mg, 3.52 mmol, 1 eq) in THF (8.4 ml), benzyl bromide (0.46 ml, 3.87 mmol, 1 eq) and triethylamine (0.55 ml, 3.87 mmol, 1.1 eq) was added sequentially. The solution was warmed to room temperature overnight. After concentrated in vacuo, the crude mixture was purified by flash chromatography (15-30% EtOAc/hexanes (v/v)) to obtain 9e (720 mg, 35% over four steps). $^1$H NMR (700 MHz, CDCl$_3$): δ=7.37-7.29 (m, 5H), 5.25 (br, 2H), 4.68 (br, 1H), 4.05 (d, 1H, J=8.61 Hz), 3.81 (d, 1H, J=8.61 Hz), 3.31 (s, 3H), 3.16 (s, 3H), 1.42 and 1.36 (each s, 9H in total). $^{13}$C NMR (176 MHz, CDCl$_3$): δ=167.02, 135.82, 128.54, 128.26, 98.26, 80.58, 66.89, 50.27, 49.89, 28.30. MS (ESI): Calcd for C$_{18}$H$_{26}$NO$_6$ [M+H]$^+$: 352.2, found: 296.1 [M-C(CH$_3$)$_3$+2H]$^+$.

tert-butyl 2-(hydroxymethyl)-3,3-dimethoxyazetidine-1-carboxylate (9f): Into an ice-cold solution of 9e (720 mg, 2.05 mmol, 1 eq) in THF (10 ml), LAH (86 mg, 2.26 mmol, 1.1 eq). The reaction mixture was kept at this temperature for at least 1 h. The reaction was monitored by TLC or MS and additional LAH was added if necessary. After completion of the reaction, the crude was poured into ice-cold 1M HCl and extracted by DCM twice. The combined organic layers were dried over Na$_2$SO$_4$ and concentrated in vacuo to obtain crude 9f (552 mg), which was used for next step without further purification. The formation of 9f was confirmed by MS. MS (ESI): Calcd for C$_{11}$H$_{22}$NO$_5$ [M+H]$^+$: 248.1, found: 248.1.

tert-butyl 3,3-dimethoxy-2-((tosyloxy)methyl)azetidine-1-carboxylate (9g): The preparation of 9g followed similar procedure for 1c using the crude 9f (552 mg, 2.23 mmol, 1 eq), TsCl (2.13 g, 11.15 mmol, 5 eq) in pyridine (10 ml). The reaction crude was purified by flash chromatography (20% to 25% EtOAc/hexanes (v/v)) to obtain 9g (630 mg, 77% over two steps). $^1$H NMR (700 MHz, CDCl$_3$): δ=7.79 (d, 2H, J=8.19 Hz), 7.34 (d, 2H, J=8.05 Hz), 4.25-4.15 (m, 3H), 3.77-3.69 (m, 2H), 3.16 (s, 3H), 3.10 (s, 3H), 2.44 (s, 3H), 1.39 (s, 9H). $^{13}$C NMR (176 MHz, CDCl$_3$): δ=165.24, 144.90, 133.00, 129.84, 128.18, 97.93, 80.73, 67.43, 66.22, 57.33, 49.88, 49.54, 28.34, 21.75. MS (ESI): Calcd for C$_{18}$H$_{28}$NO$_7$S [M+H]$^+$: 402.2, found: 346.0 [M-C(CH$_3$)$_3$+2H]$^+$.

tert-butyl 3,3-dimethoxy-2-methyleneazetidine-1-carboxylate (9 h): The preparation of 9 h followed similar procedure for 1d using 9g (422 mg, 1.05 mmol, 1 eq), NaI (473 mg, 3.15 mmol, 3 eq), DBU (0.31 ml, 2.10 mmol, 2 eq) in glyme (10 ml). The reaction was quenched by adding H$_2$O, followed by extraction with ether. The organic layer was collected and washed with brine twice, dried over Na$_2$SO$_4$, concentrated in vacuo, the crude 9 h (216 mg) was obtained. The crude 9 h was used without further purification. $^1$H NMR (500 MHz, CNCD$_3$): δ=4.85 (br, 0.5H), 4.65 (br, 0.5H), 4.45 (d, 1H, J=2.1 Hz), 3.79 (s, 2H), 3.29 (s, 6H), 1.46 (s, 9H).

tert-butyl 1,1-dibromo-6,6-dimethoxy-4-azaspiro[2.3]hexane-4-carboxylate (9i): The preparation of 9i followed similar procedure for 1e using crude 9 h (216 mg, 1.03 mmol, 1 eq), CTAB (5.6 mg, 0.015 mmol, 0.015 eq), bromoform (0.37 ml, 4.12 mmol, 4 eq) and 50% NaOH (0.52 ml). The reaction crude was purified by flash chromatography (10-15% EtOAc/hexanes (v/v)) to obtain 9i (246 mg, 58% over two steps). $^1$H NMR (500 MHz, CDCl$_3$): δ=4.21 (d, 1H, J=9.05 Hz), 3.96 (d, 1H, J=9.05 Hz), 3.43 (s, 3H), 3.36 (s, 3H), 3.03-3.02 (m, 1H), 2.13 (d, 1H, J=9.5 Hz), 1.43 (s, 9H). $^{13}$C NMR (126 MHz, CDCl$_3$): δ=155.01, 101.41, 81.59, 62.97, 57.86, 51.30, 50.82, 28.48, 28.43, 27.15, 25.81. MS (ESI): Calcd for C$_{12}$H$_{20}$Br$_2$NO$_4$ [M+H]$^+$: 402.0, found: 313.8 [M-C(CH$_3$)$_3$—OCH$_3$+H]$^+$.

tert-butyl 1-bromo-6,6-dimethoxy-4-azaspiro[2.3]hexane-4-carboxylate (9j): The preparation of 9j followed similar procedure for 1f using 9i (123 mg, 0.31 mmol, 1 eq), 2.0 M iPrMgCl (0.18 ml, 0.37 mmol, 1.2 eq) in dry THF (3 ml). Additional iPrMgCl was added if necessary and the reaction was monitored by MS. After the complete consumption of the starting material, the reaction was quenched with by saturated NH$_4$Cl. The organic layer was collected and the aqueous layer was further washed with DCM. The combined organic layers were dried over anhydrous Na$_2$SO$_4$, concentrated in vacuo to give crude 9j, which was used without further purification. The formation of 9j was confirmed by MS. MS (ESI): Calcd for C$_{12}$H$_{21}$BrNO$_4$ [M+H]$^+$: 322.1, found: 266.0 [M-C(CH$_3$)$_3$+2H]$^+$.

tert-butyl 6,6-dimethoxy-4-azaspiro[2.3]hex-1-ene-4-carboxylate (9k): To the solution of crude 9j (100 mg, 0.31 mmol, 1 eq) in dry THF (3 ml) at −78° C., tBuOK (52 mg, 0.46 mmol, 1.5 eq) was added in one portion. The reaction mixture was slowly warmed to r.t. and stirred overnight. Additional tBuOK was added if necessary. The reaction was quenched with water, concentrated in vacuo, and diluted with DCM. The organic layer was collected and the aqueous layer was further washed with DCM. The combined organic layers were dried over anhydrous Na$_2$SO$_4$, concentrated in vacuo. We could clearly see the right mass corresponding to 9k on the MS in the crude. However, we cannot obtain the pure 9k by HPLC or silica gel column purifications due to its poor stability. Instead, a crude proton NMR was obtained. $^1$H NMR (500 MHz, CNCD$_3$): δ=7.58 (d, 2H), 3.97 (d, 2H), 3.27 (s, 6H), 1.46 (s, 9H). MS (ESI): Calcd for C$_{12}$H$_{20}$NO$_4$ [M+H]$^+$: 242.1, found: 242.1.

Example 7. Cell Based Assay Data

Figure 22:
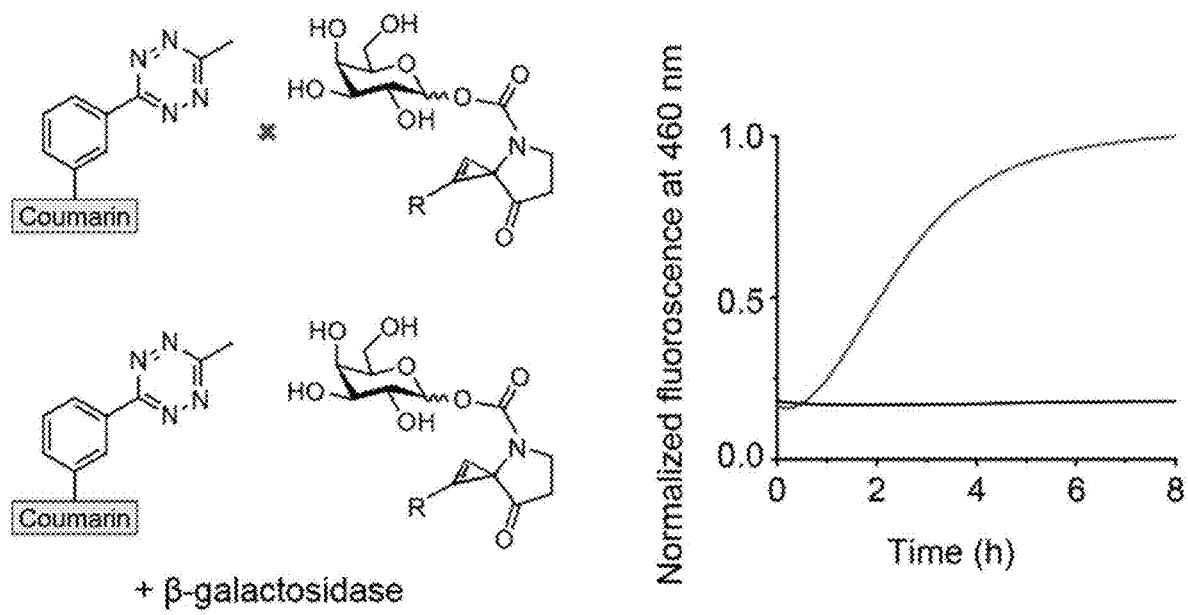
FIG. 22—CP-β-OH (100 μM) and tetrazine-coumarin (20 μM) were mixed in 10% DMSO in PBS (Black curve), and CP-β-OH (100 μM) and tetrazine-coumarin (20 μM) plus β-galactosidase (10 unit) was mixed together in 10% DMSO in PBS (red curve), the reaction was monitored by reading the coumarin's fluorescence intensity every 4 minutes for 8 h at room temperature using a 380 nm excitation filter and 460 nm emission filter.

Ketone cyclopropene (CP-β-OH) connected to β-glucopyranoside group is inert to tetrazine. However, upon deprotection of acetyl group by lipase and cleavage by β-galactosidase, it is activated to react with a tetrazine (FIG. 22).

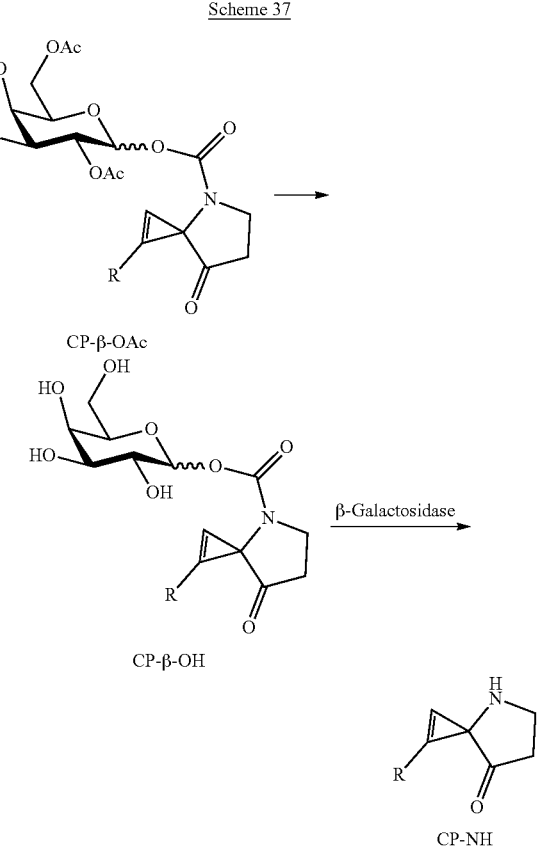

Scheme 37

Figure 23:
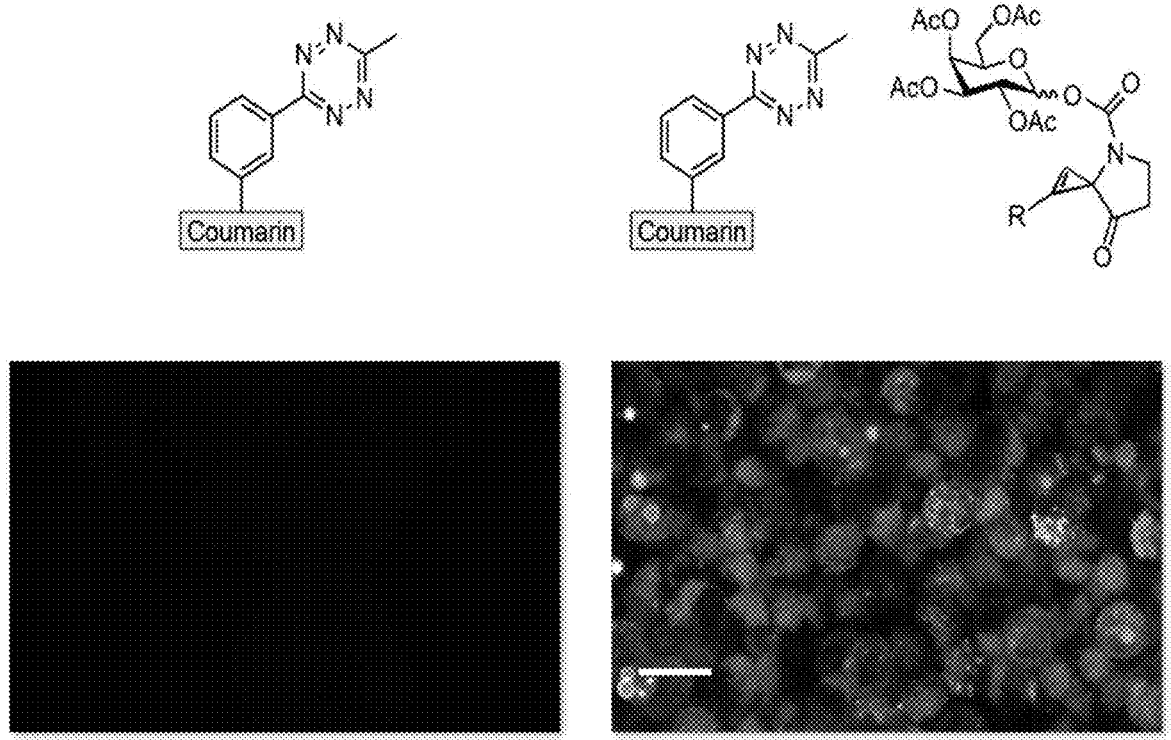
FIG. 23—HEK 293T cells were transfected with β-galactosidase (ordered from Addgene, plasmid number 83943) and then incubated with tetrazine-coumarin alone (20 μM) (left) or CP-β-OH (100 μM) and tetrazine-coumarin (20 μM) (right) for around 16 hours. Then cells are washed twice with pre-warmed PBS and imaged on the confocal microscopy with a 20× NA 0.5 water immersion objective and with 50 ms exposure time. The resulting confocal images were analyzed using ImageJ (NIH) to produce maximum intensity z projections and prepared for presentation using Adobe Illustrator. Scale bar 20 μm.

Ketone cyclopropene (CP-β-OH) connected to β-glucopyranoside group is inert to tetrazine. However, upon deprotection of acetyl group by lipase and cleavage by D-galactosidase, it is activated to react with a tetrazine (FIG. 23). This data confirms compatibility of the technology with living mammalian cells for enzyme induced activation of bioorthogonal reactivity. In this experiment, HEK293T cells were transfected with a plasmid encoding the enzyme β-galactosidase. One group of cells was bathed with a coumarin-tetrazine (20 um) and the other group was bathed with a β-galactosidase labile caged cyclopropene (CP-beta-OAc (100 uM)) and tetrazine-coumarin (20 uM). The cells were incubated for 16 hours, at which point CP-beta-OAc had entered the cells and become activated through the action of β-galactosidase to form the reactive cyclopropene (CP-NH), which reacted with the supplied profluorescent tetrazine to turn on the coumarin fluorescent signal.

DISCUSSION

Disclosed herein are cyclopropenes as modular activatable bioorthogonal reagents. Modification of the molecule design permits control of their reactivity, the stimulus (or stimuli) that activate them, and modular activation, i.e., by different wavelengths, enzymes, or metabolic by-products.

This technology enables targeting and release of bioorthogonal reactivity at specified times and places in biological systems. This has the potential to enrich many approaches that utilize bioorthogonal chemistry. For example, bioorthogonal chemistry is routinely used to visualize the localization and production of glycans during disease and development using monosaccharides tagged with bioorthogonal groups. The described technology will enable delivery of the tagged monosaccharides to only cell types of interest (e.g., only in a particular type of neuron, a cancer cell, or a particular cell type in the gut) to the experimenter by expressing an uncaging enzyme only in that cell type. In another example, bioorthogonal chemistry is frequently employed to label biomolecules of interest for analysis by proteomics. The technology described herein will enable researchers to control the cell type, subcellular localization, and/or time that the reaction occurs to obtain fine control of the dataset. The described technology could also enable the targeting of bioorthogonal reactions to cells and tissues for therapeutic applications. For example, uncaging of the bioorthogonal reactivity by an enzyme released by diseased cells to permit reaction in that cellular environment for diagnostics or drug delivery.

Figure 24:
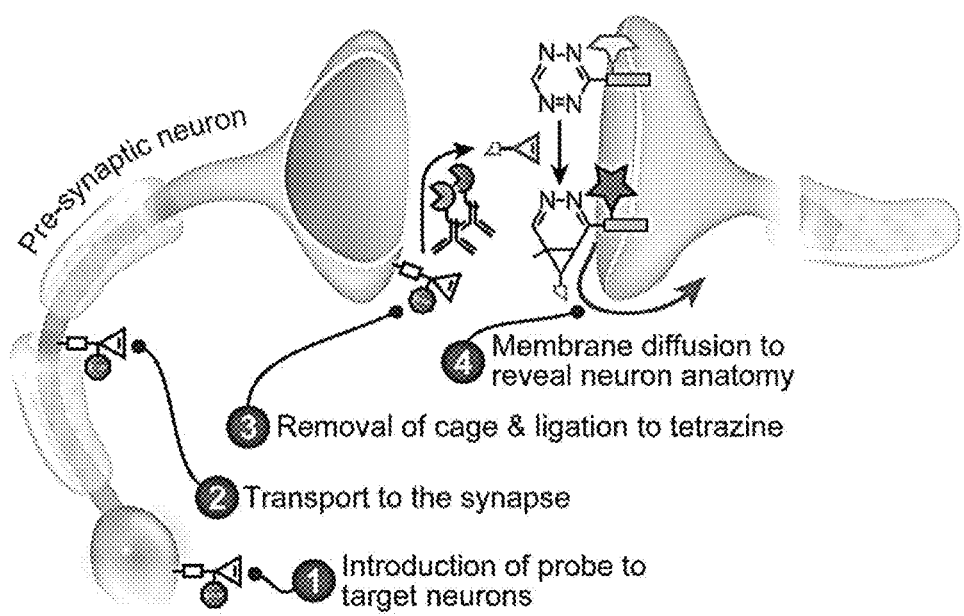
FIG. 24—Schematic describing a strategy for imaging cell connectivity in post-mortem specimens. Release of cyclopropene reactivity at the synapse via a synapse-targeted enzyme activates fluorescence on connected cells.
Figure 25:
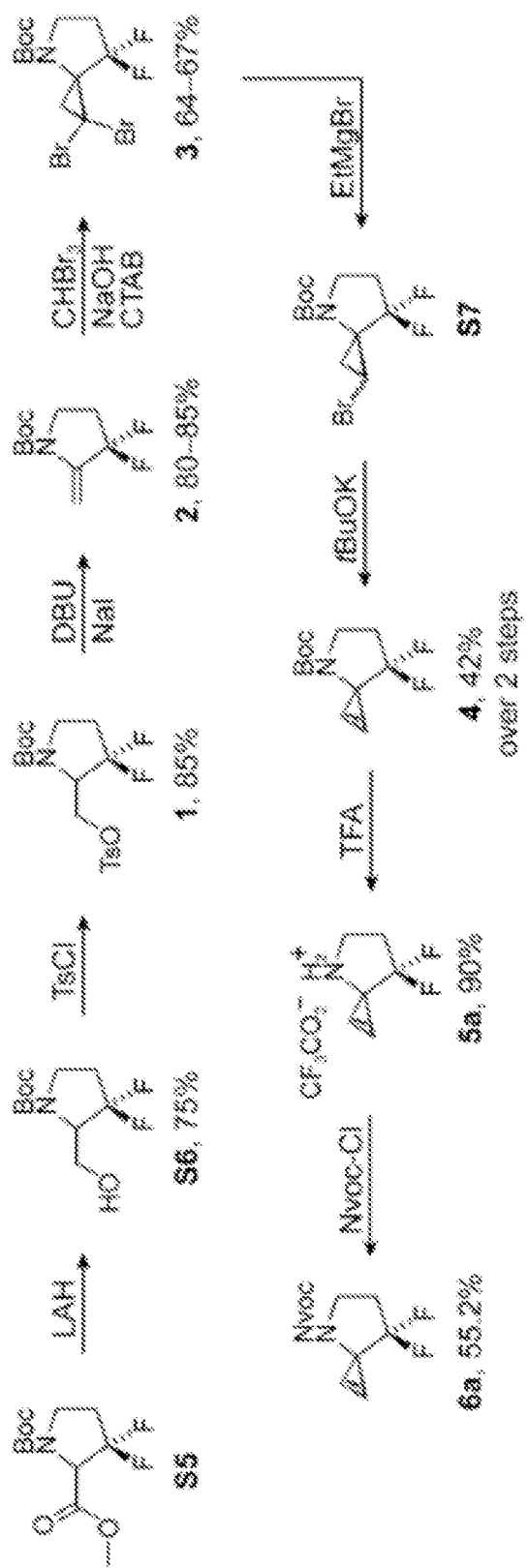
Figure 26:
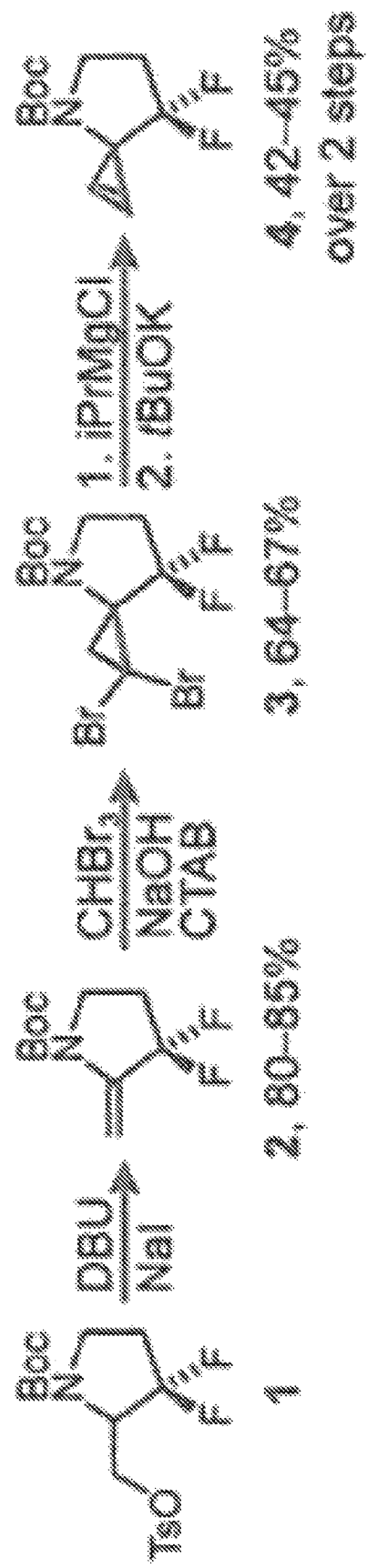
FIG. 26. Scheme 10—Synthesis of Boc-protected 3-N, difluoro spirocyclopropene
Figure 27:
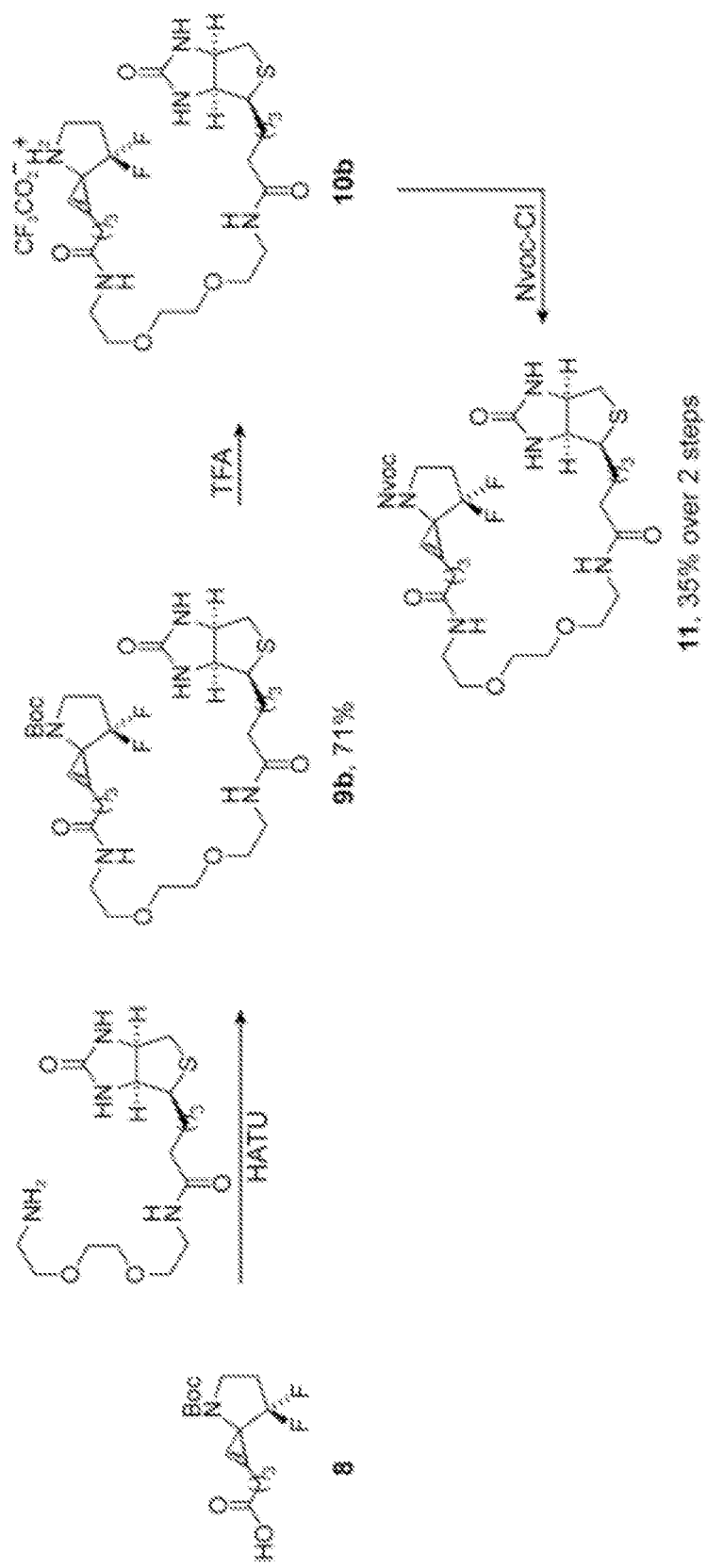
FIG. 27. Scheme 11—Methods for synthesis of compounds 9b, 10b, and 11
Figure 28:
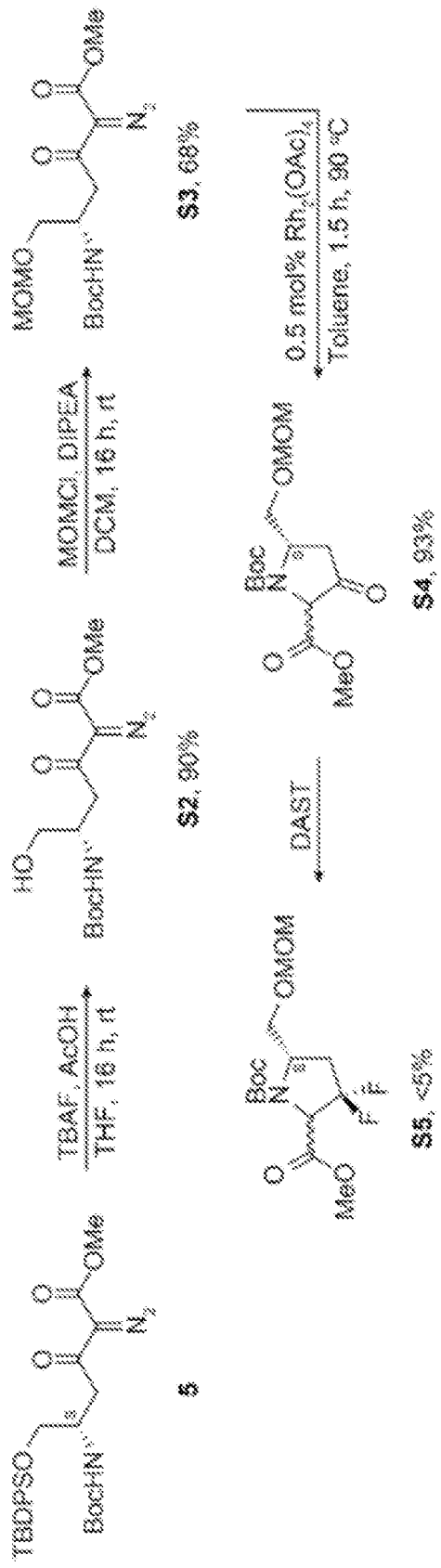
FIG. 28. Scheme 15—Synthesis and characterization of compounds S2-S5
Figure 29:
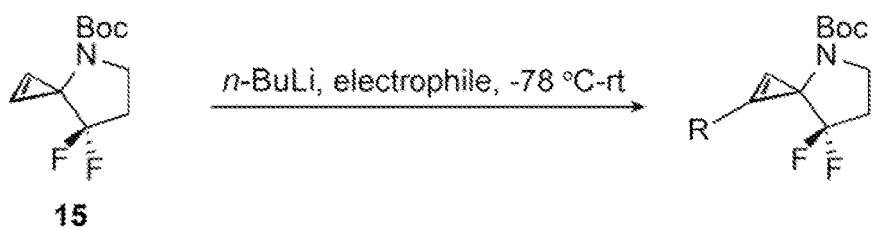
FIG. 29. Scheme 16—Attempts at installation of linker at C1 on cyclopropene 15
Figure 30:
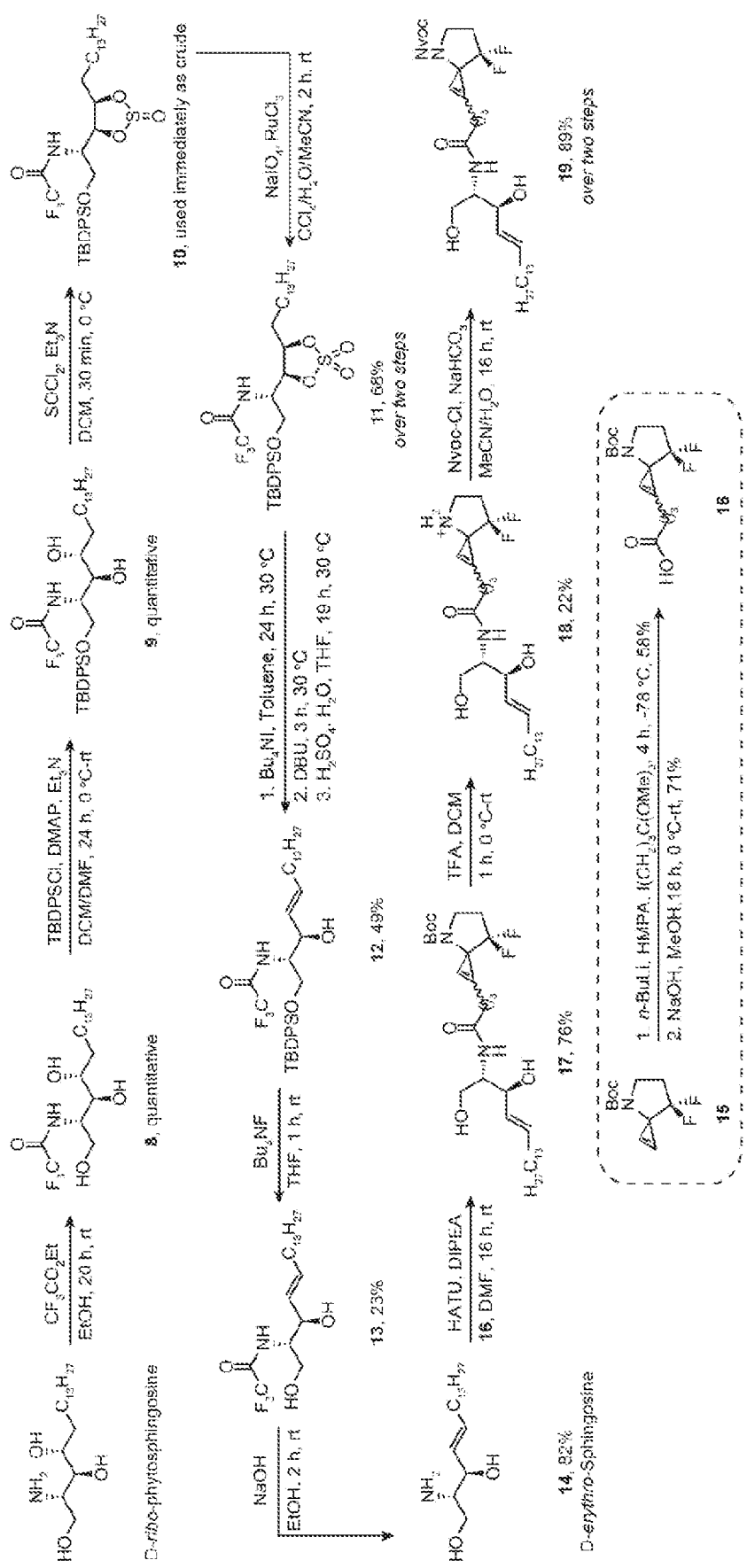
FIG. 30. Scheme 17.—Synthesis of C1-ceramide, photocaged 3-N spirocyclopropene after installation of a C1-acid.
Figure 31:
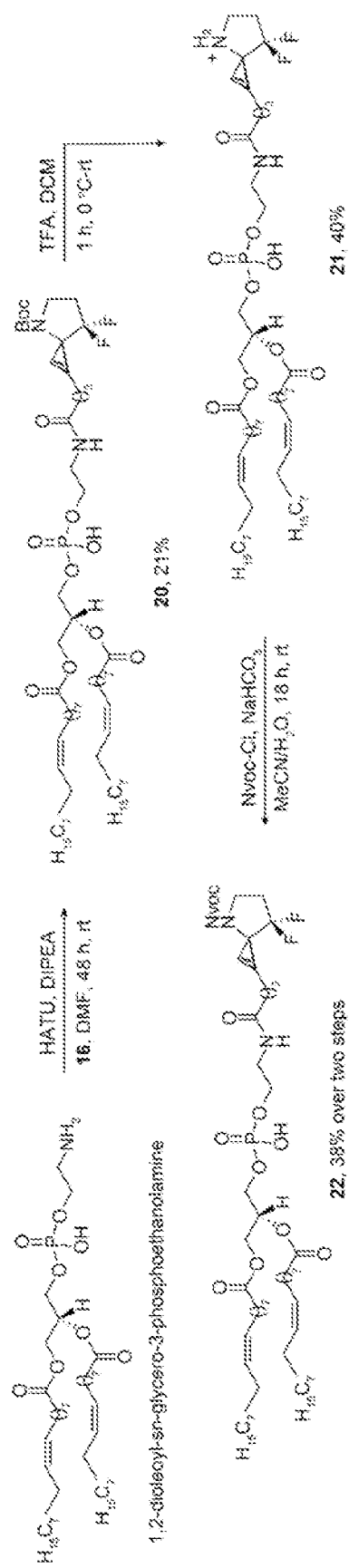
FIG. 31. Scheme 18.—Synthesis of C1-phospholipid, photocaged 3-N spirocyclopropene via a C1-acid containing cyclopropene.
Figure 32:
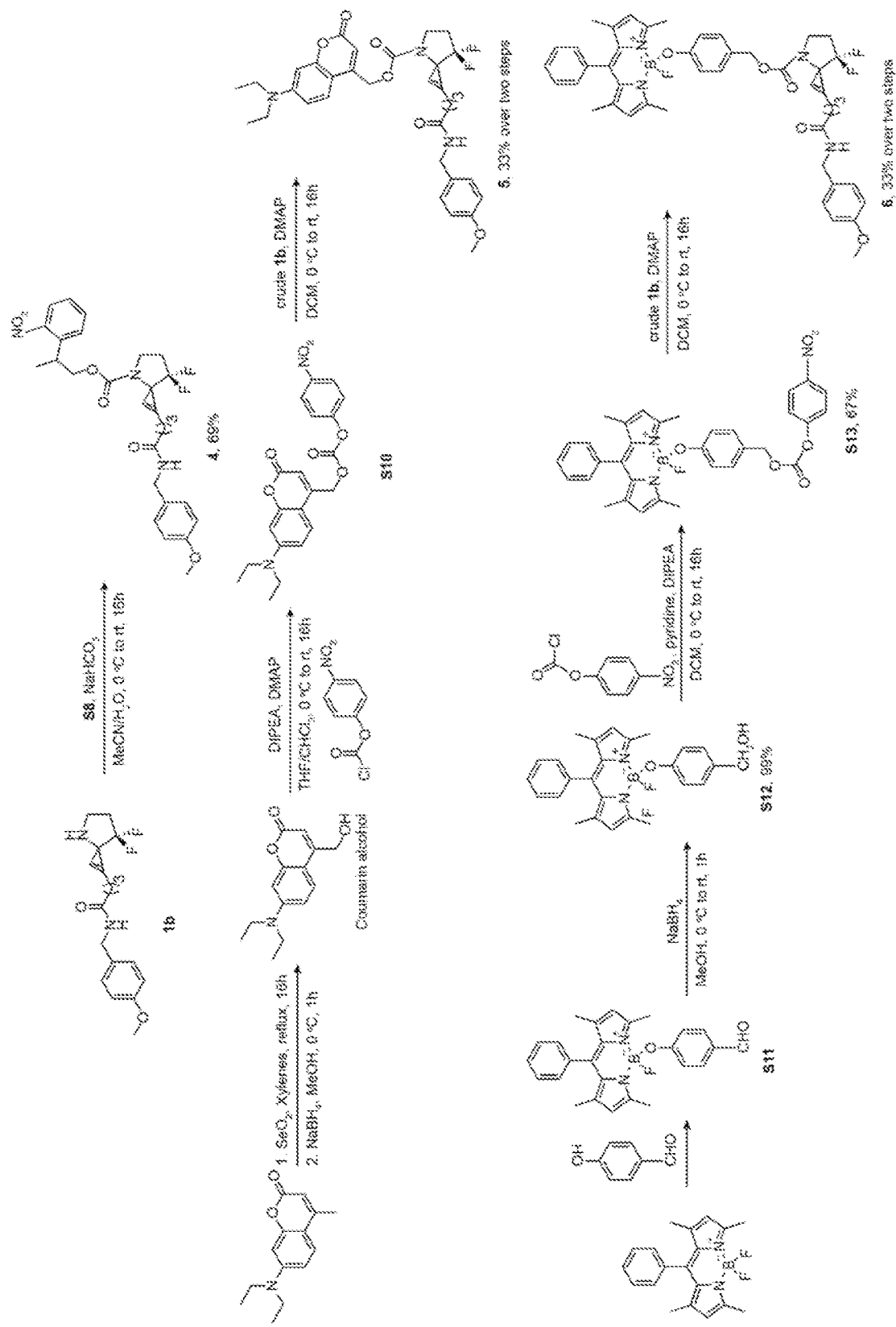
FIG. 32. Scheme 19—Methods synthesis of compounds 4, 5, S11, S12, S13 and 6.

Another anticipated use of this technology that is currently not possible with any existing reactions is a strategy for visualizing neural connectivity with light microscopy in fixed specimens, such as the brains and peripheral nervous systems of pre-natal mammals during embryonic development, non-human primates, and, potentially, post-mortem human specimens to better understand the underpinnings of neurological disorders. Essentially, in a manner similar to lipophilic tracer dyes DiO and DiI, delivery of lipid-linked, reactivity-caged reagents to cells of interest is performed where they diffuse throughout the membranes (FIG. 24, Steps 1 & 2). Once the cyclopropenes reach the synapse, an enzyme targeted to the synapse through its conjugation to an antibody liberates the cyclopropenes' reactivity so that it can react with a cognate, lipid-linked pro-fluorescent tetrazine to produce a fluorescent marker on synaptically connected cells (FIG. 24).

In more detail, the proposed strategy combines aspects of lipophilic tracers (e.g., DiI and DiO) and immunohistochemistry, two common methods for interrogating the post-mortem brain (Sparks, D. L. et al. 2000; Lukas, J.-R. et al. 1998), to create lipophilic tracers that report on cell-cell connectivity in fixed specimens. We envision a molecular scaffold containing a lipid anchor and polyethylene glycol spacer (to span the ~200 Å between membranes at the synapse) linked to a caged cyclopropene via a protease consensus sequence. Similar to the routine application of classic lipophilic tracers (which do not label synaptically connected cells), we anticipate applying this lipid to the cell membranes of neurons of interest (Sparks, D. L. et al. 2000; Lukas, J.-R. et al. 1998) or obtaining sparse labeling across a collection of cells by injection of cyclopropene-lipid-coated particles with a modified gene gun (Sherazee, N. et al. 2013). Importantly, labeling target populations of neurons with lipids is routinely done in diverse organisms by simply placing a concentrated solution of the lipid in proximity to the cells of interest for seconds to minutes.

After application of the reactive lipid to the neuron of interest, it will diffuse along the cell's membrane until it reaches the synapse. Once at the synapse, the reactivity of the cyclopropene will be activated by an enzyme that is targeted to the synapse by conjugation to an antibody. Importantly, the choice of antibody has the potential to enable the selection of the type of connection visualized with this system. This would simplify data analysis and enrich the information obtained by providing clues to the molecular identity of the synaptic connection. For example, antibodies directed against Bassoon or PSD-95, which label the components of the synapse called the active zone or post-synaptic density, respectively, could be used to map neural connectivity indiscriminately with respect to synapse type. However, an antibody directed against Shank3, a scaffolding protein localized to the postsynaptic density of excitatory glutamatergic synapses (Sheng, M. et al. 2000), has the potential to reveal connectivity between the cells of interest and cells connected by excitatory glutamatergic synapses. Importantly, antibodies or nanobodies developed in the future that target specific synapse types would be directly applicable to this approach.

Once activated at the synapse, the cyclopropene component reacts with a pro-fluorescent tetrazine on the connected cell and the synapse-targeted protease releases the fluorophore lipid to diffuse throughout the connected neuron's membrane. The pro-fluorescent tetrazine lipid will be uniformly applied throughout the system, a feat facilitated by our ability to use high concentrations, lipid delivery agents such as cyclodextrins, long incubation times, and applied electric fields due to the fixed nature of the specimens (Swift, M. J. et al. 2005).

This method functions in post-mortem specimens. Visualizing the anatomy of neural connectivity in fixed systems presents unique challenges and opportunities compared to doing so in living specimens. This is because the few available strategies for visualizing neuronal connectivity like neurotrophic viruses rely on functional (i.e., living) neurophysiology. The evolution or extension of these current strategies will not provide a convenient method for visualizing neural connectivity in fixed or non-genetically malleable systems, so a novel strategy like that envisioned here is required.

REFERENCES

Abbaspour Tehrani, Kourosch, and Norbert De Kimpe. 2000. "New Synthesis of 2-Methyleneaziridines and 2-Methyleneazetidines by Dimethyl Titanocene Mediated Methylenation of α- and β-Lactams." *Tetrahedron Letters* 41 (12): 1975-78.

Abid, Imen, Pascal Gosselin, Monique Mathé-Allainmat, Souhir Abid, Gilles Dujardin, and Catherine Gaulon-Nourry. 2015. "TBAF-Triggered Aldol-Type Addition of α-Triethylsilyl-α-Diazoacetone." *J. Org. Chem.* 80 (20): 9980-88.

Adams, Julian, and Denice M. Spero. 1991. "Rhodium (II) Catalyzed Reactions of Diazo-Carbonyl Compounds." *Tetrahedron* 47 (10-11): 1765-1808.

Agard, Nicholas J., Jennifer A. Prescher, and Carolyn R. Bertozzi. 2004. "A Strain-Promoted [3+2] Azide-Alkyne Cycloaddition for Covalent Modification of Biomolecules in Living Systems." *J. Am. Chem. Soc.* 126 (46): 15046-47.

Agarwal, Paresh, Brendan J. Beahm, Peyton Shieh, and Carolyn R. Bertozzi. 2015. "Systemic Fluorescence Imaging of Zebrafish Glycans with Bioorthogonal Chemistry." *Angewandte Chemie International Edition* 54 (39): 11504-10.

Amatrudo, Joseph M, Jeremy P Olson, Hitesh K Agarwal, and Graham C R Ellis-Davies. 2015. "Caged Compounds for Multichromic Optical Interrogation of Neural Systems." *The European Journal of Neuroscience* 41 (1): 5-16.

Baird, Mark S., Cynthia M. Dale, William Lytollis, and Michael J. Simpson. 1992. "A New Approach to Cyclopropene Fatty Acids." *Tetrahedron Letters* 33 (11): 1521-22.

Bertus, Philippe, and Jan Szymoniak. 2003. "Ti-Mediated Chemoselective Conversion of Cyanoesters and Cyanoamides into β-Aminoesters and 1-Aza-Spirolactams Bearing a Cyclopropane Ring." *Synlett*, no. 2: 265-67.

Bieberich, Erhard. 2008. "Ceramide Signaling in Cancer and Stem Cells." *Future Lipidology*.

Blackman, Melissa L., Maksim Royzen, and Joseph M. Fox. 2008. "Tetrazine Ligation: Fast Bioconjugation Based on Inverse-Electron-Demand Diels-Alder Reactivity." *J. Am. Chem. Soc.* 130 (41): 13518-19.

Borrmann, Annika, Olumide Fatunsin, Jan Dommerholt, Anika M. Jonker, Dennis W. P. M. Löwik, Jan C. M. van Hest, and Floris L. van Delft. 2015. "Strain-Promoted Oxidation-Controlled Cyclooctyne-1,2-Quinone Cycloaddition (SPOCQ) for Fast and Activatable Protein Conjugation." *Bioconjugate Chemistry* 26 (2): 257-61.

Borrmann, Ruediger, Rene M. Koenigs, Jochen Zoller, and Magnus Rueping. 2017. "Asymmetric Hydrogenation of Cyclic Imines and Enamines: Access to 1,5-Benzodiazepine Pharmacophores." *Synthesis* (Germany) 49 (2): 310-18.

Brasca, Maria Gabriella, Clara Albanese, Raffaella Amici, Dario Ballinari, Luca Corti, Valter Croci, Daniele Fancelli, et al. 2007. "6-Substituted Pyrrolo[3,4-c]Pyrazoles: An Improved Class of CDK2 Inhibitors." *ChemMedChem* 2 (6): 841-52.

Bumpus, Timothy W., and Jeremy M. Baskin. 2017. "Clickable Substrate Mimics Enable Imaging of Phospholipase D Activity." *ACS Central Science* 3 (10): 1070-77.

Cabrera, Ricardo, Oscar Filevich, Beatriz Garcia-Acosta, Jegath Athilingam, Kevin J. Bender, Kira E. Poskanzer, and Roberto Etchenique. 2017. "A Visible-Light-Sensitive Caged Serotonin." *ACS Chemical Neuroscience* 8 (5): 1036-42.

Campbell, Craig D, Rebecca L Greenaway, Oliver T Holton, P Ross Walker, Helen A Chapman, C Adam Russell, Greg Carr, Amber L Thomson, and Edward A Anderson. 2015. "Ynamide Carbopalladation: A Flexible Route to Mono-, Bi- and Tricyclic Azacycles." *Chemistry* (Weinheim an Der Bergstrasse, Germany) 21 (36): 12627-39.

Canepari, M., L. Nelson, G. Papageorgiou, J. E. T. Corrie, and D. Ogden. 2001. "Photochemical and Pharmacological Evaluation of 7-Nitroindolinyl- and 4-Methoxy-7-Nitroindolinyl-Amino Acids as Novel, Fast Caged Neurotransmitters." *Journal of Neuroscience Methods* 112 (1): 29-42.

Carboni, R. A., and R. V. Lindsey. 1959. "Reactions of Tetrazines with Unsaturated Compounds. A New Synthesis of Pyridazines." *J. Am. Chem. Soc.* 81 (16): 4342-46.

Chang, Pamela V., Danielle H. Dube, Ellen M. Sletten, and Carolyn R. Bertozzi. 2010. "A Strategy for the Selective Imaging of Glycans Using Caged Metabolic Precursors." *J. Am. Chem. Soc.* 132 (28): 9516-18.

Chintalapudi, V., E. A. Galvin, R. L. Greenaway, and E. A. Anderson. 2016. "Combining Cycloisomerization with Trienamine Catalysis: A Regiochemically Flexible Enantio- and Diastereoselective Synthesis of Hexahydroindoles." *Chemical Communications* 52 (4): 693-96.

Cole, Christian M, Jun Yang, Jolita Šečkutė, and Neal K Devaraj. 2013. "Fluorescent Live-Cell Imaging of Metabolically Incorporated Unnatural Cyclopropene-Mannosamine Derivatives." *Chembiochem: A European Journal of Chemical Biology* 14 (2): 205-8.

Cordeiro, Alessandra, Ernesto Quesada, Maria-Cruz Bonache, Sonsoles Velazquez, Maria-José Camarasa, and Ana San-Félix. 2006. "A Cyclic Enamine Derived from 1,2-O-Isopropylidene-Alpha-D-Xylofuranose as a Novel Carbohydrate Intermediate to Achieve Skeletal Diversity." *J. Org. Chem.* 71 (19): 7224-35.

Curado, Silvia, Didier Y. R. Stainier, and Ryan M. Anderson. 2008. "Nitroreductase-Mediated Cell/Tissue Ablation in Zebrafish: A Spatially and Temporally Controlled Ablation Method with Applications in Developmental and Regeneration Studies." *Nature Protocols* 3 (6): 948-54.

Debets, Marjoke F, Jan C M van Hest, and Floris P J T Rutjes. 2013. "Bioorthogonal Labelling of Biomolecules: New Functional Handles and Ligation Methods." *Organic & Biomolecular Chemistry* 11 (38): 6439-55.

DeBoer, C. D. 1973. "Polym. Lett. Ed." J. Polym. Sci. 11: 25-27.

Devaraj, Neal K., Ralph Weissleder, and Scott A. Hilderbrand. 2008. "Tetrazine-Based Cycloadditions: Application to Pretargeted Live Cell Imaging." *Bioconjugate Chemistry* 19 (12): 2297-99.

Dieterich, Daniela C, A James Link, Johannes Graumann, David A Tirrell, and Erin M Schuman. 2006. "Selective Identification of Newly Synthesized Proteins in Mammalian Cells Using Bioorthogonal Noncanonical Amino Acid Tagging (BONCAT)." *Proceedings of the National Academy of Sciences of the United States of America* 103 (25): 9482-87.

Doebelin, Christelle, Yuanjun He, and Theodore M Kamenecka. 2016. "Multigram-Scale Synthesis of Enantiopure 3,3-Difluoroproline." *Tetrahedron Letters* 57 (50): 5658-60.

Dowd, Paul, and Avram Gold. 1969. "The Thermal Dimerization of Cyclopropene." *Tetrahedron Letters* 10 (2): 85-86.

Drabek, D, J Guy, R Craig, and F Grosveld. 1997. "The Expression of Bacterial Nitroreductase in Transgenic Mice Results in Specific Cell Killing by the Prodrug CB1954." *Gene Therapy* 4 (2): 93-100.

Dulayymi, Juma'a R. Al, Mark S. Baird, Ivan G. Bolesov, Alexey V. Nizovtsev, and Viacheslav V. Tverezovsky. 2000. "Hydrodehalogenation of 1,1-Dibromocyclopropanes by Grignard Reagents Promoted by Titanium Compounds." *Journal of the Chemical Society. Perkin Transactions* 2, no. 7 (July): 1603-17.

Edwards, Andrew, Marina Rubina, and Michael Rubin. 2016. "Nucleophilic Addition of Cyclopropenes." *Current Organic Chemistry* 20 (18): 1862-77.

Eggert, F, and S Kath-Schorr. 2016. "A Cyclopropene-Modified Nucleotide for Site-Specific RNA Labeling Using Genetic Alphabet Expansion Transcription." *Chemical Communications* (Cambridge, England) 52 (45): 7284-87.

El-Sagheer, Afaf H., and Tom Brown. 2010. "Click Chemistry with DNA." *Chemical Society Reviews*.

Elling, Benjamin R, Jessica K Su, and Yan Xia. 2016. "Ring-Opening Metathesis Polymerization of 1,2-Disubstituted Cyclopropenes." *Chemical Communications* (Cambridge, England) 52 (58): 9097-9100.

Ellis-Davies, Graham C R. 2007. "Caged Compounds: Photorelease Technology for Control of Cellular Chemistry and Physiology." *Nature Methods* 4 (8): 619-28.

Erdmann, Roman S., Hideo Takakura, Alexander D. Thompson, Felix Rivera-Molina, Edward S. Allgeyer, Joerg Bewersdorf, Derek Toomre, and Alanna Schepartz. 2014. "Super-Resolution Imaging of the Golgi in Live Cells with a Bioorthogonal Ceramide Probe." *Angewandte Chemie—International Edition* 53 (38): 10242-46.

Fardis, Maria, Haolun Jin, Salman Jabri, Ruby Z Cai, Michael Mish, Manuel Tsiang, and Choung U Kim. 2006. "Effect of Substitution on Novel Tricyclic HIV-1 Integrase Inhibitors." *Bioorganic & Medicinal Chemistry Letters* 16 (15): 4031-35.

Furuta, Toshiaki, Samuel S. H. Wang, Jami L. Dantzker, Timothy M. Dore, Wendy J. Bybee, Edward M. Callaway, Winfried Denk, and Roger Y. Tsien. 1999. "Brominated 7-Hydroxycoumarin-4-Ylmethyls: Photolabile Protecting Groups with Biologically Useful Cross-Sections for Two Photon Photolysis." *Proceedings of the National Academy of Sciences of the United States of America* 96 (4): 1193-1200.

Gahtory, Digvijay, Rickdeb Sen, Andriy R. Kuzmyn, Jorge Escorihuela, and Han Zuilhof. 2018. "Strain-Promoted Cycloaddition of Cyclopropenes with o-Quinones: A Rapid Click Reaction." *Angewandte Chemie—International Edition* 57 (32): 10118-22.

Goswami, Pratik P., Aleem Syed, Christie L. Beck, Toshia R. Albright, Kaitlyn M. Mahoney, Ryan Unash, Emily A. Smith, and Arthur H. Winter. 2015. "BODIPY-Derived Photoremovable Protecting Groups Unmasked with Green Light." *J. Am. Chem. Soc.* 137 (11): 3783-86.

Granik, Vladimir G., Vadim A. Makarov, and Cyril Párkányi. 1998. "Enamines as Synthons in the Synthesis of Heterocycles." *Advances in Heterocyclic Chemistry* 72 (January): 283-359.

Greenaway, Rebecca L., Craig D. Campbell, Helen A. Chapman, and Edward A. Anderson. 2012. "Reductive Cyclization of Bromoenynamides with Alcohols as Hydride Source: Synthesis and Reactions of 2-Amidodienes." *Advanced Synthesis & Catalysis* 354 (17): 3187-94.

Grimm, Jonathan B., Todd D. Gruber, Gloria Ortiz, Timothy A. Brown, and Luke D. Lavis. 2016. "Virginia Orange: A Versatile, Red-Shifted Fluorescein Scaffold for Single- and Dual-Input Fluorogenic Probes." *Bioconjugate Chemistry* 27 (2): 474-80.

Gruber, Todd D, Chithra Krishnamurthy, Jonathan B Grimm, Michael R Tadross, Laura M Wysocki, Zev J Gartner, and Luke D Lavis. 2018. "Cell-Specific Chemical Delivery Using a Selective Nitroreductase-Nitroaryl Pair." *ACS Chemical Biology* 13 (10): 2888-96.

Guo, Fenghai, Michael D Clift, and Regan J Thomson. 2012. "Oxidative Coupling of Enolates, Enol Silanes and Enamines: Methods and Natural Product Synthesis." *European Journal of Organic Chemistry* 2012 (26): 4881-96.

Hao, Pan, Intisar Q M Alaraj, Juma'a R Al Dulayymi, Mark S Baird, Jing Liu, and Qun Liu. 2016. "Sterculic Acid and Its Analogues Are Potent Inhibitors of *Toxoplasma Gondii*." *The Korean Journal of Parasitology* 54 (2): 139-45.

Hazelden, Ian R, Xiaofeng Ma, Thomas Langer, and John F Bower. 2016. "Diverse N-Heterocyclic Ring Systems via Aza-Heck Cyclizations of N-(Pentafluorobenzoyloxy)Sulfonamides." *Angewandte Chemie* (International Ed. in English) 55 (37): 11198-202.

Herner, András, and Qing Lin. 2016. "Photo-Triggered Click Chemistry for Biological Applications." *Topics in Current Chemistry*. Springer International Publishing.

Izquierdo, Eduardo, and Antonio Delgado. 2018. "Click Chemistry in Sphingolipid Research." *Chemistry and Physics of Lipids*. Elsevier Ireland Ltd.

Jiang, Heng, Jian He, Tao Liu, and Jin-Quan Yu. 2016. "Ligand-Enabled γ-C(Sp(3))-H Olefination of Amines: En Route to Pyrrolidines." *J. Am. Chem. Soc.* 138 (6): 2055-59.

Jiang, Ting, Pratik Kumar, Wei Huang, Wei-Siang Kao, Adrian O. Thompson, Frank M. Camarda, and Scott T. Laughlin. 2019. "Modular Enzyme- and Light-Based Activation of Cyclopropene-Tetrazine Ligation." *ChemBioChem* 20 (17): 2222-26.

Jiang, Xiqian, Jianwei Chen, Aleksandar Bajid, Chengwei Zhang, Xianzhou Song, Shaina L. Carroll, Zhao Lin Cai, et al. 2017. "Quantitative Real-Time Imaging of Glutathione." *Nature Communications* 8 (July).

Kamber, David N., Yong Liang, Robert J. Blizzard, Fang Liu, Ryan A. Mehl, K. N. Houk, and Jennifer A. Prescher. 2015. "1,2,4-Triazines Are Versatile Bioorthogonal Reagents." *J. Am. Chem. Soc.* 137 (26): 8388-91.

Kamber, David N, Lidia A Nazarova, Yong Liang, Steven A Lopez, David M Patterson, Hui-Wen Shih, K N Houk, and Jennifer A Prescher. 2013. "Isomeric Cyclopropenes Exhibit Unique Bioorthogonal Reactivities." *J. Am. Chem. Soc.* 135 (37): 13680-83.

Kantevari, Srinivas, Masanori Matsuzaki, Yuya Kanemoto, Haruo Kasai, and Graham C R Ellis-Davies. 2010. "Two-Color, Two-Photon Uncaging of Glutamate and GABA—Supplementary Information." *Nature Methods* 7 (2): 123-25.

Kantevari, Srinivas, Stefan Passlick, Hyung-Bae Kwon, Matthew T Richers, Bernardo L Sabatini, and Graham C R Ellis-Davies. 2016. "Development of Anionically Decorated Caged Neurotransmitters: In Vitro Comparison of 7-Nitroindolinyl- and 2-(p-Phenyl-o-Nitrophenyl)Propyl-Based Photochemical Probes." *Chembiochem: A European Journal of Chemical Biology* 17 (10): 953-61.

Kao, James, and Leo Radom. 1978. "An Ab Initio Molecular Orbital Study of Structures and Energies of Spiro Compounds: Spiropentane, Spiropentene, Spiropentadiene, Spiro [2.4]Hepta-4,6-Diene, Spiro[2.4]Heptatriene, and Spiro[4.4]Nonatetraene." *J. Am. Chem. Soc.* 100 (3): 760-67.

Karver, Mark R, Ralph Weissleder, and Scott A Hilderbrand. 2011. "Synthesis and Evaluation of a Series of 1,2,4,5-Tetrazines for Bioorthogonal Conjugation." *Bioconjugate Chemistry* 22 (11): 2263-70.

Kaur, Gurpreet, Gurjaspreet Singh, and Jandeep Singh. 2018. "Photochemical Tuning of Materials: A Click Chemistry Perspective." *Materials Today Chemistry*. Elsevier Ltd.

Kaya, Ferdinand, Abdelkrim Mannioui, Albert Chesneau, Sowmya Sekizar, Emmanuelle Maillard, Chantal Ballagny, Ludivine Houel-Renault, et al. 2012. "Live Imaging of Targeted Cell Ablation in *Xenopus*: A New Model to Study Demyelination and Repair." *The Journal of Neuroscience: The Official Journal of the Society for Neuroscience* 32 (37): 12885-95.

Kim, Ryan, William M. Sherrill, and Michael Rubin. 2010. "Ring-Retentive Deprotonation of Cyclopropene-3-Carboxamides." *Tetrahedron* 66 (27-28): 4947-53.

Kimpe, Norbert De, and Marc Boeykens. 1994. "Synthesis of .Beta.-Lactam Derivatives by Cycloaddition of 2-Methyleneazetidines with Azides." *J. Org. Chem.* 59 (18): 5189-91.

Kitani, Satoru, Kazuki Sugawara, Ken Tsutsumi, Tsumoru Morimoto, and Kiyomi Kakiuchi. 2008. "Synthesis and Characterization of Thiochromone S,S-Dioxides as New Photolabile Protecting Groups." *Chemical Communications* (Cambridge, England), no. 18 (May): 2103-5.

Klán, Petr, Tomáš Šolomek, Christian G. Bochet, Aurélien Blanc, Richard Givens, Marina Rubina, Vladimir Popik, Alexey Kostikov, and Jakob Wirz. 2013. "Photoremovable Protecting Groups in Chemistry and Biology: Reaction Mechanisms and Efficacy." *Chemical Reviews*.

Kogen, Hiroshi, Toshihiro Kiho, Keiko Tago, Shuichi Miyamoto, Tomoyuki Fujioka, Noriko Otsuka, Keiko Suzuki-Konagai, and Takeshi Ogita. 2000. "Alutacenoic Acids A and B, Rare Naturally Occurring Cyclopropenone Derivatives Isolated from Fungi: Potent Non-Peptide Factor XIIIa Inhibitors." *J. Am. Chem. Soc.* 122 (8): 1842-43.

Kumar, Pratik, Ting Jiang, Sining Li, Omar Zainul, and Scott T Laughlin. 2018. "Caged Cyclopropenes for Controlling Bioorthogonal Reactivity." *Organic & Biomolecular Chemistry* 16 (22): 4081-85.

Kumar, Pratik, Ting Jiang, Omar Zainul, Alyssa N. Preston, Sining Li, Joshua D. Farr, Pavit Suri, and Scott T. Laughlin. 2018. "Lipidated Cyclopropenes via a Stable 3-N Spirocyclopropene Scaffold." *Tetrahedron Letters* 59 (37): 3435-38.

Kumar, Pratik, and Scott T Laughlin. 2019. "Modular Activatable Bioorthogonal Reagents." *Methods in Enzymology* 622: 153-82.

Kumar, Pratik, David Shukhman, and Scott T Laughlin. 2016. "A Photocaged, Cyclopropene-Containing Analog of the Amino Acid Neurotransmitter Glutamate." *Tetrahedron Letters* 57 (51): 5750-52.

Kumar, Pratik, Omar Zainul, and Scott T. Laughlin. 2018. "Inexpensive Multigram-Scale Synthesis of Cyclic Enamines and 3-N Spirocyclopropyl Systems." *Organic and Biomolecular Chemistry* 16 (4): 652-56.

Lang, Kathrin, and Jason W. Chin. 2014. "Bioorthogonal Reactions for Labeling Proteins." *ACS Chemical Biology* 9 (1): 16-20.

Laroche, Christophe, Dominique Harakat, Philippe Bertus, and Jan Szymoniak. 2005. "Studies on the Titanium-Catalyzed Cyclopropanation of Nitriles." *Organic & Biomolecular Chemistry* 3 (19): 3482-87.

Lee, D J, J H Wales, J L Ayres, and R O Sinnhuber. 1968. "Synergism between Cyclopropenoid Fatty Acids and Chemical Carcinogens in Rainbow Trout (Salmo Gairdneri)." *Cancer Research* 28 (11): 2312-18.

Lee, Min Hee, Ji Hye Han, Pil Seung Kwon, Sankarprasad Bhuniya, Jin Young Kim, Jonathan L. Sessler, Chulhun Kang, and Jong Seung Kim. 2012. "Hepatocyte-Targeting Single Galactose-Appended Naphthalimide: A Tool for Intracellular Thiol Imaging in Vivo." *J. Am. Chem. Soc.* 134 (2): 1316-22.

Lee, Yun Mi, Seokwoo Lee, Hongjun Jeon, Dong Jae Baek, Jae Hong Seo, Deukjoon Kim, and Sanghee Kim. 2011. "A Practical and Cost-Effective Synthesis of d-Erythro-Sphingosine from d-Ribo-Phytosphingosine via a Cyclic Sulfate Intermediate." *Synthesis*, no. 6: 867-72.

Levandowski, Brian J., Raymond F. Gamache, Jennifer M. Murphy, and K. N. Houk. 2018. "Readily Accessible Ambiphilic Cyclopentadienes for Bioorthogonal Labeling." *J. Am. Chem. Soc.* 140 (20): 6426-31.

Li, He, Xinqi Fan, and Xing Chen. 2016. "Near-Infrared Light Activation of Proteins Inside Living Cells Enabled by Carbon Nanotube-Mediated Intracellular Delivery." *ACS Applied Materials and Interfaces* 8 (7): 4500-4507.

Li, Jie, and Peng R Chen. 2016. "Development and Application of Bond Cleavage Reactions in Bioorthogonal Chemistry." *Nature Chemical Biology* 12 (3): 129-37.

Li, Jinbo, Hao Kong, Lei Huang, Bo Cheng, Ke Qin, Mengmeng Zheng, Zheng Yan, and Yan Zhang. 2018. "Visible Light-Initiated Bioorthogonal Photoclick Cycloaddition." *J. Am. Chem. Soc.* 140 (44): 14542-46.

Li, Zhengqiu, Linghui Qian, Lin Li, Jan C Bernhammer, Han Vinh Huynh, Jun-Seok Lee, and Shao Q Yao. 2016. "Tetrazole Photoclick Chemistry: Reinvestigating Its Suitability as a Bioorthogonal Reaction and Potential Applications." *Angewandte Chemie* (International Ed. in English) 55 (6): 2002-6.

Li, Zhengqiu, Danyang Wang, Lin Li, Sijun Pan, Zhenkun Na, Chelsea Y. J. Tan, and Shao Q. Yao. 2014. "'Minimalist' Cyclopropene-Containing Photo-Cross-Linkers Suitable for Live-Cell Imaging and Affinity-Based Protein Labeling." *J. Am. Chem. Soc.* 136 (28): 9990-98.

Liao, Lian-an, Ni Yan, and Joseph M Fox. 2004. "Dianion Approach to Chiral Cyclopropene Carboxylic Acids." *Organic Letters* 6 (26): 4937-39.

Lin, Kuo Wei, Shiuan Yan, I. Lin Hsieh, and Tu Hsin Yan. 2006. "Unusual Ambiphilic Carbenoid Equivalent in Amide Cyclopropanation." *Organic Letters* 8 (11): 2265-67.

Lin, Tao-Yan, Chao-Ze Zhu, Peichao Zhang, Yidong Wang, Hai-Hong Wu, Jian-Jun Feng, and Junliang Zhang. 2016. "Regiodivergent Intermolecular [3+2] Cycloadditions of Vinyl Aziridines and Allenes: Stereospecific Synthesis of Chiral Pyrrolidines." *Angewandte Chemie* (International Ed. in English) 55 (36): 10844-48.

Liu, Fang, Yong Liang, and K. N. Houk. 2017. "Bioorthogonal Cycloadditions: Computational Analysis with the Distortion/Interaction Model and Predictions of Reactivities." *Accounts of Chemical Research* 50 (9): 2297-2308.

Lopez Aguilar, Aime, Jennie Grace Briard, Linette Yang, Ben Ovryn, Matthew Scott Macauley, and Peng Wu. 2017. "Tools for Studying Glycans: Recent Advances in Chemoenzymatic Glycan Labeling." *ACS Chemical Biology* 12 (3): 611-21.

Lu, Hongjian, and Chaozhong Li. 2006. "General and Highly Efficient Synthesis of 2-Alkylideneazetidines and Beta-Lactams via Copper-Catalyzed Intramolecular N-Vinylation." *Organic Letters* 8 (23): 5365-67.

Lu, Hongjian, Xinting Yuan, Shana Zhu, Changhui Sun, and Chaozhong Li. 2008. "Copper-Catalyzed Intramolecular N-Vinylation of Sulfonamides: General and Efficient Synthesis of Heterocyclic Enamines and Macrolactams." *J. Org. Chem.* 73 (21): 8665-68.

MACFARLANE, J J, F S SHENSTONE, and J R VICKERY. 1957. "Malvalic Acid and Its Structure." *Nature* 179 (4564) 830-31.

Madelaine, Claire, Yvan Six, and Olivier Buriez. 2007. "Electrochemical Aerobic Oxidation of Aminocyclopropanes to Endoperoxides." *Angewandte Chemie—International Edition* 46 (42): 8046-49.

Mangelinckx, Sven, Marc Boeykens, and Norbert De Kimpe. 2008. "2-(Dichloromethylene)Azetidines: Stable Strained Cyclic Enamines." *Synlett*, no. 9 (May): 1394-98.

Meimetis, Labros G., Jonathan C. T. Carlson, Randy J. Giedt, Rainer H. Kohler, and Ralph Weissleder. 2014. "Ultrafluorogenic Coumarin-Tetrazine Probes for Real-Time Biological Imaging." *Angewandte Chemie International Edition* 53 (29): 7531-34.

Morad, Samy A. F., and Myles C. Cabot. 2013. "Ceramide-Orchestrated Signalling in Cancer Cells." *Nature Reviews Cancer*.

Moreau, Robert J., and Erik J. Sorensen. 2007. "Classical Carbonyl Reactivity Enables a Short Synthesis of the Core Structure of Acutumine." *Tetrahedron* 63 (28): 6446-53.

Mukherjee, Santanu, Jung Woon Yang, Sebastian Hoffmann, and Benjamin List. 2007. "Asymmetric Enamine Catalysis." *Chemical Reviews*. American Chemical Society.

Narayanam, Maruthi Kumar, Yong Liang, K. N. Houk, and Jennifer M. Murphy. 2016. "Discovery of New Mutually Orthogonal Bioorthogonal Cycloaddition Pairs through Computational Screening." *Chemical Science* 7 (2): 1257-61.

Nunn, J. R. 1952. "66. The Structure of Sterculic Acid." *Journal of the Chemical Society* (Resumed), 313.

Olejniczak, Jason, Carl-Johan Carling, and Adah Almutairi. 2015. "Photocontrolled Release Using One-Photon Absorption of Visible or NIR Light." *Journal of Controlled Release: Official Journal of the Controlled Release Society* 219 (December): 18-30.

Orski, Sara V, Andrei A Poloukhtine, Selvanathan Arumugam, Leidong Mao, Vladimir V Popik, and Jason Locklin. 2010. "High Density Orthogonal Surface Immobilization via Photoactivated Copper-Free Click Chemistry." *J. Am. Chem. Soc.* 132 (32): 11024-26.

Patterson, David M., Krysten A. Jones, and Jennifer A. Prescher. 2014. "Improved Cyclopropene Reporters for Probing Protein Glycosylation." *Molecular BioSystems* 10 (7): 1693-97.

Patterson, David M., Lidia A. Nazarova, and Jennifer A. Prescher. 2014. "Finding the Right (Bioorthogonal) Chemistry." *ACS Chemical Biology*. American Chemical Society.

Patterson, David M, Lidia a Nazarova, Bryan Xie, David N Kamber, and Jennifer a Prescher. 2012. "Tetrazine+Synthesis of Some Functionalised Cyclopropenes." *J. Am. Chem. Soc.* 134 (45): 18638-43.

Paulini, Klaus, and H.-U. Reissig. 1992. "Efficient Synthesis of a Novel GABA Analogue Incorporating a Cyclopropene Ring." *Synlett* 1992 (06): 505-6.

Phukan, Prodeep, Matthias Bauer, and Martin E. Maier. 2003. "Facile Generation of Alkenes and Dienes from Tosylates." *Synthesis*, no. 9: 1324-28.

Poloukhtine, Andrei A., Ngalle Eric Mbua, Margreet A. Wolfert, Geert Jan Boons, and Vladimir V. Popik. 2009. "Selective Labeling of Living Cells by a Photo-Triggered Click Reaction." *J. Am. Chem. Soc.* 131 (43): 15769-76.

Ramil, Carlo P, and Qing Lin. 2014. "Photoclick Chemistry: A Fluorogenic Light-Triggered in Vivo Ligation Reaction." *Current Opinion in Chemical Biology* 21 (August): 89-95.

Ravasco, João M. J. M., Carlos M. Monteiro, and Alexandre F. Trindade. 2017. "Cyclopropenes: A New Tool for the Study of Biological Systems." *Organic Chemistry Frontiers*. Royal Society of Chemistry.

Row, R. David, and Jennifer A. Prescher. 2018. "Constructing New Bioorthogonal Reagents and Reactions." *Accounts of Chemical Research* 51 (5): 1073-81.

Rubin, Michael, Marina Rubina, and Vladimir Gevorgyan. 2006. "Recent Advances in Cyclopropene Chemistry." *Synthesis*.

Sauer, Jürgen, Dieter K. Heldmann, Josef Hetzenegger, Josef Krauthan, Heinz Sichert, and Johann Schuster. 1998. "1,2,4,5-Tetrazine: Synthesis and Reactivity in [4+2] Cycloadditions." *European Journal of Organic Chemistry* 1998 (12): 2885-96.

Searle, Peter F, Ming-Jen Chen, Longqin Hu, Paul R Race, Andrew L Lovering, Jane I Grove, Chris Guise, et al. 2004. "Nitroreductase: A Prodrug-Activating Enzyme for Cancer Gene Therapy." *Clinical and Experimental Pharmacology & Physiology* 31 (11): 811-16.

Sebej, Peter, Jürgen Wintner, Pavel Müller, Tomáš Slanina, Jamaludin Al Anshori, Lovely Angel Panamparambil Antony, Petr Klán, and Jakob Wirz. 2013. "Fluorescein Analogues as Photoremovable Protecting Groups Absorbing at ~520 Nm." *J. Org. Chem.* 78 (5): 1833-43.

Šečkutė, Jolita, Jun Yang, and Neal K. Devaraj. 2013. "Rapid Oligonucleotide-Templated Fluorogenic Tetrazine Ligations." *Nucleic Acids Research* 41 (15): e148-e148.

Shah, Lisa, Scott T. Laughlin, and Isaac S. Carrico. 2016. "Light-Activated Staudinger-Bertozzi Ligation within Living Animals." *J. Am. Chem. Soc.* 138 (16): 5186-89.

Shintani, Ryo, Takaoki Tsuji, Soyoung Park, and Tamio Hayashi. 2010. "Mechanistic Investigation of the Palladium-Catalyzed Decarboxylative Cyclization of Gamma-Methylidene-Delta-Valerolactones with Isocyanates: Kinetic Studies and Origin of the Site Selectivity in the Nucleophilic Attack at a (Pi-Allyl)Palladium." *J. Am. Chem. Soc.* 132 (21): 7508-13.

Singh, Kamaljeet, Christopher J. Fennell, Evangelos A. Coutsias, Reza Latifi, Steve Hartson, and Jimmie D. Weaver. 2018. "Light Harvesting for Rapid and Selective Reactions: Click Chemistry with Strain-Loadable Alkenes." *Chem* 4 (1): 124-37.

Singh, Rojendra, Constantin Czekelius, and Richard R. Schrock. 2006. "Living Ring-Opening Metathesis Polymerization of Cyclopropenes." *Macromolecules* 39 (4): 1316-17.

Smith, Natalee J, Katarina Rohlfing, Lisa A Sawicki, Prathamesh M Kharkar, Samantha J Boyd, April M Kloxin, and Joseph M Fox. 2018. "Fast, Irreversible Modification of Cysteines through Strain Releasing Conjugate Additions of Cyclopropenyl Ketones." *Organic & Biomolecular Chemistry* 16 (12): 2164-69.

Spangler, Benjamin, Charles W Morgan, Shaun D Fontaine, Mark N Vander Wal, Christopher J Chang, James A Wells, and Adam R Renslo. 2016. "A Reactivity-Based Probe of the Intracellular Labile Ferrous Iron Pool." *Nature Chemical Biology* 12 (9): 680-85.

Spate, Anne-Katrin, Holger Bußkamp, Andrea Niederwieser, Verena F. Schart, Andreas Marx, and Valentin Wittmann. 2014. "Rapid Labeling of Metabolically Engineered Cell-Surface Glycoconjugates with a Carbamate-Linked Cyclopropene Reporter." *Bioconjugate Chemistry* 25 (1): 147-54.

Stork, Gilbert., A. Brizzolara, H. Landesman, J. Szmuszkovicz, and R. Terrell. 1963. "The Enamine Alkylation and Acylation of Carbonyl Compounds." *J. Am. Chem. Soc.* 85 (2): 207-22.

Stutz, Alfred, and Stefan Pitsch. 1999. "Automated RNA-Synthesis with Photocleavable Sugar and Nucleobase Protecting Groups." *Synlett* 1999 (Sup. 1): 930-34.

Sulmon, Paul, Norbert De Kimpe, and Niceas Schamp. 1988. "New Synthesis of N-Aryl-2-Methyleneazetidines." *J. Org. Chem.* 53 (19): 4462-65.

Sun, Jianwei, Yanmei Dong, Liya Cao, Xinyan Wang, Shaozhong Wang, and Yuefei Hu. 2004. "Highly Efficient Chemoselective Deprotection of O,O-Acetals and O,O-Ketals Catalyzed by Molecular Iodine in Acetone." *J. Org. Chem.* 69 (25): 8932-34.

Tasdelen, Mehmet Atilla, and Yusuf Yagci. 2013. "Light-Induced Click Reactions." *Angewandte Chemie International Edition* 52 (23): 5930-38.

Thalhammer, Franz, Uwe Wallfahrer, and Jürgen Sauer. 1990. "Reaktivität Einfacher Offenkettiger Und Cyclischer Dienophile Bei Diels-Alder-Reaktionen Mit Inversem Elektronenbedarf." *Tetrahedron Letters* 31 (47): 6851-54.

Umeda, Nobuhiro, Hironori Takahashi, Mako Kamiya, Tasuku Ueno, Toru Komatsu, Takuya Terai, Kenjiro Hanaoka, Tetsuo Nagano, and Yasuteru Urano. 2014. "Boron Dipyrromethene As a Fluorescent Caging Group for Single-Photon Uncaging with Long-Wavelength Visible Light." *ACS Chemical Biology* 9 (10): 2242-46.

Vorobyeva, Anzhelika G, Michael Stanton, Aurélien Godinat, Kjetil B Lund, Grigory G Karateev, Kevin P Francis, Elizabeth Allen, et al. 2015. "Development of a Bioluminescent Nitroreductase Probe for Preclinical Imaging." *PloS One* 10 (6): e0131037.

Vu, Viet Anh, Ilan Marek, Kurt Polborn, and Paul Knochel. 2002. "Preparation of New Functionalized Cyclopropylmagnesium Reagents." *Angewandte Chemie* (International Ed. in English) 41 (2): 351-52.

Walsh, Robin. 2005. "The Cyclopropene Pyrolysis Story." *Chemical Society Reviews* 34 (8): 714-32.

Wolf, Larissa B., Kim C. M. F. Tjen, Hefziba T. ten Brink, Richard H. Blaauw, Henk Hiemstra, Hans E. Schoemaker, and Floris P. J. T. Rutjes. 2002. "Palladium-Catalyzed Cyclization Reactions of Acetylene-Containing Amino Acids." *Advanced Synthesis & Catalysis* 344 (1): 70.

Wong, Pamela T., Edward W. Roberts, Shengzhuang Tang, Jhindan Mukherjee, Jayme Cannon, Alyssa J. Nip, Kaitlin Corbin, Matthew F. Krummel, and Seok Ki Choi. 2017. "Control of an Unusual Photo-Claisen Rearrangement in Coumarin Caged Tamoxifen through an Extended Spacer." *ACS Chemical Biology* 12 (4): 1001-10.

Wu, Haoxing, and Neal K. Devaraj. 2016. "Inverse Electron-Demand Diels-Alder Bioorthogonal Reactions." *Topics in Current Chemistry*. Springer International Publishing.

Xi Hing. 2012. COMPOUNDS COMPRISING A SPIRO-RING AND METHODS OF USE. 8293897, issued 2012.

Xie, Jian Hua, Shou Fei Zhu, and Qi Lin Zhou. 2011. "Transition Metal-Catalyzed Enantioselective Hydrogenation of Enamines and Imines." *Chemical Reviews*.

Xiong, De-Cai, Jingjing Zhu, Ming-Jie Han, Hui-Xin Luo, Cong Wang, Yang Yu, Yugian Ye, Guihua Tai, and Xin-Shan Ye. 2015. "Rapid Probing of Sialylated Glycoproteins in Vitro and in Vivo via Metabolic Oligosaccharide Engineering of a Minimal Cyclopropene Reporter." *Organic & Biomolecular Chemistry* 13 (13): 3911-17.

Yang, Jun, Yong Liang, Jolita Šečkutė, K N Houk, and Neal K Devaraj. 2014. "Synthesis and Reactivity Comparisons of 1-Methyl-3-Substituted Cyclopropene Mini-Tags for Tetrazine Bioorthogonal Reactions." *Chemistry* (Weinheim an Der Bergstrasse, Germany) 20 (12):

Yang, Jun, Jolita Šečkutė, Christian M. Cole, and Neal K. Devaraj. 2012. "Live-Cell Imaging of Cyclopropene Tags with Fluorogenic Tetrazine Cycloadditions." *Angewandte Chemie International Edition* 51 (30): 7476-79.

Yik-Sham Chung, Clive, Greg A. Timblin, Kaoru Saijo, and Christopher J. Chang. 2018. "Versatile Histochemical Approach to Detection of Hydrogen Peroxide in Cells and Tissues Based on Puromycin Staining." *J. Am. Chem. Soc.* 140 (19): 6109-21.

Yu, Zhipeng, Lok Yin Ho, and Qing Lin. 2011. "Rapid, Photoactivatable Turn-On Fluorescent Probes Based on an Intramolecular Photoclick Reaction." *J. Am. Chem. Soc.* 133 (31): 11912-15.

Yu, Zhipeng, and Qing Lin. 2014. "Design of Spiro[2.3] Hex-1-Ene, a Genetically Encodable Double-Strained Alkene for Superfast Photoclick Chemistry." *J. Am. Chem. Soc.* 136 (11): 4153-56.

Yu, Zhipeng, Tymish Y. Ohulchanskyy, Peng An, Paras N. Prasad, and Qing Lin. 2013. "Fluorogenic, Two-Photon-Triggered Photoclick Chemistry in Live Mammalian Cells." *J. Am. Chem. Soc.* 135 (45): 16766-69.

Yu, Zhipeng, Yanchao Pan, Zhiyong Wang, Jiangyun Wang, and Qing Lin. 2012. "Genetically Encoded Cyclopropene Directs Rapid, Photoclick-Chemistry-Mediated Protein Labeling in Mammalian Cells." *Angewandte Chemie International Edition* 51 (42): 10600-604.

Zeng, Dexing, Brian M. Zeglis, Jason S. Lewis, and Carolyn J. Anderson. 2013. "The Growing Impact of Bioorthogonal Click Chemistry on the Development of Radiopharmaceuticals." *Journal of Nuclear Medicine*.

Zengeya, Thomas T., Julie M. Garlick, Rhushikesh A. Kulkarni, Mikayla Miley, Allison M. Roberts, Youfeng Yang, Daniel R. Crooks, Carole Sourbier, W. Marston Linehan, and Jordan L. Meier. 2016. "Co-Opting a Bioorthogonal Reaction for Oncometabolite Detection." *J. Am. Chem. Soc.* 138 (49): 15813-16.

Zhang, Fan, and Joseph M. Fox. 2006. "Synthesis of Cyclopropene α-Amino Acids via Enantioselective Desymmetrization." *Organic Letters* 8 (14): 2965-68.

Zhang, Han, William S. Trout, Shuang Liu, Gabriel A. Andrade, Devin A. Hudson, Samuel L. Scinto, Kevin T. Dicker, et al. 2016. "Rapid Bioorthogonal Chemistry Turn-on through Enzymatic or Long Wavelength Photocatalytic Activation of Tetrazine Ligation." *J. Am. Chem. Soc.* 138 (18): 5978-83.

Zhu, Zhi Bin, Yin Wei, and Min Shi. 2011. "Recent Developments of Cyclopropene Chemistry." *Chemical Society Reviews*.

What is claimed:

1. A compound having the structure:

wherein $R_1$ is H or a protecting group;

$R_2$ and $R_3$ are each independently H, halo, $C_1$-$C_6$ alkyl, $C_2$-$C_6$ alkenyl, $C_2$-$C_6$ alkynyl, $C_1$-$C_6$ alkyl-C(O)NHR$_6$, or $C_1$-$C_6$ alkyl-C(O)OR$_6$, wherein $R_6$ is H, $C_1$-$C_6$ alkyl, $C_2$-$C_6$ alkenyl, $C_2$-$C_6$ alkynyl, $C_1$-$C_6$ alkylaryl or $L_1$-$Y_1$, wherein $R_6$ is substituted or unsubstituted;

wherein $L_1$ is a chemical linker that is present or absent and $Y_1$ is biotin or a lipid, or $R_2$ and $R_3$ combine to form a 3-7 membered cycloalkyl, heterocycloalkyl, aryl or heteroaryl ring; and $R_4$ and $R_5$ are each independently halo;

wherein when $R_2$ and $R_3$ are H, then the dashed line represents a bond that is present;

or a salt thereof.

2. The compound of claim 1, wherein $R_1$ is H, Boc, Nvoc or a light cleavable protecting group;

$R_2$ and $R_3$ are each independently H, halo, $C_1$-$C_3$ alkyl, $C_2$-$C_3$ alkenyl, $C_2$-$C_3$ alkynyl, $C_1$-$C_3$ alkyl-C(O)NHR$_6$, or $C_1$-$C_3$ alkyl-C(O)OR$_6$, wherein R_6 is H, C_1-C_3 alkyl, C_2-C_3 alkenyl or C_2-C_3 alkynyl, or R_2 and R_3 combine to form a 3-7 membered cycloalkyl, heterocycloalkyl, aryl or heteroaryl ring; and
R_4 and R_5 are each independently F, Cl or Br.
3. The compound of claim 1, wherein
R_1 is H, Boc or Nvoc;
R_2 and R_3 are each independently H or C_1-C_3 alkyl; and
R_4 and R_5 are each F.
4. The compound of claim 1 having the structure:
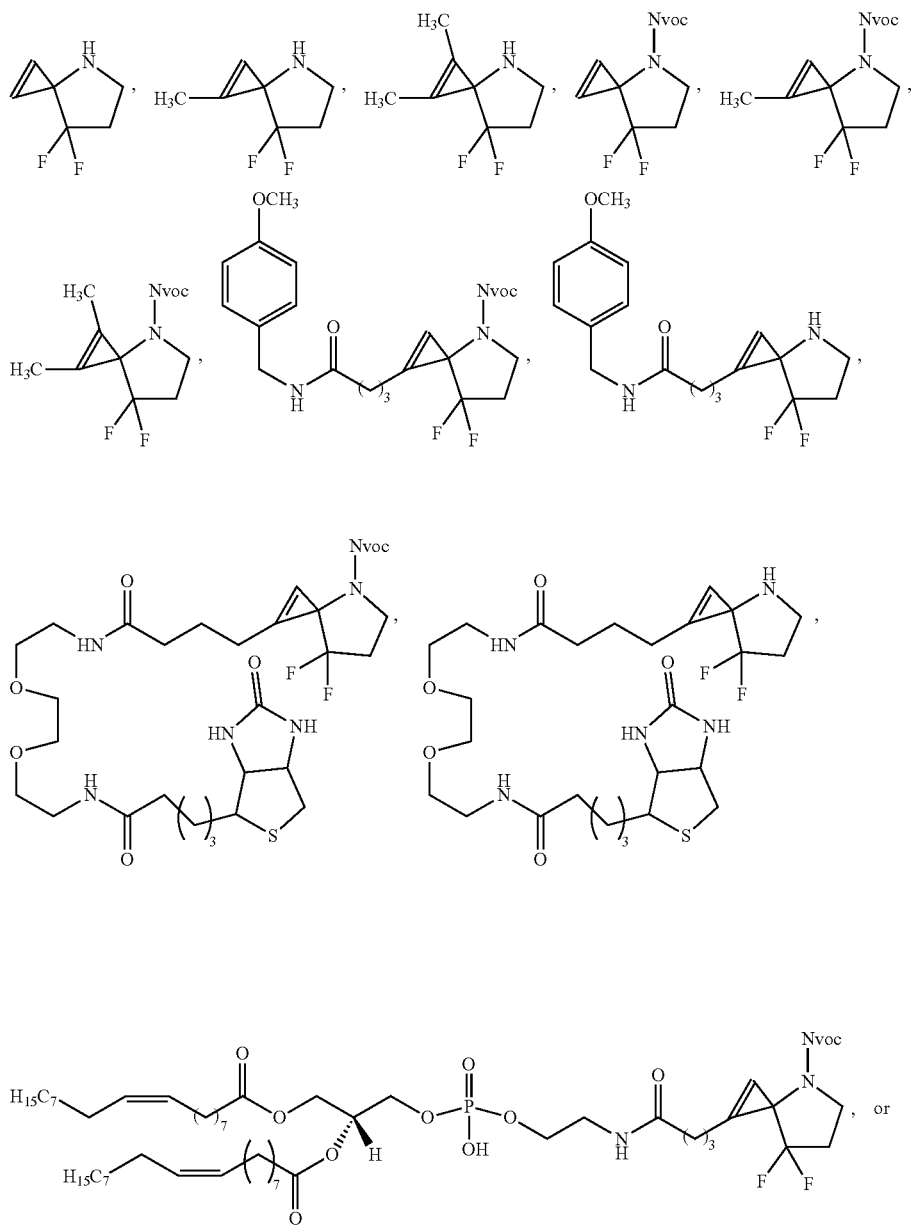
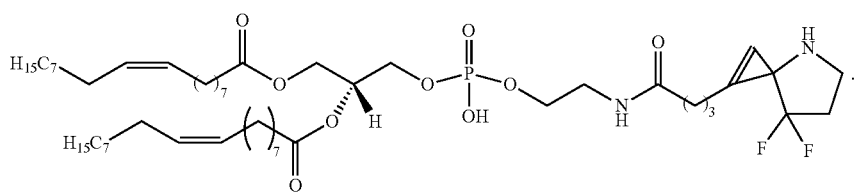

5. A compound having the structure:

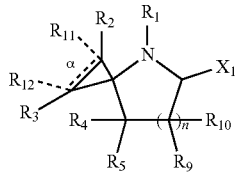

wherein
n is 0 or 1;
α is a bond which is absent or present,
wherein when α is present, then $R_{11}$ and $R_{12}$ are absent and when α is absent, $R_{11}$ and $R_{12}$ are present;
$X_1$ is H or $L_3$-$Y_3$,
wherein $L_3$ is a chemical linker that is present or absent and $Y_3$ is a lipid, peptide, protein, sugar, nucleotide, antibody or imaging moiety;
$R_1$ is H or a protecting group;
$R_2$ and $R_3$ are each independently H, halo, alkyl, alkenyl, alkynyl, alkyl-C(O) $NHR_{13}$, or alkyl-C(O)$OR_{13}$,
wherein $R_{13}$ is H or substituted or unsubstituted alkyl, alkenyl, alkynyl, heteroalkyl, amidoalkyl, amidoheteroalkyl, alkylaryl, alkylheteroaryl or $L_4$-$Y_4$,
wherein $L_4$ is a chemical linker that is present or absent and $Y_4$ is a lipid, peptide, protein, sugar, nucleotide, antibody or imaging moiety;
$R_4$ and $R_5$ combine to form a carbonyl, or are each H, or one of $R_4$ and $R_5$ is H and the other is halo, —O(alkyl), substituted or unsubstituted —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;
$R_9$ and $R_{10}$ are each independently H, halo, alkyl, —O(alkyl), substituted or unsubstituted O (alkylaryl), $CF_3$, $OCF_3$, $OCHF_2$ or $OSO_3^-$;
wherein one of $R_4$ and $R_5$ or one of $R_9$ and $R_{10}$ is other than H; and
$R_{11}$ and $R_{12}$, when present, combine to form a 5-6 membered substituted or unsubstituted heterocycloalkyl, aryl or heteroaryl ring which is fused to the cyclopropanyl;
or a salt thereof.

6. The compound of claim 5 having the structure:

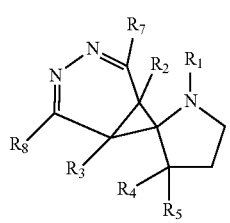

wherein
$R_1$ is H;
$R_2$ and $R_3$ are each independently H, halo, $C_1$-$C_6$ alkyl, $C_2$-$C_6$ alkenyl, $C_2$-$C_6$ alkynyl, $C_1$-$C_6$ alkyl-C(O) $NHR_6$, or $C_1$-$C_6$ alkyl-C(O)$OR_6$,
wherein $R_6$ is H, $C_1$-$C_6$ alkyl, $C_2$-$C_6$ alkenyl, $C_2$-$C_6$ alkynyl, $C_1$-$C_6$ alkylaryl or $L_1$-$Y_1$ wherein $L_1$ is a chemical linker that is present or absent and
$Y_1$ is biotin or a lipid;
$R_7$ and $R_8$ are each independently H, substituted or unsubstituted aryl or $L_2$-$Y_2$,
wherein $L_2$ is a chemical linker that is present or absent and $Y_2$ is bovine serum albumin protein; and
$R_4$ and $R_5$ are each independently halo;
or a salt thereof.

7. The compound of claim 6, wherein $R_7$ and $R_8$ are each independently H, phenyl, or substituted phenyl.

8. The compound of claim 6 having the structure:

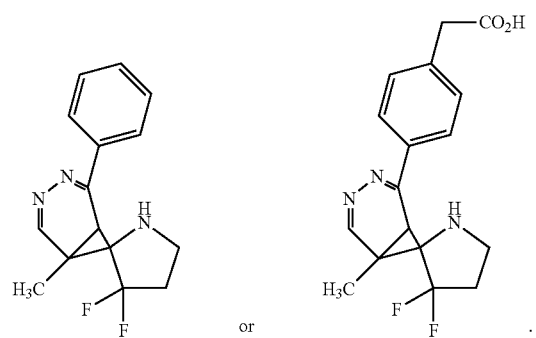 [SMILES: CC12C=NN=C(c3ccccc3)C1C21NCCC1(F)F ; CC12C=NN=C(c3ccc(CC(=O)O)cc3)C1C21NCCC1(F)F]

9. A compound having the structure:

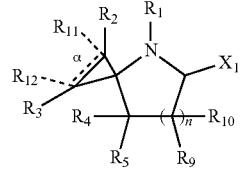

wherein
n is 0 or 1;
α is a bond which is absent or present,
wherein when α is present, then $R_{11}$ and $R_{12}$ are absent and when α is absent, $R_{11}$ and $R_{12}$ are present;
$X_1$ is H or $L_3$-$Y_3$,
wherein $L_3$ is a chemical linker that is present or absent and $Y_3$ is a lipid, peptide, protein, sugar, nucleotide, antibody or imaging moiety;
$R_1$ is H or a protecting group;
$R_2$ and $R_3$ are each independently H, halo, alkyl, alkenyl, alkynyl, alkyl-C(O) $NHR_{13}$, or alkyl-C(O)$OR_{13}$,
wherein $R_{13}$ is H or substituted or unsubstituted alkyl, alkenyl, alkynyl, heteroalkyl, amidoalkyl, amidoheteroalkyl, alklyaryl, alkylheteroaryl or $L_4$-$Y_4$,
wherein $L_4$ is a chemical linker that is present or absent and $Y_4$ is a lipid, peptide, protein, sugar, nucleotide, antibody or imaging moiety;
$R_4$ and $R_5$ combine to form a carbonyl, or are each H, or one of $R_4$ and $R_5$ is H and the other is halo, —O(alkyl), —O(alkylaryl), $CF_3$, $OCF_3$, $OCHF_2$ or $OSO_3^-$, or $R_4$ and $R_5$ are each independently halo, alkyl, —O(alkyl), $CF_3$, $OCF_3$, $OCHF_2$ or $OSO_3^-$;
$R_9$ and $R_{10}$ are each independently H, halo, alkyl, —O(alkyl), O(alkylaryl), $CF_3$, $OCF_3$, $OCHF_2$ or $OSO_3^-$;
wherein two of $R_4$ and $R_5$ are other than H and $R_9$ and $R_{10}$ are each H; or wherein two of $R_9$ and $R_{10}$ are other than H and R$_4$ and R$_5$ are each H; or wherein one of R$_4$ and R$_5$ is other than H and one of R$_9$ and R$_{10}$ is other than H, and R$_{11}$ and R$_{12}$, when present, combine to form a 5-6 membered substituted or unsubstituted heterocycloalkyl, aryl or heteroaryl ring which is fused to the cyclopropanyl.

10. The compound of claim 5 having the structure:

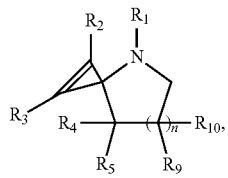

wherein
n is 0 or 1;
R$_1$ is H or a protecting group;
R$_2$ and R$_3$ are each independently H, halo, alkyl, alkenyl, alkynyl, alkyl-C(O) NHR$_{13}$, or alkyl-C(O)OR$_{13}$,
wherein R$_{13}$ is H or substituted or unsubstituted alkyl, alkenyl, alkynyl, heteroalkyl, amidoalkyl, amidoheteroalkyl, alklyaryl, alkylheteroaryl or L$_4$-Y$_4$,
wherein L$_4$ is a chemical linker that is present or absent and Y$_4$ is a lipid, peptide, protein, sugar, nucleotide, antibody or imaging moiety;
R$_4$ and R$_5$ combine to form a carbonyl, or are each H, or one of R$_4$ and R$_5$ is H and the other is halo, —O(alkyl), —O(alkylaryl), CF$_3$, OCF$_3$, OCHF$_2$ or OSO$_3^-$, or R$_4$ and R$_5$ are each independently halo, alkyl, —O(alkyl), CF$_3$, OCF$_3$, OCHF$_2$ or OSO$_3^-$;
R$_9$ and R$_{10}$ are each independently H, halo, alkyl, —O(alkyl), —O (alkylaryl), CF$_3$, OCF$_3$, OCHF$_2$ or OSO$_3^-$; wherein one of R$_4$ and R$_5$ or one of R$_9$ and R$_{10}$ is other than H;
or a salt thereof.

11. The compound of claim 10, wherein
(a) R$_1$ is H, a light cleavable amine protecting group, an enzyme cleavable protecting group, or a carbamate protecting group having the structure

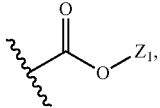

wherein Z$_1$ is substituted or unsubstituted alkylaryl, substituted or unsubstituted alkylheteroaryl or a pyranoside; and/or
(b) one of R$_9$ and R$_{10}$ is H and the other is —O(alkylaryl).

12. The compound of claim 11, wherein Z$_1$ is

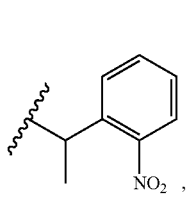 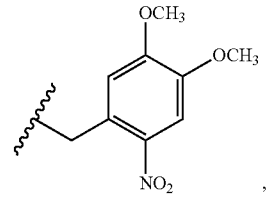

-continued

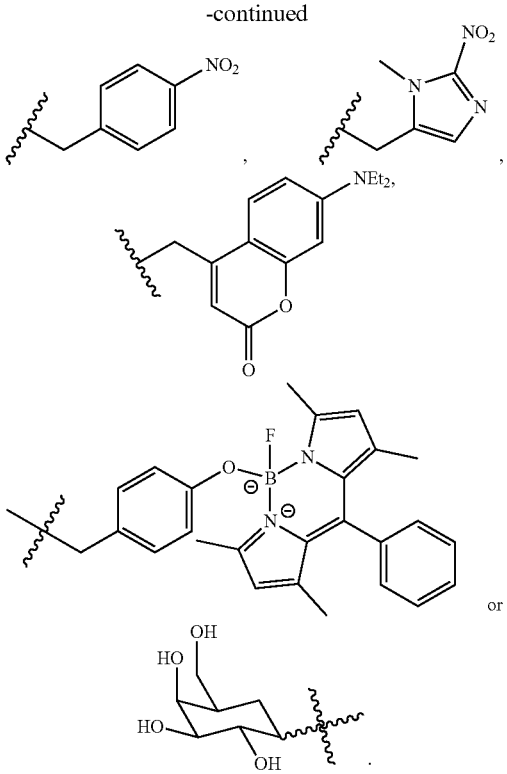

or

13. The compound of claim 5, having the structure:

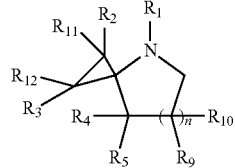

wherein
n is 0 or 1;
R$_1$ is H;
R$_2$ and R$_3$ are each independently H, halo, alkyl, alkenyl, alkynyl, alkyl-C(O)NHR$_{13}$, or alkyl-C(O)OR$_{13}$,
wherein R$_{13}$ is H or a substituted or unsubstituted alkyl, alkenyl, alkynyl, heteroalkyl, amidoalkyl, amidoheteroalkyl, alklyaryl, alkylheteroaryl or L$_4$-Y$_4$,
wherein L$_4$ is a chemical linker that is present or absent and Y$_4$ is a lipid, peptide, protein, sugar, nucleotide, antibody or imaging moiety,
R$_4$ and R$_5$ combine to form a carbonyl, or are each H, or one of R$_4$ and R$_5$ is H and the other is halo, —O(alkyl), —O(alkylaryl), CF$_3$, OCF$_3$, OCHF$_2$ or OSO$_3^-$, or R$_4$ and R$_5$ are each independently halo, alkyl, —O(alkyl), CF$_3$, OCF$_3$, OCHF$_2$ or OSO$_3^-$;
R$_9$ and R$_{10}$ are each independently H, halo, alkyl, —O(alkyl), —O(alkylaryl), CF$_3$, OCF$_3$, OCHF$_2$ or OSO$_3^-$, wherein one of R$_4$ and R$_5$ or one of R$_9$ and R$_{10}$ is other than H;
R$_{11}$ and R$_{12}$ combine to form a 5-6 membered substituted or unsubstituted heterocycloalkyl, aryl or heteroaryl ring which is fused to the cyclopropanyl; or $R_{11}$ and $R_{12}$ combine to form a dihydropyridazine, which is fused to the cyclopropanyl;

or a salt thereof.

14. The compound of claim 13 having the structure:

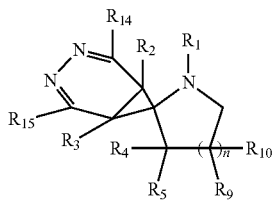

wherein $R_{14}$ and $R_{15}$ are each independently H, halo, alkyl, alkenyl, alkynyl, alkyl-C(O) $NHR_{16}$, or alkyl-C(O)$OR_{16}$, wherein $R_{16}$ is H, or a substituted or unsubstituted alkyl, alkenyl, alkynyl, heteroalkyl, amidoalkyl, amidoheteroalkyl, alkylaryl, alkylheteroaryl or $L_5$-$Y_5$, wherein $L_5$ is a chemical linker that is present or absent and $Y_5$ is a lipid, peptide, protein, sugar, nucleotide, antibody or imaging moiety; or a salt thereof.

15. The compound of claim 10, wherein the —O(alkylaryl) is

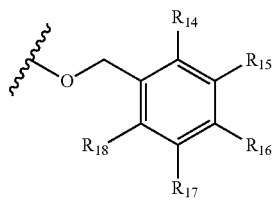

wherein $R_{14}$, $R_{15}$, $R_{16}$, $R_{17}$ and $R_{18}$ are each independently H, halo, alkyl, —O(alkyl), $CF_3$, $OCF_3$, $OCHF_2$, $OSO_3^-$, $SO_3H$, $NO_2$ or CN.

16. The compound of claim 5 having the structure:

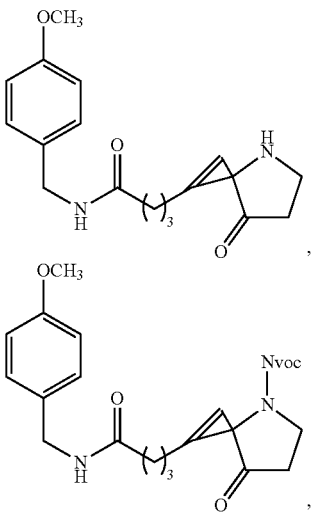

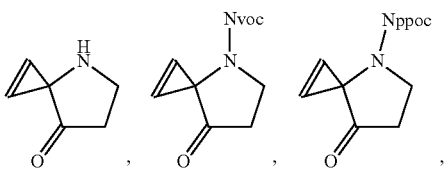

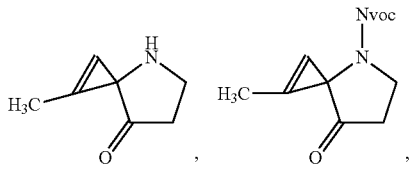

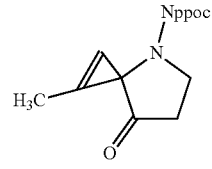

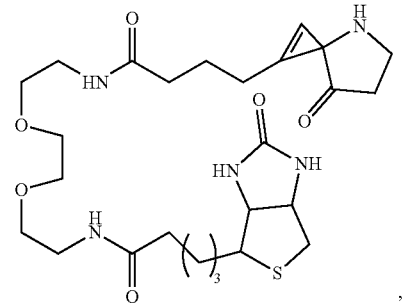

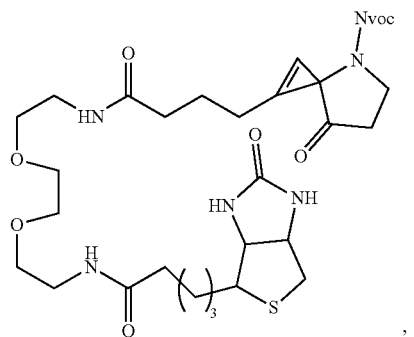

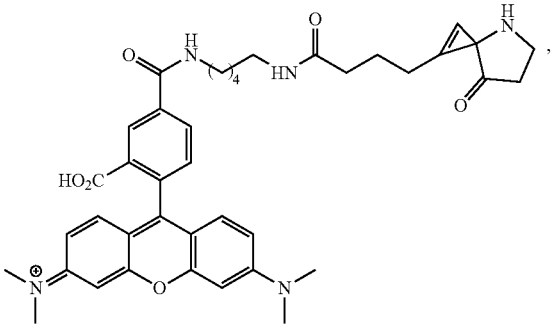

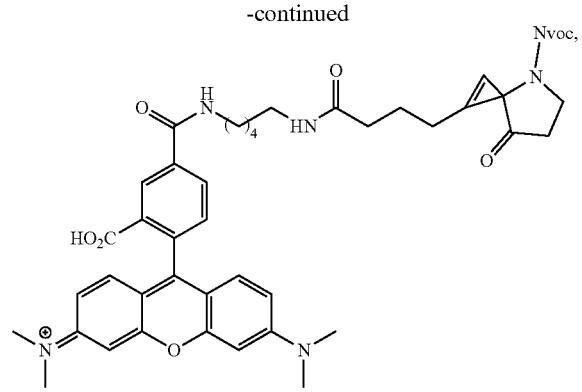
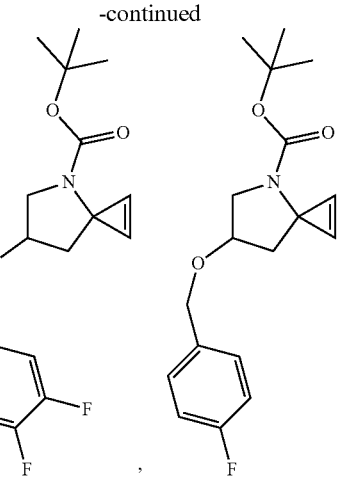
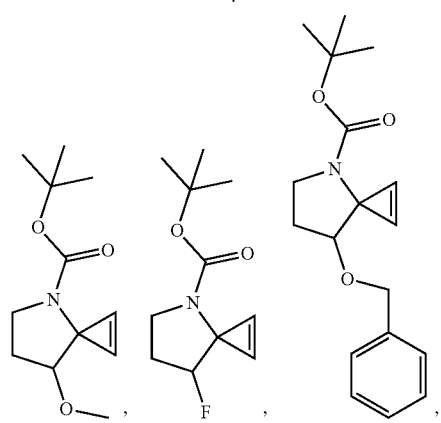
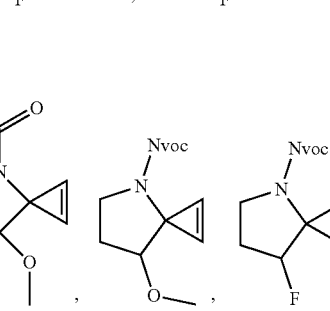
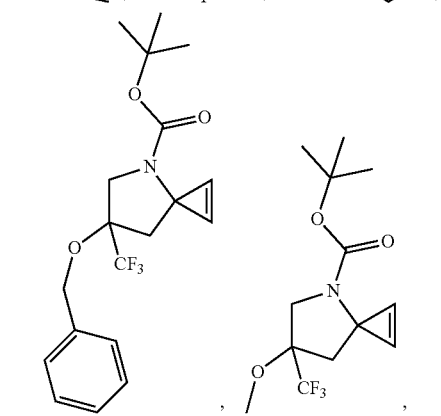
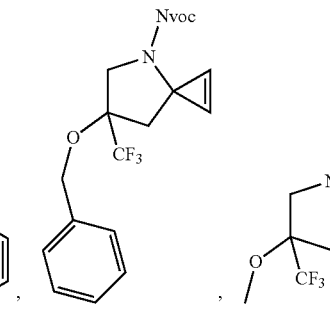
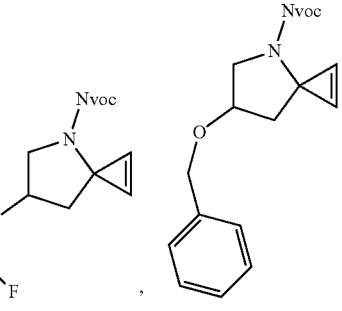
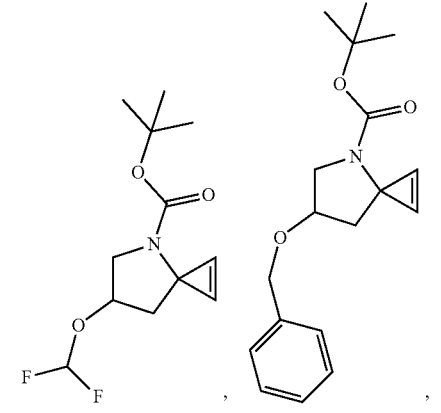
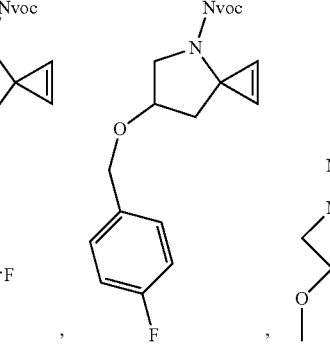

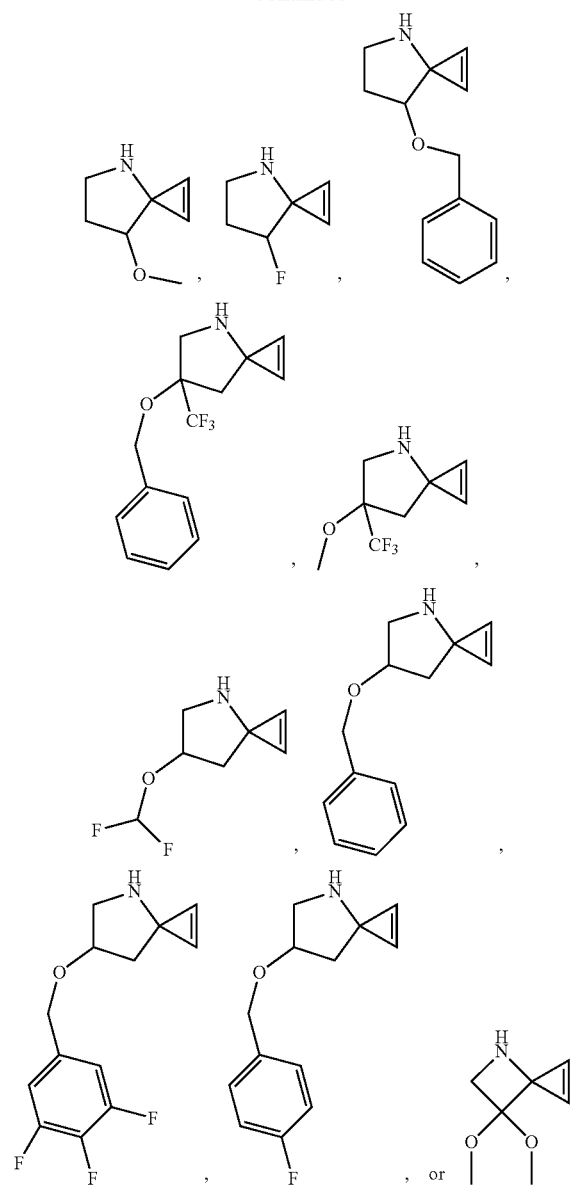
17. The compound of claim 5 having the structure:
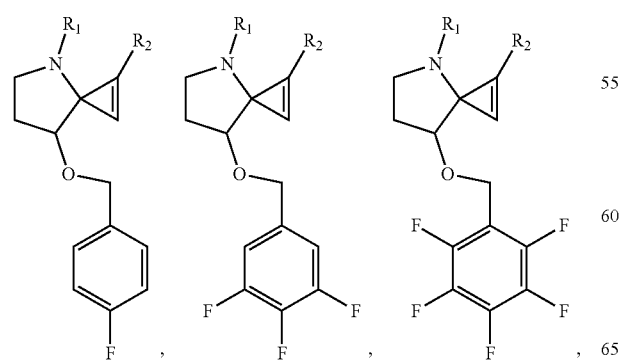
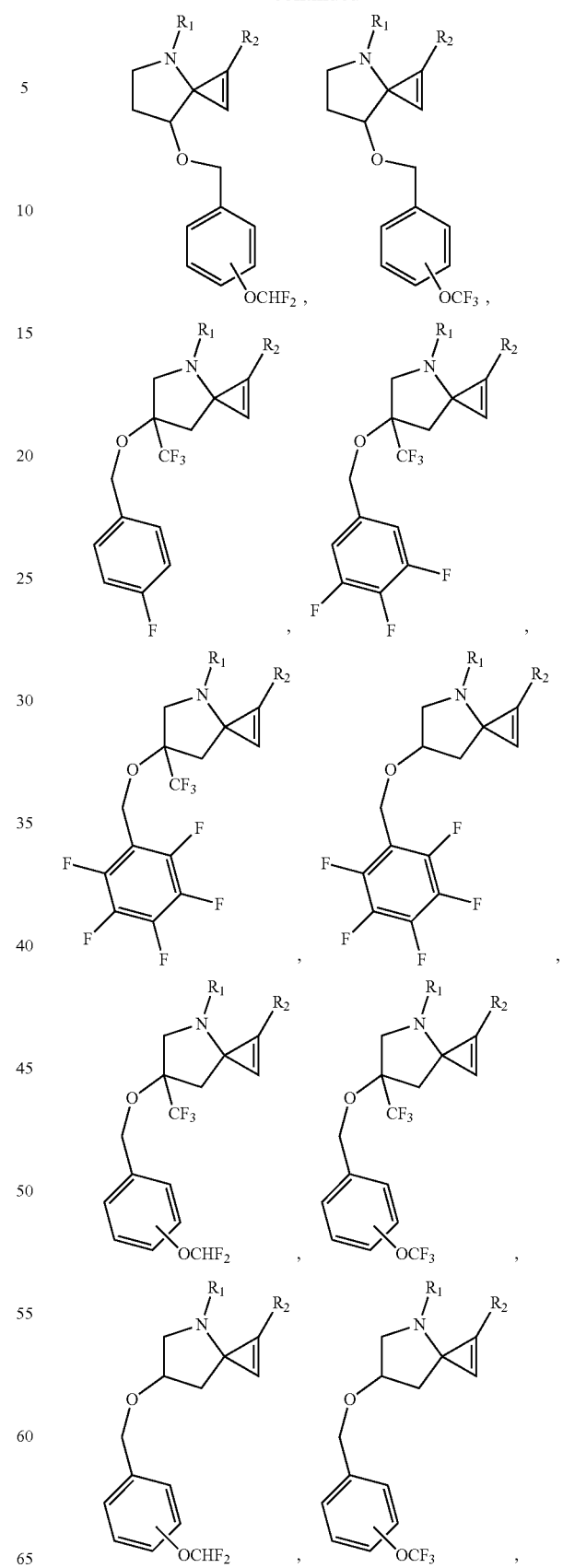

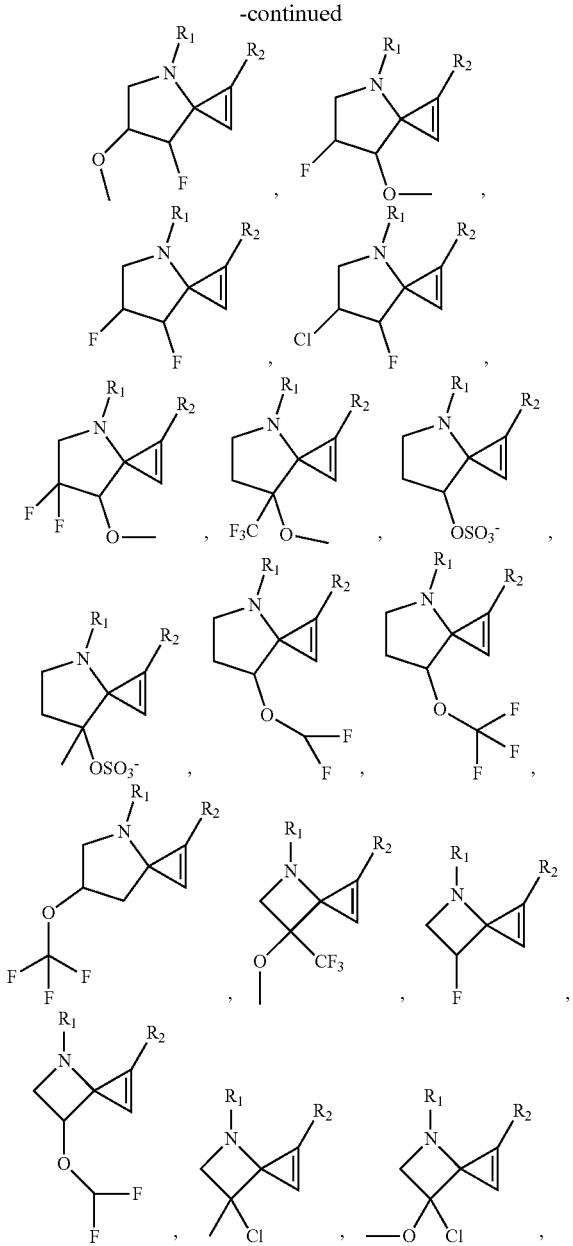
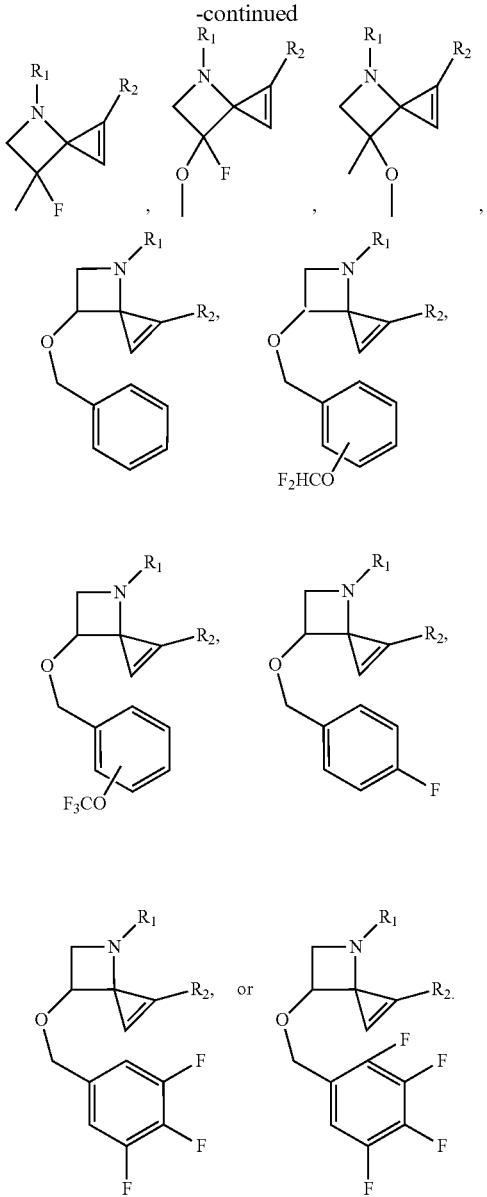
* * * * *